United States Patent
Ziemer et al.

(10) Patent No.: US 9,102,623 B2
(45) Date of Patent: Aug. 11, 2015

(54) PYRIDINECARBOXAMIDES, USEFUL-PLANT-PROTECTING COMPOSITION COMPRISING THEM AND PROCESSES FOR THEIR PREPARATION AND THEIR USE

(75) Inventors: Frank Ziemer, Kriftel (DE); Lothar Willms, Hofheim (DE); Christopher Rosinger, Hofheim (DE); Thomas Auler, Leichlingen (DE); Erwin Hacker, Hochheim (DE); Udo Bickers, Wietmarschen (DE)

(73) Assignee: Bayer Cropscience AG, Monheim (DE)

( * ) Notice: Subject to any disclaimer, the term of this patent is extended or adjusted under 35 U.S.C. 154(b) by 153 days.

(21) Appl. No.: 13/523,794

(22) Filed: Jun. 14, 2012

(65) Prior Publication Data

US 2012/0252670 A1   Oct. 4, 2012

Related U.S. Application Data

(63) Continuation of application No. 12/111,419, filed on Apr. 29, 2008.

(30) Foreign Application Priority Data

Apr. 30, 2007   (EP) .................................... 07400013

(51) Int. Cl.
| | |
|---|---|
| A01N 25/32 | (2006.01) |
| C07D 211/76 | (2006.01) |
| C07D 213/82 | (2006.01) |
| C07D 401/06 | (2006.01) |
| C07D 413/06 | (2006.01) |
| C07D 417/06 | (2006.01) |

(52) U.S. Cl.
CPC .............. *C07D 211/76* (2013.01); *A01N 25/32* (2013.01); *C07D 213/82* (2013.01); *C07D 401/06* (2013.01); *C07D 413/06* (2013.01); *C07D 417/06* (2013.01)

(58) Field of Classification Search
None
See application file for complete search history.

(56) References Cited

U.S. PATENT DOCUMENTS

| | | | |
|---|---|---|---|
| 4,965,266 A | | 10/1990 | Uno et al. |
| 5,235,060 A | | 8/1993 | Bullock et al. |
| 5,344,813 A | * | 9/1994 | Theobald et al. ............. 504/244 |
| 5,393,734 A | | 2/1995 | Andrea et al. |
| 6,794,397 B2 | | 9/2004 | Cai et al. |
| 7,732,375 B2 | | 6/2010 | Dunkel et al. |
| 8,138,118 B2 | | 3/2012 | Bickers et al. |
| 2002/0177578 A1 | | 11/2002 | Ricks et al. |
| 2004/0116479 A1 | | 6/2004 | Haviv et al. |
| 2004/0224844 A1 | | 11/2004 | Bickers et al. |
| 2005/0037922 A1 | | 2/2005 | Bickers et al. |
| 2005/0256000 A1 | | 11/2005 | Schaper et al. |
| 2007/0037858 A1 | | 2/2007 | Dunkel et al. |
| 2007/0196406 A1 | | 8/2007 | Dunkel et al. |
| 2007/0265164 A1 | | 11/2007 | Bartsch et al. |

FOREIGN PATENT DOCUMENTS

| | | |
|---|---|---|
| EP | 0298134 | 1/1989 |
| EP | 502740 | 9/1992 |
| EP | 0544151 | 11/1992 |
| EP | 0522392 | 1/1993 |
| GB | 2305174 | 4/1997 |
| WO | WO 01/14339 | 3/2001 |
| WO | WO 01/55115 | 8/2001 |
| WO | WO 2004/084631 | 10/2004 |
| WO | WO 2005/015994 | 2/2005 |
| WO | WO 2005/042492 | 5/2005 |
| WO | WO 2005/042493 | 5/2005 |
| WO | WO 2005/112630 | 12/2005 |
| WO | WO 2006/007981 | 1/2006 |
| WO | WO 2007/041052 | 4/2007 |

OTHER PUBLICATIONS

R. Lang & P. Wenk, "Synthesis of Selectivity Trifluoromethylated Pyridine Derivatives as Potential Antihypersensitives". *Ilelvetica Chimica Acta*, vol. 71, p. 596-601, (1988).

M. Gorbunova, I. Genus & V. Kukhar, "Synthesis and Properties of β-Ethoxyvinyl Polyfluoroalkyl Ketones", *Synthesis 2000*, vol. 5, p. 738-742, (2000).

P. Hapiot & Médebielle, "Electrochemically induces free-radical tandem cyclisation of chlorodifluoromethylaled ketones Application to the synthesis of gem-difluorinated heterocycles". Journal of Fluorine Chemistry, vol. 107, p. 285-300, (2001).

H.V. Dias & H. Kim, "Novel Tris(pyrazolyl)borates Bearing Perfluoroalkyl Pigtails. Syntheses and Characterization of the Sodium and Copper(I) Complexes of [HB(3-(R)Pz)₃ ] (R=C₂F₅, C₃F₇, Pz=Pyrazolyl)". *Organometallics*, vol. 15, p. 5374-5379, (1996).

* cited by examiner

*Primary Examiner* — Sue Liu
*Assistant Examiner* — Thor Nielsen
(74) *Attorney, Agent, or Firm* — Frommer Lawrence & Haug

(57) ABSTRACT

Compounds of the formula (I), or salts thereof,

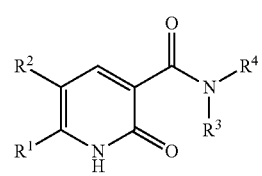

in which $R^1$ to $R^4$ are as defined in formula (I) of claim 1 are suitable as useful-plant-protecting agents for reducing or preventing harmful effects of agrochemicals on the useful plants and their method of preparation are described.

17 Claims, No Drawings

PYRIDINECARBOXAMIDES, USEFUL-PLANT-PROTECTING COMPOSITION COMPRISING THEM AND PROCESSES FOR THEIR PREPARATION AND THEIR USE

INCORPORATION BY REFERENCE

The present application is a continuation of U.S. patent application Ser. No. 12/111,419 filed Apr. 29, 2008, which claims benefit under 35 U.S.C. 119(a) of European patent application 07400013.4, filed on Apr. 30, 2007.

Any foregoing applications, including U.S. patent application Ser. No. 12/111,419 and European patent application EP 07400013.4, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

DESCRIPTION

The present invention relates to useful-plant-protecting compounds and compositions comprising specific compounds as safeners for reducing phytotoxic actions of agrochemicals, in particular of herbicides. The invention relates in particular to pyridone derivatives as safeners and to processes for their preparation.

When controlling unwanted organisms in crops of plants which are useful for agriculture or forestry by using pesticides, the useful plants are frequently also damaged to a greater or lesser extent, by the pesticides employed. This unwanted phytotoxic effect is encountered in particular with the use of a considerable number of herbicides in crops of useful plants such as, for example, corn, rice or cereals- and there primarily in the post-emergence application. In some instances, the useful plants can be protected against the phytotoxic properties of the pesticides by employing safeners or antidotes, without diminishing or substantially impairing the pesticidal activity against the harmful organisms. In some cases, even an improved pesticidal action against harmful organisms such as weeds was observed.

The compounds hitherto known as safeners belong to a large number of different chemical structure classes, their suitability as safeners generally also depending on the chemical structures of the pesticides and on the crops of useful plants.

Known for a long time have been the safener actions of compounds from the group of the phenoxy- or heteroaryloxy-alkanecarboxylic acids, provided these compounds are applied in combination with herbicides. Examples of such compounds are MCPA and similar compounds which are at the same time herbicidally active against harmful plants, or cloquintocet-mexyl.

Known are furthermore safeners from the group of the derivatives of N-phenyl-substituted heteroaromatic carboxylic esters having a plurality of heteroatoms in the heterocycle. Examples of such safeners are the safeners mefenpyr-diethyl and isoxadifen-ethyl, which are used in commercial products.

WO 2004/084631 (us 2004-0224844) discloses the use of hydroxyl-substituted aromatic carboxylic acid derivatives. WO 2005/015994 (US 2005-037922) describes specific derivatives of salicylic acid as safeners. These compounds are suitable in particular for use as safeners in crops of corn and soybeans.

Furthermore, WO 2005/112630 (US 2005-256000) discloses 1,2-dihydroquinoxalin-2-one derivatives as safeners.

Active compounds from the chemical class of the pyridones with pesticidal properties are known from the literature. Various biological actions are described; thus, for example, WO 2001/014339 (US 2002-177578) describes the fungicidal action of certain substituted pyridonecarboxamides, WO 2005/042492 (US 2007-196406) and WO 2005/042493 (US 2007-037858) describe inter alia the fungicidal action of heterocyclylcarboxanilides. EP-A-544151 (U.S. Pat. No. 5,344,813) describes the action of hydroxyl-substituted pyridonecarboxamides as herbicides.

Also known are representatives having pharmacological properties. Thus, WO 2001/055115 (U.S. Pat. No. 6,794,397) describes nicotinanilides as inductors of apoptosis, and US 2004/0116479 describes dialkylnicotinamides as inhibitors of angiogenesis.

Furthermore, EP-A-522392 (U.S. Pat. No. 5,235,060) describes 6-trifluoromethyl-substituted pyridonecarboxamides as precursors for the synthesis of herbicidally active sulfonylureas. Helv. Chim. Acta 71 (1988) 596-601 and GB 2305174 mention 1,2-dihydro-2-oxo-6-trifluoromethylpyridine-3-carboxamide, 6-chloro(difluoro)methyl-1,2-dihydro-2-oxopyridine-3-carboxamide and 6-difluoromethyl-1,2-dihydro-2-oxopyridine-3-carboxamide as intermediates in the synthesis of pyranopyridines. WO 2007/041052 mentions 1,2-dihydro-2-oxo-6-trifluoromethylpyridine-3-carboxamide as an intermediate in the synthesis of pharmacologically active spiropiperidines.

The use of such compounds as safeners in combination with certain pesticides has hitherto not been disclosed.

WO 2006/007981 (US 2007-265164) describes a method for identifying compounds which induce the defense of plants against pathogens, where the increase of the expression of plant-endogenous genes is considered to be an indication for the induction.

Here, 1,2-dihydro-2-oxo-6-trifluoromethylpyridine-3-carboxamide is mentioned as part of a group of six compounds which may be referred to as safeners. A safener action confirmed by biological tests on plants has hitherto not been disclosed for this compound, and is also not sufficiently disclosed by WO 2006/007981.

In particular the expression values obtained according to WO 2006/007981 for the compound, which in some cases are at a considerably lower level than those for commercially available safeners also mentioned, lead it to be expected in the best case that, as safeners, they are considerably less suitable, if at all.

When safeners were used to protect useful plants against damage by pesticides, it was found that the known safeners may in many cases have disadvantages. These include:
the safener reduces the efficacy of the pesticides, in particular that of herbicides, against the harmful plants,
the useful-plant-protecting properties are insufficient,
in combination with a certain herbicide, the spectrum of the useful plants in which the safener/herbicide is to be employed is not sufficiently wide,
a certain safener can only be combined with a small number of herbicides,
by using safeners, the application rate to be applied and the amount of formulation is increased, which may cause problems during the application.

For the reasons mentioned, there is a need to provide alternative compounds having safener action.

The invention provides the use of compounds of the formula (I) or salts thereof

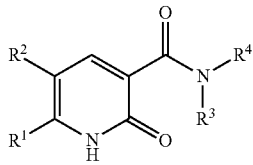

in which
R¹ is a $(C_1-C_6)$-haloalkyl radical, preferably a radical of the formula $CF_3$, $CF_2Cl$, $CF_2H$, $CF_2CF_3$, $CF_2CF_2H$, $CF_2CF_2Cl$, $CFClCF_3$, $CFHCF_3$, $CF(CF_3)_2$, $CH(CF_3)_2$, $CF_2CF_2CF_3$, or $C(CH_3)_2F$ and
R² is hydrogen or halogen and
R³ is hydrogen, $(C_1-C_{16})$-alkyl, $(C_2-C_{16}$-alkenyl or $(C_2-C_{16})$-alkynyl,
  where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted,
  or $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring,
  where each of the 4 lastmentioned radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted,
  and
R⁴ is $(C_1-C_{16})$-alkyl, $(C_2-C_{16})$-alkenyl or $(C_2-C_{16})$-alkynyl,
  where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted
  or $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring,
  where each of the 4 lastmentioned radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted,
  or
R³ is $(C_1-C_4)$-alkoxy, $(C_2-C_4)$-alkenyloxy, $(C_2-C_6)$-alkynyloxy or $(C_2-C_4)$-haloalkoxy and
R⁴ is hydrogen or $(C_1-C_4)$-alkyl or
R³ and R⁴ together with the directly attached nitrogen atom are a four- to eight-membered heterocyclic ring which, in addition to the nitrogen atom, may also comprise further hetero ring atoms, preferably up to two further hetero ring atoms selected from the group consisting of N, O and S, and which is unsubstituted or substituted by one or more radicals selected from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, or
R³ and R⁴ together with the directly attached nitrogen atom are the group $-N=CR^5-NR^6R^7$, in which
  R⁵ is hydrogen or $(C_1-C_6)$-alkyl, with hydrogen being preferred, and
  R⁶, R⁷ independently of one another are hydrogen or $(C_1-C_4)$-alkyl, preferably $(C_1-C_2)$-alkyl, or R⁶ and R⁷ together with the directly attached nitrogen atom form a five- to seven-membered, preferably saturated heterocyclic ring, such as, for example, piperidinyl, pyrrolidinyl or morpholinyl,
  or
R¹ is a $(C_1-C_6)$-haloalkyl radical, preferably a radical of the formula $CF_3$, $CF_2Cl$, $CF_2H$, $CF_2CF_3$, $CF_2CF_2H$, $CF_2CF_2Cl$, $CFClCF_3$, $CFHCF_3$, $CF(CF_3)_2$, $CH(CF_3)_2$, $CF_2CF_2CF_3$ or $C(CH_3)_2F$, more preferably a radical of the formula $CF_3$, $CF_2Cl$, $CF_2H$, $CF_2CF_3$, $CF_2CF_2H$, $CF_2CF_2Cl$, $CF_2CF_2CF_3$ or $C(CH_3)_2F$, in particular $CF_2Cl$, $CF_2H$, $CF_2CF_3$, $CF_2CF_2H$, $CF_2CF_2Cl$, $CF_2CF_2CF_3$ or $C(CH_3)_2F$, even more preferably $CF_2Cl$, $CF_2H$, $CF_2CF_3$, $CF_2CF_2H$, $CF_2CF_2Cl$ or $CF_2CF_2CF_3$,
R² is halogen,
R³ is hydrogen and
R⁴ is hydrogen
or
R¹ is a radical of the formula $CF_2Cl$, $CF_2H$, $CF_2CF_3$, $CF_2CF_2H$, $CF_2CF_2Cl$, $CFClCF_3$, $CFHCF_3$, $CF(CF_3)_2$, $CH(CF_3)_2$, $CF_2CF_2CF_3$ or $C(CH_3)_2F$, more preferably $CF_2Cl$, $CF_2H$, $CF_2CF_3$, $CF_2CF_2H$, $CF_2CF_2Cl$, $CF_2CF_2CF_3$ or $C(CH_3)_2F$, even more preferably $CF_2Cl$, $CF_2H$, $CF_2CF_3$, $CF_2CF_2H$, $CF_2CF_2Cl$ or $CF_2CF_2CF_3$,
R² is hydrogen,
R³ is hydrogen and
R⁴ is hydrogen,
as a useful-plant-protecting agent for reducing or preventing harmful actions of agrochemicals, preferably pesticides, in particular herbicides, on the useful plants.

Hereinbelow, the compounds of the formula (I) and their salts are in some cases also referred to as "compounds (I)" according to the invention or used according to the invention.

The compounds of the formula (I) also include tautomers which can be formed by hydrogen shifts and whose structure is formally not embraced by the formula (I). These tautomers are nevertheless included in the definition of the compounds of the formula (I) according to the invention. The definition of the compounds of the formula (I) includes in particular the tautomeric structures of the formula (Ia) (2-hydroxypyridine-3-carboxamides) or salts thereof

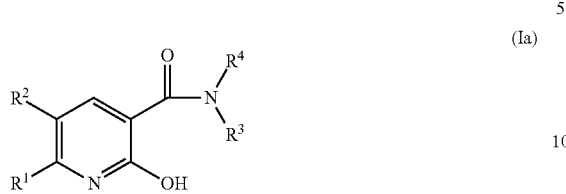

in which
$R^1$, $R^2$, $R^3$ and $R^4$ are as defined in formula (I).

Some compounds of the formula (I) according to the invention or salts thereof are novel and also form part of the subject matter of the invention.

It is noted that in this disclosure and particularly in the claims and/or paragraphs, terms such as "comprises", "comprised", "comprising" and the like can have the meaning attributed to it in U.S. patent law, e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

The invention also provides useful-plant-protecting compositions comprising compounds of the formula (I) or salts thereof and formulation auxiliaries. The invention also provides useful-plant-protecting compositions comprising compounds of the formula (I) or salts thereof in combination with further agrochemicals, preferably pesticides, in particular herbicides, and, if appropriate, formulation auxiliaries.

Some compounds of the formula (I) are already described as intermediates for preparing active compounds, see the abovementioned GB-A-2305174 (comp. (I) in which $R^1$=CF$_3$, CF$_2$Cl or CF$_2$H and $R^3$=$R^4$=H). EP-A-522392, which has already been mentioned, described in a general manner inter alia compounds (I) as intermediates for preparing sulfonylureas. The safener actions of the compounds have not been described.

The invention also provides compounds of the formula (I) or salts thereof

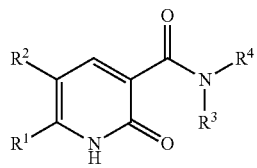

(I)

in which
$R^1$ is a $(C_1-C_6)$-haloalkyl radical, preferably a radical of the formula CF$_3$, CF$_2$Cl, CF$_2$H, CF$_2$CF$_3$, CF$_2$CF$_2$H, CF$_2$CF$_2$Cl, CFClCF$_3$, CFHCF$_3$, CF(CF$_3$)$_2$, CH(CF$_3$)$_2$, CF$_2$CF$_2$CF$_3$ or C(CH$_3$)$_2$F, in particular a radical of the formula CF$_3$, CF$_2$Cl, CF$_2$H, CF$_2$CF$_3$, CF$_2$CF$_2$H, CF$_2$CF$_2$Cl, CF$_2$CF$_2$CF$_3$ or C(CH$_3$)$_2$F, more preferably CF$_3$, CF$_2$Cl, CF$_2$H, CF$_2$CF$_3$, CF$_2$CF$_2$H, CF$_2$CF$_2$Cl or CF$_2$CF$_2$CF$_3$ and $R^2$ is hydrogen or halogen and $R^3$ is hydrogen, $(C_1-C_{16})$-alkyl, $(C_2-C_{16})$-alkenyl or $(C_2-C_{16})$-alkynyl,
where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, and [$(C_1-C_4)$-haloalkoxy]-carbonyl,
or $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring,
where each of the 4 lastmentioned radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted,
and $R^4$ is $(C_1-C_{16})$-alkyl, $(C_2-C_{26})$-alkenyl or $(C_2-C_{16})$-alkynyl,
where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, and [$(C_1-C_4)$-haloalkoxy]-carbonyl,
or $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring,
where each of the 4 lastmentioned radicals is unsubstituted or substituted by one or more radicals selected from the group consisting of halogen, hydroxyl, cyano, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted,
or $R^3$ is $(C_1-C_4)$-alkoxy, $(C_2-C_4)$-alkenyloxy, $(C_2-C_6)$-alkynyloxy or $(C_2-C_4)$-haloalkoxy and $R^4$ is hydrogen or $(C_1-C_4)$-alkyl or $R^3$ and $R^4$ together with the directly attached nitrogen atom are a four- to eight-membered heterocyclic ring which, in addition to the nitrogen atom, may also comprise further hetero ring atoms, preferably up to two further hetero ring atoms selected from the group consisting of N, O and S, and which is unsubstituted or substituted by one or more radicals selected from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, or $R^3$ and $R^4$ together with the directly attached nitrogen atom are the group —N=CR$^5$—NR$^6$R$^7$ in which $R^5$ is hydrogen or $(C_1-C_6)$-alkyl, with hydrogen being preferred, and $R^6$, $R^7$ independently of one another are hydrogen or $(C_1-C_4)$-alkyl, preferably $(C_1-C_2)$-alkyl, or $R^6$ and $R^7$ together with the directly attached nitrogen atom form a five- to seven-membered, preferably saturated heterocyclic ring, such as, for example, piperidinyl, pyrrolidinyl or morpholinyl, or $R^1$ is a $(C_1-C_6)$-haloalkyl radical, preferably a radical of the formula $CF_3$, $CF_2Cl$, $CF_2H$, $CF_2CF_3$, $CF_2CF_2H$, $CF_2CF_2Cl$, $CFClCF_3$, $CFHCF_3$, $CF(CF_3)_2$, $CH(CF_3)_2$, $CF_2CF_2CF_3$ or $C(CH_3)_2F$, more preferably $CF_3$, $CF_2Cl$, $CF_2H$, $CF_2CF_3$, $CF_2CF_2H$, $CF_2CF_2Cl$, $CF_2CF_2CF_3$ or $C(CH_3)_2F$, in particular $CF_2Cl$, $CF_2H$, $CF_2CF_3$, $CF_2CF_2H$, $CF_2CF_2Cl$, $CF_2CF_2CF_3$ or $C(CH_3)_2F$, even more preferably $CF_2Cl$, $CF_2CF_3$, $CF_2CF_2Cl$ or $CF_2CF_2CF_3$, $R^2$ is halogen, $R^3$ is hydrogen and $R^4$ is hydrogen or $R^1$ is a radical of the formula $CF_2CF_3$, $CF_2CF_2H$, $CF_2CF_2Cl$, $CFClCF_3$, $CFHCF_3$, $CF(CF_3)_2$, $CH(CF_3)_2$, $CF_2CF_2CF_3$ or $C(CH_3)_2F$, preferably $CF_2CF_3$, $CF_2CF_2H$, $CF_2CF_2Cl$, $CFClCF_3$, $CF_2CF_2CF_3$ or $C(CH_3)_2F$, in particular $CF_2CF_3$, $CF_2CF_2H$, $CF_2CF_2Cl$, $CFClCF_3$ or $CF_2CF_2CF_{3,}$ even more preferably $CF_2CF_3$, $CF_2CF_2H$, $CF_2CF_2Cl$ or $CF_2CF_2CF_3$, $R^2$ is hydrogen, $R^3$ is hydrogen and $R^4$ is hydrogen.

Preferably excluded are compounds of the formula (I) and salts thereof in which $R^1$ is $(C_1-C_3)$-alkyl which is substituted by one to three fluorine atoms, $R^2$ is hydrogen, $R^3$ is $(C_1-C_2)$-alkyl and $R^4$ is $(C_1-C_2)$-alkyl.

The lastmentioned preferably excluded compounds are described in a general manner in the abovementioned EP-A-0522392 as intermediates for preparing sulfonylureas.

Depending on the nature and the attachment of the substituents, the compounds of the formula (I) may be present as stereoisomers. All possible stereoisomers defined by their specific spatial form, such as enantiomers, diastereomers, Z- and E-isomers, are embraced by the formula (I).

If, for example, one or more alkenyl groups are present, it is possible for diastereomers (Z- and E-isomers) to occur. If, for example, one or more asymmetric carbon atoms are present, it is possible for enantiomers and diastereomers to occur. Stereoisomers can be obtained by customary separation methods, for example by chromatographic separation procedures, from the mixtures obtained in the preparation. It is also possible to selectively prepare stereoisomers by employing stereoselective reactions using optically active starting materials and/or auxiliaries. Thus, the invention also relates to all stereoisomers embraced by the formula (I) but not shown in their specific stereoform and mixtures thereof.

The possibilities of combining the various substituents of the formula (I) are to be understood in such a way that the general principles of the synthesis of chemical compounds are to be observed, i.e. the formula (I) does not embrace compounds which the skilled worker knows to be chemically impossible.

The terms used above and further below are familiar to the person skilled in the art and have in particular the meanings illustrated below:

The term "$(C_1-C_4)$-alkyl" is a short notation for open-chain alkyl having 1 to 4 carbon atoms corresponding to the stated range of carbon atoms, i.e. it includes the radicals methyl, ethyl, 1-propyl, 2-propyl, 1-butyl, 2-butyl, 2-methylpropyl and tert-butyl. Correspondingly, general alkyl radicals having a wider stated range of carbon atoms, for example "$(C_1-C_6)$-alkyl", also include straight-chain or branched alkyl radicals having a larger number of carbon atoms, i.e. in the example also the alkyl radicals having 5 and 6 carbon atoms.

Unless specifically indicated, the lower carbon skeletons, for example those having 1 to 6 carbon atoms or, in the case of unsaturated groups, having 2 to 6 carbon atoms, are preferred for the hydrocarbon radicals such as alkyl, alkenyl and alkynyl radicals, including in composite radicals. Alkyl radicals, including in the composite meanings, such as alkoxy, haloalkyl, etc., are, for example, methyl, ethyl, n- or isopropyl, n-, iso, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals have the meanings of the possible unsaturated radicals which correspond to the alkyl radicals; alkenyl is, for example, vinyl, allyl, 1-methyl-2-propenyl, 2-methyl-2-propenyl, 2-butenyl, pentenyl, 2-methylpentenyl or hexenyl, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl. $(C_2-C_6)$-alkynyl is, for example, ethynyl, propargyl, 1-methyl-2-propynyl, 2-methyl-2-propynyl, 2-butynyl, 2-pentynyl or 2-hexynyl, preferably propargyl, but-2-yn-1-yl, but-3-yn-1-yl or 1-methylbut-3-yn-1-yl.

Alkylidene, including, for example, in the form $(C_1-C_{10})$-alkylidene, is the radical of a straight-chain or branched alkane which is attached via a double bond, where the position of the point of attachment has not yet been fixed. The only possible positions in the case of a branched alkane are, of course, positions in which two hydrogen atoms may be replaced by the double bond; radicals are, for example, =CH$_2$, =CH—CH$_3$, =C(CH$_3$)—CH$_3$, =C(CH$_3$)—C$_2$H$_5$ or =C(C$_2$H$_5$)—C$_2$H$_5$.

Cycloalkyl is a carbocyclic saturated ring system having preferably 3-8 carbon atoms, for example cyclopropyl, cyclobutyl, cyclopentyl or cyclohexyl. Substituted cycloalkyl embraces cyclic systems having substituents, substituents having a double bond at the cycloalkyl radical, for example an alkylidene group, such as methylidene, also being included. Substituted cycloalkyl also embraces polycyclic aliphatic systems, such as, for example, bicyclo[1.1.0]butan-1-yl, bicyclo[1.1.0]butan-2-yl, bicyclo[2.1.0]-pentan-1-yl, bicyclo[2.1.0]pentan-2-yl, bicyclo[2.1.0]pentan-5-yl, adamantan-1-yl and adamantan-2-yl.

Cycloalkenyl is a carbocyclic, non-aromatic, partially unsaturated ring system having preferably 4-8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. The explanations given for substituted cycloalkyl apply correspondingly to substituted cycloalkenyl.

The term "halogen" denotes, for example, fluorine, chlorine, bromine or iodine. Haloalkyl, haloalkenyl and haloalkynyl are alkyl, alkenyl and alkynyl, respectively, which are partially or fully substituted by identical or different halogen atoms, preferably from the group consisting of fluorine, chlorine and bromine, in particular from the group consisting of fluorine and chlorine, for example monohaloalkyl, such as $CH_2CH_2Cl$, $CH_2CH_2F$, $CH_2ClCH_3$, $CH_2FCH_3$, $CH_2Cl$, $CH_2F$; perhaloalkyl such as $CCl_3$ or $CF_3$ or $CF_3CF_2$; polyhaloalkyl, such as $CHF_2$, $CH_2F$, $CH_2FCHCl$, $CHCl_2$, $CF_2CF_2H$, $CH_2CF_3$, $CH_2ClCH_3$, $CH_2FCH_3$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

If a skeleton is substituted "by one or more radicals" from a list of radicals (=group) or a generically defined group of radicals, this includes in each case the simultaneous substitution by a plurality of identical and/or structurally different radicals.

Substituted radicals, such as a substituted alkyl, alkenyl, alkynyl, cycloalkyl, cycloalkenyl, phenyl, benzyl, heterocyclyl and heteroaryl radical, are, for example, substituted radicals derived from an unsubstituted skeleton, the substituents being, for example, one or more, preferably 1, 2 or 3, radicals from the group consisting of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, trialkylsilyl and optionally substituted cycloalkyl, optionally substituted phenyl, optionally substituted heterocyclyl, where each of the lastmentioned cyclic groups may also be attached via heteroatoms or divalent functional groups as in the alkyl radicals mentioned, and alkylsulfinyl, alkylsulfonyl and, in the case of cyclic radicals (="cyclic skeleton"), also alkyl, haloalkyl, alkylthioalkyl, alkoxyalkyl, optionally substituted mono- and dialkylaminoalkyl and hydroxyalkyl; the term "substituted radicals", such as substituted alkyl, etc., includes as substituents, in addition to the saturated hydrocarbon-containing radicals mentioned, the corresponding unsaturated aliphatic and aromatic radicals, such as optionally substituted alkenyl, alkynyl, alkenyloxy, alkynyloxy, phenyl, phenoxy etc. In the case of substituted cyclic radicals having aliphatic moieties in the ring, this also embraces cyclic systems having substituents which are attached to the ring via a double bond, for example substituted by an alkylidene group, such as methylidene or ethylidene, or an oxo group, imino group or substituted imino group.

The substituents mentioned by way of example ("first substituent level") can, if they contain hydrocarbon-containing moieties, be, if appropriate, substituted further in the moieties ("second substituent level"), for example by one of the substituents as defined for the first substituent level. Corresponding further substituent levels are possible. The term "substituted radical" preferably embraces only one or two substituent levels.

Preferred substituents for the substituent levels are, for example, amino, hydroxyl, halogen, nitro, cyano, mercapto, carboxyl, carboxamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkyl-aminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

In the case of radicals having carbon atoms, preference is given to those having 1 to 6 carbon atoms, preferably 1 to 4 carbon atoms, in particular 1 or 2 carbon atoms. Preference is generally given to substituents selected from the group consisting of halogen, for example fluorine and chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano. Here, particular preference is given to the substituents methyl, methoxy, fluorine and chlorine.

Substituted amino, such as mono- or disubstituted amino, denotes a radical from the group of the substituted amino radicals which are N-substituted, for example, by one or two identical or different radicals selected from the group consisting of alkyl, alkoxy, acyl and aryl; preferably mono- and dialkylamino, mono- and diarylamino, acylamino, N-alkyl-N-acylamino, N-alkyl-N-acylamino and saturated N-heterocycles; here, preference is given to alkyl radicals having 1 to 4 carbon atoms; aryl is preferably phenyl or substituted phenyl; for acyl, the definition given further down applies, preference is given to ($C_1$-$C_4$)-alkanoyl. This applies correspondingly to substituted hydroxylamino or hydrazino.

Substituted amino also includes quarternary ammonium compounds (salts) with four organic substituents at the nitrogen atom.

Optionally substituted phenyl is preferably phenyl which is unsubstituted or mono- or polysubstituted, preferably up to trisubstituted, by identical or different radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted cycloalkyl is preferably cycloalkyl which is unsubstituted or mono- or polysubstituted, preferably up to trisubstituted, by identical or different radicals from the group consisting of halogen, ($C_1$-$C_4$)-alkyl, ($C_1$-$C_4$)-alkoxy, ($C_1$-$C_4$)-haloalkyl and ($C_1$-$C_4$)-haloalkoxy, in particular by one or two ($C_1$-$C_4$)-alkyl radicals.

Optionally substituted heterocyclyl is preferably heterocyclyl which is unsubstituted or mono- or polysubstituted, preferably up to trisubstituted, by identical or different radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy, nitro and oxo, in particular mono- or polysubstituted by radicals from the group consisting of halogen, ($C_1$-$C_4$)-alkyl, ($C_1$-$C_4$)-alkoxy, ($C_1$-$C_4$)-haloalkyl and oxo, very particularly substituted by one or two ($C_1$-$C_4$)-alkyl radicals.

Acyl denotes a radical of an organic acid which, formally, is formed by removing a hydroxyl group from the acid function, it also being possible for the organic radical in the acid to be attached to the acid function via a heteroatom. Examples of acyl are the radical —CO—R of a carboxylic acid HO—CO—R and radicals of acids derived therefrom, such as thiocarboxylic acid, unsubstituted or N-substituted iminocarboxylic acids or the radical of carbonic acid monoesters, N-substituted carbamic acid, sulfonic acids, sulfinic acids, N-substituted sulfonamido acids, phosphonic acids, phosphinic acids.

Acyl denotes, for example, formyl, alkylcarbonyl such as [($C_1$-$C_4$)-alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl, N-alkyl- and N,N-dialkylcarbamoyl and other radicals of organic acids. Here, the radicals may in each case be substituted further in the alkyl or phenyl moiety, for example in the alkyl moiety by one or more radicals selected from the group consisting of halogen, alkoxy, phenyl and phenoxy; examples of substituents in the phenyl moiety are the substituents which have already been mentioned further above in a general manner for substituted phenyl.

Acyl denotes preferably an acyl radical in the narrower sense, i.e. a radical of an organic acid where the acid group is attached directly to the carbon atom of an organic radical, for example alkanoyl, such as formyl and acetyl, aroyl, such as phenylcarbonyl, and other radicals of saturated or unsaturated organic acids.

"Aroyl" denotes an aryl radical as defined above which is attached via a carbonyl group, for example the benzoyl group.

If a general radical is defined as "hydrogen", this means a hydrogen atom.

The "yl-position" of a radical denotes its point of attachment.

In accordance with the general definitions:

"$(C_1-C_6)$-alkyl" is a methyl, ethyl, propyl, isopropyl, 1-butyl, 2-butyl, 2-methylpropyl or tert-butyl radical;

"$(C_1-C_{10})$-alkyl" thus includes the alkyl radicals mentioned above, and also isomeric pentyl radicals, such as n-pentyl, 1,1-dimethylpropyl or 2-methylbutyl, isomeric hexyl, heptyl, octyl, nonyl or decyl radicals.

Accordingly, "$(C_2-C_4)$-alkenyl" denotes, for example, the vinyl, allyl, 2-methyl-2-propen-1-yl-, 2- or 3-buten-1-yl group, accordingly, "$(C_3-C_{10})$-alkenyl" denotes, for example, the allyl, 2-methyl-2-propen-1-yl, 2- or 3-buten-1-yl, pentenyl, 2-methylpentenyl, hexenyl, heptenyl, octenyl, nonenyl or decenyl group.

"$(C_2-C_4)$-Alkynyl" denotes, for example, the ethynyl, propargyl or 2-butyn-1-yl group, "$(C_3-C_{10})$-alkynyl" denotes, for example, the propargyl, 2-butyn-1-yl, 2-pentyn-1-yl, 2-methylpentyn-3-yl, hexynyl, heptynyl, octynyl, nonynyl or the decynyl group.

If the carbon chain of an alkyl radical is interrupted by more than one oxygen atom, this means that two oxygen atoms must not be directly adjacent.

"$(C_3-C_6)$-Cycloalkyl" denotes the cyclopropyl, cyclobutyl, cyclopentyl or cyclohexyl radical, "$(C_3-C_{10})$-cycloalkyl" denotes monocycle alkyl radicals, such as the cyclopropyl, cyclobutyl, cyclopentyl, cyclohexyl, cycloheptyl, cyclooctyl or cyclodecyl radical, denotes bicyclic alkyl radicals, such as the norbornyl or bicyclo[2.2.2]octyl radical, or denotes fused systems, such as the decahydronaphthyl radical.

"$(C_4-C_{10})$-Cycloalkenyl" denotes monocycle cycloalkylene radicals, such as the cyclobutenyl, cyclopentenyl, cyclohexenyl, cycloheptenyl, cyclooctenyl or cyclodecenyl radical, denotes bicyclic alkyl radicals, such as the norbornenyl or bicyclo[2.2.2]octenyl radical, or denotes fused systems, such as the tetra-, hexa- or octahydronaphthyl radical.

"$(C_1-C_4)$-Alkoxy" and "$(C_1-C_{10})$-alkoxy" are alkoxy groups whose hydrocarbon radicals have the meanings given under the terms "$(C_1-C_4)$-alkyl" and "$(C_1-C_{10})$-alkyl".

In particular for reasons of better crop-plant- or useful-plant-protecting action (safener action), better selectivity and/or better preparability, the use according to the invention of compounds of the formula (I) mentioned or salts thereof is of particular interest in which individual radicals have one of the preferred meanings already mentioned or mentioned below, and in particular those which contain a combination of one or more of the preferred meanings already mentioned or mentioned below.

Preferably, if embraced by the above mentioned general definition of formula (I), $R^1$ is a $(C_1-C_4)$-haloalkyl radical, more preferably $CF_3$, $CF_2Cl$, $CF_2H$, $CF_2CF_3$, $CF_2CF_2H$, $CF_2CF_2Cl$, $C(CH_3)_2F$ or $CF_2CF_2CF_3$, more preferably $CF_3$, $CF_2Cl$, $CF_2H$, $CF_2CF_2CF_3$ or $CF_2CF_3$, more preferably $CF_3$, $CF_2Cl$, $CF_2CF_2CF_3$ or $CF_2CF_3$, in particular $CF_3$, $CF_2Cl$ or $CF_2CF_3$.

Preferably, $R^2$ is hydrogen or halogen. Here, halogen is preferably fluorine, chlorine, bromine or iodine, in particular chlorine, bromine or iodine, very particularly chlorine or bromine.

Preferably, $R^3$ is hydrogen, $(C_1-C_{10})$-alkyl, $(C_2-C_{10})$-alkenyl or $(C_2-C_{10})$-alkynyl, where each of the 3 last mentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted by one or more radicals from the group consisting of halogen, $(C_1-C_4)$-alkyl and $(C_1-C_4)$-haloalkyl, preferably unsubstituted or substituted by $(C_1-C_4)$-alkyl, phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, and heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, preferably unsubstituted or substituted by one or more radicals from the group consisting of $(C_1-C_4)$-alkyl ($C_1-C_4)$-haloalkyl and $(C_1-C_4)$-alkoxy, or $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring, where each of the 4 lastmentioned radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, [$(C_1-C_4)$-alkoxy]-carbonyl, [$(C_1-C_4)$-haloalkoxy]-carbonyl, $(C_3-C_6)$-cycloalkyl, which is unsubstituted or substituted by one or more radicals selected from the group consisting of halogen, $(C_1-C_4)$-alkyl and $(C_1-C_4)$-haloalkyl, preferably unsubstituted or substituted by $(C_1-C_4)$-alkyl, phenyl, which is unsubstituted or substituted by one or more radicals selected from the group consisting of halogen, $(C_1-C_4)$-alkyl, $(C_1-C_4)$-alkoxy, $(C_1-C_4)$-haloalkoxy and $(C_1-C_4)$-alkylthio, and heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, preferably unsubstituted or substituted by one or more radicals from the group consisting of $(C_1-C_4)$-alkyl, $(C_1-C_4)$-haloalkyl and $(C_1-C_4)$-alkoxy, more preferably hydrogen, $(C_1-C_6)$-alkyl, $(C_2-C_6)$-alkenyl or $(C_2-C_6)$-alkynyl, where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl, more preferably hydrogen or $(C_1-C_4)$-alkyl, in particular hydrogen, and $R^4$ is $(C_1-C_{10})$-alkyl, $(C_2-C_{10})$-alkenyl or $(C_2-C_{10})$-alkynyl, where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]-carbonyl, [$(C_1-C_4)$-haloalkoxy]-carbonyl, $(C_3-C_6)$-cycloalkyl, which is unsubstituted or substituted by one or more radicals selected from the group consisting of halogen, $(C_1-C_4)$-alkyl and $(C_1-C_4)$-haloalkyl, preferably unsubstituted or substituted by $(C_1-C_4)$-alkyl, phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, and heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, preferably unsubstituted or substituted by one or more radicals selected from the group consisting of $(C_1-C_4)$-alkyl $(C_1-C_4)$-haloalkyl and $(C_1-C_4)$-alkoxy, or $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring, where each of the 4 lastmentioned radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted by one or more radicals selected from the group consisting of halogen, $(C_1-C_4)$-alkyl and $(C_1-C_4)$-haloalkyl, preferably unsubstituted or substituted by $(C_1-C_4)$-alkyl, phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, and heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, preferably unsubstituted or substituted by one or more radicals selected from the group consisting of $(C_1-C_4)$-alkyl, $(C_1-C_4)$-haloalkyl and $(C_1-C_4)$-alkoxy.

Here, heterocyclyl is preferably a heterocyclic 3- to 9-membered, in particular 5- or 6-membered, ring having 1 to 3 hetero ring atoms from the group consisting of N, O and S.

More preferably, $R^3$ is hydrogen, $(C_1-C_{10})$-alkyl, $(C_2-C_{10})$-alkenyl or $(C_2-C_{10})$-alkynyl, where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted by one or more radicals selected from the group consisting of halogen, $(C_1-C_4)$-alkyl and $(C_1-C_4)$-haloalkyl, preferably unsubstituted or substituted by $(C_1-C_4)$-alkyl, phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, and heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, or $(C_3-C_6)$-cycloalkyl or $(C_3-C_6)$-cycloalkyl which is condensed at one side of the ring to a 4- to 6-membered saturated or unsaturated carbocyclic ring, where each of the 2 lastmentioned radicals is unsubstituted or substituted by one or more radicals selected from the group consisting of $(C_1-C_4)$-alkyl, more preferably hydrogen, $(C_1-C_6)$-alkyl, $(C_2-C_6)$-alkenyl or $(C_2-C_6)$-alkynyl, where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl, more preferably hydrogen or $(C_1-C_4)$-alkyl, in particular hydrogen, and $R^4$ is as already defined above for $R^4$ or preferably $(C_1-C_{10})$-alkyl, $(C_2-C_{10})$-alkenyl or $(C_2-C_{10})$-alkynyl, where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted by one or more radicals selected from the group consisting of halogen, $(C_1-C_4)$-alkyl and $(C_1-C_4)$-haloalkyl, preferably unsubstituted by $(C_1-C_4)$-alkyl, phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, and heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, or $(C_3-C_6)$-cycloalkyl or $(C_3-C_6)$-cycloalkyl which is condensed at one side of the ring to a 4- to 6-membered saturated or unsaturated carbocyclic ring, where each of the 2 lastmentioned radicals is unsubstituted or substituted by one or more radicals from the group consisting of $(C_1-C_4)$-alkyl.

More preferably.

$R^3$ is hydrogen, $(C_1-C_{10})$-alkyl, $(C_2-C_{10})$-alkenyl or $(C_2-C_{10})$-alkynyl, where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and [$(C_1-C_4)$-alkoxy]-carbonyl, preferably hydrogen, $(C_1-C_6)$-alkyl, $(C_2-C_6)$-alkenyl or $(C_2-C_6)$-alkynyl, where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl,
more preferably hydrogen or $(C_1-C_4)$-alkyl, in particular hydrogen,
and
$R^4$ is as already defined above for $R^4$ or preferably
$(C_1-C_{10})$-alkyl, $(C_2-C_{10})$-alkenyl or $(C_2-C_{10})$-alkynyl,
where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $[(C_1-C_4)$-alkoxy]-carbonyl,
preferably $(C_1-C_6)$-alkyl, $(C_2-C_6)$-alkenyl or $(C_2-C_6)$-alkynyl, where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl.

Particular preference is given to the use according to the invention of compounds of the formula (I) or salts thereof in which
$R^1$ is $CF_3$, $CF_2Cl$, $CF_2H$, $CF_2CF_2CF_3$ or $CF_2CF_3$, preferably $CF_3$, $CF_2Cl$, $CF_2CF_2CF_3$ or $CF_2CF_3$, in particular $CF_3$, $CF_2Cl$ or $CF_2CF_3$ and
$R^2$ is hydrogen or halogen, preferably hydrogen, and
$R^3$ is hydrogen, $(C_1-C_{10})$-alkyl, $(C_1-C_{10})$-alkenyl or $(C_2-C_{10})$-alkynyl,
where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl,
preferably hydrogen, $(C_1-C_6)$-alkyl, $(C_2-C_6)$-alkenyl or $(C_2-C_6)$-alkynyl, where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl,
in particular hydrogen or $(C_1-C_4)$-alkyl, and
$R^4$ is $(C_1-C_{10})$-alkyl, $(C_3-C_{10})$-alkenyl or $(C_3-C_{10})$-alkynyl,
where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, $[(C_1-C_4)$-alkoxy]-carbonyl, $[(C_1-C_4)$-haloalkoxy]-carbonyl,
$(C_3-C_6)$-cycloalkyl, which is unsubstituted or substituted by one or more radicals selected from the group consisting of halogen, $(C_1-C_4)$-alkyl and $(C_1-C_4)$-haloalkyl, preferably unsubstituted or substituted by $(C_1-C_4)$-alkyl,
phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio, and
heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo,
or $(C_3-C_6)$-cycloalkyl or $(C_3-C_6)$-cycloalkyl which is condensed at one side of the ring to a 4- to 6-membered saturated or unsaturated carbocyclic ring,
where each of the 2 lastmentioned radicals is unsubstituted or substituted by one or more radicals selected from the group consisting of $(C_1-C_4)$-alkyl,
preferably $(C_1-C_{10})$-alkyl, $(C_2-C_{10})$-alkenyl or $(C_2-C_{10})$-alkynyl,
where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl,
more preferably $(C_1-C_6)$-alkyl, $(C_2-C_6)$-alkenyl or $(C_2-C_6)$-alkynyl, where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio and $(C_1-C_4)$-alkoxycarbonyl,
or
$R^3$ and $R^4$ together with the directly attached nitrogen atom are a four- to eight-membered heterocyclic ring, preferably a 5- or 6-membered heterocyclic ring, which, in addition to the nitrogen atom, may also contain further hetero ring atoms, preferably up to two further hetero ring atoms from the group consisting of N, O and S, and which is unsubstituted or substituted by one or more radicals selected from the group consisting of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio,
or
$R^3$ and $R^4$ together with the directly attached nitrogen atom are the group —N=CR$^5$—NR$^6$R$^7$, in which
$R^5$ is hydrogen or $(C_1-C_4)$-alkyl, with hydrogen being preferred, and
$R^6$, $R^7$ independently of one another are hydrogen or $(C_1-C_4)$-alkyl, preferably $(C_1-C_2)$-alkyl, or $R^5$ and $R^7$ together with the directly attached nitrogen atom form a five- or six-membered, preferably saturated heterocyclic ring, such as, for example, piperidinyl, pyrrolidinyl or morpholinyl.

Particular preference is also given to the use according to the invention of compounds of the formula (I) or salts thereof in which
$R^1$ is a $(C_1-C_6)$-haloalkyl radical, preferably from the group consisting of $CF_3$, $CF_2Cl$, $CF_2H$, $CF_2CF_3$, $CF_2CF_2H$, $CF_2CF_2Cl$, $CF_2CF_2CF_3$ and $C(CH_3)_2F$, more preferably $CF_3$, $CF_2Cl$, $CF_2H$, $CF_2CF_2CF_3$ or $CF_2CF_3$, even more preferably $CF_3$, $CF_2Cl$, $CF_2CF_2CF_3$ or $CF_2CF_3$, in particular $CF_3$, $CF_2CF_3$ or $CF_2Cl$, and
$R^2$ is halogen and
$R^3$ is hydrogen and
$R^4$ is hydrogen.

Likewise particularly preferred is the use according to the invention of compounds of the formula (I) or salts thereof in which
$R^1$ is $CF_2Cl$, $CF_2H$, $CF_2CF_3$, $CF_2CF_2H$ or $CF_2CF_2Cl$, more preferably $CF_2Cl$ or $CF_2H$ or $CF_2CF_3$, more preferably $CF_2Cl$ or $CF_2CF_3$, in particular $CF_2Cl$,
$R^2$ is hydrogen and
$R^3$ is hydrogen or $(C_1-C_4)$-alkyl and
$R^4$ is hydrogen.

Particular preference is also given to the use according to the invention of compounds of the formula (I) or salts thereof in which the general radicals correspond to the radicals mentioned for $R^1$, $R^2$, $R^3$ and $R^4$, respectively, in the examples given in the tables, or embrace them.

Particular preference is also given to the use according to the invention of novel compounds of the formula (I) or salts thereof in which $R^1$, $R^2$, $R^3$ and $R^4$ furthermore preferably have the meanings mentioned for the preferred uses.

The compounds of the general formula (I) can be prepared, for example, by (a) reacting a carboxylic acid of the general formula (II)

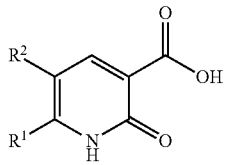
(II)

in which $R^1$ and $R^2$ are as defined for the compound of the formula (I) to be prepared, with an amine of the formula (III) or a salt thereof,

(III)

in which $R^3$ and $R^4$ are as defined for the compound of the formula (I) to be prepared, if appropriate in the presence of a carboxylic acid-activating reagent, for example N,N-carbonyldiimidazole (CDI), or a dehydrating agent, for example dicyclohexylcarbodiimide (DCC), to give the compound of the formula (I) or (b) reacting a carboxylic ester of the general formula (IV)

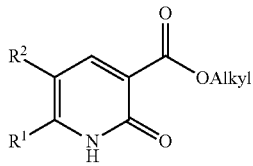
(IV)

in which $R^1$ and $R^2$ are as defined for the compound of the formula (I) to be prepared and "Alkyl" is an alkyl radical, for example methyl or ethyl, with an amine of the formula (III) or a salt thereof,

(III)

in which $R^3$ and $R^4$ are as defined for the compound of the formula (I) to be prepared, to give the compound of the formula (I) or (c) reacting a carbonyl halide or a carboxylic anhydride of the general formula (V),

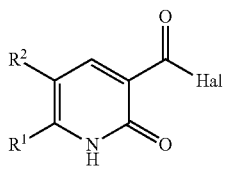
(V)

in which $R^1$ and $R^2$ are as defined for the compound of the formula (I) to be prepared and Hal is a halogen atom, for example chlorine, or an acyloxy radical, with an amine of the formula (III) or a salt thereof,

(III)

in which $R^3$ and $R^4$ are as defined for the compound of the formula (I) to be prepared, to give the compound of the formula (I), (d), if $R^3$ and $R^4$ in the compound of the formula (I) to be prepared are each hydrogen, reacting a compound of the formula (VI),

(VI)

in which $R^1$ is as defined for the compound of the formula (I) to be prepared, and "Alkyl" is an alkyl radical, for example methyl or ethyl,
with malonamide to give the compound of the formula (I).

The amide formations according to variant (a) can be carried out, for example, in an inert organic solvent in a temperature range between 0° C. and 150° C., preferably between 0° C. and 50° C. Suitable organic solvents are, for example, polar prone or aprotic solvents, such as ethers, for example diethyl ether, tetrahydrofuran and dioxane, or nitrites, such as acetonitrile, or amides, such as dimethylformamide.

The amide formations according to variant (b) can be carried out, for example, in an inert organic solvent in a temperature range between 0° C. and 150° C., preferably between 50° C. and 100° C. Suitable organic solvents are, for example, polar protic or aprotic solvents, such as ethers, for example tetrahydrofuran and dioxane, or nitriles, such as acetonitrile, or amides, such as dimethylformamide. However, preference is given to the amide formation according to variant (b) at elevated temperatures by reacting the undiluted reactants.

The amide formations according to variant (c) can be carried out, for example, in the presence of an acid binder in an inert organic solvent in a temperature range between 0° C. and 150° C., preferably between 50° C. and 100° C. Suitable organic solvents are, for example, polar protic or aprotic solvents, such as ethers, for example diethyl ether, tetrahydrofuran and dioxane, or nitriles, such as acetonitrile, or amides, such as dimethylformamide. Acid binders are, for example, alkali metal or alkaline earth metal carbonates, such as, for example, sodium carbonate, potassium carbonate or calcium carbonate, alkali metal or alkaline earth metal hydroxides, such as sodium hydroxide, potassium hydroxide or calcium hydroxide, or alkali metal hydrides or amides, such as sodium hydride or potassium hydride or sodium amide or potassium amide, or else organic bases, such as triethylamine, pyridine, dimethylaminopyridine, DBU (1,8-diazabicyclo[5.4.0]-undec-7-ene), DBN (1,5-diazabicyclo[4.3.0]non-5-ene) and 1,4-diaza-bicyclo[2.2.2]octane.

The amide formations according to variant (d) can be carried out analogously to the processes described in EP 522392 and Helv. Chim. Acta 71 (1988) 596-601 and GB 2305174. In general, the malonamide can be converted in an organic anhydrous polar prone or aprotic solvent, for example in an alcohol, with a strong base, such as an alkali metal, alkali metal hydride or alkali metal alkoxide, into a reactive salt, and then be reacted with the compound of the formula (VI). The reaction with the compound (VI) can generally be carried out in a temperature range between 0° C. and the boiling point of the solvent (depending on the solvent up to about 150° C.).

The compounds of the general formulae (II), (III), (IV) and (V) are either commercially available or can be prepared by or analogously to methods known to the person skilled in the art (for example Helv. Chim. Acta 71 (1988) 596; EP 502740 (U.S. Pat. No. 5,393,734); EP 522392).

Thus, for example, the compounds of the formula (IVa)

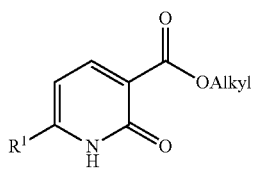

(IVa)

can be obtained by reacting alkoxyvinyl ethers of the formula (VI) with alkyl malonamides of the formula (VII).

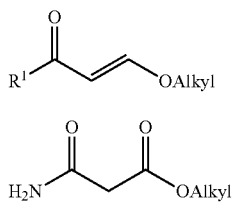

(VI)

(VII)

The starting materials of the formula (VI) are either commercially available or can be prepared by known methods (for example Synthesis 2000, 738-742; J. Fluor. Chem., 107, 2001, 285-300; Organometallics 15, 1996, 5374-5379).

The compounds of the formula (IV) in which $R^2$ is a halogen atom can be prepared by customary halogenations from the compounds of the formula (IVa).

Suitable for use as halogenating agents for pyridine are, for example, chlorine (J. Org. Chem. 23, 1958, 1614), bromine (Synth. Commun. 19, 1989, 553-560; U.S. Pat. No. 2,532, 055), iodine (Tetrahedron Lett. 45, 2004, 6633-6636), sodium hypochlorite (J. Org. Chem. 49, 1984, 4784-4786; J. Med. Chem. 36, 1993, 2676-2688, U.S. Pat. No. 4,960,896), sodium hypobromite (J. Med. Chem. 32, 1989, 2178-2199), thionyl chloride (Organic Letters, 6, 2004, 3-5), N-chlorosuccinimide (J. Med. Chem. 46, 2003, 702-715), N-bromosuccinimide (Chem. Pharm. Bull. 48, 2000, 1847-1853), N-iodosuccinimide (J. Med. Chem. 36, 1993, 2676-2788).

Furthermore, the compounds of the formula (IV) can be prepared from the compounds of the formula (IVa) by successive nitration (for example J. Med. Chem. 36, 1993, 2676-2688; J. Heterocycl. Chem. 33, 1996, 287-294), reduction (for example J. Med. Chem. 33, 1990, 1859-1865), diazotation and subsequent reaction of the diazonium salts in a Sandmeyer or Schiemann reaction.

The compounds of the formula (I) in which $R^3$ and $R^4$ together with the directly attached nitrogen atom are the group $-N=CR^5-NR^6R^7$ can be prepared by reacting a compound of the formula (I) in which $R^3$ and $R^4$ are hydrogen with compounds of the formula (VIII) in which $R^5$, $R^6$ and $R^7$ are as defined above

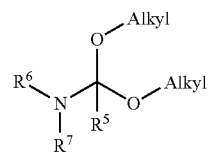

(VIII)

according to known methods (see, for example Synthesis 1980, 119-121; J. Med. Chem., 33, 1990, 2052-2059).

The invention also provides a method for protecting crop plants or useful plants against phytotoxic actions of agrochemicals, such as pesticides or, in particular, herbicides which cause damage to crop plants or useful plants, which method comprises using compounds of the formula (I) or salts thereof as safeners, preferably by applying an effective amount of the compounds of the formula (I) or salts thereof to the plants, to parts of plants or their seeds (or seed).

The compounds (I) (=safeners), together with active compounds (pesticides), are suitable for use in the selective control of harmful organisms in a number of plant crops, for example in crops of economic importance, such as cereals (wheat, barley, triticale, rye, rice, corn, millet), sugar beet, sugar cane, oilseed rape, cotton, sunflower, peas, beans and soybeans. Of particular interest is the use in monocotyledonous crops, such as cereals (wheat, barley, rye, triticale, sorghum), including corn and rice, and monocotyledonous vegetable crops, but also in dicotyledonous crops, such as, for example, soybean, oilseed rape, cotton, grape vines, vegetable plants, fruit plants and ornamental plants. The herbicide/safener combinations with the safeners (I) are also suitable for controlling harmful plants in beds and plots of useful plants and ornamental plants, such as, for example, lawn plots with useful or ornamental lawn, especially lolium, meadow grass or Bermuda grass.

Also of interest from among the useful plants and crop plants in which the herbicide/safener combinations with safeners (I) may be used are mutant crops which are completely or partially tolerant to certain pesticides or completely or partially tolerant transgenic crops, for example corn crops which are resistant to glufosinate or glyphosate, or soybean crops which are resistant to herbicidal imidazolinones. However, the particular advantage of the safeners used in this novel way is their efficient action in crops which normally are insufficiently tolerant to the pesticides being applied.

For the joint use with pesticides, the compounds of the formula (I) according to the invention can be applied simultaneously with the active compounds or in any order, and they are then capable of reducing or completely eliminating harmful side effects of these active compounds in crop plants, without negatively affecting or substantially reducing the activity of these active compounds against unwanted harmful organisms. Here, even damage caused by using a plurality of pesticides, for example a plurality of herbicides or herbicides in combination with insecticides or fungicides, can be reduced substantially or eliminated completely. In this manner, it is possible to extend the field of use of conventional pesticides considerably.

If the compositions according to the invention comprise pesticides, these compositions are, after appropriate dilution, applied either directly to the area under cultivation, to the already germinated harmful and/or useful plants or to the already emerged harmful and/or useful plants. If the compositions according to the invention do not comprise any pesticide, these compositions can be employed by the tank mix method—i.e. the user mixes and dilutes the separately available products (=the pesticide and the agent protecting the useful plants) immediately prior to application to the area to be treated—or prior to the application of a pesticide, or after the application of a pesticide, or for the pretreatment of seed, i.e., for example, for dressing the seed of the useful plants. Preferably, safener and pesticide are applied within a short time of one another, in particular when the safener is applied to the plants after the herbicide.

The advantageous actions of the compounds (I) according to the invention are observed when they are used together with the pesticides by the pre-emergence method or the post-emergence method, for example in the case of simultaneous application as a tank mix or a coformulation or in the case of a separate application, in parallel or in succession (split application). It is also possible to repeat the application a number of times. In some cases, it may be expedient to combine a pre-emergence application with a post-emergence application. In most cases, one option is a post-emergence application to the useful plant or crop plant together with a simultaneous or later application of the pesticide. Also possible is the use of the compounds (I) according to the invention for seed dressing, for (dip) treatment of seedlings (for example rice) or for the treatment of other propagation material (for example potato tubers).

When using the compounds (I) according to the invention in combination with herbicides, in addition to the safener action, enhanced action, in the herbicidal action, against harmful plants is frequently also observed. Furthermore, in many cases, there is an improved growth of the useful plants and crop plants, and it is possible to increase the harvest yields.

The compositions according to the invention may comprise one or more pesticides. Suitable pesticides are, for example, herbicides, insecticides, fungicides, acaricides and nematicides, which, when used on their own, would cause phytotoxic damage to the crop plants or would probably cause damage. Of particular interest are corresponding pesticidally active compounds from the groups of the herbicides, insecticides, acaricides, nematicides and fungicides, in particular herbicides.

The weight ratio of safener to pesticide can be varied within wide limits and is generally in the range from 1:100 to 100:1, preferably from 1:20 to 20:1, in particular from 1:10 to 10:1. The optimum weight ratio of safener to pesticide depends both on the respective safener used and the respective pesticide, and on the type of useful plant or crop plant to be protected. The required application rate of safener can, depending on the pesticide used and the type of useful plant to be protected, be varied within wide limits and is generally in the range from 0.001 to 10 kg, preferably from 0.01 to 1 kg, in particular from 0.05 to 0.5 kg, of safener per hectare. The weight ratios and amounts required for a successful treatment can be determined by simple preliminary experiments.

For seed dressing, for example, from 0.005 to 20 g of safener per kilogram of seed, preferably from 0.01 to 10 g of safener per kilogram of seed, in particular from 0.05 to 5 g of safener per kilogram of seed, are used.

If solutions of safener are used for seed treatment and the seeds or seedlings are wetted with the solutions, the suitable concentration is generally in the range from 1 to 10 000 ppm, preferably from 100 to 1000 ppm, based on the weight. The weight ratios and amounts required for a successful treatment can be determined by simple preliminary experiments.

The safeners can be formulated in the customary manner, separately or together with the pesticides. Accordingly, the present invention also provides the useful-plant-protecting or crop-plant-protecting compositions.

Preferred is the joint application of safener and pesticide, in particular that of safener and herbicide as a readymix or the use by the tankmix method.

Preference is also given to using the safener (I) in the treatment of seed, followed by the application of pesticides, preferably herbicides, after sowing by the pre- or post-emergence method.

The compounds of the formula (I) or their salts, as such or in the form of their preparations (formulations), can be used in combination with other pesticidally active compounds, such as, for example, insecticides, acaricides, nematicides, herbicides, fungicides, safeners, fertilizers and/or growth regulators, for example as finished formulation or as tank mixes. Here, the combination formulations can be prepared based on the formulations mentioned above, taking into account the physical properties and stabilities of the active compounds to be combined. Suitable as combination partners for the active compounds according to the invention in formulations of mixtures or in tank-mixes are, for example, known, preferably herbicidally active compounds whose action is based on the inhibition of, for example, acetolactate synthase, acetyl-coenzyme-A carboxylase, PS I, PS II, HPPDO, phytoene desaturase, protoporphyrinogen oxidase, glutamine synthetase, cellulose biosynthesis, 5-enolpyruvylshikimate 3-phosphate synthetase. Such compounds and also other compounds which can be used, in some cases having an unknown or a different mechanism of action, are described, for example, in Weed Research 26, 441-445 (1986), or in "The Pesticide Manual", 12th edition 2000, or 13th edition 2003 or 14h edition 2006/2007, or in the corresponding "e-Pesticide Manual", version 4 (2006), all published by the British Crop Protection Council, (hereinbelow also referred to in short as "PM"), and in the literature cited therein. Lists of "common names" are also available in "The Compendium of Pesticide Common Names" on the Internet. Examples of herbicides known from the literature which may be combined with the compounds of the formula (I) are, for example, the following active compounds (note: the compounds are referred to either by the "common name" according to the International Organization for Standardization (ISO) or by the chemical name, if appropriate together with a customary code number):

acetochlor; acibenzolar-5-methyl; acifluorfen(-sodium); aclonifen; AD-67; AKH 7088, i.e. [[[1-[5-[2-chloro-4-(trifluoromethyl)phenoxy]-2-nitrophenyl]-2-methoxyethylidene]amino]oxy]acetic acid and methyl [[[1-[5-[2-chloro-4-(trifluoromethyl)phenoxy]-2-nitrophenyl]-2-methoxyethylidene]-amino]oxy]acetate; alachlor; alloxydim (-sodium); ametryn; amicarbazone, amidochlor, amidosulfuron; aminopyralid; amitrol; AMS, i.e. ammonium sulfamate; ancimidol; anilofos; asulam; atrazine; aviglycine; azafenidin, azimsulfuron (DPX-A8947); aziprotryn; barban; BAS 516 H, i.e. 5-fluoro-2-phenyl-4H-3,1-benzoxazin-4-one; beflubutamid (UBH-509), benazolin(-ethyl); bencarbazone; benfluralin; benfuresate; benoxacor; bensulfuron(-methyl); bensulide; bentazone; benzfendizone; benzobicyclon, benzofenap; benzofluor; benzoylprop(-ethyl); benzthiazuron; bialaphos; bifenox; bispyribac(-sodium) (KIH-2023); borax; bromacil; bromobutide; bromofenoxim; bromoxynil; bromuron; buminafos; busoxinone; butachlor; butafenacil, butamifos; butenachlor (KH-218); buthidazole; butralin; butroxydim, butylate; cafenstrole (CH-900); carbetamide; carfentrazone(-ethyl); CDAA, i.e. 2-chloro-N,N-di-2-propenylacetamide; CDEC, i.e. 2-chlorallyl diethyldithiocarbamate; chlomethoxyfen; chloramben; chlorazifop-butyl, chlorbromuron; chlorbufam; chlorfenac; chlorfenprop; chlorflurecol(-methyl); chlorflurenol(-methyl); chloridazon; chlorimuron(-ethyl); chlormequat(chloride); chlornitrofen; chlorophthalim (MK-616); chlorotoluron; chloroxuron; chlorpropham; chlorsulfuron; chlorthal-dimethyl; chlorthiamid; chlortoluron, cinidon(-methyl and -ethyl), cinmethylin; cinosulfuron; clefoxydim, clethodim; clodinafop and its ester derivatives (for example clodinafop-propargyl); clofencet; clomazone; clomeprop; cloprop; cloproxydim; clopyralid; clopyrasulfuron(-methyl), cloquintocet(-mexyl); cloransulam(-methyl), cumyluron (JC 940); cyanamide; cyanazine; cycloate; cyclosulfamuron (AC 104); cycloxydim; cycluron; cyhalofop and its ester derivatives (for example the butyl ester, DEH-112); cyperquat; cyprazine; cyprazole; cyprosulfamide; daimuron; 2,4-D, 2,4-DB; dalapon; daminozide; dazomet; n-decanol; desmedipham; desmetryn; di-allate; dicamba; dichlobenil; dichlormid; dichlorprop(-P) salts; diclofop and its esters, such as diclofop-methyl; diclofop-P(-methyl); diclosulam, diethatyl(-ethyl); difenoxuron; difenzoquat(metilsulfate); diflufenican; diflufenzopyr(-sodium); dimefuron; dimepiperate, dimethachlor; dimethametryn; dimethazone; dimethenamid (SAN-582H); dimethenamide-P; dimethylarsinic acid; dimethipin; dimetrasulfuron, dinitramine; dinoseb; dinoterb; diphenamid; dipropetryn; diquat salts; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethephon; ethidimuron; ethiozin; ethofumesate; ethoxyfen and its esters (for example the ethyl ester, HN-252); ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]phenyl] ethanesulfonamide; fenchlorazole(-ethyl); fenclorim; fenoprop; fenoxan, fenoxaprop and fenoxaprop-P and also their esters, for example fenoxaprop-P-ethyl and fenoxaprop-ethyl; fenoxydim; fentrazamide, fenuron; ferrous sulfate; flamprop(-methyl or -isopropyl or -isopropyl-L); flamprop-M(-methyl or -isopropyl); flazasulfuron; florasulam, fluazifop and fluazifop-P and their esters, for example fluazifop-butyl and fluazifop-P-butyl; fluazolate, flucarbazone(-sodium), flucetosulfuron; fluchloralin; flufenacet; flufenpyr(-ethyl); flumetralin; flumetsulam; flumeturon; flumiclorac(-pentyl), flumioxazin (S-482); flumipropyn; fluometuron, fluorochloridone, fluorodifen; fluoroglycofen(-ethyl); flupoxam (KNW-739); flupropacil (UBIC-4243); flupropanoate; flupyrsulfuron(-methyl)(-sodium); flurazole; flurenol(-butyl); fluridone; flurochloridone; fluoroxypyr(-meptyl); flurprimidol, flurtamone; fluthiacet(-methyl) (KIH-9201); fluthiamide, fluxofenim; fomesafen; foramsulfuron, forchlorfenuron; fosamine; furilazole; furyloxyfen; gibberillic acid; glufosinate(-ammonium); glyphosate(-isopropylammonium); halosafen; halosulfuron(-methyl); haloxyfop and its esters; haloxyfop-P(═R-haloxyfop) and its esters; HC-252; hexazinone; imazamethabenz(-methyl); imazamethapyr, imazamox, imazapic, imazapyr; imazaquin and salts, such as the ammonium salt; imazethamethapyr; imazethapyr; imazosulfuron; inabenfide; indanofan; indole-3-acetic acid; 4-indol-3-ylbutyric acid; iodosulfuron-methyl(-sodium); ioxynil; isocarbamid; isopropalin; isoproturon; isouron; isoxaben; isoxachlortole; isoxadifen(-ethyl); isoxaflutole, isoxapyrifop; karbutilate; lactofen; lenacil; linuron; maleic hydrazide (MH), MCPA; MCPB; mecoprop(-P); mefenacet; mefenpyr(diethyl); mefluidid; mepiquat(-chloride); mesosulfuron(-methyl); mesotrione, metam; metamifop; metamitron; metazachlor; methabenzthiazuron; metham; methazole; methoxyphenone; methylarsonic acid; methylcyclopropene; methyldymron; methyl isothiocyanate; methabenzthiazuron; metobenzuron; metobromuron; (alpha-)metolachlor; metosulam (XRD 511); metoxuron; metribuzin; metsulfuron-methyl; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclofen; nitralin; nitrofen; nitrophenolate mixture; nitrofluorfen; nonanoic acid; norflurazon; orbencarb; orthasulfamuron; oxabetrinil; oryzalin; oxadiargyl (RP-020630); oxadiazon; oxasulfuron, oxaziclomefone, oxyfluorfen; paclobutrazol; paraquat(dichloride); pebulate; pelargonic acid, pendimethalin; penoxsulam; pentachlorophenol; pentanochlor, pentoxazone, perfluidone; pethoxamid; phenisopham; phenmedipham; picloram; picolinafen, pinoxaden, piperophos; piributicarb; pirifenop-butyl; pretilachlor; primisulfuron(-methyl); probenazole; procarbazone-(sodium), propazine; prodiamine; profluralin; profoxydim; prohexadione(-calcium); prohydrojasmon; proglinazine(-ethyl); prometon; prometryn; propachlor; propanil; propaquizafop; propazine; propham; propisochlor; propoxycarbazone(-sodium) (MKH-6561); n-propyl dihydrojasmonate; propyzamide; prosulfalin; prosulfocarb; prosulfuron (CGA-152005); prynachlor; pyraclonil; pyraflufen(ethyl) (ET-751); pyrasulfotole; pyrazolynate; pyrazon; pyrazosulfuron(-ethyl); pyrazoxyfen; pyribenzoxim, pyributicarb, pyridafol, pyridate; pyriftalid; pyriminobac(-methyl) (KIH-6127); pyrimisulfan (KIH-5996); pyrithiobac(-sodium) (KIH-2031); pyroxasulfone (KIH-485); pyroxofop and its esters (for example the propargyl ester); pyroxsulam; quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazol; saflufenacil (N'-[2-chloro-4-fluoro-5-(3-methyl-2,6-dioxo-4-(trifluoromethyl)-3,6-dihydro-1(2H)-pyrimidinyl)benzoyl]-N-isopropyl-N-methylsulfamide), secbumeton; sethoxydim; siduron; simazine; simetryn; sintofen; SN 106279, i.e. 2-[[7-[2-chloro-4-(trifluoromethyl)phenoxy]-2-naphthalenyl]oxy]propanoic acid and methyl 2-[[7-[2-chloro-4-(trifluoromethyl)phenoxy]-2-naphthalenyl]oxy]propanoate; sulcotrione, sulfentrazone (FMC-97285, F-6285); sulfazuron; sulfometuron(-methyl); sulfosate (ICI-A0224); sulfosulfuron, TCA; tebutam (GCP-5544); tebuthiuron; tecnacene; tembotrione; tefuryltrione; tepraloxydim, terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide, thiazafluoron; thiazopyr (Mon-13200); thidiazimin (SN-24085); thidiazuron; thiencarbazone; thifensulfuron(-methyl); thiobencarb; Ti 35; tiocarbazil; topramezone; tralkoxydim; tri-allate; triasulfuron; triaziflam, triazofenamide; tribenuron(-methyl); triclopyr; tridiphane; trietazine; trifloxysulfuron; trifluralin; triflusulfuron and esters (for example the methyl ester, DPX-66037); trimeturon; trinexapac; tritosulfuron, tsitodef; uniconazole; vernolate; WL 110547, i.e. 5-phenoxy-1-[3-(trifluoromethyl)phenyl]-1H-tetrazole; D-489; LS 82-556; KPP-300; NC-324; NC-330; DPX-N8189; SC-0774; DOWCO-535; DK-8910; V-53482; PP-600 and MBH-001.

Insecticides which may cause damage to plants when used on their own or together with herbicides are, for example, the following:

Organophosphates, for example terbufos (Counter®), fonofos (Dyfonate®), phorate (Thimet®), chlorpyriphos (Reldan®), carbamates, such as carbofuran (Furadan®), pyrethroid insecticides, such as tefluthrin (Force®), deltamethrin (Decis®) and tralomethrin (Scout®), and other insecticidal agents having a different mechanism of action.

Herbicides, whose phytotoxic side effects on crop plants can be reduced using compounds of the formula (I) are, for example, herbicides from the group of the carbamates, thiocarbamates, haloacetanilides, substituted phenoxy-, naphthoxy- and phenoxyphenoxycarboxylic acid derivatives and heteroaryloxyphenoxyalkanecarboxylic acid derivatives, such as quinolyloxy-, quinoxalyloxy-, pyridyloxy-, benzoxazolyloxy- and benzothiazolyloxyphenoxyalkanecarboxylic acid esters, cyclohexanedione oximes, benzoylcyclohexanediones, benzoylisoxazoles, benzoylpyrazoles, imidazolinones, pyrimidinyloxypyridinecarboxylic acid derivatives, pyrimidyloxybenzoic acid derivatives, sulfonylureas, sulfonylaminocarbonyltriazolinones, triazolopyrimidinesulfonamide derivatives, phosphinic acid derivatives and salts thereof, glycine derivatives, triazolinones, triazinones and also S—(N-aryl-N-alkylcarbamoylmethyl)dithiophosphoric esters, pyridinecarboxylic acids, pyridines, pyridinecarboxamides, 1,3,5-triazines and others.

Preference is given here to phenoxyphenoxy- and heteroaryloxyphenoxycarboxylic acid esters and salts, cyclohexanedione oximes, benzoylcyclohexanediones, benzoylisoxazoles, benzoylpyrazoles sulfonylureas, sulfonylaminocarbonyltriazolinones, imidazolinones and mixtures of the active compounds mentioned with one another and/or with active compounds used for broadening the activity spectrum of the herbicides, for example bentazone, cyanazine, atrazine, bromoxynil, dicamba and other leaf-acting herbicides.

Herbicides which are suitable for combination with the safeners according to the invention are, for example:

A) herbicides of the type of the phenoxyphenoxy- and heteroaryloxyphenoxycarboxylic acid derivatives, such as A1) phenoxyphenoxy- and benzyloxyphenoxycarboxylic acid derivatives, for example methyl 2-(4-(2,4-dichlorophenoxy)phenoxy)propionate (diclofop-methyl),
methyl 2-(4-(4-bromo-2-chlorophenoxy)phenoxy)propionate (DE-A 26 01 548 (U.S. Pat. No. 4,370,489)),
methyl 2-(4-(4-bromo-2-fluorophenoxy)phenoxy)propionate (U.S. Pat. No. 4,808,750),
methyl 2-(4-(2-chloro-4-trifluoromethylphenoxy)phenoxy) propionate (DE-A 24 33 067 (U.S. Pat. No. 4,332,960)),
methyl 2-(4-(2-fluoro-4-trifluoromethylphenoxy)phenoxy) propionate (U.S. Pat. No. 4,808,750),
methyl 2-(4-(2,4-dichlorobenzyl)phenoxy)propionate (DE-A 24 17 487 (U.S. Pat. No. 4,088,474)),
ethyl 4-(4-(4-trifluoromethylphenoxy)phenoxy)pent-2-enoate,
methyl 2-(4-(4-trifluoromethylphenoxy)phenoxy)propionate (DE-A 24 33 067),
butyl (R)-2-[4-(4-cyano-2-fluorophenoxy)phenoxy]propionate (cyhalofop-butyl)

A2) "monocyclic" heteroaryloxyphenoxyalkanecarboxylic acid derivatives, for example ethyl 2-(4-(3,5-dichloropyridyl-2-oxy)phenoxy)propionate (EP-A 0 002 925),
propargyl 2-(4-(3,5-dichloropyridyl-2-oxy)phenoxy)propionate (EP-A 0 003 114 (U.S. Pat. No. 4,300,944)),
methyl (RS)- or (R)-2-(4-(3-chloro-5-trifluoromethyl-2-pyridyloxy)phenoxy)propionate (haloxyfop-methyl or haloxyfop-P-methyl),
ethyl 2-(4-(3-chloro-5-trifluoromethyl-2-pyridyloxy)phenoxy)propionate (EP-A 0 003 890 (U.S. Pat. No. 4,840,664)),
propargyl 2-(4-(5-chloro-3-fluoro-2-pyridyloxy)phenoxy) propionate (clodinafop-propargyl),
butyl (RS)- or (R)-2-(4-(5-trifluoromethyl-2-pyridyloxy) phenoxy)propionate (fluazifop-butyl or fluazifop-P-butyl),
(R)-2-[4-(3-chloro-5-trifluoromethyl-2-pyridyloxy)phenoxy]propionic acid A3) "bicyclic" heteroaryloxyphenoxyalkanecarboxylic acid derivatives, for example methyl and ethyl (RS)- or (R)-2-(4-(6-chloro-2-quinoxalyloxy)phenoxy)propionate (quizalofop-methyl and -ethyl or quizalofop-P-methyl and -P-ethyl),
methyl 2-(4-(6-fluoro-2-quinoxalyloxy)phenoxy)propionate (see J. Pest. Sci. Vol. 10, 61 (1985)),
2-isopropylidenaminooxyethyl (R)-2-(4-(6-chloro-2-quinoxalyloxy)phenoxy)propionate (propaquizafop),
ethyl (RS)- or (R)-2-(4-(6-chlorobenzoxazol-2-yloxy)phenoxy)propionate (fenoxaprop-ethyl or fenoxaprop-P-ethyl),
ethyl 2-(4-(6-chlorobenzthiazol-2-yloxy)phenoxy)propionate (DE-A-26 40 730 (U.S. Pat. No. 4,130,413)),
tetrahydro-2-furylmethyl (RS)- or (R)-2-(4-(6-chloroquinoxalyloxy)phenoxy) propionate (EP-A-0 323 727 (U.S. Pat. No. 5,120,348));
(R)-2-[4-(6-chloro-1,3-benzoxazol-2-yloxy)phenoxy]-2'-fluoro-N-methylpropionanilide (metamifop);

B) herbicides from the group of the sulfonylureas, such as pyrimidinyl- or triazinylaminocarbonyl[benzene-, -pyridine-, -pyrazole-, -thiophene- and -(alkyl-sulfonyl)alkylamino]sulfamides. Preferred substituents on the pyrimidine ring or the triazine ring are alkoxy, alkyl, haloalkoxy, haloalkyl, halogen or dimethylamino, it being possible to combine all substituents independently of one another. Preferred substituents in the benzene, pyridine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkanesulfonyl)alkylamino. Such suitable sulfonylureas are, for example, B1) phenyl- and benzylsulfonylureas and related compounds, for example 1-(2-chlorophenylsulfonyl)-3-(4-methoxy-6-methyl-1,3,5-triazin-2-yl)urea (chlorsulfuron),
1-(2-ethoxycarbonylphenylsulfonyl)-3-(4-chloro-6-methoxypyrimidin-2-yl)urea (chlorimuron-ethyl),
1-(2-methoxyphenylsulfonyl)-3-(4-methoxy-6-methyl-1,3,5-triazin-2-yl)urea (metsulfuron-methyl),
1-(2-chloroethoxyphenylsulfonyl)-3-(4-methoxy-6-methyl-1,3,5-triazin-2-yl)urea (triasulfuron),
1-(2-methoxycarbonylphenylsulfonyl)-3-(4,6-dimethylpyrimidin-2-yl)urea (sulfumeturon-methyl),
1-(2-methoxycarbonylphenylsulfonyl)-3-(4-methoxy-6-methyl-1,3,5-triazin-2-yl)-3-methylurea (tribenuron-methyl),
1-(2-methoxycarbonylbenzylsulfonyl)-3-(4,6-dimethoxypyrimidin-2-yl)urea (bensulfuron-methyl),
1-(2-methoxycarbonylphenylsulfonyl)-3-(4,6-bis-(difluoromethoxy)pyrimidin-2-yl)urea (primisulfuron-methyl),
3-(4-ethyl-6-methoxy-1,3,5-triazin-2-yl)-1-(2,3-dihydro-1,1-dioxo-2-methylbenzo[b]thiophene-7-sulfonyl)urea (EP-A 0 079 683 (U.S. Pat. No. 4,492,596), 3-(4-ethoxy-6-ethyl-1,3,5-triazin-2-yl)-1-(2,3-dihydro-1,1-dioxo-2-methylbenzo[b]-thiophene-7-sulfonyl)urea (EP-A 0 079 683), 3-(4-methoxy-6-methyl-1,3,5-triazin-2-yl)-1-(2-methoxycarbonyl-5-iodophenylsulfonyl)urea (WO 92/13845 (U.S. Pat. No. 5,463,081)), methyl 2-[4-dimethylamino-6-(2,2,2-trifluoroethoxy)-1,3,5-triazin-2-ylcarbamoylsulfamoyl]-3-methylbenzoate (DPX-66037, triflusulfuron-methyl), oxetan-3-yl 2-[(4,6-dimethylpyrimidin-2-yl)carbamoylsulfamoyl]benzoate (CGA-277476, oxasulfuron), methyl 4-iodo-2-[3-(4-methoxy-6-methyl-1,3,5-triazin-2-yl)ureidosulfonyl]benzoate, sodium salt (iodosulfuron-methyl-sodium), methyl 2-[3-(4,6-dimethoxypyrimidin-2-yl)ureidosulfonyl]-4-methanesulfonylaminomethylbenzoate (mesosulfuron-methyl, WO 95/10507 (U.S. Pat. No. 5,648,315)), N,N-dimethyl-2-[3-(4,6-dimethoxypyrimidin-2-yl)ureidosulfonyl]-4-formylaminobenzamide (foramsulfuron, WO 95/01344 (U.S. Pat. No. 5,658,854)), 1-(4,6-dimethoxy-1,3,5-triazin-2-yl)-3-[2-(2-methoxyethoxy)phenylsulfonyl]urea (cinosulfuron), methyl 2-[(4-ethoxy-6-methylamino-1,3,5-triazin-2-yl)carbamoylsulfamoyl]benzoate (ethametsulfuron-methyl), 1-(4-methoxy-6-methyl-1,3,5-triazin-2-yl)-3-[2-(3,3,3-trifluoropropyl)phenylsulfonyl]urea (prosulfuron), 1-(4-methoxy-6-trifluoromethyl-1,3,5-triazin-2-yl)-3-(2-trifluoromethylbenzenesulfonyl)urea (tritosulfuron);

N-[(4-methylpyrimidin-2-yl)carbamoyl]-2-nitrobenzenesulfonamide (monosulfuron), methyl-2-[({[4-methoxy-6-(methylthio)pyrimidin-2-yl]carbamoyl}amino)sulfonyl]benzoate B2) thienylsulfonylureas, for example
1-(2-methoxycarbonylthiophen-3-yl)-3-(4-methoxy-6-methyl-1,3,5-triazin-2-yl)urea (thifensulfuron-methyl);

B3) pyrazolylsulfonylureas, for example
1-(4-ethoxycarbonyl-1-methylpyrazol-5-ylsulfonyl)-3-(4,6-dimethoxypyrimidin-2-yl)urea (pyrazosulfuron-ethyl), methyl 3-chloro-5-(4,6-dimethoxypyrimidin-2-ylcarbamoylsulfamoyl)-1-methylpyrazole-4-carboxylate (halosulfuron-methyl), methyl 5-(4,6-dimethylpyrimidin-2-yl-carbamoylsulfamoyl)-1-(2-pyridyl)pyrazole-4-carboxylate (NC-330, see Brighton Crop Prot. Conference 'Weeds' 1991, Vol. 1, p. 45 et seq.), 1-(4,6-dimethoxypyrimidin-2-yl)-3-[1-methyl-4-(2-methyl-2H-tetrazol-5-yl)pyrazol-5-ylsulfonyl]urea (DPX-A8947, azimsulfuron);

N-[(4,6-dimethoxypyrimidin-2-yl)carbamoyl]-4-(5,5-dimethyl-4,5-dihydroisoxazol-3-yl)-1,3-dimethyl-1H-pyrazole-5-sulfonamide;

B4) sulfonediamide derivatives, for example
3-(4,6-dimethoxypyrimidin-2-yl)-1-(N-methyl-N-methylsulfonylaminosulfonyl)urea (amidosulfuron) and its structural analogs (EP-A 0 131 258 (U.S. Pat. No. 4,601,747) and Z. Pfl. Krankh. Pfl. Schutz, special issue XII, 489-497 (1990));

B5) pyridylsulfonylureas, for example
1-(3-N,N-dimethylaminocarbonylpyridin-2-ylsulfonyl)-3-(4,6-dimethoxypyrimidin-2-yl)urea (nicosulfuron), 1-(3-ethylsulfonylpyridin-2-ylsulfonyl)-3-(4,6-dimethoxypyrimidin-2-yl)urea (rimsulfuron), methyl 2-[3-(4,6-dimethoxypyrimidin-2-yl)ureidosulfonyl]-6-trifluoromethyl-3-pyridinecarboxylate, sodium salt (DPX-KE 459, flupyrsulfuron-methyl-sodium), 3-(4,6-dimethoxypyrimidin-2-yl)-1-(3-N-methylsulfonyl-N-methylaminopyridin-2-yl)sulfonylurea or its salts (DE-A 40 00 503 (U.S. Pat. No. 5,494,886) and DE-A 40 30 577), 1-(4,6-dimethoxypyrimidin-2-yl)-3-(3-trifluoromethyl-2-pyridylsulfonyl)urea (flazasulfuron), 1-(4,6-dimethoxypyrimidin-2-yl)-3-[3-(2,2,2-trifluoroethoxy)-2-pyridylsulfonyl]urea sodium salt (trifloxysulfuron-sodium);

(1RS,2RS; 1RS,2SR)-1-{3-[(4,6-dimethoxypyrimidin-2-ylcarbamoyl)sulfamoyl]-2-pyridyl}-2-fluoropropyl methoxyacetate (flucetosulfuron);

B6) alkoxyphenoxysulfonylureas, for example
3-(4,6-dimethoxypyrimidin-2-yl)-1-(2-ethoxyphenoxy)sulfonylurea or its salts (ethoxysulfuron);

B7) imidazolylsulfonylureas, for example
1-(4,6-dimethoxypyrimidin-2-yl)-3-(2-ethylsulfonylimidazo[1,2-a]pyridin-3-yl)sulfonylurea (MON 37500, sulfosulfuron), 1-(2-chloroimidazo[1,2-a]pyridin-3-ylsulfonyl)-3-(4,6-dimethoxypyrimidin-2-yl)urea (imazosulfuron);

2-chloro-N-[(4,6-dimethoxypyrimidin-2-yl)carbamoyl]-6-propylimidazo[1,2-b]pyridazine-3-sulfonamide;

B8) phenylaminosulfonylureas, for example
1-[2-(cyclopropylcarbonyl)phenylaminosulfonyl]-3-(4,6-dimethoxypyrimidin-2-yl)urea (cyclosulfamuron);

1-(4,6-dimethoxypyrimidin-2-yl)-3-[2-(dimethylcarbamoyl)phenylsulfamoyl]urea (orthosulfamuron);

C) chloroacetanilides, for example
acetochlor, alachlor, butachlor, dimethachlor, dimethenamid, dimethenamid-P; metazachlor, metolachlor, S-metolachlor, pethoxamid, pretilachlor, propachlor, propisochlor and thenylchlor;

D) thiocarbamates, for example
S-ethyl N,N-dipropylthiocarbamate (EPTC),
S-ethyl N,N-diisobutylthiocarbamate (butylate);
cycloate, dimepiperate, esprocarb, molinate, orbencarb, pebulate, prosulfocarb, thiobencarb, tiocarbazil, tri-allate and vernolate;

E) cyclohexanedione oximes, for example
alloxydim, butroxydim, clethodim, cloproxydim, cycloxydim, profoxydim, sethoxydim, tepraloxydim and tralkoxydim;

F) imidazolinones, for example
imazamethabenz-methyl, imazapic, imazamox, imazapyr, imazaquin and imazethapyr;

G) triazolopyrimidinesulfonamide derivatives, for example
chloransulam-methyl, diclosulam, florasulam, flumetsulam, metosulam and penoxsulam, i.e. 2-(2,2-difluoroethoxy)-N-(5,8-dimethoxy[1,2,4]triazolo[1,5-c]pyrimidin-2-yl)-6-(trifluoromethyl)benzenesulfonamide, and pyroxsulam, i.e. N-(5,7-dimethoxy[1,2,4]triazolo[1,5-a]pyrimidin-2-yl)-2-methoxy-4-(trifluoromethyl)-3-pyridinesulfonamide;

H) benzoylcyclohexanediones, for example
2-(2-chloro-4-methylsulfonylbenzoyl)cyclohexane-1,3-dione (SC-0051, sulcotrione), 2-(2-nitrobenzoyl)-4,4-dimethylcyclohexane-1,3-dione (EP-A 0 274 634), 2-(2-nitro-3-methylsulfonylbenzoyl)-4,4-dimethylcyclohexane-1,3-dione (WO 91/13548), 2-[4-(methylsulfonyl)-2-nitrobenzoyl]-1,3-cyclohexanedione (mesotrione), 2-[2-chloro-3-(5-cyanomethyl-4,5-dihydroisoxazol-3-yl)-4-(ethylsulfonyl)benzoyl]-1,3-cyclohexanedione, 2-[2-chloro-3-(5-cyanomethyl-4,5-dihydroisoxazol-3-yl)-4-(methylsulfonyl)benzoyl]-1,3-cyclohexanedione,
2-[2-chloro-3-(5-ethoxymethyl-4,5-dihydroisoxazol-3-yl)-4-(ethylsulfonyl)benzoyl]-1,3-cyclohexanedione,
2-[2-chloro-3-(5-ethoxymethyl-4,5-dihydroisoxazol-3-yl)-4-(methylsulfonyl)benzoyl]-1,3-cyclohexanedione,
2-[2-chloro-3-[(2,2,2-trifluoroethoxy)methyl]-4-(ethylsulfonyl)benzoyl]-1,3-cyclohexanedione,
2-[2-chloro-3-[(2,2,2-trifluoroethoxy)methyl]-4-(methylsulfonyl)benzoyl]-1,3-cyclohexanedione (tembotrione),
2-[2-chloro-3-[(2,2-difluoroethoxy)methyl]-4-(ethylsulfonyl)benzoyl]-1,3-cyclohexanedione,
2-[2-chloro-3-[(2,2-difluoroethoxy)methyl]-4-(methylsulfonyl)benzoyl]-1,3-cyclohexanedione,
2-[2-chloro-3-[(2,2,3,3-tetrafluoropropoxy)methyl]-4-(ethylsulfonyl)benzoyl]-1,3-cyclohexanedione,
2-[2-chloro-3-[(2,2,3,3-tetrafluoropropoxy)methyl]-4-(methylsulfonyl)benzoyl]-1,3-cyclohexanedione,
2-[2-chloro-3-(cyclopropylmethoxy)-4-(ethylsulfonyl)benzoyl]-1,3-cyclohexanedione,
2-[2-chloro-3-(cyclopropylmethoxy)-4-(methylsulfonyl)benzoyl]-1,3-cyclohexanedione,
2-[2-chloro-3-(tetrahydrofuran-2-ylmethoxymethyl)-4-(ethylsulfonyl)benzoyl]-1,3-cyclohexanedione,
2-[2-chloro-3-(tetrahydrofuran-2-ylmethoxymethyl)-4-(methylsulfonyl)benzoyl]-1,3-cyclohexanedione (tefuryltrione),
2-[2-chloro-3-[2-(2-methoxyethoxy)ethoxymethyl]-4-(ethylsulfonyl)benzoyl]-1,3-cyclohexanedione,
2-[2-chloro-3-[2-(2-methoxyethoxy)ethoxymethyl]-4-(methylsulfonyl)benzoyl]-1,3-cyclohexanedione,
3-({2-[(2-methoxyethoxy)methyl]-6-(trifluoromethyl)pyridin-3-yl}carbonyl)-bicyclo[12.1]octane-2,4-dione (WO 2001094339);
I) benzoylisoxazoles, for example
5-cyclopropyl-[2-(methylsulfonyl)-4-(trifluoromethyl)benzoyl]isoxazole (isoxaflutole);
(4-chloro-2-mesylphenyl)(5-cyclopropyl-1,2-oxazol-4-yl)methanone (isoxachlortole);
j) benzoylpyrazoles, for example
2-[4-(2,4-dichloro-m-toluoyl)-1,3-dimethylpyrazol-5-yloxy]-4'-methylacetophenone (benzofenap),
4-(2,4-dichlorobenzoyl)-1,3-dimethylpyrazol-5-yltoluene-4-sulfonate (pyrazolynate),
2-[4-(2,4-dichlorobenzoyl)-1,3-dimethylpyrazol-5-yloxy]acetophenone (pyrazoxyfen);
5-hydroxy-1-methyl-4-[2-(methylsulfonyl)-4-trifluoromethylbenzoyl]pyrazole (WO 01/74785 (U.S. Pat. No. 6,420,317)),
1-ethyl-5-hydroxy-4-[2-(methylsulfonyl)-4-trifluoromethylbenzoyl]pyrazole (WO 01/74785),
1,3-dimethyl-5-hydroxy-4-[2-(methylsulfonyl)-4-trifluoromethylbenzoyl]pyrazole (WO 01/74785),
1-ethyl-5-hydroxy-3-methyl-4-[2-(methylsulfonyl)-4-trifluoromethylbenzoyl]pyrazole (pyrasulfotole, WO 01/74785),
5-hydroxy-1-methyl-4-[-2-chlor-3-(4,5-dihydroisoxazol-3-yl)-4-methylsulfonylbenzoyl]pyrazole (WO 99/58509 (U.S. Pat. No. 6,525,204)),
5-hydroxy-1-methyl-4-[3-(4,5-dihydroisoxazol-3-yl)-2-methyl-4-methylsulfonylbenzoyl]pyrazole (topramezone, WO 99/58509),
1-ethyl-5-hydroxy-3-methyl-4-[2-methyl-4-methylsulfonyl-3-(2-methoxyethylamino)benzoyl]pyrazole (WO 96/26206 (U.S. Pat. No. 5,846,907)),
3-cyclopropyl-5-hydroxy-1-methyl-4-[2-methyl-4-methylsulfonyl-3-(2-methoxy-ethylamino)benzoyl]pyrazole (WO 96/26206),
5-benzoxy-1-ethyl-4-[2-methyl-4-methylsulfonyl-3-(2-methoxyethylamino)benzoyl]pyrazole (WO 96/26206),
1-ethyl-5-hydroxy-4-(3-dimethylamino-2-methyl-4-methylsulfonylbenzoyl)pyrazole (WO 96/26206),
5-hydroxy-1-methyl-4-(2-chloro-3-dimethylamino-4-methylsulfonylbenzoyl)pyrazole (WO 96/26206),
1-ethyl-5-hydroxy-4-(3-allylamino-2-chloro-4-methylsulfonylbenzoyl)pyrazole (WO 96/26206),
1-ethyl-5-hydroxy-4-(2-methyl-4-methylsulfonyl-3-morpholinobenzoyl)pyrazole (WO 96/26206),
5-hydroxy-1-isopropyl-4-(2-chloro-4-methylsulfonyl-3-morpholinobenzoyl)pyrazole (WO 96/26206),
3-cyclopropyl-5-hydroxy-1-methyl-4-(2-chloro-4-methylsulfonyl-3-morpholinobenzoyl)pyrazole (WO 96/26206),
1,3-dimethyl-5-hydroxy-4-(2-chloro-4-methylsulfonyl-3-pyrazol-1-ylbenzoyl)pyrazole WO 96/26206),
1-ethyl-5-hydroxy-3-methyl-4-(2-chloro-4-methylsulfonyl-3-pyrazol-1-ylbenzoyl)pyrazole (WO 96/26206),
1-ethyl-5-hydroxy-4-(2-chloro-4-methylsulfonyl-3-pyrazol-1-ylbenzoyl)pyrazole (WO 96/26206),
(5-hydroxy-1-methyl-1H-pyrazol-4-yl)(3,3,4-trimethyl-1,1-dioxido-2,3-dihydro-1-benzothien-5-yl)methanone (US2002/0016262),
1-methyl-4-[(3,3,4-trimethyl-1,1-dioxido-2,3-dihydro-1-benzothien-5-yl)carbonyl]-1H-pyrazol-5-ylpropane-1-sulfonate (US2002/0016262, WO 2002/015695 (US 2002052296));
3-(2-chloro-4-mesylbenzoyl)-2-phenylthiobicyclo[3.2.1]oct-2-en-4-one (benzobicyclon);
K) sulfonylaminocarbonyltriazolinones, for example
4,5-dihydro-3-methoxy-4-methyl-5-oxo-N-(2-trifluoromethoxyphenylsulfonyl)-1H-1,2,4-triazole-1-carboxamide sodium salt (flucarbazone-sodium),
methyl 2-(4,5-dihydro-4-methyl-5-oxo-3-propoxy-1H-1,2,4-triazol-1-yl)carboxamido-sulfonylbenzoate sodium salt (propoxycarbazone-Na);
methyl 4-[(4,5-dihydro-3-methoxy-4-methyl-5-oxo-1H-1,2,4-triazol-1-yl)carbonyl-sulfamoyl]-5-methylthiophene-3-carboxylate (thiencarbazone-methyl);
L) triazolinones, for example
4-amino-N-ten-butyl-4,5-dihydro-3-isopropyl-5-oxo-1,2,4-1H-triazole-1-carboxamide (amicarbazone),
2-(2,4-dichloro-5-prop-2-ynyloxyphenyl)-5,6,7,8-tetrahydro-1,2,4-triazolo[4,3-a]pyridin-3(2H)-one (azafenidin),
ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate (carfentrazone-ethyl),
2',4'-dichloro-5'-(4-difluoromethyl-4,5-dihydro-3-methyl-5-oxo-1H-1,2,4-triazol-1-yl)-methanesulfonanilide (sulfentrazone);
4-[4,5-dihydro-4-methyl-5-oxo-3-(trifluoromethyl)-1H-1,2,4-triazol-1-yl]-2-[(ethylsulfonyl)amino]-5-fluorobenzenecarbothioamide (bencarbazone);
M) phosphinic acids and derivatives, for example
4-[hydroxy(methyl)phosphinoyl]-L-homoalanyl-L-alanyl-L-alanine (bilanafos),
DL-homoalanin-4-yl(methyl)phosphinic acid ammonium salt (glufosinate-ammonium);
N) glycine derivatives, for example
N-(phosphonomethyl)glycine and its salts (glyphosate and salts, for example the sodium salt or the isopropylammonium salt),
N-(phosphonomethyl)glycine trimesium salt (sulfosate);

O) pyrimidinyloxypyridinecarboxylic acid derivatives; pyrimidinyloxybenzoic acid derivatives and pyrimidinylthiobenzoic acid derivatives, for example benzyl 3-(4,6-dimethoxypyrimidin-2-yl)oxypyridine-2-carboxylate (EP-A 0 249 707 (U.S. Pat. No. 4,832,729)), methyl 3-(4,6-dimethoxypyrimidin-2-yl)oxypyridine-2-carboxylate (EP-A 0 249 707), 1-(ethoxycarbonyloxyethyl) 2,6-bis[(4,6-dimethoxypyrimidin-2-yl)oxy]benzoate (EP-A 0 472 113 (U.S. Pat. No. 5,154,750)), 2,6-bis[(4,6-dimethoxypyrimidin-2-yl)oxy]benzoic acid (bispyribac-sodium), isopropyl 4-[[[2-[(4,6-dimethoxy-2-pyrimidinyl)oxy]phenyl]methyl]amino]benzoate (pyribambenz-isopropyl, WO 2002034724 (U.S. Pat. No. 6,800,590)), propyl 4-[[[2-[(4,6-dimethoxy-2-pyrimidinyl)oxy]phenyl]methyl]amino]benzoate (pyribambenz-propyl, WO 2002034724), pyribenzoxim, pyriftalid, pyriminobac-methyl, pyrithiobac-sodium, pyrirmisulfan;

P) S—(N-aryl-N-alkylcarbamoylmethyl)dithiophosphonic acid esters, such as S—[N-(4-chlorophenyl)-N-isopropylcarbamoylmethyl]O,O-dimethyl dithiophosphate (anilophos);

Q) triazinones, for example 3-cyclohexyl-6-dimethylamino-1-methyl-1,3,5-triazine-2,4-(1H,3H)-dione (hexazinone), 4-amino-4,5-dihydro-3-methyl-6-phenyl-1,2,4-triazin-5-one (metamitron), 4-amino-6-tert-butyl-4,5-dihydro-3-methylthio-1,2,4-triazin-5-one (metribuzin);

R) pyridinecarboxylic acids, for example aminopyralid, clopyralid, fluoroxypyr, picloram and triclopyr;

S) pyridines, for example dithiopyr and thiazopyr;

T) pyridinecarboxamides, for example diflufenican and picolinafen;

U) 1,3,5-triazines, for example ametryn, atrazine, cyanazine, dimethametrin, prometon, prometryn, propazine, simazine, symetryn, terbumeton, terbuthylazine, terbutryn and trietazine;

V) plant growth regulators, for example forchlorfenuron and thidiazuron;

W) ketoenoles, for example 8-(2,6-diethyl-p-tolyl)-1,2,4,5-tetrahydro-7-oxo-7H-pyrazolo[1,2-d][1,4,5]oxadiazepin-9-yl 2,2-dimethylpropionate (pinoxaden);

X) pyrazoles, for example

3-[5-(difluoromethoxy)-1-methyl-3-(trifluoromethyl)pyrazol-4-ylmethylsulfonyl]-4,5-dihydro-5,5-dimethyl-1,2-oxazole (pyroxasulfone).

The herbicides of groups A to W are known, for example, from the respective abovementioned publications and from "The Pesticide Manual", The British Crop Protection Council, 14th Edition, 2006, or the e-Pesticide Manual, Version 4.0, British Crop Protection Council 2006 or else from the "Compendium of Pesticide Common Names".

When used as active compound formulations or coformulations, they generally comprise, if appropriate, the respective customary tackifiers, wetting agents, dispersing agents, emulsifiers, penetrants, preservatives, antifreeze agents and solvents, fillers, carriers and colorants, antifoams, evaporation inhibitors and pH- and viscosity-modifying agents.

The compounds of the formula I and their combinations with one or more of the abovementioned pesticides can be formulated in various ways, depending on the prevailing physicochemical and biological parameters. Examples of suitable formulation types are:

emulsifiable concentrates which are prepared by dissolving the active compounds in an organic solvent, for example butanol, cyclohexanone, dimethylformamide, xylene or else relatively high-boiling hydrocarbons or mixtures of the organic solvents with addition of one or more ionic and/or nonionic surfactants (emulsifiers). Suitable emulsifiers are, for example, calcium alkylarylsulfonates, fatty acid polyglycol esters, alkylaryl polyglycol ethers, fatty alcohol polyglycol ethers, propylene oxide/ethylene oxide condensates, alkyl polyethers, sorbitan esters and polyoxyethylenesorbitan fatty acid esters;

dusts, which are obtained by grinding the active compounds with finely dispersed solid inorganic or organic substances, for example talc, natural clays, such as kaolin, bentonite and pyrophyllite, diatomaceous earth or meals;

water- or oil-based suspension concentrates, which can be prepared, for example, by wet grinding using bead mills;

water-soluble powders;

water-soluble concentrates;

granules, such as water-soluble granules, water-dispersible granules and granules for application by broadcasting and soil application;

wettable powders which, in addition to active compound, also contain diluents or inert substances and surfactants;

capsule suspensions and microcapsules;

ultra-low-volume formulations.

The abovementioned formulation types are known to the person skilled in the art and described, for example, in: K. Martens, "Spray Drying Handbook", 3rd Ed., G. Goodwin Ltd., London, 1979; W. van Valkenburg, "Pesticide Formulations", Marcel Dekker, N.Y. 1973; Winnaker-Küchler, "Chemische Technologie" [Chemical Technology], volume 7, C. Hanser Verlag Munich, 4th edition 1986; "Perry's Chemical Engineer's Handbook", 5th Ed., McGraw-Hill, N.Y. 1973, pages 8-57.

The formulation auxiliaries required, such as inert materials, surfactants, solvents and other additives are also known and are described, for example, in: McCutcheon's "Detergents and Emulsifiers Annual", MC Publ. Corp., Ridgewood N.J.; C. Marsden, "Solvents Guide", 2nd Ed., Interscience, N.Y. 1963; H. von Olphen, "Introduction to Clay Colloid Chemistry", 2nd Ed., J. Wiley & Sons, N.Y.; Schönfeldt, "Grenzflächenaktive Äthylenoxidaddukte" [Surface-active ethylene oxide adducts], Wiss. Verlagsgesellschaft, Stuttgart 1976; Sisley and Wood, "Encyclopedia of Surface Active Agents", Chem. Publ. Co. Inc., N.Y. 1964; Watkins, "Handbook of Insecticide Dust Diluents and Carriers", 2nd Ed., Darland Books, Caldwell N.J.; Winnacker-Küchler, "Chemische Technologie" [Chemical Technology], volume 7, C. Hanser Verlag Munich, 4th edition 1986.

In addition to the abovementioned formulation auxiliaries, the useful-plant-protecting compositions may comprise, if appropriate, customary tackifiers, wetting agents, dispersants, penetrants, emulsifiers, preservatives, antifreeze agents, fillers, carriers, colorants, anti-foams, evaporation inhibitors and pH or viscosity regulators.

Depending on the formulation type, the useful-plant-protecting compositions generally comprise 0.1 to 99% by weight, in particular 0.2 to 95% by weight, of one or more safeners of the formula I or a combination of safener and pesticide. Furthermore, they comprise 1 to 99.9, in particular 4 to 99.5,% by weight of one or more solid or liquid additives and 0 to 25, in particular 0.1 to 25,% by weight of a surfactant.

In emulsifiable concentrates, the concentration of active compound, i.e. the concentration of safener and/or pesticide, is generally 1 to 90, in particular 5 to 80,% by weight. Dusts usually comprise 1 to 30, preferably 5 to 20,% by weight of active compound. In wettable powders, the concentration of active compound is generally 10 to 90% by weight. In water-dispersible granules, the content of active compound is, for example, between 1 and 95% by weight, preferably between 10 and 80% by weight.

For use, the formulations, which are present in commercially available form, are, if appropriate, diluted in a customary manner, for example in the case of wettable powders, emulsifiable concentrates, dispersions and water-dispersible granules, with water. Preparations in the form of dusts, granules and sprayable solutions are usually not diluted with any further inert substances prior to use. The required application rate of the safeners varies with the external conditions such as, inter alia, temperature, humidity and the type of herbicide used.

In the examples below, which illustrate the invention but do not limit it, the amounts are based on weight, unless defined otherwise.

EXAMPLES

1 Formulation Examples 1.1 Dusting Agent

A dusting agent is obtained by mixing 10 parts by weight of a compound of the formula (I) or of an active compound mixture of a pesticide (eg. herbicide) and a safener of the formula (I) and 90 parts by weight of talc as inert material and comminuting in a hammer mill.

1.2 Water-Dispersible Powder

A wettable powder which is readily dispersible in water is obtained by mixing 25 parts by weight of a compound of the formula (I) or of an active compound mixture of a pesticide (eg. herbicide) and a safener of the formula (I), 64 parts by weight of kaolin-containing quartz as inert material, 10 parts by weight of potassium ligninsulfonate and 1 part by weight of sodium oleoylmethyltaurinate as wetting and dispersing agent, and grinding in a pin mill.

1.3 Water-Dispersible Concentrate

A dispersion concentrate which is readily dispersible in water is obtained by mixing 20 parts by weight of a compound of the formula (I) or of an active compound mixture of a pesticide (eg. herbicide) and a safener of the formula (I) with 6 parts by weight of alkylphenol polyglycol ether (®Triton X 207), 3 parts by weight of isotridecanol polyglycol ether and 71 parts by weight of paraffinic mineral oil and grinding in a ball mill to a fineness of below 5 microns.

1.4 Emulsifiable Concentrate

An emulsifiable concentrate is obtained from 15 parts by weight of a compound of the formula (I) or of an active compound mixture of a pesticide (eg. herbicide) and a safener of the formula (I), 75 parts by weight of cyclohexanone as solvent and 10 parts by weight of ethoxylated nonylphenol as emulsifier.

1.5 Water-Dispersible Granules

Water-dispersible granules are obtained by mixing

| | |
|---|---|
| 75 parts by weight | of a safener of the formula (I) or of a mixture of a pesticide and a safener of the formula (I), |
| 10 parts by weight | of calcium ligninsulfonate, |
| 5 parts by weight | of sodium lauryl sulfate, |
| 3 parts by weight | of polyvinyl alcohol and |
| 7 parts by weight | of kaolin, | grinding in a pin mill and granulating the powder in a fluidized bed by spraying on water as granulation liquid.

Water-dispersible granules are also obtained by homogenizing

| | |
|---|---|
| 25 parts by weight | of a safener of the formula (I) or of a mixture of a pesticide and a safener of the formula (I), |
| 5 parts by weight | of sodium 2,2'-dinaphthylmethane-6,6'-disulfonate, |
| 2 parts by weight | of sodium oleoylmethyltaurinate, |
| 17 parts by weight | of calcium carbonate, |
| 50 parts by weight | of water and |
| 1 part by weight | of polyvinyl alcohol | in a colloid mill, comminuting, then grinding in a bead mill and atomizing and drying the resulting suspension in a spray tower using a single-fluid nozzle.

2. Preparation Examples

Example A1

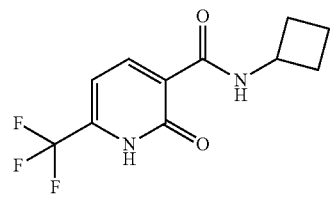 [SMILES: O=C(NC1CCC1)c1ccc(C(F)(F)F)[nH]c1=O]

N-Cyclobutyl-2-oxo-6 (trifluoromethyl)-1,2-dihydropyridine-3-carboxamide

A1.1) 4-Butoxy-1,1,1-trifluorobut-3-en-2-one

At 5° C., 79.9 g (0.38 mol) of trifluoroacetic anhydride—dissolved in 100 ml of trichloromethane—were added with stirring to a mixture of 29.9 g (0.38 mol) of pyridine and 50.0 g (0.38 mol) of butyl vinyl ether in 200 ml of trichloromethane. After the addition, stirring was continued at room temperature for another 15 h. 300 ml of water were then added to the mixture, and the organic phase was separated off, dried and concentrated. This gave 59 g (79% of theory) of a yellowish oil.

$^1$H-NMR: [CDCl$_3$] 0.96 (t, 3H); 1.41 (m, 2H); 1.73 (m, 2H); 4.04 (t, 2H); 5.85 (d, 1H); 7.90 (d, 1H).

A1.2) Methyl 2-oxo-6-(trifluoromethyl)-1,2-dihydropyridine-3-carboxylate 2.15 g (94 mmol) of sodium were dissolved in 300 ml of methanol, 15.3 g (78 mmol) of 4-butoxy-1,1,1-trifluorobut-3-en-2-one and 9.13 g (78 mmol) of methyl malonatemonoamide were added and the mixture was heated under reflux for 18 h. The mixture was concentrated, and the residue was taken up in water and washed with dichloromethane. The aqueous phase was then adjusted to pH 2 by addition of 2N hydrochloric acid and extracted with dichloromethane. Drying and concentration of the extract gave 12 g (69% of theory) of a colorless powder.

$^1$H-NMR: [CDCl$_3$] 4.03 (s, 3H); 7.31 (d, 1H); 8.39 (d, 1H).

A1.3) 2-Oxo-6-(trifluoromethyl)-1,2-dihydropyridine-3-carboxylic acid

At room temperature, 4.73 g (21.4 mmol) of methyl 2-oxo-6-(trifluoromethyl)-1,2-dihydropyridine-3-carboxylate were dissolved in 45 ml of methanol and 15 ml of water, 1.80 g (42.8 mmol) of lithium hydroxide monohydrate were added and the mixture was then heated under reflux for 2 h. The mixture was concentrated to about 15 ml and then washed with dichloromethane and the aqueous phase was adjusted to pH 2 by addition of 2N hydrochloric acid. The mixture was again extracted with dichloromethane, and the organic phase was dried and concentrated. This gave 4.2 g (94% of theory) of a colorless powder.

$^1$H-NMR: [DMSO] 7.41 (d, 1H); 8.35 (d, 1H).

A1.4) N-Cyclobutyl-2-oxo-6-(trifluoromethyl)-1,2-dihydropyridine-3-carboxamide 600 mg (2.9 mmol) of 2-oxo-6-(trifluoromethyl)-1,2-dihydropyridine-3-carboxylic acid were dissolved in 5 ml of tetrahydrofuran, 658 mg (4.1 mmol) of N,N-carbonyldiimidazole were added and the mixture was heated initially at room temperature for 30 min and then under reflux for 30 min. A solution of 247 mg (3.5 mmol) of cyclobutylamine in 5 ml tetrahydrofuran was then added dropwise, and the mixture was heated under reflux for a further 2 h. The solution was evaporated to dryness and then taken up in ethyl acetate, washed with 1 N hydrochloric acid and water, dried and concentrated. Purification by column chromatography gave 160 mg (19% of theory) of a light-brown powder.

$^1$H-NMR: [CDCl$_3$] 1.80 (m, 2H); 2.00 (m, 2H); 2.42 (m, 2H); 4.55 (m, 1H); 6.88 (d, 1H); 8.65 (d, 1H); 9.50 (br, 1H).

Example A2

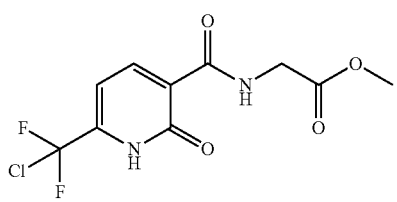 [SMILES: COC(=O)CNC(=O)c1ccc(C(F)(F)Cl)[nH]c1=O]

6-[Chloro(difluoro)methyl]-N-(2-methoxyethyl)-2-oxo-1,2-dihydropyridine-3-carboxamide

A2.1) 4-Butoxy-1-chloro-1,1-difluorobut-3-en-2-one

Under stirring at 5° C., 5.0 g (20.2 mmol) of chlorodifluoroacetic anhydride—dissolved in 10 ml of trichloromethane—were added to a mixture of 1.60 g (20.2 mmol) of pyridine and 2.1 g (20.2 mmol) of butyl vinyl ether in 30 ml of trichloromethane. After the addition, stirring was continued at room temperature for another 15 h. 100 ml of water were then added to the mixture, and the organic phase was separated off, dried and concentrated. This gave 3.4 g (80% of theory) of a yellowish oil.

$^1$H-NMR: [DMSO] 0.90 (t, 3H); 1.35 (m, 2H); 1.65 (m, 2H); 4.20 (t, 2H); 6.04 (d, 1H); 8.10 (d, 1H).

A2.2) Methyl 6-[chloro(difluoro)methyl]-2-oxo-1,2-dihydropyridine-3-carboxylate 1.47 g (61 mmol) of sodium were dissolved in 220 ml of methanol, 10 g (47 mmol) of 4-butoxy-1-chloro-1,1-difluorobut-3-en-2-one and 5.51 g (47 mmol) of methyl malonatemonoamide were added and the mixture was heated under reflux for 21 h. The pH was adjusted to 4-5 by addition of 2N hydrochloric acid, and about 200 ml were then distilled off. The solution that remained was extracted with ethyl acetate, and the extract was dried and concentrated. The residue was triturated with diisopropyl ether, filtered off with suction and dried. This gave 7.4 g (66% of theory) of a colorless powder.

$^1$H-NMR: [CDCl$_3$] 4.01 (s, 3H); 7.30 (d, 1H); 8.38 (d, 1H); 11.5 (br, 1H).

A2.3a) 6-[Chloro(difluoro)methyl]-2-oxo-1,2-dihydropyridine-3-carboxylic acid 1.70 g (74 mmol) of sodium were dissolved in 250 ml of methanol, 13.1 g (61.7 mmol) of 4-butoxy-1-chloro-1,1-difluorobut-3-en-2-one and 7.22 g (61.7 mmol) of methyl malonatemonoamide were added and the mixture was heated under reflux for 21 h. 250 ml of water and 2.9 g (67.9 mmol) of lithium hydroxide monohydrate were then added, and heating under reflux was continued for a further 2 h. The mixture was concentrated to about 200 ml and washed with dichloromethane, and the aqueous phase was acidified with 2N hydrochloric acid to pH 2. The precipitated solid was filtered off with suction and dried under reduced pressure. 9.3 g (68% of theory).

A2.3b) 6-[Chloro(difluoro)methyl]-2-oxo-1,2-dihydropyridine-3-carboxylic acid 11.0 g (49.4 mmol) of 6-[chloro(difluoro)methyl]-2-oxo-1,2-dihydropyridine-3-carboxamide were heated in 77 ml of 50% strength sulfuric acid. The mixture was then added to ice water, and the precipitate was filtered off with suction and dried. This gave 7.2 g (65% of theory) of a yellowish powder.

m.p.: 145-147° C.

$^1$H-NMR: [DMSO] 7.36 (d, 1H); 8.34 (d, 1H).

A2.4) 6-[Chloro(difluoro)methyl]-N-(2-methoxyethyl)-2-oxo-1,2-dihydropyridine-3-carboxamide 500 mg (2.2 mmol) of 6-[chloro(difluoro)methyl]-2-oxo-1,2-dihydropyridine-3-carboxylic acid were dissolved in 10 ml of tetrahydrofuran, 508 mg (3.1 mmol) of N,N-carbonyldiimidazole were added and the mixture was then stirred initially at room temperature for 30 min and then under reflux for min. A solution of 202 mg (2.7 mmol) of 2-methoxyethylamine in 2 ml of tetrahydrofuran was then added dropwise, and the mixture was heated under reflux for a further 2 h. The solution was evaporated to dryness, the residue was taken up in ethyl acetate and the solution was washed with 1N hydrochloric acid and water, dried and concentrated. This gave 360 mg (54% of theory) of a light-brown powder.

¹H-NMR: [CDCl₃] 3.40 (s, 3H); 3.58 (m, 2H); 3.67 (m, 2H); 6.84 (d, 1H), 8.62 (d, 1H); 9.40 (br, 1H).

Example A3

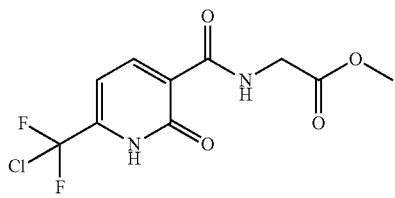 [SMILES: COC(=O)CNC(=O)c1ccc(C(F)(F)Cl)[nH]c1=O]

Methyl N-({6-[chloro(difluoro)methyl]2 oxo-1,2-dihydropyridin-3-yl}carbonyl)glycinate 300 mg (1.34 mmol) of 6-[chloro(difluoro)methyl]-2-oxo-1,2-dihydropyridine-3-carboxylic acid were dissolved in 5 ml of tetrahydrofuran, 435 mg (2.68 mmol) of N,N-carbonyldiimidazole were added and the mixture was stirred initially at room temperature for 30 min and then under reflux for 30 min. A mixture of 168 mg (1.34 mmol) of glycine methyl ester hydrochloride in 3 ml of tetrahydrofuran was then added, and the mixture was heated under reflux for a further 2 h. The solution was evaporated to dryness, the residue was taken up in ethyl acetate and the solution was washed with 1N hydrochloric acid and water, dried and concentrated. This gave 92 mg (23% of theory) of a light-brown powder.

¹H-NMR: [DMSO] 3.65 (s, 3H); 4.12 (d, 2H); 7.28 (d, br, 1H); 8.42 (d, 1H); 9.25 (t, br, 1H), 13.6 (br, 1H)

Example A4

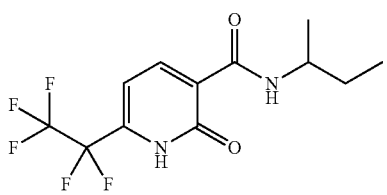 [SMILES: CCC(C)NC(=O)c1ccc(C(F)(F)C(F)(F)F)[nH]c1=O]

N-(1-Methylpropyl)-2-oxo-6 (pentafluoroethyl)-1,2-dihydropyridine-3-carboxamide

A4.1) 1-Butoxy-4,4,5,5,5-pentafluoropent-1-en-3-one

With stirring at −10° C., 17.0 g (93.2 mmol) of pentafluoropropionyl chloride—dissolved in 20 ml of dichloromethane—were added to a mixture of 8.11 g (102 mmol) pyridine and 9.33 g (93.2 mmol) of butyl vinyl ether in 200 ml of dichloromethane. After the addition, stirring was continued at room temperature for a further 15 h. 200 ml of water were then added to the mixture, and the organic phase was separated off, dried and concentrated. This gave 18.9 g (82% of theory) of a yellowish oil.

¹H-NMR: [DMSO] 0.85 (t, 3H); 1.32 (m, 2H); 1.63 (m, 2H); 4.20 (t, 2H); 6.06 (d, 1H); 8.11 (d, 1H).

A4.2) Ethyl 2-oxo-6-(pentafluoroethyl)-1,2-dihydropyridine-3-carboxylate 0.56 g (24.4 mmol) of sodium was dissolved in 150 ml of ethanol, 5 g (20.3 mmol) of 1-butoxy-4,4,5,5,5-pentafluoropent-1-en-3-one and 2.66 g (20.3 mmol) of methyl malonatemonoamide were added and the mixture was heated under reflux for 6 h. The mixture was concentrated to about 50 ml, 500 ml of 1N hydrochloric acid were added and the mixture was then extracted with ethyl acetate. Drying and concentration gave 2.3 g (40% of theory) of a yellowish resin.

¹H-NMR: [CDCl₃] 1.45 (t, 3H); 4.50 (q, 2H); 7.35 (d, 1H); 8.40 (d, 1H); 11.4 (br, 1H).

A4.3) N-(1-Methylpropyl)-2-oxo-6-(pentafluoroethyl)-1,2-dihydropyridine-3-carboxamide At room temperature, 160 mg (0.56 mmol) of ethyl 2-oxo-6-(pentafluoroethyl)-1,2-dihydropyridine-3-carboxylate were stirred in 5 ml of 2-butylamine for 14 h. The pH was then adjusted to 2 by addition of 1N hydrochloric acid, which resulted in the precipitation of a colorless solid. Filtration with suction and drying gave 160 mg (91% of theory) of the product.

¹H-NMR: [CDCl₃] 0.97 (t, 3H); 1.22 (d, 3H); 1.59 (m, 2H); 4.10 (m, 1H); 6.88 (d, 1H); 8.72 (d, 1H); 9.24 (d, br, 1H); 13.6 (br).

Example A5

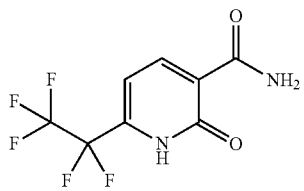 [SMILES: NC(=O)c1ccc(C(F)(F)C(F)(F)F)[nH]c1=O]

2-Oxo-6-(pentafluoroethyl)-1,2-dihydropyridine-3-carboxamide 0.22 g (9.7 mmol) of sodium was dissolved in 50 ml of ethanol, 2 g (8.1 mmol) of 1-butoxy-4,4,5,5,5-pentafluoropent-1-en-3-one and 0.86 g (8.1 mmol) malonamide were added and the mixture was heated under reflux for 7 h. The mixture was concentrated, and 1N hydrochloric acid was added. The resulting precipitate was filtered off with suction and dried. This gave 1.9 g (94% of theory) of a yellow powder.

¹H-NMR: [DMSO] 7.45 (d, 1H); 8.15 (br, 1H); 8.45 (br, 1H); 8.50 (d, 1H); 13.7 (br, 1H).

Example A6

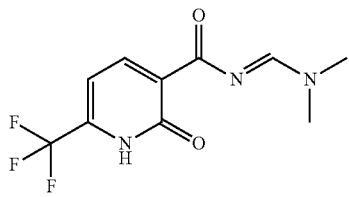 [SMILES: CN(C)/C=N/C(=O)c1ccc(C(F)(F)F)[nH]c1=O]

N-[(Dimethylamino)methylene]-2-oxo-6-(trifluoromethyl)-1,2-dihydropyridine-3-carboxamide 0.87 g (7.28 mmol) of N,N-dimethylformamide dimethyl acetal was added to 1.00 g (4.85 mmol) of 2-oxo-6-(trifluoromethyl)-1,2-dihydropyridine-3-carboxamide in 5 ml of toluene, and the mixture was heated under reflux for 4 h. After cooling, the resulting precipitate was filtered off with suction and dried: 0.5 g (39% of theory).
$^1$H-NMR: [CDCl$_3$] 3.25 (s, 3H); 3.35 (3. 3H); 7.25 (d, 1H); 8.58 (d, 1H); 8.76 (s, 1H)
$^{13}$C-NMR. [CDCl$_3$] 35 (NMe$_2$); 106 (C-5); 115 (C-3); 122 (q, CF$_3$); 143 (C-4); 151 (C-6); 164 (N=CN); 167 (C-2); 171 (CON).

Example A7

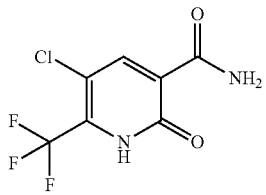 [SMILES: NC(=O)c1cc(Cl)c(C(F)(F)F)[nH]c1=O]

5-Chloro-2-oxo-6-(trifluoromethyl)-1,2-dihydropyridine-3-carboxamide

At room temperature, 0.39 g (2.9 mmol) of sulfuryl chloride was added to 300 mg (1.46 mmol) of 2-oxo-6-(trifluoromethyl)-1,2-dihydropyridine-3-carboxamide in 5 ml of 1,2-dichloroethane and 2.3 g (0.25 ml) of pyridine, and the mixture was heated under reflux for 2 h. The mixture was then added to 0.5N hydrochloric acid. The organic phase was removed and then dried and concentrated, which gave 144 mg (41% of theory) of a brownish powder.
$^1$H-NMR: [DMSO] 8.25 (br, 1H); 8.35 (br, 1H); 8.50 (s, 1H); 13.8 (br, 1H)
$^{13}$C-NMR. [DMSO] 118 (C-5); 120 (C-6); 120.5 (q, CF$_3$); 144 (C-4), 161 (C-2); 166 (COONH$_2$).

Example A8

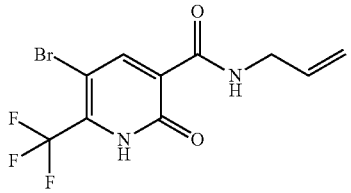 [SMILES: C=CCNC(=O)c1cc(Br)c(C(F)(F)F)[nH]c1=O]

N-Allyl-5-bromo-2-oxo-6-(trifluoromethyl)-1,2-dihydropyridine-3-carboxamide

A8.1) Methyl 5-bromo-2-oxo-6-(trifluoromethyl)-1,2-dihydropyridine-3-carboxylate At room temperature, 0.36 g (2.04 mmol) of N-bromosuccinimide was added to a suspension of 0.3 g (1.36 mmol) of methyl 2-oxo-6-(trifluoromethyl)-1,2-dihydropyridine-3-carboxylate in 10 ml of glacial acetic acid, and the mixture was then heated under reflux for 2 days. The reaction mixture was then added to water and extracted with dichloromethane. The extract was concentrated, and the residue was purified further by preparative HPLC. This gave 227 mg (56% of theory) of a colorless powder.
$^1$H-NMR: [DMSO] 3.85 (s, 3H); 8.45 (s, 1H); 12.80 (br, 1H);
$^{13}$C-NMR. [DMSO] 53 (OCH$_3$); 105 (C-3); 148 (C-4), 161 (C-2); 164 (COOMe).

A8.2) N-Allyl-5-bromo-2-oxo-6-(trifluoromethyl)-1,2-dihydropyridine-3-carboxamide At room temperature, 250 mg (0.83 mmol) of methyl 5-bromo-2-oxo-6-(trifluoromethyl)-1,2-dihydropyridine-3-carboxylate were stirred in 5 ml of allylamine for 18 h. By addition of 2N hydrochloric acid, the pH was then adjusted to 2, resulting in the precipitation of a colorless solid. Filtration with suction and drying gave 134 mg (50% of theory) of the product.
$^1$H-NMR: [DMSO] 3.94 (t, 2H); 5.18 (dd, 2H); 5.89 (m, 1H); 8.52 (s, 1H); 8.85 (t, br, 1H).

Example A9

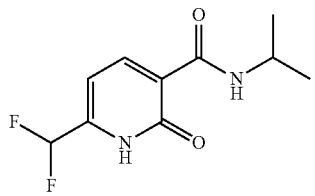 [SMILES: CC(C)NC(=O)c1ccc(C(F)F)[nH]c1=O]

6-Difluoromethyl-N-isopropyl-2-oxo-1,2-dihydropyridine-3-carboxamide

A9.1) 4-Butoxy-1,1-difluorobut-3-en-2-one

With stirring at 5° C., 10.0 g (55.7 mmol) of difluoroacetic anhydride were added to a mixture of 4.41 g (4.5 ml, 55.7 mmol) of pyridine and 5.7 g (55.7 mmol) butyl vinyl ether in 330 ml of trichloromethane. After the addition, stirring was continued at room temperature for a further 15 h. 300 ml of water were then added to the mixture, and the organic phase was separated off, dried and concentrated. This gave 5.7 g (57% of theory) of a yellowish oil.
$^1$H-NMR: [CDCl$_3$] 0.95 (t, 3H); 1.42 (m, 2H); 1.72 (m, 2H); 4.00 (t, 2H); 5.78 (t, 1H); 5.90 (d, 1H); 7.85 (d, 1H).

A9.2) Methyl 6-(difluoromethyl)-2-oxo-1,2-dihydropyridine-3-carboxylate 1.21 g (52.9 mmol) of sodium were dissolved in 200 ml of methanol, 7.9 g (44 mmol) of 4-butoxy-1,1-difluorobut-3-en-2-one and 5.3 g (44 mmol) of methyl malonatemonoamide were then added and the mixture was heated under reflux for 15 h. The mixture was concentrated and the residue was then triturated with 100 ml of 1N hydrochloric acid. The solid obtained was filtered off with suction and dried: 7.4 g (82% of theory).
$^1$H-NMR: [DMSO] 3.82 (s, 3H); 6.85 (t, 1H); 7.02 (d, br, 1H); 8.20 (d, 1H); 12.4 (br, 1H).

A9.3) 6-(Difluoromethyl)-2-oxo-1,2-dihydropyridine-3-carboxylic acid 7.4 g (36.4 mmol) of methyl 6-(difluoromethyl)-2-oxo-1,2-dihydropyridine-3-carboxylate were dissolved in 100 ml of methanol, and a solution of 1.3 g (54.6 mmol) of lithium hydroxide in 50 ml of water was added. After two hours of heating under reflux, the mixture was concentrated to a volume of about 50 ml and the solution was washed with dichloromethane. The aqueous phase was then acidified with 2N hydrochloric acid and extracted with ethyl acetate. Drying and concentration of the extract gave 5.6 g (82% of theory) of a brownish powder.

A9.4) 6-(Difluoromethyl)-N-isopropyl-2-oxo-1,2-dihydropyridine-3-carboxamide After dissolution of 200 mg (1.1 mmol) of 6-(difluoromethyl)-2-oxo-1,2-dihydropyridine-3-carboxylic acid in 25 ml of tetrahydrofuran and addition of 206 mg (1.3 mmol) of N,N-carbonyldiimidazole, the mixture was stirred initially at room temperature for 30 min and then under reflux for 30 min. A solution of 66 mg (1.1 mmol) of isopropylamine in 5 ml of tetrahydrofuran was then added dropwise, and the mixture was heated under reflux for a further 2 h. The solution was evaporated to dryness, the residue was then taken up in ethyl acetate and the mixture was washed with 2N hydrochloric acid and water, dried and concentrated. Purification by column chromatography gave 150 mg (61% of theory) of a colorless powder.

$^1$H-NMR: [CDCl$_3$] 1.25 (d, 6H); 4.22 (m, 1H); 6.55 (t, 1H); 6.69 (d, 1H); 8.64 (d, 1H); 9.42 (d, br, 1H); 13.0 (br, 1H).

Example A10

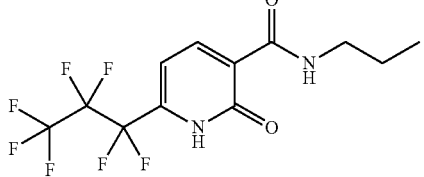

6-(Heptafluoropropyl)-2-oxo-N-propyl-1,2-dihydropyridine-3-carboxamide

A10.1) 1-Butoxy-4,4,5,5,6,6,6-heptafluorohex-1-en-3-one

With stirring and at −10° C., 21.7 g (93.2 mmol) of heptafluorobutyryl chloride—dissolved in 50 ml of dichloromethane—were added to a mixture of 8.11 g (102 mmol) of pyridine and 9.33 g (93.2 mmol) of butyl vinyl ether in 200 ml of dichloromethane. After the addition, stirring was continued at room temperature for another 15 h. 300 ml of water were then added to the mixture, and the organic phase was separated off, dried and concentrated.

This gave 28.2 g (82% of theory) of a yellowish oil which was reacted further without further purification.

$^1$H-NMR: [CDCl$_3$] 0.96 (t, 3H); 1.40 (m, 2H); 1.75 (m, 2H); 4.04 (t, 2H); 5.95 (d, 1H); 7.93 (d, 1H).

A10.2) Methyl 6-(heptafluoropropyl)-2-oxo-1,2-dihydropyridine-3-carboxylate

After dissolution of 2.63 g (114 mmol) of sodium in 250 ml of methanol, 28.2 g (95.5 mmol) of 1-butoxy-4,4,5,5,6,6,6-heptafluorohex-1-en-3-one and 11.18 g (95.5 mmol) of methyl malonatemonoamide were added, and the mixture was heated under reflux for 18 h. The mixture was concentrated and the residue was then taken up in water and washed with dichloromethane. The aqueous phase was then adjusted to pH 2 by addition of 2N hydrochloric acid and extracted with dichloromethane, Drying, concentration and purification of the extract by column chromatography gave 15.2 g (49% of theory) of a yellow powder.

$^1$H-NMR: [CDCl$_3$] 4.06 (s, 3H); 7.35 (d, 1H); 8.40 (d, 1H); 11.4 (br, 1H).

A10.3) 6-(Heptafluoropropyl) 2 oxo-N-propyl-1,2-dihydropyridine-3-carboxamide 250 mg (0.78 mmol) of methyl 6-(heptafluoropropyl)-2-oxo-1,2-dihydropyridine-3-carboxylate in 5 ml of propylamine were heated under reflux for 5 h. The mixture was then adjusted to pH 2 by addition of 1N hydrochloric acid and extracted with dichloromethane. Drying and concentration gave 240 mg (88% of theory) of a beige powder.

$^1$H-NMR: [DMSO] 0.90 (t, 3H); 1.54 (m, 2H); 3.25 (q, 2H); 7.41 (d, 1H); 8.40 (d, 1H); 8.85 (br, 1H); 13.45 (br, 1H).

Example A11

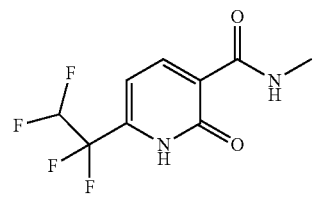 [SMILES: CNC(=O)c1ccc(C(F)(F)C(F)F)[nH]c1=O]

N-Methyl-2-oxo-6-(1,1,2,2-tetrafluoroethyl)-1,2-dihydropyridine-3-carboxamide

A11.1) 1-Butoxy-4,4,5,5-tetrafluoropent-1-en-3-one

With stirring and at 0° C., 25.0 g (152 mmol) of 3H-tetrafluoropropionyl chloride—dissolved in 20 ml dichloromethane—were added to a mixture of 14.4 g (182 mmol) of pyridine and 15.2 g (152 mmol) of butyl vinyl ether in 250 ml of dichloromethane. After the addition, stirring was continued at room temperature for another 15 h. 250 ml of water were then added to the mixture, and the organic phase was separated off, dried and concentrated. This gave 12.5 g (36% of theory) of a yellowish oil.

$^1$H-NMR: [CDCl$_3$] 0.96 (t, 3H); 1.46 (m, 2H); 1.75 (m, 2H); 4.03 (t, 2H); 6.00 (d, 1H); 6.09 (tt, 1H); 7.90 (d, 1H).

A11.2) Methyl 2-oxo-6-(1,1,2,2-tetrafluoroethyl)-1,2-dihydropyridine-3-carboxylate After dissolution of 1.39 g (60.3 mmol) of sodium in 500 ml of methanol, 11.5 g (50.3 mmol) of 1-butoxy-4,4,5,5-tetrafluoropent-1-en-3-one and 6.07 g (50.3 mmol) of methyl malonatemonoamide were added, and the mixture was heated under reflux for 6 h. The mixture was concentrated to about 100 ml, 500 ml of 1N hydrochloric acid were then added and the mixture was subsequently extracted with ethyl acetate. Drying and concentration gave 10.3 g (67% of theory) of a yellowish resin.

$^1$H-NMR: [CDCl$_3$] 4.03 (s, 3H); 6.40 (tt, 1H); 7.38 (d, 1H); 8.39 (d, 1H).

A11.3) N-Methyl-2-oxo-6-(1,1,2,2-tetrafluoroethyl)-1,2-dihydropyridine-3-carb oxamide At room temperature, 300 mg (1.19 mmol) of methyl 2-oxo-6-(1,1,2,2-tetrafluoroethyl)-1,2-dihydropyridine-3-carboxylate were stirred in 3.3 ml of a 40% strength aqueous methylamine solution for 14 h. The pH was then adjusted to 2 by addition of 1N hydrochloric acid, and the mixture was extracted with dichloromethane. Drying and concentration of the extract gave 230 mg (77% of theory) of the product.

$^1$H-NMR: [DMSO] 2.83 (d, 3H); 6.81 (tt, 1H); 7.22 (br, 1H); 8.41 (d, 1H); 9.00 (br, 1H); 13.4 (br, 1H).

Example A12

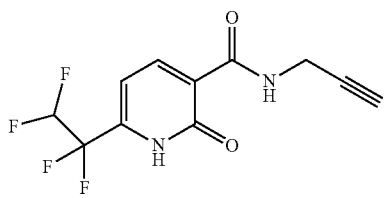 [SMILES: C#CCNC(=O)c1ccc(C(F)(F)C(F)F)[nH]c1=O]

2-Oxo-N-(2-propynyl)-6-(1,1,2,2-tetrafluoroethyl)-1,2-dihydropyridine-3-carboxamide At room temperature, 300 mg (1.19 mmol) of methyl 2-oxo-6-(1,1,2,2-tetrafluoroethyl)-1,2-dihydropyridine-3-carboxylate were stirred in 3.3 ml (41 mmol) of propargylamine for 14 h. The pH was then adjusted to 2 by addition of 1N hydrochloric acid, and the mixture was extracted with dichloromethane. Drying and concentration of the extract gave 280 mg (85% of theory) of the product.

$^1$H-NMR: [DMSO] 3.15 (t, 1H); 4.13 (m, 2H); 6.82 (tt, 1H); 7.18 (br, 1H); 8.41 (d, 1H); 9.35 (br, 1H); 13.3 (br, 1H).

Example A13

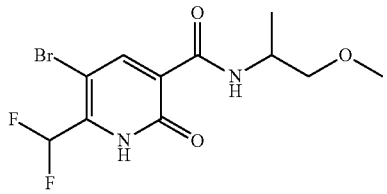 [SMILES: COCC(C)NC(=O)c1cc(Br)c(C(F)F)[nH]c1=O]

5-Bromo-6-(difluoromethyl)-N-(2-methoxy-1-methylethyl)-2-oxo-1,2-dihydropyridine-3-carboxamide A13.1) Methyl 5-bromo-6-(difluoromethyl)-2-oxo-1,2-dihydropyridine-3-carboxylate 4.1 g (20 mmol) of methyl 6-(difluoromethyl)-2-oxo-1,2-dihydropyridine-3-carboxylate were dissolved in 20 ml of N,N-dimethylformamide, and 5.35 g (30 mmol) of N-bromosuccinimide were added at room temperature. After 2 hours of stirring, the reaction mixture was added to water and extracted with tert-butyl methyl ether. The extract was subsequently washed repeatedly with water. Drying and concentration finally gave 3.7 g (65% of theory) of the product.

$^1$H-NMR: [DMSO] 3.83 (s, 3H); 7.07 (t, 1H); 8.34 (s, 1H); 12.5 (s, br, 1H).

A13.2) 5-Bromo-6-(difluoromethyl)-N-(2-methoxymethylethyl)-2-oxo-1,2-dihydropyridine-3-carboxamide At room temperature, 334 mg (1.19 mmol) of methyl 5-bromo-6-(difluoromethyl)-2-oxo-1,2-dihydropyridine-3-carboxylate in 3.3 ml (41 mmol) of 2-amino-1-methoxypropane were stirred for 14 h. The pH was then adjusted to 2 by addition of 1N hydrochloric acid, and the mixture was extracted with dichloromethane. Drying and concentration of the extract gave 360 mg (89% of theory) of the product.

$^1$H-NMR: [CDCl3] 1.27 (d, 3H); 3.40 (s, 3H); 3.43 (m, 2H); 4.37 (m, 1H); 6.85 (t, 1H); 8.68 (s, 1H); 9.42 (d, br, 1H); 12.7 (br, 1H).

Example A14

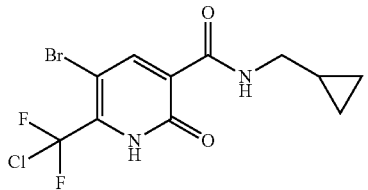 [SMILES: O=C(NCC1CC1)c1cc(Br)c(C(F)(F)Cl)[nH]c1=O]

5-Bromo-6-[chloro(difluoro)methyl]-N-(cyclopropylmethyl)-2-oxo-1,2-dihydropyridine-3-carboxamide A14.1) Methyl 5-bromo-6-[chloro(difluoro)methyl]-2-oxo-1,2-dihydropyridine-3-carboxylate 1.30 g (5.47 mmol) of methyl 6-[chloro(difluoro)methyl]-2-oxo-1,2-dihydropyridinecarboxylate were dissolved in 50 ml of N,N-dimethylformamide, and 1.46 g (8.21 mmol) of N-bromosuccinimide were added at room temperature. After 3 hours of stirring, the reaction mixture was added to water, resulting in the formation of a colorless precipitate. Drying and concentration gave 1.23 g (71% of theory) of the product.

$^1$H-NMR: [DMSO] 3.85 (s, 3H); 8.45 (s, 1H); 12.7 (s, br, 1H).

A14.2) 5-Bromo-6-[chloro(difluoro)methyl]-N-(cyclopropylmethyl)-2-oxo-1,2-dihydropyridine-3-carboxamide At room temperature, 350 mg (1.11 mmol) of methyl 5-bromo-6-[chloro(difluoro)methyl]-2-oxo-1,2-dihydropyridine-3-carboxylate were dissolved in 5 ml of acetonitrile and stirred with 0.5 ml of aminomethylcyclopropane for 12 h. The reaction mixture was then added to 1N hydrochloric acid, and the resulting precipitate was filtered off with suction. The precipitate was dried, again triturated with 1N hydrochloric acid, filtered off with suction and washed with water. Drying gave 240 mg (62% of theory) of the product.

¹H-NMR: [DMSO] 0.25 (m, 2H); 0.46 (m, 2H); 1.04 (m, 1H); 3.20 (t, 2H); 8.55 (s, 1H); 8.82 (t, br, 1H); 13.6 (br, 1H).

Example A15

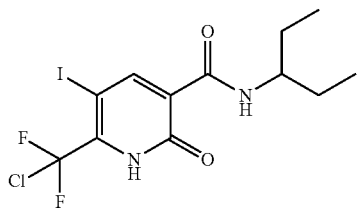 [SMILES: CCC(CC)NC(=O)c1cc(I)c(C(F)(F)Cl)[nH]c1=O]

6-[Chloro(difluoro)methyl]-N-(1-ethylpropyl)-5-iodo-2-oxo-1,2-dihydropyridine-3-carboxamide A15.1) Methyl 6-[chloro(difluoro)methyl]-5-iodo-2-oxo-1,2-dihydropyridine-3-carboxylate 10.0 g (42.1 mmol) of methyl 6-[chloro(difluoro)methyl]-2-oxo-1,2-dihydropyridinecarboxylate were dissolved in 50 ml of N,N-dimethylformamide, and 6.32 g (63.1 mmol) of calcium carbonate and 20.5 g (126 mmol) of iodine chloride were added at room temperature. After 6 hours of stirring at 50° C., the reaction mixture was added to water, resulting in the formation of a colorless precipitate, which was washed with dilute sodium bisulfite solution and water. Filtration with suction and drying gave 13.6 g (89% of theory) of the product.

¹H-NMR: [DMSO] 3.84 (s, 3H); 8.61 (s, 1H); 12.6 (s, br, 1H).

A15.2) 6-[Chloro(difluoro)methyl]-N-(1-ethylpropyl)-5-iodo-2-oxo-1,2-dihydropyridine-3-carboxamide At room temperature, 400 mg (1.1 mmol) of methyl 6-[chloro(difluoro)methyl]-5-iodo-2-oxo-1,2-dihydropyridine-3-carboxylate were dissolved in 5 ml of acetonitrile and stirred with 0.5 ml of 3-pentylamine for 12 h. The reaction mixture was then added to 1N of hydrochloric acid, and the resulting precipitate was filtered off with suction and washed with water. Drying gave 370 mg (72% of theory) of the product.

¹H-NMR: [DMSO] 0.87 (t, 6H); 1.43 (m, 21H); 1.55 (m, 2H); 3.78 (m, 1H); 8.55 (br, 1H); 8.67 (s, 1H); 13.5 (br, 1H).

Example A16

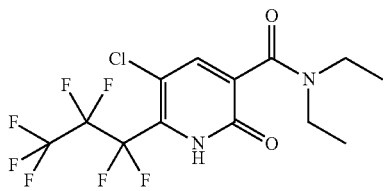 [SMILES: CCN(CC)C(=O)c1cc(Cl)c(C(F)(F)C(F)(F)C(F)(F)F)[nH]c1=O]

5-Chloro-N,N-diethyl-6-(heptafluoropropyl)-2-oxo-1,2-dihydropyridine-3-carboxamide A16.1) Methyl 5-chloro-6-(heptafluoropropyl)-2-oxo-1,2-dihydropyridine-3-carboxylate 16.7 g (52 mmol) of methyl 6-(heptafluoropropyl)-2-oxo-1,2-dihydropyridine-3-carboxylate were dissolved in 160 ml of N,N-dimethylformamide, and 7.08 g (52 mmol) of N-chlorosuccinimide were added at room temperature. After 3 hours of stirring at 50° C., the reaction mixture was added to water and extracted repeatedly with ethyl acetate. The organic phase was then separated off, washed with water and dried. The resulting crude product was then purified by preparative RP-HPLC. This gave 10.1 g (54% of theory) of the product as a colorless powder.

¹H-NMR: [DMSO] 3.85 (s, 3H); 8.35 (s, 1H); 12.8 (s, br, 1H).

A16.2) 5-Chloro-6-(heptafluoropropyl)-2-oxo-1,2-dihydropyridine-3-carboxylic acid 1.54 g (4.33 mmol) of methyl 5-chloro-6-(heptafluoropropyl)-2-oxo-1,2-dihydropyridine-3-carboxylate were dissolved in 23 ml of methanol, and a solution of 0.16 g (6.5 mmol) of lithium hydroxide in 13 ml of water was added. After two hours of heating under reflux, the methanol was distilled off, and the aqueous solution that remained was washed with dichloromethane. The aqueous phase was then acidified with 2N hydrochloric acid and extracted with dichloromethane. Drying and concentration of the extract gave 1.45 g (98% o of theory) of a brownish powder.

¹H-NMR: [DMSO] 8.30 (s, 1H).

A16.3) 5-Chloro-N,N-diethyl-6-(heptafluoropropyl)-2-oxo-1,2-dihydropyridine-3-carboxamide After dissolution of 355 mg (1.04 mmol) of 5-chloro-6-(heptafluoropropyl)-2-oxo-1,2-dihydropyridine-3-carboxylic acid in 30 ml tetrahydrofuran and addition of 337 mg (2.08 mmol) of N,N-carbonyldiimidazole, the mixture was stirred initially at room temperature for 30 min and then under reflux for 30 min. 152 mg (0.22 ml, 2.08 mmol) of diethylamine were then added, and the mixture was heated under reflux for a further 2 h. The solution was evaporated to dryness and then taken up in dichloromethane, washed with 1N hydrochloric acid and water, dried and concentrated. This gave 300 mg (72% of theory) of the product.

¹H-NMR: [DMSO] 1.03 (t, 3H); 1.15 (t, 3H); 3.12 (q, 2H); 3.45 (q, 2H); 8.05 (s, 1H); 12.5 (br, 1H).

Example A17

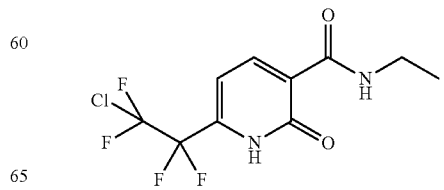

6-(2-Chloro-1,1,2,2-tetrafluoroethyl)-N-ethyl-2-oxo-1,2-dihydropyridine-3-carboxamide A17.1) 1-Butoxy-5-chloro-4,4,5,5-tetrafluoropent-1-en-3-one With stirring and at 0° C., 10.0 g (50.2 mmol) of 3-chlorotetrafluoropropionyl chloride—dissolved in ml of chloroform—were added to a mixture of 3.97 g (50.2 mmol) of pyridine and 5.03 g (50.2 mmol) of butyl vinyl ether in 80 ml of chloroform. After the addition, stirring was continued at room temperature for a further 15 h. 100 ml of water were then added to the mixture, and the organic phase was separated off, dried and concentrated. This gave 10.4 g (78% of theory) of a yellowish oil.
$^1$H-NMR: [CDCl$_3$] 0.96 (t, 3H); 1.43 (m, 2H); 1.75 (m, 2H); 4.04 (t, 2H); 5.97 (d, 1H); 7.91 (d, 1H).

A17.2) Methyl 6-(2-chloro-1,1,2,2-tetrafluoroethyl)-2-oxo-1,2-dihydropyridine-3-carboxylate 0.32 g (13.7 mmol) of sodium were dissolved in 50 ml of methanol, 3.0 g (11.4 mmol) of 1-butoxy-5-chloro-4,4,5,5-tetrafluoropent-1-en-3-one and 1.34 g (11.4 mmol) of methyl malonatemonoamide were added and the mixture was heated under reflux for 6 h. The mixture was concentrated to about ml, 50 ml of 1N hydrochloric acid were then added and the mixture was subsequently extracted repeatedly with ethyl acetate. After drying and concentration, the resulting residue was taken up in diethyl ether and filtered. Concentration of the filtrate gave 1.74 g (52% of theory) of a yellowish powder.
$^1$H-NMR: [DMSO] 3.84 (s, 3H); 7.44 (d, 1H); 8.32 (d, 1H); 12.4 (br, 1H).

A17.3) 6-(2-Chloro-1,1,2,2-tetrafluoroethyl)-N-ethyl-2-oxo-1,2-dihydropyridine-3-carboxamide At room temperature, 300 mg (1.04 mmol) of methyl 6-(2-chloro-1,1,2,2-tetrafluoroethyl)-2-oxo-1,2-dihydropyridine-3-carboxylate were stirred in 5 ml of aqueous ethylamine solution (70%) for 14 h. The pH was then adjusted to 2 by addition of 1N hydrochloric acid, and the mixture was extracted with dichloromethane. Drying and concentration of the extract gave 310 mg (98% of theory) of the product.
$^1$H-NMR: [CDCl$_3$] 1.27 (t, 3H); 3.50 (m, 2H); 6.88 (d, 1H); 8.68 (d, 1H); 9.32 (br, 1H); 12.6 (br, 1H).

Example A18

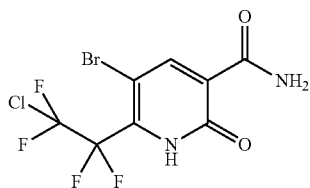 [SMILES: NC(=O)c1cc(Br)c(C(F)(F)C(F)(F)Cl)[nH]c1=O]

5-Bromo-6-(2-chloro-1,1,2,2-tetrafluoroethyl)-2-oxo-1,2-dihydropyridine-3-carboxamide A18.1) 6-(2-Chloro-1,1,2,2-tetrafluoroethyl)-2-oxo-1,2-dihydropyridine-3-carboxamide 0.53 g (22.8 mmol) of sodium were dissolved in 50 ml of methanol, 5.0 g (19.0 mmol) of 1-butoxy-5-chloro-4,4,5,5-tetrafluoropent-1-en-3-one and 2.0 g (19.0 mmol) of malonamide were then added and the mixture was heated under reflux for 6 h. The mixture was concentrated, and 1N hydrochloric acid was then added. The resulting precipitate was filtered off with suction and dried. This gave 3.8 g (73% of theory) of a brownish powder.
$^1$H-NMR: [DMSO] 7.42 (br, 1H); 8.10 (br, 1H); 8.40 (br, 1H); 8.46 (d, 1H), 13.6 (br, 1H).

A18.2) 5-Bromo-6-(2-chloro-1,1,2,2-tetrafluoroethyl)-2-oxo-1,2-dihydropyridine-3-carboxamide 0.49 g (1.8 mmol) of 6-(2-chloro-1 µl, 2,2-tetrafluoroethyl)-2-oxo-1,2-dihydropyridine-3-carboxamide were dissolved in 5 ml of N,N-dimethylformamide, and 0.48 g (2.7 mmol) of N-bromosuccinimide was added at room temperature. After 2 hours of stirring at room temperature, the reaction mixture was poured into water, resulting in the formation of a precipitate. Filtration with suction, washing with water and drying gave 610 mg (96% of theory) of the product as a yellowish powder.
$^1$H-NMR: [DMSO] 8.25 (br, 1H); 8.35 (br, 1H); 8.61 (s, 1H); 13.7 (br, 1H).

Example A19

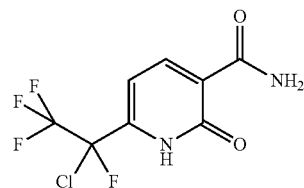 [SMILES: NC(=O)c1ccc(C(F)(Cl)C(F)(F)F)[nH]c1=O]

6-(1 Chloro-1,2,2,2-tetrafluoroethyl)-2-oxo-1,2-dihydropyridine-3-carboxamide

A19.1) 1-Butoxy-4-chloro-4,5,5,5-tetrafluoropent-1-en-3-one

With stirring and at 0° C., 9.59 g (48.2 mmol) of 2-chlorotetrafluoropropionyl chloride were added dropwise to a mixture of 4.19 g (50.0 mmol) of pyridine and 4.83 g (48.2 mmol) of butyl vinyl ether in 75 ml of dichloromethane. After the addition, stirring was continued at room temperature for another 15 h. The mixture was then washed with 1N hydrochloric acid and 2×100 ml of water, and the organic phase was separated off, dried and concentrated. This gave 6.33 g (50% of theory) of a brown oil.
$^1$H-NMR: [CDCl$_3$] 0.97 (t, 3H); 1.48 (m, 2H); 1.75 (m, 2H); 4.03 (t, 2H); 5.98 (d, 1H); 7.89 (d, 1H).

A19.2) 6-(1-Chloro-1,2,2,2-tetrafluoroethyl)-2-oxo-1,2-dihydropyridine-3-carboxamide 0.33 g (14.4 mmol) of sodium were dissolved in 50 ml of methanol, 3.16 g (12.03 mmol) of 1-butoxy-4-chloro-4,5,5,5-tetrafluoropent-1-en-3-one and 1.27 g (12.03 mmol) of malonamide were added and the mixture was heated under reflux for 7 h. The mixture was concentrated, and 1N hydrochloric acid was then added. The resulting precipitate was filtered off with suction and dried. This gave 380 mg (12% of theory) of a yellowish powder.

$^1$H-NMR: [DMSO] 7.45 (d, 1H); 8.14 (br, 1H); 8.42 (br, 1H); 8.48 (d, 1H); 13.7 (br, 1H).

In an exemplary manner, Table 1 below lists a number of compounds of the general formula (I) which can be obtained in a manner analogous to Examples A1 to A10 above and to the methods mentioned further above.

In the table:
Bu=butyl
Me=methyl
Pr=propyl
i=iso
t=tertiary
Et=ethyl
Ph=phenyl
s=secondary
c=cyclo This applies correspondingly to composite terms such as
iPr=isopropyl
iBu=isobutyl
sBu=sec-butyl
tBu=tert-butyl
cPr=cyclopropyl
cPentyl=cyclopentyl
cHexyl=cyclohexyl If an alkyl radical is listed in the tables without further specification, the radical in question is the straight-chain alkyl radical, i.e., for example, Bu=n-Bu=n-butyl.

In the table, the number indices in the formula are not subscript but arranged in the same line height and font size as the symbols for the atoms.

For example, the formula CF3 in the table corresponds to the formula $CF_3$ according to the customary notation with subscript index, or the formula CH2CH(CH2CH3)2 corresponds to the formula $CH_2CH(CH_2CH_3)_2$ with subscript indices.

For some compounds (I) in Table 1, physicochemical data (in general $^1$H-NMR data) are listed in Table 2. Here, the data are assigned to the compounds via the example number according to Table 1.

TABLE 1

Compounds of the formula (I)

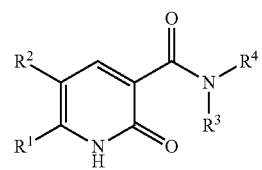

(I)

| Ex. | R$^1$ | R$^2$ | R$^3$ | R$^4$ |
|---|---|---|---|---|
| 1 | CF3 | H | H | Me |
| 2 | CF3 | H | H | Et |
| 3 | CF3 | H | H | Pr |
| 4 | CF3 | H | H | iPr |
| 5 | CF3 | H | H | cPr |
| 6 | CF3 | H | H | Bu |
| 7 | CF3 | H | H | cBu |
| 8 | CF3 | H | H | tBu |
| 9 | CF3 | H | Me | Me |
| 10 | CF3 | H | Me | Et |
| 11 | CF3 | H | Me | Bu |
| 12 | CF3 | H | Me | Pr |
| 13 | CF3 | H | Me | iPr |
| 14 | CF3 | H | Et | Et |
| 15 | CF3 | H | Et | Pr |
| 16 | CF3 | H | Et | iPr |

TABLE 1-continued

Compounds of the formula (I)

(I)

| Ex. | R$^1$ | R$^2$ | R$^3$ | R$^4$ |
|---|---|---|---|---|
| 17 | CF3 | H | Pr | Pr |
| 18 | CF3 | H | H | cPentyl |
| 19 | CF3 | H | H | cHexyl |
| 20 | CF3 | H | H | CH2(CH2)3CH3 |
| 21 | CF3 | H | H | CH2(CH2)4CH3 |
| 22 | CF3 | H | H | CH2—cPr |
| 23 | CF3 | H | H | CH2—CN |
| 24 | CF3 | H | H | CH2—C(CH3)3 |
| 25 | CF3 | H | H | CH2CF2CF3 |
| 26 | CF3 | H | H | CH2CF3 |
| 27 | CF3 | H | H | CH2(CF2)2CF3 |
| 28 | CF3 | H | H | CH2CH(CH3)CH2CH3 |
| 29 | CF3 | H | H | CH2C(CH3)2CH2F |
| 30 | CF3 | H | H | CH2CH(CH3)2 |
| 31 | CF3 | H | H | CH2CH(CH2CH3)2 |
| 32 | CF3 | H | H | CH2CH2CH(CH3)2 |
| 33 | CF3 | H | H | CH2CH2C(CH3)3 |
| 34 | CF3 | H | H | CH2CH=CH2 |
| 35 | CF3 | H | Me | CH2CH=CH2 |
| 36 | CF3 | H | CH2CH=CH2 | CH2CH=CH2 |
| 37 | CF3 | H | H | CH2CH=CHCH3 |
| 38 | CF3 | H | H | CH2—C(CH3)=CH2 |
| 39 | CF3 | H | H | CH2—C≡CH |
| 40 | CF3 | H | Me | CH2—C≡CH |
| 41 | CF3 | H | H | CH(CH3)CH2CH3 |
| 42 | CF3 | H | H | CH(CH3)cPr |
| 43 | CF3 | H | H | CH(CH3)(CH2)2CH3 |
| 44 | CF3 | H | H | CH(CH3)(CH2)4CH3 |
| 45 | CF3 | H | H | CH(CH3)(CH2)5CH3 |
| 46 | CF3 | H | H | CH(CH2CH3)(CH2)3CH3 |
| 47 | CF3 | H | H | CH(CH3)CH2CH(CH3)2 |
| 48 | CF3 | H | H | CH(CH3)C(CH3)3 |
| 49 | CF3 | H | H | CH(CH3)CH(CH3)2 |
| 50 | CF3 | H | H | CH(CH3)CH2CH2CH(CH3)2 |
| 51 | CF3 | H | H | CH(CH2CH3)2 |
| 52 | CF3 | H | H | C(CH3)2CH2CH3 |
| 53 | CF3 | H | H | C(CH3)2CH2C(CH3)3 |
| 54 | CF3 | H | H | CH2—CH(OMe)2 |
| 55 | CF3 | H | H | CH2—CH(OEt)2 |
| 56 | CF3 | H | H | CH2CH2—OH |
| 57 | CF3 | H | H | CH2CH2—OMe |
| 58 | CF3 | H | Me | CH2CH2—OMe |
| 59 | CF3 | H | H | CH2CH2—OEt |
| 60 | CF3 | H | H | CH2CH2—SMe |
| 61 | CF3 | H | H | CH2CH2—CN |
| 62 | CF3 | H | H | CH2CH2—NMe2 |
| 63 | CF3 | H | H | CH2CH2-morpholin-4-yl |
| 64 | CF3 | H | H | CH(CH3)CH2—OMe |
| 65 | CF3 | H | H | CH(CH3)CH2—NMe2 |
| 66 | CF3 | H | H | CH2CH2CH2—OMe |
| 67 | CF3 | H | H | CH2CH2CH2—SMe |
| 68 | CF3 | H | H | CH2CH2CH2—OEt |
| 69 | CF3 | H | H | CH2CH2CH2—OiPr |
| 70 | CF3 | H | H | CH2CH2CH2—OBu |
| 71 | CF3 | H | H | CH2—COOCH3 |
| 72 | CF3 | H | Me | CH2—COOCH3 |
| 73 | CF3 | H | H | CH(CH3)COOMe |
| 74 | CF3 | H | H | CH(CH3)COOEt |
| 75 | CF3 | H | H | CH2CH2—COOCH3 |
| 76 | CF3 | H | H | CH(COOCH3)2 |
| 77 | CF3 | H | H | CH(COOEt)CH2—CH(CH3)2 |
| 78 | CF3 | H | H | CH(COOMe)CH(CH3)2 |
| 79 | CF3 | H | H | O—CH2CH3 |
| 80 | CF3 | H | Me | O—CH3 |
| 81 | CF3 | H | H | O—CH2CH=CH2 |
| 82 | CF3 | H | H | O—tBu |

TABLE 1-continued

Compounds of the formula (I)

$$\text{(I)}$$

Structure: R² and R¹ on pyridin-2(1H)-one ring with C(O)N(R³)(R⁴) carboxamide at position 3.

| Ex. | R¹ | R² | R³ | R⁴ |
|---|---|---|---|---|
| 83 | CF3 | H | H | O—Pr |
| 84 | CF3 | H | H | O—CH2cPr |
| 85 | CF3 | H | H | O—CH2CH(CH3)2 |
| 86 | CF3 | H | H | O—CH2CF3 |
| 87 | CF3 | H | H | O—CH(CH3)cPr |
| 88 | CF3 | H | H | O—CH2CH2Cl |
| 89 | CF3 | H | H | O—CH2C≡CH |
| 90 | CF3 | H | H | O—CH2C≡CCH3 |
| 91 | CF3 | H | H | O—CH(CH3)C≡CH |
| 92 | CF3 | H | H | CH2—Ph |
| 93 | CF3 | H | Me | CH2—Ph |
| 94 | CF3 | H | H | CH2-pyridin-3-yl |
| 95 | CF3 | H | H | CH2-6-Cl-pyridin-3-yl |
| 96 | CF3 | H | H | CH(CH3)Ph |
| 97 | CF3 | H | H | CH2CH2—Ph |
| 98 | CF3 | H | H | CH2-2-CF3—Ph |
| 99 | CF3 | H | H | CH2CH2CHPh2 |
| 100 | CF3 | H | | morpholin-4-yl |
| 101 | CF3 | H | | piperidin-1-yl |
| 102 | CF3 | H | | thiazolidin-3-yl |
| 103 | CF3 | H | | pyrrolidin-1-yl |
| 104 | CF3 | H | | 2-methylpyrrolidin-1-yl |
| 105 | CF3 | H | | =CH—N(CH3)2 |
| 106 | CF3 | H | | =C(CH3)N(CH3)2 |
| 107 | CF3 | H | | =CH—N(C2H5)2 |
| 108 | CF3 | H | | =C(CH3)N(C2H5)2 |
| 109 | CF3 | H | | =CH-piperidine |
| 110 | CF3 | H | | =CH-morpholine |
| 111 | CF3 | H | | =CH-pyrrolidine |
| 112 | CF3 | H | H | indan-1-yl |
| 113 | CF3 | H | H | tetrahydrofuran-2-ylmethyl |
| 114 | CF2Cl | H | H | H |
| 115 | CF2Cl | H | H | Me |
| 116 | CF2Cl | H | H | Et |
| 117 | CF2Cl | H | H | Pr |
| 118 | CF2Cl | H | H | iPr |
| 119 | CF2Cl | H | H | cPr |
| 120 | CF2Cl | H | H | Bu |
| 121 | CF2Cl | H | H | cBu |
| 122 | CF2Cl | H | H | tBu |
| 123 | CF2Cl | H | Me | Me |
| 124 | CF2Cl | H | Me | Et |
| 125 | CF2Cl | H | Me | Bu |
| 126 | CF2Cl | H | Me | Pr |
| 127 | CF2Cl | H | Me | iPr |
| 128 | CF2Cl | H | Et | Et |
| 129 | CF2Cl | H | Et | Pr |
| 130 | CF2Cl | H | Et | iPr |
| 131 | CF2Cl | H | Pr | Pr |
| 132 | CF2Cl | H | H | cPentyl |
| 133 | CF2Cl | H | H | cHexyl |
| 134 | CF2Cl | H | H | CH2(CH2)3CH3 |
| 135 | CF2Cl | H | H | CH2(CH2)4CH3 |
| 136 | CF2Cl | H | H | CH2—cPr |
| 137 | CF2Cl | H | H | CH2—CN |
| 138 | CF2Cl | H | H | CH2—C(CH3)3 |
| 139 | CF2Cl | H | H | CH2CF2CF3 |
| 140 | CF2Cl | H | H | CH2CF3 |
| 141 | CF2Cl | H | H | CH2(CF2)2CF3 |
| 142 | CF2Cl | H | H | CH2CH(CH3)2CH3 |
| 143 | CF2Cl | H | H | CH2C(CH3)2CH2F |
| 144 | CF2Cl | H | H | CH2CH(CH3)2 |
| 145 | CF2Cl | H | H | CH2CH(CH2CH3)2 |
| 146 | CF2Cl | H | H | CH2CH2CH(CH3)2 |
| 147 | CF2Cl | H | H | CH2CH2C(CH3)3 |
| 148 | CF2Cl | H | H | CH2CH=CH2 |
| 149 | CF2Cl | H | Me | CH2CH=CH2 |
| 150 | CF2Cl | H | CH2CH=CH2 | CH2CH=CH2 |
| 151 | CF2Cl | H | H | CH2CH=CHCH3 |
| 152 | CF2Cl | H | H | CH2—C(CH3)=CH2 |
| 153 | CF2Cl | H | H | CH2—C≡CH |
| 154 | CF2Cl | H | Me | CH2—C≡CH |
| 155 | CF2Cl | H | H | CH(CH3)CH2CH3 |
| 156 | CF2Cl | H | H | CH(CH3)cPr |
| 157 | CF2Cl | H | H | CH(CH3)(CH2)2CH3 |
| 158 | CF2Cl | H | H | CH(CH3)(CH2)4CH3 |
| 159 | CF2Cl | H | H | CH(CH3)(CH3)5CH3 |
| 160 | CF2Cl | H | H | CH(CH2CH3)(CH2)3CH3 |
| 161 | CF2Cl | H | H | CH(CH3)CH2CH(CH3)2 |
| 162 | CF2Cl | H | H | CH(CH3)C(CH3)3 |
| 163 | CF2Cl | H | H | CH(CH3)CH(CH3)2 |
| 164 | CF2Cl | H | H | CH(CH3)CH2CH2CH(CH3)2 |
| 165 | CF2Cl | H | H | CH(CH2CH3)2 |
| 166 | CF2Cl | H | H | C(CH3)2CH2CH3 |
| 167 | CF2Cl | H | H | C(CH3)2CH2C(CH3)3 |
| 168 | CF2Cl | H | H | CH2—CH(OMe)2 |
| 169 | CF2Cl | H | H | CH2—CH(OEt)2 |
| 170 | CF2Cl | H | H | CH2CH2—OH |
| 171 | CF2Cl | H | H | CH2CH2—OMe |
| 172 | CF2Cl | H | Me | CH2CH2—OMe |
| 173 | CF2Cl | H | H | CH2CH2—OEt |
| 174 | CF2Cl | H | H | CH2CH2—SMe |
| 175 | CF2Cl | H | H | CH2CH2—CN |
| 176 | CF2Cl | H | H | CH2CH2—NMe2 |
| 177 | CF2Cl | H | H | CH2CH2-morpholin-4-yl |
| 178 | CF2Cl | H | H | CH(CH3)CH2—OMe |
| 179 | CF2Cl | H | H | CH(CH3)CH2—NMe2 |
| 180 | CF2Cl | H | H | CH2CH2CH2—OMe |
| 181 | CF2Cl | H | H | CH2CH2CH2—SMe |
| 182 | CF2Cl | H | H | CH2CH2CH2—OEt |
| 183 | CF2Cl | H | H | CH2CH2CH2—OiPr |
| 184 | CF2Cl | H | H | CH2CH2CH2—OBu |
| 185 | CF2Cl | H | H | CH2—COOCH3 |
| 186 | CF2Cl | H | Me | CH2—COOCH3 |
| 187 | CF2Cl | H | H | CH(CH3)COOMe |
| 188 | CF2Cl | H | H | CH(CH3)COOEt |
| 189 | CF2Cl | H | H | CH2CH2—COOCH3 |
| 190 | CF2Cl | H | H | CH(COOCH3)2 |
| 191 | CF2Cl | H | H | CH(COOEt)CH2—CH(CH3)2 |
| 192 | CF2Cl | H | H | CH(COOMe)CH(CH3)2 |
| 193 | CF2Cl | H | H | O—CH2CH3 |
| 194 | CF2Cl | H | H | O—CH3 |
| 195 | CF2Cl | H | H | O—CH2CH=CH2 |
| 196 | CF2Cl | H | H | O—tBu |
| 197 | CF2Cl | H | H | O—Pr |
| 198 | CF2Cl | H | H | O—CH2cPr |
| 199 | CF2Cl | H | H | O—CH2CH(CH3)2 |
| 200 | CF2Cl | H | H | O—CH2CF3 |
| 201 | CF2Cl | H | H | O—CH(CH3)cPr |
| 202 | CF2Cl | H | H | O—CH2CH2Cl |
| 203 | CF2Cl | H | H | O—CH2C≡CH |
| 204 | CF2Cl | H | H | O—CH2C≡CCH3 |
| 205 | CF2Cl | H | H | O—CH(CH3)C≡CH |
| 206 | CF2Cl | H | H | CH2—Ph |
| 207 | CF2Cl | H | Me | CH2—Ph |
| 208 | CF2Cl | H | H | CH2-pyridin-3-yl |
| 209 | CF2Cl | H | H | CH2-6-Cl-pyridin-3-yl |
| 210 | CF2Cl | H | H | CH(CH3)Ph |
| 211 | CF2Cl | H | H | CH2CH2—Ph |
| 212 | CF2Cl | H | H | CH2-2-CF3—Ph |
| 213 | CF2Cl | H | H | CH2CH2CHPh |
| 214 | CF2Cl | H | | morpholin-4-yl |

TABLE 1-continued

Compounds of the formula (I)

| Ex. | R¹ | R² | R³ | R⁴ |
|---|---|---|---|---|
| 215 | CF2Cl | H | | piperidin-1-yl |
| 216 | CF2Cl | H | | thiazolidin-3-yl |
| 217 | CF2Cl | H | | pyrrolidin-1-yl |
| 218 | CF2Cl | H | | 2-methylpyrrolidin-1-yl |
| 219 | CF2Cl | H | | =CH—N(CH3)2 |
| 220 | CF2Cl | H | | =C(CH3)N(CH3)2 |
| 221 | CF2Cl | H | | =CH—N(C2H5)2 |
| 222 | CF2Cl | H | | =C(CH3)N(C2H5)2 |
| 223 | CF2Cl | H | | =CH-piperidine |
| 224 | CF2Cl | H | | =CH-morpholine |
| 225 | CF2Cl | H | | =CH-pyrrolidine |
| 226 | CF2Cl | H | H | indan-1-yl |
| 227 | CF2Cl | H | H | tetrahydrofuran-2-ylmethyl |
| 228 | CHF2 | H | H | H |
| 229 | CHF2 | H | H | Me |
| 230 | CHF2 | H | H | Et |
| 231 | CHF2 | H | H | Pr |
| 232 | CHF2 | H | H | iPr |
| 233 | CHF2 | H | H | cPr |
| 234 | CHF2 | H | H | Bu |
| 235 | CHF2 | H | H | cBu |
| 236 | CHF2 | H | H | tBu |
| 237 | CHF2 | H | Me | Me |
| 238 | CHF2 | H | Me | Et |
| 239 | CHF2 | H | Me | Bu |
| 240 | CHF2 | H | Me | Pr |
| 241 | CHF2 | H | Me | iPr |
| 242 | CHF2 | H | Et | Et |
| 243 | CHF2 | H | Et | Pr |
| 244 | CHF2 | H | Et | iPr |
| 245 | CHF2 | H | Pr | Pr |
| 246 | CHF2 | H | H | cPentyl |
| 247 | CHF2 | H | H | cHexyl |
| 248 | CHF2 | H | H | CH2(CH2)3CH3 |
| 249 | CHF2 | H | H | CH2(CH2)4CH3 |
| 250 | CHF2 | H | H | CH2—cPr |
| 251 | CHF2 | H | H | CH2—CN |
| 252 | CHF2 | H | H | CH2—C(CH3)3 |
| 253 | CHF2 | H | H | CH2CF2CF3 |
| 254 | CHF2 | H | H | CH2CF3 |
| 255 | CHF2 | H | H | CH2(CF2)2CF3 |
| 256 | CHF2 | H | H | CH2CH(CH3)CH2CH3 |
| 257 | CHF2 | H | H | CH2C(CH3)2CH2F |
| 258 | CHF2 | H | H | CH2CH(CH3)2 |
| 259 | CHF2 | H | H | CH2CH(CH2CH3)2 |
| 260 | CHF2 | H | H | CH2CH2CH(CH3)2 |
| 261 | CHF2 | H | H | CH2CH2C(CH3)3 |
| 262 | CHF2 | H | H | CH2CH=CH2 |
| 263 | CHF2 | H | Me | CH2CH=CH2 |
| 264 | CHF2 | H | CH2CH=CH2 | CH2CH=CH2 |
| 265 | CHF2 | H | H | CH2CH=CHCH3 |
| 266 | CHF2 | H | H | CH2—C(CH3)=CH2 |
| 267 | CHF2 | H | H | CH2—C≡CH |
| 268 | CHF2 | H | Me | CH2—C≡CH |
| 269 | CHF2 | H | H | CH(CH3)CH2CH3 |
| 270 | CHF2 | H | H | CH(CH3)cPr |
| 271 | CHF2 | H | H | CH(CH3)(CH2)2CH3 |
| 272 | CHF2 | H | H | CH(CH3)(CH2)4CH3 |
| 273 | CHF2 | H | H | CH(CH3)(CH2)5CH3 |
| 274 | CHF2 | H | H | CH(CH2CH3)(CH2)3CH3 |
| 275 | CHF2 | H | H | CH(CH3)CH2CH(CH3)2 |
| 276 | CHF2 | H | H | CH(CH3)C(CH3)3 |
| 277 | CHF2 | H | H | CH(CH3)CH(CH3)2 |
| 278 | CHF2 | H | H | CH(CH3)CH2CH2CH(CH3)2 |
| 279 | CHF2 | H | H | CH(CH2CH3)2 |
| 280 | CHF2 | H | H | C(CH3)2CH2CH3 |
| 281 | CHF2 | H | H | C(CH3)2CH2C(CH3)3 |
| 282 | CHF2 | H | H | CH2—CH(OMe)2 |
| 283 | CHF2 | H | H | CH2—CH(OEt)2 |
| 284 | CHF2 | H | H | CH2CH2—OH |
| 285 | CHF2 | H | H | CH2CH2—OMe |
| 286 | CHF2 | H | H | CH2CH2—OEt |
| 287 | CHF2 | H | H | CH2CH2—SMe |
| 288 | CHF2 | H | H | CH2CH2—CN |
| 289 | CHF2 | H | H | CH2CH2—NMe2 |
| 290 | CHF2 | H | H | CH2CH2-morpholin-4-yl |
| 291 | CHF2 | H | H | CH(CH3)CH2—OMe |
| 292 | CHF2 | H | H | CH(CH3)CH2—NMe2 |
| 293 | CHF2 | H | H | CH2CH2CH2—OMe |
| 294 | CHF2 | H | H | CH2CH2CH2—SMe |
| 295 | CHF2 | H | H | CH2CH2CH2—OEt |
| 296 | CHF2 | H | H | CH2CH2CH2—OiPr |
| 297 | CHF2 | H | H | CH2CH2CH2—OBu |
| 298 | CHF2 | H | H | CH2—COOCH3 |
| 299 | CHF2 | H | Me | CH2—COOCH3 |
| 300 | CHF2 | H | H | CH(CH3)COOMe |
| 301 | CHF2 | H | H | CH(CH3)COOEt |
| 302 | CHF2 | H | H | CH2CH2—COOCH3 |
| 303 | CHF2 | H | H | CH(COOCH3)2 |
| 304 | CHF2 | H | H | CH(COOEt)CH2—CH(CH3)2 |
| 305 | CHF2 | H | H | CH(COOMe)CH(CH3)2 |
| 306 | CHF2 | H | H | O—CH2CH3 |
| 307 | CHF2 | H | H | O—CH3 |
| 308 | CHF2 | H | H | O—CH2CH=CH2 |
| 309 | CHF2 | H | H | O—tBu |
| 310 | CHF2 | H | H | O—Pr |
| 311 | CHF2 | H | H | O—CH2cPr |
| 312 | CHF2 | H | H | O—CH2CH(CH3)2 |
| 313 | CHF2 | H | H | O—CH2CF3 |
| 314 | CHF2 | H | H | O—CH(CH3)cPr |
| 315 | CHF2 | H | H | O—CH2CH2Cl |
| 316 | CHF2 | H | H | O—CH2C≡CH |
| 317 | CHF2 | H | H | O—CH2C≡CCH3 |
| 318 | CHF2 | H | H | O—CH(CH3)C≡CH |
| 319 | CHF2 | H | H | CH2—Ph |
| 320 | CHF2 | H | Me | CH2—Ph |
| 321 | CHF2 | H | H | CH2-pyridin-3-yl |
| 322 | CHF2 | H | H | CH2-6-Cl-pyridin-3-yl |
| 323 | CHF2 | H | H | CH(CH3)Ph |
| 324 | CHF2 | H | H | CH2CH2—Ph |
| 325 | CHF2 | H | H | CH2-2-CF3—Ph |
| 326 | CHF2 | H | H | CH2CH2CHPh |
| 327 | CHF2 | H | | morpholin-4-yl |
| 328 | CHF2 | H | | piperidin-1-yl |
| 329 | CHF2 | H | | thiazolidin-3-yl |
| 330 | CHF2 | H | | pyrrolidin-1-yl |
| 331 | CHF2 | H | | 2-methylpyrrolidin-1-yl |
| 332 | CHF2 | H | | =CH—N(CH3)2 |
| 333 | CHF2 | H | | =C(CH3)N(CH3)2 |
| 334 | CHF2 | H | | =CH—N(C2H5)2 |
| 335 | CHF2 | H | | =C(CH3)N(C2H5)2 |
| 336 | CHF2 | H | | =CH-piperidine |
| 337 | CHF2 | H | | =CH-morpholine |
| 338 | CHF2 | H | | =CH-pyrrolidine |
| 339 | CHF2 | H | H | indan-1-yl |
| 340 | CHF2 | H | H | tetrahydrofuran-2-ylmethyl |
| 341 | CF2CF3 | H | H | H |
| 342 | CF2CF3 | H | H | Me |
| 343 | CF2CF3 | H | H | Et |
| 344 | CF2CF3 | H | H | Pr |
| 345 | CF2CF3 | H | H | iPr |
| 346 | CF2CF3 | H | H | cPr |

TABLE 1-continued

Compounds of the formula (I)

| Ex. | R¹ | R² | R³ | R⁴ |
|---|---|---|---|---|
| 347 | CF2CF3 | H | H | Bu |
| 348 | CF2CF3 | H | H | cBu |
| 349 | CF2CF3 | H | H | tBu |
| 350 | CF2CF3 | H | Me | Me |
| 351 | CF2CF3 | H | Me | Et |
| 352 | CF2CF3 | H | Me | Bu |
| 353 | CF2CF3 | H | Me | Pr |
| 354 | CF2CF3 | H | Me | iPr |
| 355 | CF2CF3 | H | Et | Et |
| 356 | CF2CF3 | H | Et | Pr |
| 357 | CF2CF3 | H | Et | iPr |
| 358 | CF2CF3 | H | Pr | Pr |
| 359 | CF2CF3 | H | H | cPentyl |
| 360 | CF2CF3 | H | H | cHexyl |
| 361 | CF2CF3 | H | H | CH2(CH2)3CH3 |
| 362 | CF2CF3 | H | H | CH2(CH2)4CH3 |
| 363 | CF2CF3 | H | H | CH2—cPr |
| 364 | CF2CF3 | H | H | CH2—CN |
| 365 | CF2CF3 | H | H | CH2—C(CH3)3 |
| 366 | CF2CF3 | H | H | CH2CF2CF3 |
| 367 | CF2CF3 | H | H | CH2CF3 |
| 368 | CF2CF3 | H | H | CH2(CF2)2CF3 |
| 369 | CF2CF3 | H | H | CH2CH(CH3)CH2CH3 |
| 370 | CF2CF3 | H | H | CH2C(CH3)2CH2F |
| 371 | CF2CF3 | H | H | CH2CH(CH3)2 |
| 372 | CF2CF3 | H | H | CH2CH(CH2CH3)2 |
| 373 | CF2CF3 | H | H | CH2CH2CH(CH3)2 |
| 374 | CF2CF3 | H | H | CH2CH2C(CH3)3 |
| 375 | CF2CF3 | H | H | CH2CH=CH2 |
| 376 | CF2CF3 | H | Me | CH2CH=CH2 |
| 377 | CF2CF3 | H | CH2CH=CH2 | CH2CH=CH2 |
| 378 | CF2CF3 | H | H | CH2CH=CHCH3 |
| 379 | CF2CF3 | H | H | CH2—C(CH3)=CH2 |
| 380 | CF2CF3 | H | H | CH2—C≡CH |
| 381 | CF2CF3 | H | Me | CH2—C≡CH |
| 382 | CF2CF3 | H | H | CH(CH3)CH2CH3 |
| 383 | CF2CF3 | H | H | CH(CH3)cPr |
| 384 | CF2CF3 | H | H | CH(CH3)(CH2)2CH3 |
| 385 | CF2CF3 | H | H | CH(CH3)(CH2)4CH3 |
| 386 | CF2CF3 | H | H | CH(CH3)(CH2)5CH3 |
| 387 | CF2CF3 | H | H | CH(CH2CH3)(CH2)3CH3 |
| 388 | CF2CF3 | H | H | CH(CH3)CH2CH(CH3)2 |
| 389 | CF2CF3 | H | H | CH(CH3)C(CH3)3 |
| 390 | CF2CF3 | H | H | CH(CH3)CH(CH3)2 |
| 391 | CF2CF3 | H | H | CH(CH3)CH2CH2CH(CH3)2 |
| 392 | CF2CF3 | H | H | CH(CH2CH3)2 |
| 393 | CF2CF3 | H | H | C(CH3)2CH2CH3 |
| 394 | CF2CF3 | H | H | C(CH3)2CH2C(CH3)3 |
| 395 | CF2CF3 | H | H | CH2—CH(OMe)2 |
| 396 | CF2CF3 | H | H | CH2—CH(OEt)2 |
| 397 | CF2CF3 | H | H | CH2CH2—OH |
| 398 | CF2CF3 | H | H | CH2CH2—OMe |
| 399 | CF2CF3 | H | Me | CH2CH2—OMe |
| 400 | CF2CF3 | H | H | CH2CH2—OEt |
| 401 | CF2CF3 | H | H | CH2CH2—SMe |
| 402 | CF2CF3 | H | H | CH2CH2—CN |
| 403 | CF2CF3 | H | H | CH2CH2—NMe2 |
| 404 | CF2CF3 | H | H | CH2CH2-morpholin-4-yl |
| 405 | CF2CF3 | H | H | CH(CH3)CH2—OMe |
| 406 | CF2CF3 | H | H | CH(CH3)CH2—NMe2 |
| 407 | CF2CF3 | H | H | CH2CH2CH2—OMe |
| 408 | CF2CF3 | H | H | CH2CH2CH2—SMe |
| 409 | CF2CF3 | H | H | CH2CH2CH2—OEt |
| 410 | CF2CF3 | H | H | CH2CH2CH2—OiPr |
| 411 | CF2CF3 | H | H | CH2CH2CH2—OBu |
| 412 | CF2CF3 | H | H | CH2—COOCH3 |
| 413 | CF2CF3 | H | Me | CH2—COOCH3 |
| 414 | CF2CF3 | H | H | CH(CH3)COOMe |
| 415 | CF2CF3 | H | H | CH(CH3)COOEt |
| 416 | CF2CF3 | H | H | CH2CH2—COOCH3 |
| 417 | CF2CF3 | H | H | CH(COOCH3)2 |
| 418 | CF2CF3 | H | H | CH(COOEt)CH2—CH(CH3)2 |
| 419 | CF2CF3 | H | H | CH(COOMe)CH(CH3)2 |
| 420 | CF2CF3 | H | H | O—CH2CH3 |
| 421 | CF2CF3 | H | H | O—CH3 |
| 422 | CF2CF3 | H | H | O—CH2CH=CH2 |
| 423 | CF2CF3 | H | H | O—tBu |
| 424 | CF2CF3 | H | H | O—Pr |
| 425 | CF2CF3 | H | H | O—CH2cPr |
| 426 | CF2CF3 | H | H | O—CH2CH(CH3)2 |
| 427 | CF2CF3 | H | H | O—CH2CF3 |
| 428 | CF2CF3 | H | H | O—CH(CH3)cPr |
| 429 | CF2CF3 | H | H | O—CH2CH2Cl |
| 430 | CF2CF3 | H | H | O—CH2C≡CH |
| 431 | CF2CF3 | H | H | O—CH2C≡CCH3 |
| 432 | CF2CF3 | H | H | O—CH(CH3)C≡CH |
| 433 | CF2CF3 | H | H | CH2—Ph |
| 434 | CF2CF3 | H | Me | CH2—Ph |
| 435 | CF2CF3 | H | H | CH2-pyridin-3-yl |
| 436 | CF2CF3 | H | H | CH2-6-Cl-pyridin-3-yl |
| 437 | CF2CF3 | H | H | CH(CH3)Ph |
| 438 | CF2CF3 | H | H | CH2CH2—Ph |
| 439 | CF2CF3 | H | H | CH2-2-CF3—Ph |
| 440 | CF2CF3 | H | H | CH2CH2CHPh |
| 441 | CF2CF3 | H |  | morpholin-4-yl |
| 442 | CF2CF3 | H |  | piperidin-1-yl |
| 443 | CF2CF3 | H |  | thiazolidin-3-yl |
| 444 | CF2CF3 | H |  | pyrrolidin-1-yl |
| 445 | CF2CF3 | H |  | 2-methylpyrrolidin-1-yl |
| 446 | CF2CF3 | H |  | =CH—N(CH3)2 |
| 447 | CF2CF3 | H |  | =C(CH3)N(CH3)2 |
| 448 | CF2CF3 | H |  | =CH—N(C2H5)2 |
| 449 | CF2CF3 | H |  | =C(CH3)N(C2H5)2 |
| 450 | CF2CF3 | H |  | =CH-piperidine |
| 451 | CF2CF3 | H |  | =CH-morpholine |
| 452 | CF2CF3 | H |  | =CH-pyrrolidine |
| 453 | CF2CF3 | H | H | indan-1-yl |
| 454 | CF2CF3 | H | H | tetrahydrofuran-2-ylmethyl |
| 455 | CF3 | Cl | H | H |
| 456 | CF3 | Cl | H | Me |
| 457 | CF3 | Cl | H | Et |
| 458 | CF3 | Cl | H | Pr |
| 459 | CF3 | Cl | H | iPr |
| 460 | CF3 | Cl | H | cPr |
| 461 | CF3 | Cl | H | Bu |
| 462 | CF3 | Cl | H | cBu |
| 463 | CF3 | Cl | H | tBu |
| 464 | CF3 | Cl | Me | Me |
| 465 | CF3 | Cl | Me | Et |
| 466 | CF3 | Cl | Me | Bu |
| 467 | CF3 | Cl | Me | Pr |
| 468 | CF3 | Cl | Me | iPr |
| 469 | CF3 | Cl | Et | Et |
| 470 | CF3 | Cl | Et | Pr |
| 471 | CF3 | Cl | Et | iPr |
| 472 | CF3 | Cl | Pr | Pr |
| 473 | CF3 | Cl | H | cPentyl |
| 474 | CF3 | Cl | H | cHexyl |
| 475 | CF3 | Cl | H | CH2(CH2)3CH3 |
| 476 | CF3 | Cl | H | CH2(CH2)4CH3 |
| 477 | CF3 | Cl | H | CH2—cPr |
| 478 | CF3 | Cl | H | CH2—CN |

TABLE 1-continued

Compounds of the formula (I)

(I)

| Ex. | R¹ | R² | R³ | R⁴ |
|---|---|---|---|---|
| 479 | CF3 | Cl | H | CH2—C(CH3)3 |
| 480 | CF3 | Cl | H | CH2CF2CF3 |
| 481 | CF3 | Cl | H | CH2CF3 |
| 482 | CF3 | Cl | H | CH2(CF2)2CF3 |
| 483 | CF3 | Cl | H | CH2CH(CH3)CH2CH3 |
| 484 | CF3 | Cl | H | CH2C(CH3)2CH2F |
| 485 | CF3 | Cl | H | CH2CH(CH3)2 |
| 486 | CF3 | Cl | H | CH2CH(CH2CH3)2 |
| 487 | CF3 | Cl | H | CH2CH2CH(CH3)2 |
| 488 | CF3 | Cl | H | CH2CH2C(CH3)3 |
| 489 | CF3 | Cl | H | CH2CH=CH2 |
| 490 | CF3 | Cl | Me | CH2CH=CH2 |
| 491 | CF3 | Cl | CH2CH=CH2 | CH2CH=CH2 |
| 492 | CF3 | Cl | H | CH2CH=CHCH3 |
| 493 | CF3 | Cl | H | CH2—C(CH3)=CH2 |
| 494 | CF3 | Cl | H | CH2—C≡CH |
| 495 | CF3 | Cl | Me | CH2—C≡CH |
| 496 | CF3 | Cl | H | CH(CH3)CH2CH3 |
| 497 | CF3 | Cl | H | CH(CH3)cPr |
| 498 | CF3 | Cl | H | CH(CH3)(CH2)2CH3 |
| 499 | CF3 | Cl | H | CH(CH3)(CH2)4CH3 |
| 500 | CF3 | Cl | H | CH(CH3)(CH2)5CH3 |
| 501 | CF3 | Cl | H | CH(CH2CH3)(CH2)3CH3 |
| 502 | CF3 | Cl | H | CH(CH3)CH2CH(CH3)2 |
| 503 | CF3 | Cl | H | CH(CH3)C(CH3)3 |
| 504 | CF3 | Cl | H | CH(CH3)CH(CH3)2 |
| 505 | CF3 | Cl | H | CH(CH3)CH2CH2CH(CH3)2 |
| 506 | CF3 | Cl | H | CH(CH2CH3)2 |
| 507 | CF3 | Cl | H | C(CH3)2CH2CH3 |
| 508 | CF3 | Cl | H | C(CH3)2CH2C(CH3)3 |
| 509 | CF3 | Cl | H | CH2—CH(OMe)2 |
| 510 | CF3 | Cl | H | CH2—CH(OEt)2 |
| 511 | CF3 | Cl | H | CH2CH2—OH |
| 512 | CF3 | Cl | H | CH2CH2—OMe |
| 513 | CF3 | Cl | Me | CH2CH2—OMe |
| 514 | CF3 | Cl | H | CH2CH2—OEt |
| 515 | CF3 | Cl | H | CH2CH2—SMe |
| 516 | CF3 | Cl | H | CH2CH2—CN |
| 517 | CF3 | Cl | H | CH2CH2—NMe2 |
| 518 | CF3 | Cl | H | CH2CH2-morpholin-4-yl |
| 519 | CF3 | Cl | H | CH(CH3)CH2—OMe |
| 520 | CF3 | Cl | H | CH(CH3)CH2—NMe2 |
| 521 | CF3 | Cl | H | CH2CH2CH2—OMe |
| 522 | CF3 | Cl | H | CH2CH2CH2—SMe |
| 523 | CF3 | Cl | H | CH2CH2CH2—OEt |
| 524 | CF3 | Cl | H | CH2CH2CH2—OiPr |
| 525 | CF3 | Cl | H | CH2CH2CH2—OBu |
| 526 | CF3 | Cl | H | CH2—COOCH3 |
| 527 | CF3 | Cl | Me | CH2—COOCH3 |
| 528 | CF3 | Cl | H | CH(CH3)COOMe |
| 529 | CF3 | Cl | H | CH(CH3)COOEt |
| 530 | CF3 | Cl | H | CH2CH2—COOCH3 |
| 531 | CF3 | Cl | H | CH(COOCH3)2 |
| 532 | CF3 | Cl | H | CH(COOEt)CH2—CH(CH3)2 |
| 533 | CF3 | Cl | H | CH(COOMe)CH(CH3)2 |
| 534 | CF3 | Cl | H | O—CH2CH3 |
| 535 | CF3 | Cl | Me | O—CH3 |
| 536 | CF3 | Cl | H | O—CH2CH=CH2 |
| 537 | CF3 | Cl | H | O—tBu |
| 538 | CF3 | Cl | H | O—Pr |
| 539 | CF3 | Cl | H | O—CH2cPr |
| 540 | CF3 | Cl | H | O—CH2CH(CH3)2 |
| 541 | CF3 | Cl | H | O—CH2CF3 |
| 542 | CF3 | Cl | H | O—CH(CH3)cPr |
| 543 | CF3 | Cl | H | O—CH2CH2Cl |
| 544 | CF3 | Cl | H | O—CH2C≡CH |
| 545 | CF3 | Cl | H | O—CH2C≡CCH3 |
| 546 | CF3 | Cl | H | O—CH(CH3)C≡CH |
| 547 | CF3 | Cl | H | CH2—Ph |
| 548 | CF3 | Cl | Me | CH2—Ph |
| 549 | CF3 | Cl | H | CH2-pyridin-3-yl |
| 550 | CF3 | Cl | H | CH2-6-Cl-pyridin-3-yl |
| 551 | CF3 | Cl | H | CH(CH3)Ph |
| 552 | CF3 | Cl | H | CH2CH2—Ph |
| 553 | CF3 | Cl | H | CH2-2-CF3—Ph |
| 554 | CF3 | Cl | H | CH2CH2CHPh |
| 555 | CF3 | Cl |  | morpholin-4-yl |
| 556 | CF3 | Cl |  | piperidin-1-yl |
| 557 | CF3 | Cl |  | thiazolidin-3-yl |
| 558 | CF3 | Cl |  | pyrrolidin-1-yl |
| 559 | CF3 | Cl |  | 2-methylpyrrolidin-1-yl |
| 560 | CF3 | Cl |  | =CH—N(CH3)2 |
| 561 | CF3 | Cl |  | =C(CH3)N(CH3)2 |
| 562 | CF3 | Cl |  | =CH—N(C2H5)2 |
| 563 | CF3 | Cl |  | =C(CH3)N(C2H5)2 |
| 564 | CF3 | Cl |  | =CH-piperidine |
| 565 | CF3 | Cl |  | =CH-morpholine |
| 566 | CF3 | Cl |  | =CH-pyrrolidine |
| 567 | CF3 | Cl | H | indan-1-yl |
| 568 | CF3 | Cl | H | tetrahydrofuran-2-ylmethyl |
| 569 | CF2Cl | Cl | H | H |
| 570 | CF2Cl | Cl | H | Me |
| 571 | CF2Cl | Cl | H | Et |
| 572 | CF2Cl | Cl | H | Pr |
| 573 | CF2Cl | Cl | H | iPr |
| 574 | CF2Cl | Cl | H | cPr |
| 575 | CF2Cl | Cl | H | Bu |
| 576 | CF2Cl | Cl | H | cBu |
| 577 | CF2Cl | Cl | H | tBu |
| 578 | CF2Cl | Cl | Me | Me |
| 579 | CF2Cl | Cl | Me | Et |
| 580 | CF2Cl | Cl | Me | Bu |
| 581 | CF2Cl | Cl | Me | Pr |
| 582 | CF2Cl | Cl | Me | iPr |
| 583 | CF2Cl | Cl | Et | Et |
| 584 | CF2Cl | Cl | Et | Pr |
| 585 | CF2Cl | Cl | Et | iPr |
| 586 | CF2Cl | Cl | Pr | Pr |
| 587 | CF2Cl | Cl | H | cPentyl |
| 588 | CF2Cl | Cl | H | cHexyl |
| 589 | CF2Cl | Cl | H | CH2(CH2)3CH3 |
| 590 | CF2Cl | Cl | H | CH2(CH2)4CH3 |
| 591 | CF2Cl | Cl | H | CH2—cPr |
| 592 | CF2Cl | Cl | H | CH2—CN |
| 593 | CF2Cl | Cl | H | CH2—C(CH3)3 |
| 594 | CF2Cl | Cl | H | CH2CF2CF3 |
| 595 | CF2Cl | Cl | H | CH2CF3 |
| 596 | CF2Cl | Cl | H | CH2(CF2)2CF3 |
| 597 | CF2Cl | Cl | H | CH2CH(CH3)CH2CH3 |
| 598 | CF2Cl | Cl | H | CH2C(CH3)2CH2F |
| 599 | CF2Cl | Cl | H | CH2CH(CH3)2 |
| 600 | CF2Cl | Cl | H | CH2CH(CH2CH3)2 |
| 601 | CF2Cl | Cl | H | CH2CH2CH(CH3)2 |
| 602 | CF2Cl | Cl | H | CH2CH2C(CH3)3 |
| 603 | CF2Cl | Cl | H | CH2CH=CH2 |
| 604 | CF2Cl | Cl | Me | CH2CH=CH2 |
| 605 | CF2Cl | Cl | CH2CH=CH2 | CH2CH=CH2 |
| 606 | CF2Cl | Cl | H | CH2CH=CHCH3 |
| 607 | CF2Cl | Cl | H | CH2—C(CH3)=CH2 |
| 608 | CF2Cl | Cl | H | CH2—C≡CH |
| 609 | CF2Cl | Cl | Me | CH2—C≡CH |
| 610 | CF2Cl | Cl | H | CH(CH3)CH2CH3 |

TABLE 1-continued

Compounds of the formula (I)

(I)

| Ex. | R¹ | R² | R³ | R⁴ |
|---|---|---|---|---|
| 611 | CF2Cl | Cl | H | CH(CH3)cPr |
| 612 | CF2Cl | Cl | H | CH(CH3)(CH2)2CH3 |
| 613 | CF2Cl | Cl | H | CH(CH3)(CH2)4CH3 |
| 614 | CF2Cl | Cl | H | CH(CH3)(CH2)5CH3 |
| 615 | CF2Cl | Cl | H | CH(CH2CH3)(CH2)3CH3 |
| 616 | CF2Cl | Cl | H | CH(CH3)CH2CH(CH3)2 |
| 617 | CF2Cl | Cl | H | CH(CH3)C(CH3)3 |
| 618 | CF2Cl | Cl | H | CH(CH3)CH(CH3)2 |
| 619 | CF2Cl | Cl | H | CH(CH3)CH2CH2CH(CH3)2 |
| 620 | CF2Cl | Cl | H | CH(CH2CH3)2 |
| 621 | CF2Cl | Cl | H | C(CH3)2CH2CH3 |
| 622 | CF2Cl | Cl | H | C(CH3)2CH2C(CH3)3 |
| 623 | CF2Cl | Cl | H | CH2—CH(OMe)2 |
| 624 | CF2Cl | Cl | H | CH2—CH(OEt)2 |
| 625 | CF2Cl | Cl | H | CH2CH2—OH |
| 626 | CF2Cl | Cl | H | CH2CH2—OMe |
| 627 | CF2Cl | Cl | Me | CH2CH2—OMe |
| 628 | CF2Cl | Cl | H | CH2CH2—OEt |
| 629 | CF2Cl | Cl | H | CH2CH2—SMe |
| 630 | CF2Cl | Cl | H | CH2CH2—CN |
| 631 | CF2Cl | Cl | H | CH2CH2—NMe2 |
| 632 | CF2Cl | Cl | H | CH2CH2-morpholin-4-yl |
| 633 | CF2Cl | Cl | H | CH(CH3)CH2—OMe |
| 634 | CF2Cl | Cl | H | CH(CH3)CH2—NMe2 |
| 635 | CF2Cl | Cl | H | CH2CH2CH2—OMe |
| 636 | CF2Cl | Cl | H | CH2CH2CH2—SMe |
| 637 | CF2Cl | Cl | H | CH2CH2CH2—OEt |
| 638 | CF2Cl | Cl | H | CH2CH2CH2—OiPr |
| 639 | CF2Cl | Cl | H | CH2CH2CH2—OBu |
| 640 | CF2Cl | Cl | H | CH2—COOCH3 |
| 641 | CF2Cl | Cl | Me | CH2—COOCH3 |
| 642 | CF2Cl | Cl | H | CH(CH3)COOMe |
| 643 | CF2Cl | Cl | H | CH(CH3)COOEt |
| 644 | CF2Cl | Cl | H | CH2CH2—COOCH3 |
| 645 | CF2Cl | Cl | H | CH(COOCH3)2 |
| 646 | CF2Cl | Cl | H | CH(COOEt)CH2—CH(CH3)2 |
| 647 | CF2Cl | Cl | H | CH(COOMe)CH(CH3)2 |
| 648 | CF2Cl | Cl | H | O—CH2CH3 |
| 649 | CF2Cl | Cl | H | O—CH3 |
| 650 | CF2Cl | Cl | H | O—CH2CH=CH2 |
| 651 | CF2Cl | Cl | H | O—tBu |
| 652 | CF2Cl | Cl | H | O—Pr |
| 653 | CF2Cl | Cl | H | O—CH2cPr |
| 654 | CF2Cl | Cl | H | O—CH2CH(CH3)2 |
| 655 | CF2Cl | Cl | H | O—CH2CF3 |
| 656 | CF2Cl | Cl | H | O—CH(CH3)cPr |
| 657 | CF2Cl | Cl | H | O—CH2CH2Cl |
| 658 | CF2Cl | Cl | H | O—CH2C≡CH |
| 659 | CF2Cl | Cl | H | O—CH2C≡CCH3 |
| 660 | CF2Cl | Cl | H | O—CH(CH3)C≡CH |
| 661 | CF2Cl | Cl | H | CH2—Ph |
| 662 | CF2Cl | Cl | Me | CH2—Ph |
| 663 | CF2Cl | Cl | H | CH2-pyridin-3-yl |
| 664 | CF2Cl | Cl | H | CH2-6-Cl-pyridin-3-yl |
| 665 | CF2Cl | Cl | H | CH(CH3)Ph |
| 666 | CF2Cl | Cl | H | CH2CH2—Ph |
| 667 | CF2Cl | Cl | H | CH2-2-CF3—Ph |
| 668 | CF2Cl | Cl | H | CH2CH2CHPh |
| 669 | CF2Cl | Cl | morpholin-4-yl | |
| 670 | CF2Cl | Cl | piperidin-1-yl | |
| 671 | CF2Cl | Cl | thiazolidin-3-yl | |
| 672 | CF2Cl | Cl | pyrrolidin-1-yl | |
| 673 | CF2Cl | Cl | 2-methylpyrrolidin-1-yl | |
| 674 | CF2Cl | Cl | | =CH—N(CH3)2 |
| 675 | CF2Cl | Cl | | =C(CH3)N(CH3)2 |
| 676 | CF2Cl | Cl | | =CH—N(C2H5)2 |
| 677 | CF2Cl | Cl | | =C(CH3)N(C2H5)2 |
| 678 | CF2Cl | Cl | | =CH-piperidine |
| 679 | CF2Cl | Cl | | =CH-morpholine |
| 680 | CF2Cl | Cl | | =CH-pyrrolidine |
| 681 | CF2Cl | Cl | H | indan-1-yl |
| 682 | CF2Cl | Cl | H | tetrahydrofuran-2-ylmethyl |
| 683 | CHF2 | Cl | H | H |
| 684 | CHF2 | Cl | H | Me |
| 685 | CHF2 | Cl | H | Et |
| 686 | CHF2 | Cl | H | Pr |
| 687 | CHF2 | Cl | H | iPr |
| 688 | CHF2 | Cl | H | cPr |
| 689 | CHF2 | Cl | H | Bu |
| 690 | CHF2 | Cl | H | cBu |
| 691 | CHF2 | Cl | H | tBu |
| 692 | CHF2 | Cl | Me | Me |
| 693 | CHF2 | Cl | Me | Et |
| 694 | CHF2 | Cl | Me | Bu |
| 695 | CHF2 | Cl | Me | Pr |
| 696 | CHF2 | Cl | Me | iPr |
| 697 | CHF2 | Cl | Et | Et |
| 698 | CHF2 | Cl | Et | Pr |
| 699 | CHF2 | Cl | Et | iPr |
| 700 | CHF2 | Cl | Pr | Pr |
| 701 | CHF2 | Cl | H | cPentyl |
| 702 | CHF2 | Cl | H | cHexyl |
| 703 | CHF2 | Cl | H | CH2(CH2)3CH3 |
| 704 | CHF2 | Cl | H | CH2(CH2)4CH3 |
| 705 | CHF2 | Cl | H | CH2—cPr |
| 706 | CHF2 | Cl | H | CH2—CN |
| 707 | CHF2 | Cl | H | CH2—C(CH3)3 |
| 708 | CHF2 | Cl | H | CH2CF2CF3 |
| 709 | CHF2 | Cl | H | CH2CF3 |
| 710 | CHF2 | Cl | H | CH2(CF2)2CF3 |
| 711 | CHF2 | Cl | H | CH2CH(CH3)CH2CH3 |
| 712 | CHF2 | Cl | H | CH2C(CH3)2CH2F |
| 713 | CHF2 | Cl | H | CH2CH(CH3)2 |
| 714 | CHF2 | Cl | H | CH2CH(CH2CH3)2 |
| 715 | CHF2 | Cl | H | CH2CH2CH(CH3)2 |
| 716 | CHF2 | Cl | H | CH2CH2C(CH3)3 |
| 717 | CHF2 | Cl | H | CH2CH=CH2 |
| 718 | CHF2 | Cl | Me | CH2CH=CH2 |
| 719 | CHF2 | Cl | CH2CH=CH2 | CH2CH=CH2 |
| 720 | CHF2 | Cl | H | CH2CH=CHCH3 |
| 721 | CHF2 | Cl | H | CH2—C(CH3)=CH2 |
| 722 | CHF2 | Cl | H | CH2—C≡CH |
| 723 | CHF2 | Cl | Me | CH2—C≡CH |
| 724 | CHF2 | Cl | H | CH(CH3)CH2CH3 |
| 725 | CHF2 | Cl | H | CH(CH3)cPr |
| 726 | CHF2 | Cl | H | CH(CH3)(CH2)2CH3 |
| 727 | CHF2 | Cl | H | CH(CH3)(CH2)4CH3 |
| 728 | CHF2 | Cl | H | CH(CH3)(CH2)5CH3 |
| 729 | CHF2 | Cl | H | CH(CH2CH3)(CH2)3CH3 |
| 730 | CHF2 | Cl | H | CH(CH3)CH2CH(CH3)2 |
| 731 | CHF2 | Cl | H | CH(CH3)C(CH3)3 |
| 732 | CHF2 | Cl | H | CH(CH3)CH(CH3)2 |
| 733 | CHF2 | Cl | H | CH(CH3)CH2CH2CH(CH3)2 |
| 734 | CHF2 | Cl | H | CH(CH2CH3)2 |
| 735 | CHF2 | Cl | H | C(CH3)2CH2CH3 |
| 736 | CHF2 | Cl | H | C(CH3)2CH2C(CH3)3 |
| 737 | CHF2 | Cl | H | CH2—CH(OMe)2 |
| 738 | CHF2 | Cl | H | CH2—CH(OEt)2 |
| 739 | CHF2 | Cl | H | CH2CH2—OH |
| 740 | CHF2 | Cl | H | CH2CH2—OMe |
| 741 | CHF2 | Cl | Me | CH2CH2—OMe |
| 742 | CHF2 | Cl | H | CH2CH2—OEt |

TABLE 1-continued

Compounds of the formula (I)

$$\text{(I)}$$

Structure: pyridinone with R¹ at position 6, R² at position 5, C(=O)N(R³)(R⁴) at position 3, NH and C=O in the ring.

| Ex. | R¹ | R² | R³ | R⁴ |
|---|---|---|---|---|
| 743 | CHF2 | Cl | H | CH2CH2—SMe |
| 744 | CHF2 | Cl | H | CH2CH2—CN |
| 745 | CHF2 | Cl | H | CH2CH2—NMe2 |
| 746 | CHF2 | Cl | H | CH2CH2-morpholin-4-yl |
| 747 | CHF2 | Cl | H | CH(CH3)CH2—OMe |
| 748 | CHF2 | Cl | H | CH(CH3)CH2—NMe2 |
| 749 | CHF2 | Cl | H | CH2CH2CH2—OMe |
| 750 | CHF2 | Cl | H | CH2CH2CH2—SMe |
| 751 | CHF2 | Cl | H | CH2CH2CH2—OEt |
| 752 | CHF2 | Cl | H | CH2CH2CH2—OiPr |
| 753 | CHF2 | Cl | H | CH2CH2CH2—OBu |
| 754 | CHF2 | Cl | H | CH2—COOCH3 |
| 755 | CHF2 | Cl | Me | CH2—COOCH3 |
| 756 | CHF2 | Cl | H | CH(CH3)COOMe |
| 757 | CHF2 | Cl | H | CH(CH3)COOEt |
| 758 | CHF2 | Cl | H | CH2CH2—COOCH3 |
| 759 | CHF2 | Cl | H | CH(COOCH3)2 |
| 760 | CHF2 | Cl | H | CH(COOEt)CH2—CH(CH3)2 |
| 761 | CHF2 | Cl | H | CH(COOMe)CH(CH3)2 |
| 762 | CHF2 | Cl | H | O—CH2CH3 |
| 763 | CHF2 | Cl | H | O—CH3 |
| 764 | CHF2 | Cl | H | O—CH2CH=CH2 |
| 765 | CHF2 | Cl | H | O—tBu |
| 766 | CHF2 | Cl | H | O—Pr |
| 767 | CHF2 | Cl | H | O—CH2cPr |
| 768 | CHF2 | Cl | H | O—CH(CH3)2 |
| 769 | CHF2 | Cl | H | O—CH2CF3 |
| 770 | CHF2 | Cl | H | O—CH(CH3)cPr |
| 771 | CHF2 | Cl | H | O—CH2CH2Cl |
| 772 | CHF2 | Cl | H | O—CH2C≡CH |
| 773 | CHF2 | Cl | H | O—CH2C≡CCH3 |
| 774 | CHF2 | Cl | H | O—CH(CH3)C≡CH |
| 775 | CHF2 | Cl | H | CH2—Ph |
| 776 | CHF2 | Cl | Me | CH2—Ph |
| 777 | CHF2 | Cl | H | CH2-pyridin-3-yl |
| 778 | CHF2 | Cl | H | CH2-6-Cl-pyridin-3-yl |
| 779 | CHF2 | Cl | H | CH(CH3)Ph |
| 780 | CHF2 | Cl | H | CH2CH2—Ph |
| 781 | CHF2 | Cl | H | CH2-2-CF3—Ph |
| 782 | CHF2 | Cl | H | CH2CH2CHPh |
| 783 | CHF2 | Cl | morpholin-4-yl | |
| 784 | CHF2 | Cl | piperidin-1-yl | |
| 785 | CHF2 | Cl | thiazolidin-3-yl | |
| 786 | CHF2 | Cl | pyrrolidin-1-yl | |
| 787 | CHF2 | Cl | 2-methylpyrrolidin-1-yl | |
| 788 | CHF2 | Cl | =CH—N(CH3)2 | |
| 789 | CHF2 | Cl | =C(CH3)N(CH3)2 | |
| 790 | CHF2 | Cl | =CH—N(C2H5)2 | |
| 791 | CHF2 | Cl | =C(CH3)N(C2H5)2 | |
| 792 | CHF2 | Cl | =CH-piperidine | |
| 793 | CHF2 | Cl | =CH-morpholine | |
| 794 | CHF2 | Cl | =CH-pyrrolidine | |
| 795 | CHF2 | Cl | H | indan-1-yl |
| 796 | CHF2 | Cl | H | tetrahydrofuran-2-ylmethyl |
| 797 | CF2CF3 | Cl | H | H |
| 798 | CF2CF3 | Cl | H | Me |
| 799 | CF2CF3 | Cl | H | Et |
| 800 | CF2CF3 | Cl | H | Pr |
| 801 | CF2CF3 | Cl | H | iPr |
| 802 | CF2CF3 | Cl | H | cPr |
| 803 | CF2CF3 | Cl | H | Bu |
| 804 | CF2CF3 | Cl | H | cBu |
| 805 | CF2CF3 | Cl | H | tBu |
| 806 | CF2CF3 | Cl | Me | Me |
| 807 | CF2CF3 | Cl | Me | Et |
| 808 | CF2CF3 | Cl | Me | Bu |
| 809 | CF2CF3 | Cl | Me | Pr |
| 810 | CF2CF3 | Cl | Me | iPr |
| 811 | CF2CF3 | Cl | Et | Et |
| 812 | CF2CF3 | Cl | Et | Pr |
| 813 | CF2CF3 | Cl | Et | iPr |
| 814 | CF2CF3 | Cl | Pr | Pr |
| 815 | CF2CF3 | Cl | H | cPentyl |
| 816 | CF2CF3 | Cl | H | cHexyl |
| 817 | CF2CF3 | Cl | H | CH2(CH2)3CH3 |
| 818 | CF2CF3 | Cl | H | CH2(CH2)4CH3 |
| 819 | CF2CF3 | Cl | H | CH2—cPr |
| 820 | CF2CF3 | Cl | H | CH2—CN |
| 821 | CF2CF3 | Cl | H | CH2—C(CH3)3 |
| 822 | CF2CF3 | Cl | H | CH2CF2CF3 |
| 823 | CF2CF3 | Cl | H | CH2CF3 |
| 824 | CF2CF3 | Cl | H | CH2(CF2)2CF3 |
| 825 | CF2CF3 | Cl | H | CH2CH(CH3)CH2CH3 |
| 826 | CF2CF3 | Cl | H | CH2C(CH3)2CH2F |
| 827 | CF2CF3 | Cl | H | CH2CH(CH3)2 |
| 828 | CF2CF3 | Cl | H | CH2CH(CH2CH3)2 |
| 829 | CF2CF3 | Cl | H | CH2CH2CH(CH3)2 |
| 830 | CF2CF3 | Cl | H | CH2CH2C(CH3)3 |
| 831 | CF2CF3 | Cl | H | CH2CH=CH2 |
| 832 | CF2CF3 | Cl | Me | CH2CH=CH2 |
| 833 | CF2CF3 | Cl | CH2CH=CH2 | CH2CH=CH2 |
| 834 | CF2CF3 | Cl | H | CH2CH=CHCH3 |
| 835 | CF2CF3 | Cl | H | CH2—C(CH3)=CH2 |
| 836 | CF2CF3 | Cl | H | CH2—C≡CH |
| 837 | CF2CF3 | Cl | Me | CH2—C≡CH |
| 838 | CF2CF3 | Cl | H | CH(CH3)CH2CH3 |
| 839 | CF2CF3 | Cl | H | CH(CH3)cPr |
| 840 | CF2CF3 | Cl | H | CH(CH3)(CH2)2CH3 |
| 841 | CF2CF3 | Cl | H | CH(CH3)(CH2)4CH3 |
| 842 | CF2CF3 | Cl | H | CH(CH3)(CH2)5CH3 |
| 843 | CF2CF3 | Cl | H | CH(CH2CH3)(CH2)3CH3 |
| 844 | CF2CF3 | Cl | H | CH(CH3)CH2CH(CH3)2 |
| 845 | CF2CF3 | Cl | H | CH(CH3)C(CH3)3 |
| 846 | CF2CF3 | Cl | H | CH(CH3)CH(CH3)2 |
| 847 | CF2CF3 | Cl | H | CH(CH3)CH2CH2CH(CH3)2 |
| 848 | CF2CF3 | Cl | H | CH(CH2CH3)2 |
| 849 | CF2CF3 | Cl | H | C(CH3)2CH2CH3 |
| 850 | CF2CF3 | Cl | H | C(CH3)2CH2C(CH3)3 |
| 851 | CF2CF3 | Cl | H | CH2—CH(OMe)2 |
| 852 | CF2CF3 | Cl | H | CH2—CH(OEt)2 |
| 853 | CF2CF3 | Cl | H | CH2CH2—OH |
| 854 | CF2CF3 | Cl | H | CH2CH2—OMe |
| 855 | CF2CF3 | Cl | Me | CH2CH2—OMe |
| 856 | CF2CF3 | Cl | H | CH2CH2—OEt |
| 857 | CF2CF3 | Cl | H | CH2CH2—SMe |
| 858 | CF2CF3 | Cl | H | CH2CH2—CN |
| 859 | CF2CF3 | Cl | H | CH2CH2—NMe2 |
| 860 | CF2CF3 | Cl | H | CH2CH2-morpholin-4-yl |
| 861 | CF2CF3 | Cl | H | CH(CH3)CH2—OMe |
| 862 | CF2CF3 | Cl | H | CH(CH3)CH2—NMe2 |
| 863 | CF2CF3 | Cl | H | CH2CH2CH2—OMe |
| 864 | CF2CF3 | Cl | H | CH2CH2CH2—SMe |
| 865 | CF2CF3 | Cl | H | CH2CH2CH2—OEt |
| 866 | CF2CF3 | Cl | H | CH2CH2CH2—OiPr |
| 867 | CF2CF3 | Cl | H | CH2CH2CH2—OBu |
| 868 | CF2CF3 | Cl | H | CH2—COOCH3 |
| 869 | CF2CF3 | Cl | Me | CH2—COOCH3 |
| 870 | CF2CF3 | Cl | H | CH2CH2—COOCH3 |
| 871 | CF2CF3 | Cl | H | CH(COOCH3)2 |
| 872 | CF2CF3 | Cl | H | CH(COOEt)CH2—CH(CH3)2 |
| 873 | CF2CF3 | Cl | H | CH(COOMe)CH(CH3)2 |
| 874 | CF2CF3 | Cl | H | O—CH2CH3 |

TABLE 1-continued

Compounds of the formula (I)

(I)

| Ex. | R¹ | R² | R³ | R⁴ |
|---|---|---|---|---|
| 875 | CF2CF3 | Cl | H | O—CH3 |
| 876 | CF2CF3 | Cl | H | O—CH2CH=CH2 |
| 877 | CF2CF3 | Cl | H | O—tBu |
| 878 | CF2CF3 | Cl | H | O—Pr |
| 879 | CF2CF3 | Cl | H | O—CH2cPr |
| 880 | CF2CF3 | Cl | H | O—CH2CH(CH3)2 |
| 881 | CF2CF3 | Cl | H | O—CH2CF3 |
| 882 | CF2CF3 | Cl | H | O—CH(CH3)cPr |
| 883 | CF2CF3 | Cl | H | O—CH2CH2Cl |
| 884 | CF2CF3 | Cl | H | O—CH2C≡CH |
| 885 | CF2CF3 | Cl | H | O—CH2C≡CCH3 |
| 886 | CF2CF3 | Cl | H | O—CH(CH3)C≡CH |
| 887 | CF2CF3 | Cl | H | CH2—Ph |
| 888 | CF2CF3 | Cl | Me | CH2—Ph |
| 889 | CF2CF3 | Cl | H | CH2-pyridin-3-yl |
| 890 | CF2CF3 | Cl | H | CH2-6-Cl-pyridin-3-yl |
| 891 | CF2CF3 | Cl | H | CH(CH3)Ph |
| 892 | CF2CF3 | Cl | H | CH2CH2—Ph |
| 893 | CF2CF3 | Cl | H | CH2-2-CF3—Ph |
| 894 | CF2CF3 | Cl | H | CH2CH2CHPh |
| 895 | CF2CF3 | Cl | | morpholin-4-yl |
| 896 | CF2CF3 | Cl | | piperidin-1-yl |
| 897 | CF2CF3 | Cl | | thiazolidin-3-yl |
| 898 | CF2CF3 | Cl | | pyrrolidin-1-yl |
| 899 | CF2CF3 | Cl | | 2-methylpyrrolidin-1-yl |
| 900 | CF2CF3 | Cl | | =CH—N(CH3)2 |
| 901 | CF2CF3 | Cl | | =C(CH3)N(CH3)2 |
| 902 | CF2CF3 | Cl | | =CH—N(C2H5)2 |
| 903 | CF2CF3 | Cl | | =C(CH3)N(C2H5)2 |
| 904 | CF2CF3 | Cl | | =CH-piperidine |
| 905 | CF2CF3 | Cl | | =CH-morpholine |
| 906 | CF2CF3 | Cl | | =CH-pyrrolidine |
| 907 | CF2CF3 | Cl | H | indan-1-yl |
| 908 | CF2CF3 | Cl | H | tetrahydrofuran-2-ylmethyl |
| 909 | CF3 | Br | H | H |
| 910 | CF3 | Br | H | Me |
| 911 | CF3 | Br | H | Et |
| 912 | CF3 | Br | H | Pr |
| 913 | CF3 | Br | H | iPr |
| 914 | CF3 | Br | H | cPr |
| 915 | CF3 | Br | H | Bu |
| 916 | CF3 | Br | H | cBu |
| 917 | CF3 | Br | H | tBu |
| 918 | CF3 | Br | Me | Me |
| 919 | CF3 | Br | Me | Et |
| 920 | CF3 | Br | Me | Bu |
| 921 | CF3 | Br | Me | Pr |
| 922 | CF3 | Br | Me | iPr |
| 923 | CF3 | Br | Et | Et |
| 924 | CF3 | Br | Et | Pr |
| 925 | CF3 | Br | Et | iPr |
| 926 | CF3 | Br | Pr | Pr |
| 927 | CF3 | Br | H | cPentyl |
| 928 | CF3 | Br | H | cHexyl |
| 929 | CF3 | Br | H | CH2(CH2)3CH3 |
| 930 | CF3 | Br | H | CH2(CH2)4CH3 |
| 931 | CF3 | Br | H | CH2—cPr |
| 932 | CF3 | Br | H | CH2—CN |
| 933 | CF3 | Br | H | CH2—C(CH3)3 |
| 934 | CF3 | Br | H | CH2CF2CF3 |
| 935 | CF3 | Br | H | CH2CF3 |
| 936 | CF3 | Br | H | CH2(CF2)2CF3 |
| 937 | CF3 | Br | H | CH2CH(CH3)CH2CH3 |
| 938 | CF3 | Br | H | CH2C(CH3)2CH2F |
| 939 | CF3 | Br | H | CH2CH(CH3)2 |
| 940 | CF3 | Br | H | CH2CH(CH2CH3)2 |
| 941 | CF3 | Br | H | CH2CH2CH(CH3)2 |
| 942 | CF3 | Br | H | CH2CH2C(CH3)3 |
| 943 | CF3 | Br | H | CH2CH=CH2 |
| 944 | CF3 | Br | Me | CH2CH=CH2 |
| 945 | CF3 | Br | CH2CH=CH2 | CH2CH=CH2 |
| 946 | CF3 | Br | H | CH2CH=CHCH3 |
| 947 | CF3 | Br | H | CH2—C(CH3)=CH2 |
| 948 | CF3 | Br | H | CH2—C≡CH |
| 949 | CF3 | Br | Me | CH2—C≡CH |
| 950 | CF3 | Br | H | CH(CH3)CH2CH3 |
| 951 | CF3 | Br | H | CH(CH3)cPr |
| 952 | CF3 | Br | H | CH(CH3)(CH2)2CH3 |
| 953 | CF3 | Br | H | CH(CH3)(CH2)4CH3 |
| 954 | CF3 | Br | H | CH(CH3)(CH2)5CH3 |
| 955 | CF3 | Br | H | CH(CH2CH3)(CH2)3CH3 |
| 956 | CF3 | Br | H | CH(CH3)CH2CH(CH3)2 |
| 957 | CF3 | Br | H | CH(CH3)C(CH3)3 |
| 958 | CF3 | Br | H | CH(CH3)CH(CH3)2 |
| 959 | CF3 | Br | H | CH(CH3)CH2CH2CH(CH3)2 |
| 960 | CF3 | Br | H | CH(CH2CH3)2 |
| 961 | CF3 | Br | H | C(CH3)2CH2CH3 |
| 962 | CF3 | Br | H | C(CH3)2CH2C(CH3)3 |
| 963 | CF3 | Br | H | CH2—CH(OMe)2 |
| 964 | CF3 | Br | H | CH2—CH(OEt)2 |
| 965 | CF3 | Br | H | CH2CH2—OH |
| 966 | CF3 | Br | H | CH2CH2—OMe |
| 967 | CF3 | Br | Me | CH2CH2—OMe |
| 968 | CF3 | Br | H | CH2CH2—OEt |
| 969 | CF3 | Br | H | CH2CH2—SMe |
| 970 | CF3 | Br | H | CH2CH2—CN |
| 971 | CF3 | Br | H | CH2CH2—NMe2 |
| 972 | CF3 | Br | H | CH2CH2-morpholin-4-yl |
| 973 | CF3 | Br | H | CH(CH3)CH2—OMe |
| 974 | CF3 | Br | H | CH(CH3)CH2—NMe2 |
| 975 | CF3 | Br | H | CH2CH2CH2—OH |
| 976 | CF3 | Br | H | CH2CH2CH2—SMe |
| 977 | CF3 | Br | H | CH2CH2CH2—OEt |
| 978 | CF3 | Br | H | CH2CH2CH2—OiPr |
| 979 | CF3 | Br | H | CH2CH2CH2—OBu |
| 980 | CF3 | Br | H | CH2—COOCH3 |
| 981 | CF3 | Br | Me | CH2—COOCH3 |
| 982 | CF3 | Br | H | CH(CH3)COOMe |
| 983 | CF3 | Br | H | CH(CH3)COOEt |
| 984 | CF3 | Br | H | CH2CH2—COOCH3 |
| 985 | CF3 | Br | H | CH(COOCH3)2 |
| 986 | CF3 | Br | H | CH(COOEt)CH2—CH(CH3)2 |
| 987 | CF3 | Br | H | CH(COOMe)CH(CH3)2 |
| 988 | CF3 | Br | H | O—CH2CH3 |
| 989 | CF3 | Br | Me | O—CH3 |
| 990 | CF3 | Br | H | O—CH2CH=CH2 |
| 991 | CF3 | Br | H | O—tBu |
| 992 | CF3 | Br | H | O—Pr |
| 993 | CF3 | Br | H | O—CH2cPr |
| 994 | CF3 | Br | H | O—CH2CH(CH3)2 |
| 995 | CF3 | Br | H | O—CH2CF3 |
| 996 | CF3 | Br | H | O—CH(CH3)cPr |
| 997 | CF3 | Br | H | O—CH2CH2Cl |
| 998 | CF3 | Br | H | O—CH2C≡CH |
| 999 | CF3 | Br | H | O—CH2C≡CCH3 |
| 1000 | CF3 | Br | H | O—CH(CH3)C≡CH |
| 1001 | CF3 | Br | H | CH2—Ph |
| 1002 | CF3 | Br | Me | CH2—Ph |
| 1003 | CF3 | Br | H | CH2-pyridin-3-yl |
| 1004 | CF3 | Br | H | CH2-6-Cl-pyridin-3-yl |
| 1005 | CF3 | Br | H | CH(CH3)Ph |
| 1006 | CF3 | Br | H | CH2CH2—Ph |

TABLE 1-continued

Compounds of the formula (I)

$$\text{(I)}$$

Structure: Pyridinone with R¹ at 6-position, R² at 5-position, C(=O)N(R³)(R⁴) at 3-position, NH and C=O in ring.

| Ex. | R¹ | R² | R³ | R⁴ |
|---|---|---|---|---|
| 1007 | CF3 | Br | H | CH2-2-CF3—Ph |
| 1008 | CF3 | Br | H | CH2CH2CHPh2 |
| 1009 | CF3 | Br | | morpholin-4-yl |
| 1010 | CF3 | Br | | piperidin-1-yl |
| 1011 | CF3 | Br | | thiazolidin-3-yl |
| 1012 | CF3 | Br | | pyrrolidin-1-yl |
| 1013 | CF3 | Br | | 2-methylpyrrolidin-1-yl |
| 1014 | CF3 | Br | | =CH—N(CH3)2 |
| 1015 | CF3 | Br | | =C(CH3)N(CH3)2 |
| 1016 | CF3 | Br | | =CH—N(C2H5)2 |
| 1017 | CF3 | Br | | =C(CH3)N(C2H5)2 |
| 1018 | CF3 | Br | | =CH-piperidine |
| 1019 | CF3 | Br | | =CH-morpholine |
| 1020 | CF3 | Br | | =CH-pyrrolidine |
| 1021 | CF3 | Br | H | indan-1-yl |
| 1022 | CF3 | Br | H | tetrahydrofuran-2-ylmethyl |
| 1023 | CF2Cl | Br | H | H |
| 1024 | CF2Cl | Br | H | Me |
| 1025 | CF2Cl | Br | H | Et |
| 1026 | CF2Cl | Br | H | Pr |
| 1027 | CF2Cl | Br | H | iPr |
| 1028 | CF2Cl | Br | H | cPr |
| 1029 | CF2Cl | Br | H | Bu |
| 1030 | CF2Cl | Br | H | cBu |
| 1031 | CF2Cl | Br | H | tBu |
| 1032 | CF2Cl | Br | Me | Me |
| 1033 | CF2Cl | Br | Me | Et |
| 1034 | CF2Cl | Br | Me | Bu |
| 1035 | CF2Cl | Br | Me | Pr |
| 1036 | CF2Cl | Br | Me | iPr |
| 1037 | CF2Cl | Br | Et | Et |
| 1038 | CF2Cl | Br | Et | Pr |
| 1039 | CF2Cl | Br | Et | iPr |
| 1040 | CF2Cl | Br | Pr | Pr |
| 1041 | CF2Cl | Br | H | cPentyl |
| 1042 | CF2Cl | Br | H | cHexyl |
| 1043 | CF2Cl | Br | H | CH2(CH2)3CH3 |
| 1044 | CF2Cl | Br | H | CH2(CH2)4CH3 |
| 1045 | CF2Cl | Br | H | CH2—cPr |
| 1046 | CF2Cl | Br | H | CH2—CN |
| 1047 | CF2Cl | Br | H | CH2—C(CH3)3 |
| 1048 | CF2Cl | Br | H | CH2CF2CF3 |
| 1049 | CF2Cl | Br | H | CH2CF3 |
| 1050 | CF2Cl | Br | H | CH2(CF2)2CF3 |
| 1051 | CF2Cl | Br | H | CH2CH(CH3)CH2CH3 |
| 1052 | CF2Cl | Br | H | CH2C(CH3)2CH2F |
| 1053 | CF2Cl | Br | H | CH2CH(CH3)2 |
| 1054 | CF2Cl | Br | H | CH2CH(CH2CH3)2 |
| 1055 | CF2Cl | Br | H | CH2CH2CH(CH3)2 |
| 1056 | CF2Cl | Br | H | CH2CH2C(CH3)3 |
| 1057 | CF2Cl | Br | H | CH2CH=CH2 |
| 1058 | CF2Cl | Br | Me | CH2CH=CH2 |
| 1059 | CF2Cl | Br | CH2CH=CH2 | CH2CH=CH2 |
| 1060 | CF2Cl | Br | H | CH2CH=CHCH3 |
| 1061 | CF2Cl | Br | H | CH2—C(CH3)=CH2 |
| 1062 | CF2Cl | Br | H | CH2—C≡CH |
| 1063 | CF2Cl | Br | Me | CH2—C≡CH |
| 1064 | CF2Cl | Br | H | CH(CH3)CH2CH3 |
| 1065 | CF2Cl | Br | H | CH(CH3)cPr |
| 1066 | CF2Cl | Br | H | CH(CH3)(CH2)2CH3 |
| 1067 | CF2Cl | Br | H | CH(CH3)(CH2)4CH3 |
| 1068 | CF2Cl | Br | H | CH(CH3)(CH2)5CH3 |
| 1069 | CF2Cl | Br | H | CH(CH2CH3)(CH2)3CH3 |
| 1070 | CF2Cl | Br | H | CH(CH3)CH2CH(CH3)2 |
| 1071 | CF2Cl | Br | H | CH(CH3)C(CH3)3 |
| 1072 | CF2Cl | Br | H | CH(CH3)CH(CH3)2 |
| 1073 | CF2Cl | Br | H | CH(CH3)CH2CH2CH(CH3)2 |
| 1074 | CF2Cl | Br | H | CH(CH2CH3)2 |
| 1075 | CF2Cl | Br | H | C(CH3)2CH2CH3 |
| 1076 | CF2Cl | Br | H | C(CH3)2C(CH3)3 |
| 1077 | CF2Cl | Br | H | CH2—CH(OMe)2 |
| 1078 | CF2Cl | Br | H | CH2—CH(OEt)2 |
| 1079 | CF2Cl | Br | H | CH2CH2—OH |
| 1080 | CF2Cl | Br | H | CH2CH2—OMe |
| 1081 | CF2Cl | Br | Me | CH2CH2—OMe |
| 1082 | CF2Cl | Br | H | CH2CH2—OEt |
| 1083 | CF2Cl | Br | H | CH2CH2—SMe |
| 1084 | CF2Cl | Br | H | CH2CH2—CN |
| 1085 | CF2Cl | Br | H | CH2CH2—NMe2 |
| 1086 | CF2Cl | Br | H | CH2CH2-morpholin-4-yl |
| 1087 | CF2Cl | Br | H | CH(CH3)CH2—OMe |
| 1088 | CF2Cl | Br | H | CH(CH3)CH2—NMe2 |
| 1089 | CF2Cl | Br | H | CH2CH2CH2—OMe |
| 1090 | CF2Cl | Br | H | CH2CH2CH2—SMe |
| 1091 | CF2Cl | Br | H | CH2CH2CH2—OEt |
| 1092 | CF2Cl | Br | H | CH2CH2CH2—OiPr |
| 1093 | CF2Cl | Br | H | CH2CH2CH2—OBu |
| 1094 | CF2Cl | Br | H | CH2—COOCH3 |
| 1095 | CF2Cl | Br | Me | CH2—COOCH3 |
| 1096 | CF2Cl | Br | H | CH(CH3)COOMe |
| 1097 | CF2Cl | Br | H | CH(CH3)COOEt |
| 1098 | CF2Cl | Br | H | CH2CH2—COOCH3 |
| 1099 | CF2Cl | Br | H | CH(COOCH3)2 |
| 1100 | CF2Cl | Br | H | CH(COOEt)CH2—CH(CH3)2 |
| 1101 | CF2Cl | Br | H | CH(COOMe)CH(CH3)2 |
| 1102 | CF2Cl | Br | H | O—CH2CH3 |
| 1103 | CF2Cl | Br | Me | O—CH3 |
| 1104 | CF2Cl | Br | H | O—CH2CH=CH2 |
| 1105 | CF2Cl | Br | H | O—tBu |
| 1106 | CF2Cl | Br | H | O—Pr |
| 1107 | CF2Cl | Br | H | O—CH2cPr |
| 1108 | CF2Cl | Br | H | O—CH2CH(CH3)2 |
| 1109 | CF2Cl | Br | H | O—CH2CF3 |
| 1110 | CF2Cl | Br | H | O—CH(CH3)cPr |
| 1111 | CF2Cl | Br | H | O—CH2CH2Cl |
| 1112 | CF2Cl | Br | H | O—CH2C≡CH |
| 1113 | CF2Cl | Br | H | O—CH2C≡CCH3 |
| 1114 | CF2Cl | Br | H | O—CH(CH3)C≡CH |
| 1115 | CF2Cl | Br | H | CH2—Ph |
| 1116 | CF2Cl | Br | Me | CH2—Ph |
| 1117 | CF2Cl | Br | H | CH2-pyridin-3-yl |
| 1118 | CF2Cl | Br | H | CH2-6-Cl-pyridin-3-yl |
| 1119 | CF2Cl | Br | H | CH(CH3)Ph |
| 1120 | CF2Cl | Br | H | CH2CH2—Ph |
| 1121 | CF2Cl | Br | H | CH2-2-CF3—Ph |
| 1122 | CF2Cl | Br | H | CH2CH2CHPh2 |
| 1123 | CF2Cl | Br | | morpholin-4-yl |
| 1124 | CF2Cl | Br | | piperidin-1-yl |
| 1125 | CF2Cl | Br | | thiazolidin-3-yl |
| 1126 | CF2Cl | Br | | pyrrolidin-1-yl |
| 1127 | CF2Cl | Br | | 2-methylpyrrolidin-1-yl |
| 1128 | CF2Cl | Br | | =CH—N(CH3)2 |
| 1129 | CF2Cl | Br | | =C(CH3)N(CH3)2 |
| 1130 | CF2Cl | Br | | =CH—N(C2H5)2 |
| 1131 | CF2Cl | Br | | =C(CH3)N(C2H5)2 |
| 1132 | CF2Cl | Br | | =CH-piperidine |
| 1133 | CF2Cl | Br | | =CH-morpholine |
| 1134 | CF2Cl | Br | | =CH-pyrrolidine |
| 1135 | CF2Cl | Br | H | indan-1-yl |
| 1136 | CF2Cl | Br | H | tetrahydrofuran-2-ylmethyl |
| 1137 | CHF2 | Br | H | H |
| 1138 | CHF2 | Br | H | Me |

TABLE 1-continued

Compounds of the formula (I)

$$\text{(I)} \quad \begin{array}{c}\text{R}^2\text{-pyridinone with C(O)N(R}^3\text{)(R}^4\text{) and R}^1\end{array}$$

| Ex. | R¹ | R² | R³ | R⁴ |
|---|---|---|---|---|
| 1139 | CHF2 | Br | H | Et |
| 1140 | CHF2 | Br | H | Pr |
| 1141 | CHF2 | Br | H | iPr |
| 1142 | CHF2 | Br | H | cPr |
| 1143 | CHF2 | Br | H | Bu |
| 1144 | CHF2 | Br | H | cBu |
| 1145 | CHF2 | Br | H | tBu |
| 1146 | CHF2 | Br | Me | Me |
| 1147 | CHF2 | Br | Me | Et |
| 1148 | CHF2 | Br | Me | Bu |
| 1149 | CHF2 | Br | Me | Pr |
| 1150 | CHF2 | Br | Me | iPr |
| 1151 | CHF2 | Br | Et | Et |
| 1152 | CHF2 | Br | Et | Pr |
| 1153 | CHF2 | Br | Et | iPr |
| 1154 | CHF2 | Br | Pr | Pr |
| 1155 | CHF2 | Br | H | cPentyl |
| 1156 | CHF2 | Br | H | cHexyl |
| 1157 | CHF2 | Br | H | CH2(CH2)3CH3 |
| 1158 | CHF2 | Br | H | CH2(CH2)4CH3 |
| 1159 | CHF2 | Br | H | CH2—cPr |
| 1160 | CHF2 | Br | H | CH2—CN |
| 1161 | CHF2 | Br | H | CH2—C(CH3)3 |
| 1162 | CHF2 | Br | H | CH2CF2CF3 |
| 1163 | CHF2 | Br | H | CH2CF3 |
| 1164 | CHF2 | Br | H | CH2(CF2)2CF3 |
| 1165 | CHF2 | Br | H | CH2CH(CH3)CH2CH3 |
| 1166 | CHF2 | Br | H | CH2C(CH3)2CH2F |
| 1167 | CHF2 | Br | H | CH2CH(CH3)2 |
| 1168 | CHF2 | Br | H | CH2CH(CH2CH3)2 |
| 1169 | CHF2 | Br | H | CH2CH2CH(CH3)2 |
| 1170 | CHF2 | Br | H | CH2CH2C(CH3)3 |
| 1171 | CHF2 | Br | H | CH2CH=CH2 |
| 1172 | CHF2 | Br | Me | CH2CH=CH2 |
| 1173 | CHF2 | Br | CH2CH=CH2 | CH2CH=CH2 |
| 1174 | CHF2 | Br | H | CH2CH=CHCH3 |
| 1175 | CHF2 | Br | H | CH2—C(CH3)=CH2 |
| 1176 | CHF2 | Br | H | CH2—C≡CH |
| 1177 | CHF2 | Br | Me | CH2—C≡CH |
| 1178 | CHF2 | Br | H | CH(CH3)CH2CH3 |
| 1179 | CHF2 | Br | H | CH(CH3)cPr |
| 1180 | CHF2 | Br | H | CH(CH3)(CH2)2CH3 |
| 1181 | CHF2 | Br | H | CH(CH3)(CH2)4CH3 |
| 1182 | CHF2 | Br | H | CH(CH3)(CH2)5CH3 |
| 1183 | CHF2 | Br | H | CH(CH2CH3)(CH2)3CH3 |
| 1184 | CHF2 | Br | H | CH(CH3)CH2CH(CH3)2 |
| 1185 | CHF2 | Br | H | CH(CH3)C(CH3)3 |
| 1186 | CHF2 | Br | H | CH(CH3)CH(CH3)2 |
| 1187 | CHF2 | Br | H | CH(CH3)CH2CH2CH(CH3)2 |
| 1188 | CHF2 | Br | H | CH(CH2CH3)2 |
| 1189 | CHF2 | Br | H | C(CH3)2CH2CH3 |
| 1190 | CHF2 | Br | H | C(CH3)2CH2C(CH3)3 |
| 1191 | CHF2 | Br | H | CH2—CH(OMe)2 |
| 1192 | CHF2 | Br | H | CH2—CH(OEt)2 |
| 1193 | CHF2 | Br | H | CH2CH2—OH |
| 1194 | CHF2 | Br | H | CH2CH2—OMe |
| 1195 | CHF2 | Br | Me | CH2CH2—OMe |
| 1196 | CHF2 | Br | H | CH2CH2—OEt |
| 1197 | CHF2 | Br | H | CH2CH2—SMe |
| 1198 | CHF2 | Br | H | CH2CH2—CN |
| 1199 | CHF2 | Br | H | CH2CH2—NMe2 |
| 1200 | CHF2 | Br | H | CH2CH2-morpholin-4-yl |
| 1201 | CHF2 | Br | H | CH(CH3)CH2—OMe |
| 1202 | CHF2 | Br | H | CH(CH3)CH2—NMe2 |
| 1203 | CHF2 | Br | H | CH2CH2CH2—OMe |
| 1204 | CHF2 | Br | H | CH2CH2CH2—SMe |
| 1205 | CHF2 | Br | H | CH2CH2CH2—OEt |
| 1206 | CHF2 | Br | H | CH2CH2CH2—OiPr |
| 1207 | CHF2 | Br | H | CH2CH2CH2—OBu |
| 1208 | CHF2 | Br | H | CH2—COOCH3 |
| 1209 | CHF2 | Br | Me | CH2—COOCH3 |
| 1210 | CHF2 | Br | H | CH(CH3)COOMe |
| 1211 | CHF2 | Br | H | CH(CH3)COOEt |
| 1212 | CHF2 | Br | H | CH2CH2—COOCH3 |
| 1213 | CHF2 | Br | H | CH(COOCH3)2 |
| 1214 | CHF2 | Br | H | CH(COOEt)CH2—CH(CH3)2 |
| 1215 | CHF2 | Br | H | CH(COOMe)CH(CH3)2 |
| 1216 | CHF2 | Br | H | O—CH2CH3 |
| 1217 | CHF2 | Br | Me | O—CH3 |
| 1218 | CHF2 | Br | H | O—CH2CH=CH2 |
| 1219 | CHF2 | Br | H | O—tBu |
| 1220 | CHF2 | Br | H | O—Pr |
| 1221 | CHF2 | Br | H | O—CH2cPr |
| 1222 | CHF2 | Br | H | O—CH2CH(CH3)2 |
| 1223 | CHF2 | Br | H | O—CH2CF3 |
| 1224 | CHF2 | Br | H | O—CH(CH3)cPr |
| 1225 | CHF2 | Br | H | O—CH2CH2Cl |
| 1226 | CHF2 | Br | H | O—CH2C≡CH |
| 1227 | CHF2 | Br | H | O—CH2C≡CCH3 |
| 1228 | CHF2 | Br | H | O—CH(CH3)C≡CH |
| 1229 | CHF2 | Br | H | CH2—Ph |
| 1230 | CHF2 | Br | Me | CH2—Ph |
| 1231 | CHF2 | Br | H | CH2-pyridin-3-yl |
| 1232 | CHF2 | Br | H | CH2-6-Cl-pyridin-3-yl |
| 1233 | CHF2 | Br | H | CH(CH3)Ph |
| 1234 | CHF2 | Br | H | CH2CH2—Ph |
| 1235 | CHF2 | Br | H | CH2-2-CF3—Ph |
| 1236 | CHF2 | Br | H | CH2CH2CHPh2 |
| 1237 | CHF2 | Br | | morpholin-4-yl |
| 1238 | CHF2 | Br | | piperidin-1-yl |
| 1239 | CHF2 | Br | | thiazolidin-3-yl |
| 1240 | CHF2 | Br | | pyrrolidin-1-yl |
| 1241 | CHF2 | Br | | 2-methylpyrrolidin-1-yl |
| 1242 | CHF2 | Br | | =CH—N(CH3)2 |
| 1243 | CHF2 | Br | | =C(CH3)N(CH3)2 |
| 1244 | CHF2 | Br | | =CH—N(C2H5)2 |
| 1245 | CHF2 | Br | | =C(CH3)N(C2H5)2 |
| 1246 | CHF2 | Br | | =CH-piperidine |
| 1247 | CHF2 | Br | | =CH-morpholine |
| 1248 | CHF2 | Br | | =CH-pyrrolidine |
| 1249 | CHF2 | Br | H | indan-1-yl |
| 1250 | CHF2 | Br | H | tetrahydrofuran-2-yl |
| 1251 | CF2CF3 | Br | H | H |
| 1252 | CF2CF3 | Br | H | Me |
| 1253 | CF2CF3 | Br | H | Ey |
| 1254 | CF2CF3 | Br | H | Pr |
| 1255 | CF2CF3 | Br | H | iPr |
| 1256 | CF2CF3 | Br | H | cPr |
| 1257 | CF2CF3 | Br | H | Bu |
| 1258 | CF2CF3 | Br | H | cBu |
| 1259 | CF2CF3 | Br | H | tBu |
| 1260 | CF2CF3 | Br | Me | Me |
| 1261 | CF2CF3 | Br | Me | Et |
| 1262 | CF2CF3 | Br | Me | Bu |
| 1263 | CF2CF3 | Br | Me | Pr |
| 1264 | CF2CF3 | Br | Me | iPr |
| 1265 | CF2CF3 | Br | Et | Et |
| 1266 | CF2CF3 | Br | Et | Pr |
| 1267 | CF2CF3 | Br | Et | iPr |
| 1268 | CF2CF3 | Br | Pr | Pr |
| 1269 | CF2CF3 | Br | H | cPentyl |
| 1270 | CF2CF3 | Br | H | cHexyl |

TABLE 1-continued

Compounds of the formula (I)

(I)

| Ex. | R¹ | R² | R³ | R⁴ |
|---|---|---|---|---|
| 1271 | CF2CF3 | Br | H | CH2(CH2)3CH3 |
| 1272 | CF2CF3 | Br | H | CH2(CH2)4CH3 |
| 1273 | CF2CF3 | Br | H | CH2—cPr |
| 1274 | CF2CF3 | Br | H | CH2—CN |
| 1275 | CF2CF3 | Br | H | CH2—C(CH3)3 |
| 1276 | CF2CF3 | Br | H | CH2CF2CF3 |
| 1277 | CF2CF3 | Br | H | CH2CF3 |
| 1278 | CF2CF3 | Br | H | CH2(CF2)2CF3 |
| 1279 | CF2CF3 | Br | H | CH2CH(CH3)CH2CH3 |
| 1280 | CF2CF3 | Br | H | CH2C(CH3)2CH2F |
| 1281 | CF2CF3 | Br | H | CH2CH(CH3)2 |
| 1282 | CF2CF3 | Br | H | CH2CH(CH2CH3)2 |
| 1283 | CF2CF3 | Br | H | CH2CH2CH(CH3)2 |
| 1284 | CF2CF3 | Br | H | CH2CH2C(CH3)3 |
| 1285 | CF2CF3 | Br | H | CH2CH=CH2 |
| 1286 | CF2CF3 | Br | Me | CH2CH=CH2 |
| 1287 | CF2CF3 | Br | CH2CH=CH2 | CH2CH=CH2 |
| 1288 | CF2CF3 | Br | H | CH2CH=CHCH3 |
| 1289 | CF2CF3 | Br | H | CH2—C(CH3)=CH2 |
| 1290 | CF2CF3 | Br | H | CH2—C≡CH |
| 1291 | CF2CF3 | Br | Me | CH2—C≡CH |
| 1292 | CF2CF3 | Br | H | CH(CH3)CH2CH3 |
| 1293 | CF2CF3 | Br | H | CH(CH3)cPr |
| 1294 | CF2CF3 | Br | H | CH(CH3)(CH2)2CH3 |
| 1295 | CF2CF3 | Br | H | CH(CH3)(CH2)4CH3 |
| 1296 | CF2CF3 | Br | H | CH(CH3)(CH2)5CH3 |
| 1297 | CF2CF3 | Br | H | CH(CH2CH3)(CH2)3CH3 |
| 1298 | CF2CF3 | Br | H | CH(CH3)CH2CH(CH3)2 |
| 1299 | CF2CF3 | Br | H | CH(CH3)C(CH3)3 |
| 1300 | CF2CF3 | Br | H | CH(CH3)CH(CH3)2 |
| 1301 | CF2CF3 | Br | H | CH(CH3)CH2CH2CH(CH3)2 |
| 1302 | CF2CF3 | Br | H | CH(CH2CH3)2 |
| 1303 | CF2CF3 | Br | H | C(CH3)2CH2CH3 |
| 1304 | CF2CF3 | Br | H | C(CH3)2CH2C(CH3)3 |
| 1305 | CF2CF3 | Br | H | CH2—CH(OMe)2 |
| 1306 | CF2CF3 | Br | H | CH2—CH(OEt)2 |
| 1307 | CF2CF3 | Br | H | CH2CH2—OH |
| 1308 | CF2CF3 | Br | H | CH2CH2—OMe |
| 1309 | CF2CF3 | Br | Me | CH2CH2—OMe |
| 1310 | CF2CF3 | Br | H | CH2CH2—OEt |
| 1311 | CF2CF3 | Br | H | CH2CH2—SMe |
| 1312 | CF2CF3 | Br | H | CH2CH2—CN |
| 1313 | CF2CF3 | Br | H | CH2CH2—NMe2 |
| 1314 | CF2CF3 | Br | H | CH2CH2-morpholin-4-yl |
| 1315 | CF2CF3 | Br | H | CH(CH3)CH2—OMe |
| 1316 | CF2CF3 | Br | H | CH(CH3)CH2—NMe2 |
| 1317 | CF2CF3 | Br | H | CH2CH2CH2—OMe |
| 1318 | CF2CF3 | Br | H | CH2CH2CH2—SMe |
| 1319 | CF2CF3 | Br | H | CH2CH2CH2—OEt |
| 1320 | CF2CF3 | Br | H | CH2CH2CH2—OiPr |
| 1321 | CF2CF3 | Br | H | CH2CH2CH2—OBu |
| 1322 | CF2CF3 | Br | H | CH2—COOCH3 |
| 1323 | CF2CF3 | Br | Me | CH2—COOCH3 |
| 1324 | CF2CF3 | Br | H | CH(CH3)COOMe |
| 1325 | CF2CF3 | Br | H | CH(CH3)COOEt |
| 1326 | CF2CF3 | Br | H | CH2CH2—COOCH3 |
| 1327 | CF2CF3 | Br | H | CH(COOCH3)2 |
| 1328 | CF2CF3 | Br | H | CH(COOEt)CH2—CH(CH3)2 |
| 1329 | CF2CF3 | Br | H | CH(COOMe)CH(CH3)2 |
| 1330 | CF2CF3 | Br | H | O—CH2CH3 |
| 1331 | CF2CF3 | Br | Me | O—CH3 |
| 1332 | CF2CF3 | Br | H | O—CH2CH=CH2 |
| 1333 | CF2CF3 | Br | H | O—tBu |
| 1334 | CF2CF3 | Br | H | O—Pr |
| 1335 | CF2CF3 | Br | H | O—CH2cPr |
| 1336 | CF2CF3 | Br | H | O—CH2CH(CH3)2 |
| 1337 | CF2CF3 | Br | H | O—CH2CF3 |
| 1338 | CF2CF3 | Br | H | O—CH(CH3)cPr |
| 1339 | CF2CF3 | Br | H | O—CH2CH2Cl |
| 1340 | CF2CF3 | Br | H | O—CH2C≡CH |
| 1341 | CF2CF3 | Br | H | O—CH2C≡CCH3 |
| 1342 | CF2CF3 | Br | H | O—CH(CH3)C≡CH |
| 1343 | CF2CF3 | Br | H | CH2—Ph |
| 1344 | CF2CF3 | Br | Me | CH2—Ph |
| 1345 | CF2CF3 | Br | H | CH2-pyridin-3-yl |
| 1346 | CF2CF3 | Br | H | CH2-6-Cl-pyridin-3-yl |
| 1347 | CF2CF3 | Br | H | CH(CH3)Ph |
| 1348 | CF2CF3 | Br | H | CH2CH2—Ph |
| 1349 | CF2CF3 | Br | H | CH2-2-CF3—Ph |
| 1350 | CF2CF3 | Br | H | CH2CH2CHPh2 |
| 1351 | CF2CF3 | Br | morpholin-4-yl | |
| 1352 | CF2CF3 | Br | piperidin-1-yl | |
| 1353 | CF2CF3 | Br | thiazolidin-3-yl | |
| 1354 | CF2CF3 | Br | pyrrolidin-1-yl | |
| 1355 | CF2CF3 | Br | 2-methylpyrrolidin-1-yl | |
| 1356 | CF2CF3 | Br | =CH—N(CH3)2 | |
| 1357 | CF2CF3 | Br | =C(CH3)N(CH3)2 | |
| 1358 | CF2CF3 | Br | =CH—N(C2H5)2 | |
| 1359 | CF2CF3 | Br | =C(CH3)N(C2H5)2 | |
| 1360 | CF2CF3 | Br | =CH-piperidine | |
| 1361 | CF2CF3 | Br | =CH-morpholine | |
| 1362 | CF2CF3 | Br | =CH-pyrrolidine | |
| 1363 | CF2CF3 | Br | H | indan-1-yl |
| 1364 | CF2CF3 | Br | H | tetrahydrofuran-2-ylmethyl |
| 1365 | CF2CF3 | I | H | H |
| 1366 | CF3 | I | H | H |
| 1367 | CF2CHF2 | H | H | H |
| 1368 | CF2CHF2 | H | H | Me |
| 1369 | CF2CHF2 | H | H | Et |
| 1370 | CF2CHF2 | H | H | Pr |
| 1371 | CF2CHF2 | H | H | iPr |
| 1372 | CF2CHF2 | H | H | cPr |
| 1373 | CF2CHF2 | H | H | Bu |
| 1374 | CF2CHF2 | H | H | cBu |
| 1375 | CF2CHF2 | H | H | tBu |
| 1376 | CF2CHF2 | H | Me | Me |
| 1377 | CF2CHF2 | H | Me | Et |
| 1378 | CF2CHF2 | H | Me | Bu |
| 1379 | CF2CHF2 | H | Me | Pr |
| 1380 | CF2CHF2 | H | Me | iPr |
| 1381 | CF2CHF2 | H | Et | Et |
| 1382 | CF2CHF2 | H | Et | Pr |
| 1383 | CF2CHF2 | H | Et | iPr |
| 1384 | CF2CHF2 | H | Pr | Pr |
| 1385 | CF2CHF2 | H | H | cPentyl |
| 1386 | CF2CHF2 | H | H | cHexyl |
| 1387 | CF2CHF2 | H | H | CH2(CH2)3CH3 |
| 1388 | CF2CHF2 | H | H | CH2(CH2)4CH3 |
| 1389 | CF2CHF2 | H | H | CH2—cPr |
| 1390 | CF2CHF2 | H | H | CH2—CN |
| 1391 | CF2CHF2 | H | H | CH2—C(CH3)3 |
| 1392 | CF2CHF2 | H | H | CH2CF2CF3 |
| 1393 | CF2CHF2 | H | H | CH2CF3 |
| 1394 | CF2CHF2 | H | H | CH2(CF2)2CF3 |
| 1395 | CF2CHF2 | H | H | CH2CH(CH3)CH2CH3 |
| 1396 | CF2CHF2 | H | H | CH2C(CH3)2CH2F |
| 1397 | CF2CHF2 | H | H | CH2CH(CH3)2 |
| 1398 | CF2CHF2 | H | H | CH2CH(CH2CH3)2 |
| 1399 | CF2CHF2 | H | H | CH2CH2CH(CH3)2 |
| 1400 | CF2CHF2 | H | H | CH2CH2C(CH3)3 |
| 1401 | CF2CHF2 | H | H | CH2CH=CH2 |
| 1402 | CF2CHF2 | H | Me | CH2CH=CH2 |

TABLE 1-continued

Compounds of the formula (I)

$$\text{(I)}$$

Structure: pyridinone with R¹, R² substituents and C(=O)N(R³)(R⁴) carboxamide group.

| Ex. | R¹ | R² | R³ | R⁴ |
|---|---|---|---|---|
| 1403 | CF2CHF2 | H | CH2CH=CH2 | CH2CH=CH2 |
| 1404 | CF2CHF2 | H | H | CH2CH=CHCH3 |
| 1405 | CF2CHF2 | H | H | CH2—C(CH3)=CH2 |
| 1406 | CF2CHF2 | H | H | CH2—C≡CH |
| 1407 | CF2CHF2 | H | Me | CH2—C≡CH |
| 1408 | CF2CHF2 | H | H | CH(CH3)CH2CH3 |
| 1409 | CF2CHF2 | H | H | CH(CH3)cPr |
| 1410 | CF2CHF2 | H | H | CH(CH3)(CH2)2CH3 |
| 1411 | CF2CHF2 | H | H | CH(CH3)(CH2)4CH3 |
| 1412 | CF2CHF2 | H | H | CH(CH3)(CH2)5CH3 |
| 1413 | CF2CHF2 | H | H | CH(CH2CH3)(CH2)3CH3 |
| 1414 | CF2CHF2 | H | H | CH(CH3)CH2CH(CH3)2 |
| 1415 | CF2CHF2 | H | H | CH(CH3)C(CH3)3 |
| 1416 | CF2CHF2 | H | H | CH(CH3)CH(CH3)2 |
| 1417 | CF2CHF2 | H | H | CH(CH3)CH2CH2CH(CH3)2 |
| 1418 | CF2CHF2 | H | H | CH(CH2CH3)2 |
| 1419 | CF2CHF2 | H | H | C(CH3)2CH2CH3 |
| 1420 | CF2CHF2 | H | H | C(CH3)2CH2C(CH3)3 |
| 1421 | CF2CHF2 | H | H | CH2—CH(OMe)2 |
| 1422 | CF2CHF2 | H | H | CH2—CH(OEt)2 |
| 1423 | CF2CHF2 | H | H | CH2CH2—OH |
| 1424 | CF2CHF2 | H | H | CH2CH2—OMe |
| 1425 | CF2CHF2 | H | Me | CH2CH2—OMe |
| 1426 | CF2CHF2 | H | H | CH2CH2—OEt |
| 1427 | CF2CHF2 | H | H | CH2CH2—SMe |
| 1428 | CF2CHF2 | H | H | CH2CH2—CN |
| 1429 | CF2CHF2 | H | H | CH2CH2—NMe2 |
| 1430 | CF2CHF2 | H | H | CH2CH2-morpholin-4-yl |
| 1431 | CF2CHF2 | H | H | CH(CH3)CH2—OMe |
| 1432 | CF2CHF2 | H | H | CH(CH3)CH2—NMe2 |
| 1433 | CF2CHF2 | H | H | CH2CH2CH2—OMe |
| 1434 | CF2CHF2 | H | H | CH2CH2CH2—SMe |
| 1435 | CF2CHF2 | H | H | CH2CH2CH2—OEt |
| 1436 | CF2CHF2 | H | H | CH2CH2CH2—OiPr |
| 1437 | CF2CHF2 | H | H | CH2CH2CH2—OBu |
| 1438 | CF2CHF2 | H | H | CH2—COOCH3 |
| 1439 | CF2CHF2 | H | Me | CH2—COOCH3 |
| 1440 | CF2CHF2 | H | H | CH(CH3)COOMe |
| 1441 | CF2CHF2 | H | H | CH(CH3)COOEt |
| 1442 | CF2CHF2 | H | H | CH2CH2—COOCH3 |
| 1443 | CF2CHF2 | H | H | CH(COOCH3)2 |
| 1444 | CF2CHF2 | H | H | CH(COOEt)CH2—CH(CH3)2 |
| 1445 | CF2CHF2 | H | H | CH(COOMe)CH(CH3)2 |
| 1446 | CF2CHF2 | H | H | O—CH2CH3 |
| 1447 | CF2CHF2 | H | H | O—CH3 |
| 1448 | CF2CHF2 | H | H | O—CH2CH=CH2 |
| 1449 | CF2CHF2 | H | H | O—tBu |
| 1450 | CF2CHF2 | H | H | O—Pr |
| 1451 | CF2CHF2 | H | H | O—CH2cPr |
| 1452 | CF2CHF2 | H | H | O—CH2CH(CH3)2 |
| 1453 | CF2CHF2 | H | H | O—CH2CF3 |
| 1454 | CF2CHF2 | H | H | O—CH(CH3)cPr |
| 1455 | CF2CHF2 | H | H | O—CH2CH2Cl |
| 1456 | CF2CHF2 | H | H | O—CH2C≡CH |
| 1457 | CF2CHF2 | H | H | O—CH2C≡CCH3 |
| 1458 | CF2CHF2 | H | H | O—CH(CH3)C≡CH |
| 1459 | CF2CHF2 | H | H | CH2—Ph |
| 1460 | CF2CHF2 | H | Me | CH2—Ph |
| 1461 | CF2CHF2 | H | H | CH2-pyridin-3-yl |
| 1462 | CF2CHF2 | H | H | CH2-6-Cl-pyridin-3-yl |
| 1463 | CF2CHF2 | H | H | CH(CH3)Ph |
| 1464 | CF2CHF2 | H | H | CH2CH2—Ph |
| 1465 | CF2CHF2 | H | H | CH2-2-CF3—Ph |
| 1466 | CF2CHF2 | H | H | CH2CH2CHPh |
| 1467 | CF2CHF2 | H | morpholin-4-yl | |
| 1468 | CF2CHF2 | H | piperidin-1-yl | |
| 1469 | CF2CHF2 | H | | thiazolidin-3-yl |
| 1470 | CF2CHF2 | H | | pyrrolidin-1-yl |
| 1471 | CF2CHF2 | H | | 2-methylpyrrolidin-1-yl |
| 1472 | CF2CHF2 | H | | =CH—N(CH3)2 |
| 1473 | CF2CHF2 | H | | =C(CH3)N(CH3)2 |
| 1474 | CF2CHF2 | H | | =CH—N(C2H5)2 |
| 1475 | CF2CHF2 | H | | =C(CH3)N(C2H5)2 |
| 1476 | CF2CHF2 | H | | =CH-piperidine |
| 1477 | CF2CHF2 | H | | =CH-morpholine |
| 1478 | CF2CHF2 | H | | =CH-pyrrolidine |
| 1479 | CF2CHF2 | H | H | indan-1-yl |
| 1480 | CF2CHF2 | H | H | tetrahydrofuran-2-ylmethyl |
| 1481 | CF2CF2Cl | H | H | H |
| 1482 | CF2CF2Cl | H | H | Me |
| 1483 | CF2CF2Cl | H | H | Et |
| 1484 | CF2CF2Cl | H | H | Pr |
| 1485 | CF2CF2Cl | H | H | iPr |
| 1486 | CF2CF2Cl | H | H | cPr |
| 1487 | CF2CF2Cl | H | H | Bu |
| 1488 | CF2CF2Cl | H | H | cBu |
| 1489 | CF2CF2Cl | H | H | tBu |
| 1490 | CF2CF2Cl | H | Me | Me |
| 1491 | CF2CF2Cl | H | Me | Et |
| 1492 | CF2CF2Cl | H | Me | Bu |
| 1493 | CF2CF2Cl | H | Me | Pr |
| 1494 | CF2CF2Cl | H | Me | iPr |
| 1495 | CF2CF2Cl | H | Et | Et |
| 1496 | CF2CF2Cl | H | Et | Pr |
| 1497 | CF2CF2Cl | H | Et | iPr |
| 1498 | CF2CF2Cl | H | Pr | Pr |
| 1499 | CF2CF2Cl | H | H | cPentyl |
| 1500 | CF2CF2Cl | H | H | cHexyl |
| 1501 | CF2CF2Cl | H | H | CH2(CH2)3CH3 |
| 1502 | CF2CF2Cl | H | H | CH2(CH2)4CH3 |
| 1503 | CF2CF2Cl | H | H | CH2—cPr |
| 1504 | CF2CF2Cl | H | H | CH2—CN |
| 1505 | CF2CF2Cl | H | H | CH2—C(CH3)3 |
| 1506 | CF2CF2Cl | H | H | CH2CF2CF3 |
| 1507 | CF2CF2Cl | H | H | CH2CF3 |
| 1508 | CF2CF2Cl | H | H | CH2(CF2)2CF3 |
| 1509 | CF2CF2Cl | H | H | CH2CH(CH3)CH2CH3 |
| 1510 | CF2CF2Cl | H | H | CH2C(CH3)2CH2F |
| 1511 | CF2CF2Cl | H | H | CH2CH(CH3)2 |
| 1512 | CF2CF2Cl | H | H | CH2CH(CH2CH3)2 |
| 1513 | CF2CF2Cl | H | H | CH2CH2CH(CH3)2 |
| 1514 | CF2CF2Cl | H | H | CH2CH2C(CH3)3 |
| 1515 | CF2CF2Cl | H | H | CH2CH=CH2 |
| 1516 | CF2CF2Cl | H | Me | CH2CH=CH2 |
| 1517 | CF2CF2Cl | H | CH2CH=CH2 | CH2CH=CH2 |
| 1518 | CF2CF2Cl | H | H | CH2CH=CHCH3 |
| 1519 | CF2CF2Cl | H | H | CH2—C(CH3)=CH2 |
| 1520 | CF2CF2Cl | H | H | CH2—C≡CH |
| 1521 | CF2CF2Cl | H | Me | CH2—C≡CH |
| 1522 | CF2CF2Cl | H | H | CH(CH3)CH2CH3 |
| 1523 | CF2CF2Cl | H | H | CH(CH3)cPr |
| 1524 | CF2CF2Cl | H | H | CH(CH3)(CH2)2CH3 |
| 1525 | CF2CF2Cl | H | H | CH(CH3)(CH2)4CH3 |
| 1526 | CF2CF2Cl | H | H | CH(CH3)(CH2)5CH3 |
| 1527 | CF2CF2Cl | H | H | CH(CH2CH3)(CH2)3CH3 |
| 1528 | CF2CF2Cl | H | H | CH(CH3)CH2CH(CH3)2 |
| 1529 | CF2CF2Cl | H | H | CH(CH3)C(CH3)3 |
| 1530 | CF2CF2Cl | H | H | CH(CH3)CH(CH3)2 |
| 1531 | CF2CF2Cl | H | H | CH(CH3)CH2CH2CH(CH3)2 |
| 1532 | CF2CF2Cl | H | H | CH(CH2CH3)2 |
| 1533 | CF2CF2Cl | H | H | C(CH3)2CH2CH3 |
| 1534 | CF2CF2Cl | H | H | C(CH3)2CH2C(CH3)3 |

TABLE 1-continued

Compounds of the formula (I)

$$\text{(I)} \quad \begin{array}{c} R^2 \\ R^1 \end{array} \text{pyridinone-carboxamide with } R^3, R^4$$

| Ex. | $R^1$ | $R^2$ | $R^3$ | $R^4$ |
|---|---|---|---|---|
| 1535 | CF2CF2Cl | H | H | CH2—CH(OMe)2 |
| 1536 | CF2CF2Cl | H | H | CH2—CH(OEt)2 |
| 1537 | CF2CF2Cl | H | H | CH2CH2—OH |
| 1538 | CF2CF2Cl | H | H | CH2CH2—OMe |
| 1539 | CF2CF2Cl | H | Me | CH2CH2—OMe |
| 1540 | CF2CF2Cl | H | H | CH2CH2—OEt |
| 1541 | CF2CF2Cl | H | H | CH2CH2—SMe |
| 1542 | CF2CF2Cl | H | H | CH2CH2—CN |
| 1543 | CF2CF2Cl | H | H | CH2CH2—NMe2 |
| 1544 | CF2CF2Cl | H | H | CH2CH2-morpholin-4-yl |
| 1545 | CF2CF2Cl | H | H | CH(CH3)CH2—OMe |
| 1546 | CF2CF2Cl | H | H | CH(CH3)CH2—NMe2 |
| 1547 | CF2CF2Cl | H | H | CH2CH2CH2—OMe |
| 1548 | CF2CF2Cl | H | H | CH2CH2CH2—SMe |
| 1549 | CF2CF2Cl | H | H | CH2CH2CH2—OEt |
| 1550 | CF2CF2Cl | H | H | CH2CH2CH2—OiPr |
| 1551 | CF2CF2Cl | H | H | CH2CH2CH2—OBu |
| 1552 | CF2CF2Cl | H | H | CH2—COOCH3 |
| 1553 | CF2CF2Cl | H | Me | CH2—COOCH3 |
| 1554 | CF2CF2Cl | H | H | CH(CH3)COOMe |
| 1555 | CF2CF2Cl | H | H | CH(CH3)COOEt |
| 1556 | CF2CF2Cl | H | H | CH2CH2—COOCH3 |
| 1557 | CF2CF2Cl | H | H | CH(COOCH3)2 |
| 1558 | CF2CF2Cl | H | H | CH(COOEt)CH2—CH(CH3)2 |
| 1559 | CF2CF2Cl | H | H | CH(COOMe)CH(CH3)2 |
| 1560 | CF2CF2Cl | H | H | O—CH2CH3 |
| 1561 | CF2CF2Cl | H | H | O—CH3 |
| 1562 | CF2CF2Cl | H | H | O—CH2CH=CH2 |
| 1563 | CF2CF2Cl | H | H | O—tBu |
| 1564 | CF2CF2Cl | H | H | O—Pr |
| 1565 | CF2CF2Cl | H | H | O—CH2cPr |
| 1566 | CF2CF2Cl | H | H | O—CH2CH(CH3)2 |
| 1567 | CF2CF2Cl | H | H | O—CH2CF3 |
| 1568 | CF2CF2Cl | H | H | O—CH(CH3)cPr |
| 1569 | CF2CF2Cl | H | H | O—CH2CH2Cl |
| 1570 | CF2CF2Cl | H | H | O—CH2C≡CH |
| 1571 | CF2CF2Cl | H | H | O—CH2C≡CCH3 |
| 1572 | CF2CF2Cl | H | H | O—CH(CH3)C≡CH |
| 1573 | CF2CF2Cl | H | H | CH2—Ph |
| 1574 | CF2CF2Cl | H | Me | CH2—Ph |
| 1575 | CF2CF2Cl | H | H | CH2-pyridin-3-yl |
| 1576 | CF2CF2Cl | H | H | CH2-6-Cl-pyridin-3-yl |
| 1577 | CF2CF2Cl | H | H | CH(CH3)Ph |
| 1578 | CF2CF2Cl | H | H | CH2CH2—Ph |
| 1579 | CF2CF2Cl | H | H | CH2-2-CF3—Ph |
| 1580 | CF2CF2Cl | H | H | CH2CH2CHPh |
| 1581 | CF2CF2Cl | H | \multicolumn{2}{l}{morpholin-4-yl} |
| 1582 | CF2CF2Cl | H | \multicolumn{2}{l}{piperidin-1-yl} |
| 1583 | CF2CF2Cl | H | \multicolumn{2}{l}{thiazolidin-3-yl} |
| 1584 | CF2CF2Cl | H | \multicolumn{2}{l}{pyrrolidin-1-yl} |
| 1585 | CF2CF2Cl | H | \multicolumn{2}{l}{2-methylpyrrolidin-1-yl} |
| 1586 | CF2CF2Cl | H | \multicolumn{2}{l}{=CH—N(CH3)2} |
| 1587 | CF2CF2Cl | H | \multicolumn{2}{l}{=C(CH3)N(CH3)2} |
| 1588 | CF2CF2Cl | H | \multicolumn{2}{l}{=CH—N(C2H5)2} |
| 1589 | CF2CF2Cl | H | \multicolumn{2}{l}{=C(CH3)N(C2H5)2} |
| 1590 | CF2CF2Cl | H | \multicolumn{2}{l}{=CH-piperidine} |
| 1591 | CF2CF2Cl | H | \multicolumn{2}{l}{=CH-morpholine} |
| 1592 | CF2CF2Cl | H | \multicolumn{2}{l}{=CH-pyrrolidine} |
| 1593 | CF2CF2Cl | H | H | indan-1-yl |
| 1594 | CF2CF2Cl | H | H | tetrahydrofuran-2-ylmethyl |
| 1595 | C3F7 | H | H | H |
| 1596 | C3F7 | H | H | Me |
| 1597 | C3F7 | H | H | Et |
| 1598 | C3F7 | H | H | Pr |
| 1599 | C3F7 | H | H | iPr |
| 1600 | C3F7 | H | H | cPr |
| 1601 | C3F7 | H | H | Bu |
| 1602 | C3F7 | H | H | cBu |
| 1603 | C3F7 | H | H | tBu |
| 1604 | C3F7 | H | Me | Me |
| 1605 | C3F7 | H | Me | Et |
| 1606 | C3F7 | H | Me | Bu |
| 1607 | C3F7 | H | Me | Pr |
| 1608 | C3F7 | H | Me | iPr |
| 1609 | C3F7 | H | Et | Et |
| 1610 | C3F7 | H | Et | Pr |
| 1611 | C3F7 | H | Et | iPr |
| 1612 | C3F7 | H | Pr | Pr |
| 1613 | C3F7 | H | H | cPentyl |
| 1614 | C3F7 | H | H | cHexyl |
| 1615 | C3F7 | H | H | CH2(CH2)3CH3 |
| 1616 | C3F7 | H | H | CH2(CH2)4CH3 |
| 1617 | C3F7 | H | H | CH2—cPr |
| 1618 | C3F7 | H | H | CH2—CN |
| 1619 | C3F7 | H | H | CH2—C(CH3)3 |
| 1620 | C3F7 | H | H | CH2CF2CF3 |
| 1621 | C3F7 | H | H | CH2CF3 |
| 1622 | C3F7 | H | H | CH2(CF2)2CF3 |
| 1623 | C3F7 | H | H | CH2CH(CH3)CH2CH3 |
| 1624 | C3F7 | H | H | CH2C(CH3)2CH2F |
| 1625 | C3F7 | H | H | CH2CH(CH3)2 |
| 1626 | C3F7 | H | H | CH2CH(CH2CH3)2 |
| 1627 | C3F7 | H | H | CH2CH2CH(CH3)2 |
| 1628 | C3F7 | H | H | CH2CH2C(CH3)3 |
| 1629 | C3F7 | H | H | CH2CH=CH2 |
| 1630 | C3F7 | H | Me | CH2CH=CH2 |
| 1631 | C3F7 | H | CH2CH=CH2 | CH2CH=CH2 |
| 1632 | C3F7 | H | H | CH2CH=CHCH3 |
| 1633 | C3F7 | H | H | CH2—C(CH3)=CH2 |
| 1634 | C3F7 | H | H | CH2—C≡CH |
| 1635 | C3F7 | H | Me | CH2—C≡CH |
| 1636 | C3F7 | H | H | CH(CH3)CH2CH3 |
| 1637 | C3F7 | H | H | CH(CH3)cPr |
| 1638 | C3F7 | H | H | CH(CH3)(CH2)2CH3 |
| 1639 | C3F7 | H | H | CH(CH3)(CH2)4CH3 |
| 1640 | C3F7 | H | H | CH(CH3)(CH2)5CH3 |
| 1641 | C3F7 | H | H | CH(CH2CH3)(CH2)3CH3 |
| 1642 | C3F7 | H | H | CH(CH3)CH2CH(CH3)2 |
| 1643 | C3F7 | H | H | CH(CH3)C(CH3)3 |
| 1644 | C3F7 | H | H | CH(CH3)CH(CH3)2 |
| 1645 | C3F7 | H | H | CH(CH3)CH2CH2CH(CH3)2 |
| 1646 | C3F7 | H | H | CH(CH2CH3)2 |
| 1647 | C3F7 | H | H | C(CH3)2CH2CH3 |
| 1648 | C3F7 | H | H | C(CH3)2CH2C(CH3)3 |
| 1649 | C3F7 | H | H | CH2—CH(OMe)2 |
| 1650 | C3F7 | H | H | CH2—CH(OEt)2 |
| 1651 | C3F7 | H | H | CH2CH2—OH |
| 1652 | C3F7 | H | H | CH2CH2—OMe |
| 1653 | C3F7 | H | Me | CH2CH2—OMe |
| 1654 | C3F7 | H | H | CH2CH2—OEt |
| 1655 | C3F7 | H | H | CH2CH2—SMe |
| 1656 | C3F7 | H | H | CH2CH2—CN |
| 1657 | C3F7 | H | H | CH2CH2—NMe2 |
| 1658 | C3F7 | H | H | CH2CH2-morpholin-4-yl |
| 1659 | C3F7 | H | H | CH(CH3)CH2—OMe |
| 1660 | C3F7 | H | H | CH(CH3)CH2—NMe2 |
| 1661 | C3F7 | H | H | CH2CH2CH2—OMe |
| 1662 | C3F7 | H | H | CH2CH2CH2—SMe |
| 1663 | C3F7 | H | H | CH2CH2CH2—OEt |
| 1664 | C3F7 | H | H | CH2CH2CH2—OiPr |
| 1665 | C3F7 | H | H | CH2CH2CH2—OBu |
| 1666 | C3F7 | H | H | CH2—COOCH3 |

TABLE 1-continued

Compounds of the formula (I)

| Ex. | R¹ | R² | R³ | R⁴ |
|---|---|---|---|---|
| 1667 | C3F7 | H | Me | CH2—COOCH3 |
| 1668 | C3F7 | H | H | CH(CH3)COOMe |
| 1669 | C3F7 | H | H | CH(CH3)COOEt |
| 1670 | C3F7 | H | H | CH2CH2—COOCH3 |
| 1671 | C3F7 | H | H | CH(COOCH3)2 |
| 1672 | C3F7 | H | H | CH(COOEt)CH2—CH(CH3)2 |
| 1673 | C3F7 | H | H | CH(COOMe)CH(CH3)2 |
| 1674 | C3F7 | H | H | O—CH2CH3 |
| 1675 | C3F7 | H | H | O—CH3 |
| 1676 | C3F7 | H | H | O—CH2CH=CH2 |
| 1677 | C3F7 | H | H | O—tBu |
| 1678 | C3F7 | H | H | O—Pr |
| 1679 | C3F7 | H | H | O—CH2cPr |
| 1680 | C3F7 | H | H | O—CH2CH(CH3)2 |
| 1681 | C3F7 | H | H | O—CH2CF3 |
| 1682 | C3F7 | H | H | O—CH(CH3)cPr |
| 1683 | C3F7 | H | H | O—CH2CH2Cl |
| 1684 | C3F7 | H | H | O—CH2C≡CH |
| 1685 | C3F7 | H | H | O—CH2C≡CCH3 |
| 1686 | C3F7 | H | H | O—CH(CH3)C≡CH |
| 1687 | C3F7 | H | H | CH2—Ph |
| 1688 | C3F7 | H | Me | CH2—Ph |
| 1689 | C3F7 | H | H | CH2-pyridin-3-yl |
| 1690 | C3F7 | H | H | CH2-6-Cl-pyridin-3-yl |
| 1691 | C3F7 | H | H | CH(CH3)Ph |
| 1692 | C3F7 | H | H | CH2CH2—Ph |
| 1693 | C3F7 | H | H | CH2-2-CF3—Ph |
| 1694 | C3F7 | H | H | CH2CH2CHPh |
| 1695 | C3F7 | H | morpholin-4-yl | |
| 1696 | C3F7 | H | piperidin-1-yl | |
| 1697 | C3F7 | H | thiazolidin-3-yl | |
| 1698 | C3F7 | H | pyrrolidin-1-yl | |
| 1699 | C3F7 | H | 2-methylpyrrolidin-1-yl | |
| 1700 | C3F7 | H | =CH—N(CH3)2 | |
| 1701 | C3F7 | H | =C(CH3)N(CH3)2 | |
| 1702 | C3F7 | H | =CH—N(C2H5)2 | |
| 1703 | C3F7 | H | =C(CH3)N(C2H5)2 | |
| 1704 | C3F7 | H | =CH-piperidine | |
| 1705 | C3F7 | H | =CH-morpholine | |
| 1706 | C3F7 | H | =CH-pyrrolidine | |
| 1707 | C3F7 | H | H | indan-1-yl |
| 1708 | C3F7 | H | H | tetrahydrofuran-2-ylmethyl |
| 1709 | CF(CF3)2 | H | H | H |
| 1710 | C3F7 | Cl | H | H |
| 1711 | C3F7 | Cl | H | Me |
| 1712 | C3F7 | Cl | H | Et |
| 1713 | C3F7 | Cl | H | Pr |
| 1714 | C3F7 | Cl | H | iPr |
| 1715 | C3F7 | Cl | H | cPr |
| 1716 | C3F7 | Cl | H | Bu |
| 1717 | C3F7 | Cl | H | cBu |
| 1718 | C3F7 | Cl | H | tBu |
| 1719 | C3F7 | Cl | Me | Me |
| 1720 | C3F7 | Cl | Et | Et |
| 1721 | C3F7 | Cl | H | CH2—cPr |
| 1722 | C3F7 | Cl | H | CH2—C(CH3)3 |
| 1723 | C3F7 | Cl | H | CH2CH(CH3)2 |
| 1724 | C3F7 | Cl | H | CH2CH(CH2CH3)2 |
| 1725 | C3F7 | Cl | H | CH2CH2CH(CH3)2 |
| 1726 | C3F7 | Cl | H | CH2CH2C(CH3)3 |
| 1727 | C3F7 | Cl | H | CH2CH=CH2 |
| 1728 | C3F7 | Cl | H | CH2—C(CH3)=CH2 |
| 1729 | C3F7 | Cl | H | CH2—CCH |
| 1730 | C3F7 | Cl | Me | CH2—CCH |
| 1731 | C3F7 | Cl | H | CH(CH3)CH2CH3 |
| 1732 | C3F7 | Cl | H | CH(CH3)cPr |
| 1733 | C3F7 | Cl | H | CH(CH3)(CH2)2CH3 |
| 1734 | C3F7 | Cl | H | CH(CH3)(CH2)4CH3 |
| 1735 | C3F7 | Cl | H | CH(CH3)CH2CH(CH3)2 |
| 1736 | C3F7 | Cl | H | CH(CH3)C(CH3)3 |
| 1737 | C3F7 | Cl | H | CH(CH3)CH(CH3)2 |
| 1738 | C3F7 | Cl | H | CH(CH2CH3)2 |
| 1739 | C3F7 | Cl | H | CH2—CH(OMe)2 |
| 1740 | C3F7 | Cl | H | CH2—CH(OEt)2 |
| 1741 | C3F7 | Cl | H | CH2CH2—OH |
| 1742 | C3F7 | Cl | H | CH2CH2—OMe |
| 1743 | C3F7 | Cl | Me | CH2CH2—OMe |
| 1744 | C3F7 | Cl | H | CH(CH3)CH2—OMe |
| 1745 | C3F7 | Cl | H | CH2CH2CH2—OMe |
| 1746 | C3F7 | Cl | H | CH2—COOCH3 |
| 1747 | C3F7 | Cl | Me | CH2—COOCH3 |
| 1748 | C3F7 | Cl | H | CH(CH3)COOMe |
| 1749 | C3F7 | Cl | H | CH(CH3)COOEt |
| 1750 | C3F7 | Cl | H | CH2CH2—COOCH3 |
| 1751 | C3F7 | Br | H | H |
| 1752 | C3F7 | Br | H | Me |
| 1753 | C3F7 | Br | H | Et |
| 1754 | C3F7 | Br | H | Pr |
| 1755 | C3F7 | Br | H | iPr |
| 1756 | C3F7 | Br | H | cPr |
| 1757 | C3F7 | Br | H | Bu |
| 1758 | C3F7 | Br | H | cBu |
| 1759 | C3F7 | Br | H | tBu |
| 1760 | C3F7 | Br | Me | Me |
| 1761 | C3F7 | Br | Et | Et |
| 1762 | C3F7 | Br | H | CH2-cPr |
| 1763 | C3F7 | Br | H | CH2—C(CH3)3 |
| 1764 | C3F7 | Br | H | CH2CH(CH3)2 |
| 1765 | C3F7 | Br | H | CH2CH(CH2CH3)2 |
| 1766 | C3F7 | Br | H | CH2CH2CH(CH3)2 |
| 1767 | C3F7 | Br | H | CH2CH2C(CH3)3 |
| 1768 | C3F7 | Br | H | CH2CH=CH2 |
| 1769 | C3F7 | Br | H | CH2—C(CH3)=CH2 |
| 1770 | C3F7 | Br | H | CH2—CCH |
| 1771 | C3F7 | Br | Me | CH2—CCH |
| 1772 | C3F7 | Br | H | CH(CH3)CH2CH3 |
| 1773 | C3F7 | Br | H | CH(CH3)cPr |
| 1774 | C3F7 | Br | H | CH(CH3)(CH2)2CH3 |
| 1775 | C3F7 | Br | H | CH(CH3)(CH2)4CH3 |
| 1776 | C3F7 | Br | H | CH(CH3)CH2CH(CH3)2 |
| 1777 | C3F7 | Br | H | CH(CH3)C(CH3)3 |
| 1778 | C3F7 | Br | H | CH(CH3)CH(CH3)2 |
| 1779 | C3F7 | Br | H | CH(CH3)CH2CH2CH(CH3)2 |
| 1780 | C3F7 | Br | H | CH(CH2CH3)2 |
| 1781 | C3F7 | Br | H | CH2—CH(OMe)2 |
| 1782 | C3F7 | Br | H | CH2—CH(OEt)2 |
| 1783 | C3F7 | Br | H | CH2CH2—OH |
| 1784 | C3F7 | Br | H | CH2CH2—OMe |
| 1785 | C3F7 | Br | H | CH(CH3)CH2—OMe |
| 1786 | C3F7 | Br | H | CH2CH2CH2—OMe |
| 1787 | C3F7 | Br | H | CH2—COOCH3 |
| 1788 | C3F7 | Br | Me | CH2—COOCH3 |
| 1789 | C3F7 | Br | H | CH(CH3)COOMe |
| 1790 | C3F7 | Br | H | CH(CH3)COOEt |
| 1791 | C3F7 | Br | H | CH2CH2—COOCH3 |
| 1792 | C3F7 | I | H | H |
| 1793 | C3F7 | I | H | Me |
| 1794 | C3F7 | I | H | Et |
| 1795 | C3F7 | I | H | Pr |
| 1796 | C3F7 | I | H | iPr |
| 1797 | C3F7 | I | H | cPr |
| 1798 | C3F7 | I | H | Bu |

TABLE 1-continued

Compounds of the formula (I)

| Ex. | R¹ | R² | R³ | R⁴ |
|---|---|---|---|---|
| 1799 | C3F7 | I | H | cBu |
| 1800 | C3F7 | I | H | tBu |
| 1801 | C3F7 | I | Me | Me |
| 1802 | C3F7 | I | Et | Et |
| 1803 | C3F7 | I | H | CH2—cPr |
| 1804 | C3F7 | I | H | CH2—C(CH3)3 |
| 1805 | C3F7 | I | H | CH2CH(CH3)2 |
| 1806 | C3F7 | I | H | CH2CH(CH2CH3)2 |
| 1807 | C3F7 | I | H | CH2CH2CH(CH3)2 |
| 1808 | C3F7 | I | H | CH2CH2C(CH3)3 |
| 1809 | C3F7 | I | H | CH2CH=CH2 |
| 1810 | C3F7 | I | H | CH2—C(CH3)=CH2 |
| 1811 | C3F7 | I | H | CH2—CCH |
| 1812 | C3F7 | I | Me | CH2—CCH |
| 1813 | C3F7 | I | H | CH(CH3)CH2CH3 |
| 1814 | C3F7 | I | H | CH(CH3)cPr |
| 1815 | C3F7 | I | H | CH(CH3)(CH2)2CH3 |
| 1816 | C3F7 | I | H | CH(CH3)(CH2)4CH3 |
| 1817 | C3F7 | I | H | CH(CH3)CH2CH(CH3)2 |
| 1818 | C3F7 | I | H | CH(CH3)C(CH3)3 |
| 1819 | C3F7 | I | H | CH(CH3)CH(CH3)2 |
| 1820 | C3F7 | I | H | CH(CH2CH3)2 |
| 1821 | C3F7 | I | H | CH2—CH(OMe)2 |
| 1822 | C3F7 | I | H | CH2—CH(OEt)2 |
| 1823 | C3F7 | I | H | CH2CH2—OH |
| 1824 | C3F7 | I | H | CH2CH2—OMe |
| 1825 | C3F7 | I | Me | CH2CH2—OMe |
| 1826 | C3F7 | I | H | CH(CH3)CH2—OMe |
| 1827 | C3F7 | I | H | CH2CH2CH2—OMe |
| 1828 | C3F7 | I | H | CH2—COOCH3 |
| 1829 | C3F7 | I | Me | CH2—COOCH3 |
| 1830 | C3F7 | I | H | CH(CH3)COOMe |
| 1831 | C3F7 | I | H | CH(CH3)COOEt |
| 1832 | C3F7 | I | H | CH2CH2—COOCH3 |
| 1833 | CF3 | I | H | Me |
| 1834 | CF3 | I | H | Et |
| 1835 | CF3 | I | H | Pr |
| 1836 | CF3 | I | H | iPr |
| 1837 | CF3 | I | H | cPr |
| 1838 | CF3 | I | H | Bu |
| 1839 | CF3 | I | H | cBu |
| 1840 | CF3 | I | H | tBu |
| 1841 | CF3 | I | Me | Me |
| 1842 | CF3 | I | Et | Et |
| 1843 | CF3 | I | H | CH2(CH2)3CH3 |
| 1844 | CF3 | I | H | CH2(CH2)4CH3 |
| 1845 | CF3 | I | H | CH2—cPr |
| 1846 | CF3 | I | H | CH2—C(CH3)3 |
| 1847 | CF3 | I | H | CH2CH(CH3)2 |
| 1848 | CF3 | I | H | CH2CH(CH2CH3)2 |
| 1849 | CF3 | I | H | CH2CH2CH(CH3)2 |
| 1850 | CF3 | I | H | CH2CH2C(CH3)3 |
| 1851 | CF3 | I | H | CH2CH=CH2 |
| 1852 | CF3 | I | H | CH2—C(CH3)=CH2 |
| 1853 | CF3 | I | H | CH2—CCH |
| 1854 | CF3 | I | H | CH(CH3)CH2CH3 |
| 1855 | CF3 | I | H | CH(CH3)cPr |
| 1856 | CF3 | I | H | CH(CH3)(CH2)2CH3 |
| 1857 | CF3 | I | H | CH(CH3)(CH2)4CH3 |
| 1858 | CF3 | I | H | CH(CH3)CH2CH(CH3)2 |
| 1859 | CF3 | I | H | CH(CH3)C(CH3)3 |
| 1860 | CF3 | I | H | CH(CH3)CH(CH3)2 |
| 1861 | CF3 | I | H | CH(CH2CH3)2 |
| 1862 | CF3 | I | H | C(CH3)2CH2CH3 |
| 1863 | CF3 | I | H | C(CH3)2CH2C(CH3)3 |
| 1864 | CF3 | I | H | CH2—CH(OMe)2 |
| 1865 | CF3 | I | H | CH2—CH(OEt)2 |
| 1866 | CF3 | I | H | CH2CH2—OH |
| 1867 | CF3 | I | H | CH2CH2—OMe |
| 1868 | CF3 | I | Me | CH2CH2—OMe |
| 1869 | CF3 | I | H | CH(CH3)CH2—OMe |
| 1870 | CF3 | I | H | CH2CH2CH2—OMe |
| 1871 | CF3 | I | H | CH2—COOCH3 |
| 1872 | CF3 | I | Me | CH2—COOCH3 |
| 1873 | CF3 | I | H | CH(CH3)COOMe |
| 1874 | CF3 | I | H | CH(CH3)COOEt |
| 1875 | CF3 | I | H | CH2CH2—COOCH3 |
| 1876 | CF2Cl | I | H | H |
| 1877 | CF2Cl | I | H | Me |
| 1878 | CF2Cl | I | H | Et |
| 1879 | CF2Cl | I | H | Pr |
| 1880 | CF2Cl | I | H | iPr |
| 1881 | CF2Cl | I | H | cPr |
| 1882 | CF2Cl | I | H | Bu |
| 1883 | CF2Cl | I | H | cBu |
| 1884 | CF2Cl | I | H | tBu |
| 1885 | CF2Cl | I | Me | Me |
| 1886 | CF2Cl | I | H | CH2—cPr |
| 1887 | CF2Cl | I | H | CH2—C(CH3)3 |
| 1888 | CF2Cl | I | H | CH2CH(CH3)2 |
| 1889 | CF2Cl | I | H | CH2CH(CH2CH3)2 |
| 1890 | CF2Cl | I | H | CH2CH2CH(CH3)2 |
| 1891 | CF2Cl | I | H | CH2CH2C(CH3)3 |
| 1892 | CF2Cl | I | H | CH2CH=CH2 |
| 1893 | CF2Cl | I | Me | CH2CH=CH2 |
| 1894 | CF2Cl | I | H | CH2—C(CH3)=CH2 |
| 1895 | CF2Cl | I | H | CH2—CCH |
| 1896 | CF2Cl | I | Me | CH2—CCH |
| 1897 | CF2Cl | I | H | CH(CH3)CH2CH3 |
| 1898 | CF2Cl | I | H | CH(CH3)cPr |
| 1899 | CF2Cl | I | H | CH(CH3)(CH2)2CH3 |
| 1900 | CF2Cl | I | H | CH(CH3)(CH2)4CH3 |
| 1901 | CF2Cl | I | H | CH(CH3)(CH2)5CH3 |
| 1902 | CF2Cl | I | H | CH(CH2CH3)(CH2)3CH3 |
| 1903 | CF2Cl | I | H | CH(CH3)CH2CH(CH3)2 |
| 1904 | CF2Cl | I | H | CH(CH3)C(CH3)3 |
| 1905 | CF2Cl | I | H | CH(CH3)CH(CH3)2 |
| 1906 | CF2Cl | I | H | CH(CH3)CH2CH2CH(CH3)2 |
| 1907 | CF2Cl | I | H | CH(CH2CH3)2 |
| 1908 | CF2Cl | I | H | C(CH3)2CH2CH3 |
| 1909 | CF2Cl | I | H | C(CH3)2CH2C(CH3)3 |
| 1910 | CF2Cl | I | H | CH2—CH(OMe)2 |
| 1911 | CF2Cl | I | H | CH2—CH(OEt)2 |
| 1912 | CF2Cl | I | H | CH2CH2—OH |
| 1913 | CF2Cl | I | H | CH2CH2—OMe |
| 1914 | CF2Cl | I | Me | CH2CH2—OMe |
| 1915 | CF2Cl | I | H | CH2CH2—OEt |
| 1916 | CF2Cl | I | H | CH(CH3)CH2—OMe |
| 1917 | CF2Cl | I | H | CH2CH2CH2—OMe |
| 1918 | CF2Cl | I | H | CH2—COOCH3 |
| 1919 | CF2Cl | I | Me | CH2—COOCH3 |
| 1920 | CF2Cl | I | H | CH(CH3)COOMe |
| 1921 | CF2Cl | I | H | CH(CH3)COOEt |
| 1922 | CF2Cl | I | H | CH2CH2—COOCH3 |
| 1923 | CF2CF3 | I | H | Me |
| 1924 | CF2CF3 | I | H | Et |
| 1925 | CF2CF3 | I | H | Pr |
| 1926 | CF2CF3 | I | H | iPr |
| 1927 | CF2CF3 | I | H | cPr |
| 1928 | CF2CF3 | I | H | Bu |
| 1929 | CF2CF3 | I | H | cBu |
| 1930 | CF2CF3 | I | H | tBu |

TABLE 1-continued

Compounds of the formula (I)

(I) Structure: Pyridinone with R¹ at 6-position, R² at 5-position, C(=O)N(R³)(R⁴) at 3-position, NH at 1-position, C=O at 2-position.

| Ex. | R¹ | R² | R³ | R⁴ |
|---|---|---|---|---|
| 1931 | CF2CF3 | I | Me | Me |
| 1932 | CF2CF3 | I | Et | Et |
| 1933 | CF2CF3 | I | H | CH2—cPr |
| 1934 | CF2CF3 | I | H | CH2—C(CH3)3 |
| 1935 | CF2CF3 | I | H | CH2CH(CH3)2 |
| 1936 | CF2CF3 | I | H | CH2CH(CH2CH3)2 |
| 1937 | CF2CF3 | I | H | CH2CH2CH(CH3)2 |
| 1938 | CF2CF3 | I | H | CH2CH2C(CH3)3 |
| 1939 | CF2CF3 | I | H | CH2CH=CH2 |
| 1940 | CF2CF3 | I | Me | CH2CH=CH2 |
| 1941 | CF2CF3 | I | H | CH2—C(CH3)=CH2 |
| 1942 | CF2CF3 | I | H | CH2—CCH |
| 1943 | CF2CF3 | I | Me | CH2—CCH |
| 1944 | CF2CF3 | I | H | CH(CH3)CH2CH3 |
| 1945 | CF2CF3 | I | H | CH(CH3)cPr |
| 1946 | CF2CF3 | I | H | CH(CH3)(CH2)2CH3 |
| 1947 | CF2CF3 | I | H | CH(CH3)(CH2)4CH3 |
| 1948 | CF2CF3 | I | H | CH(CH3)CH2CH(CH3)2 |
| 1949 | CF2CF3 | I | H | CH(CH3)C(CH3)3 |
| 1950 | CF2CF3 | I | H | CH(CH3)CH(CH3)2 |
| 1951 | CF2CF3 | I | H | CH(CH2CH3)2 |
| 1952 | CF2CF3 | I | H | CH2—CH(OMe)2 |
| 1953 | CF2CF3 | I | H | CH2—CH(OEt)2 |
| 1954 | CF2CF3 | I | HH | CH2CH2—OH |
| 1955 | CF2CF3 | I | H | CH2CH2—OMe |
| 1956 | CF2CF3 | I | Me | CH2CH2—OMe |
| 1957 | CF2CF3 | I | H | CH(CH3)CH2—OMe |
| 1958 | CF2CF3 | I | H | CH2CH2CH2—OMe |
| 1959 | CF2CF3 | I | H | CH2—COOCH3 |
| 1960 | CF2CF3 | I | Me | CH2—COOCH3 |
| 1961 | CF2CF3 | I | H | CH(CH3)COOMe |
| 1962 | CF2CF3 | I | H | CH(CH3)COOEt |
| 1963 | CF2CF3 | I | H | CH2CH2—COOCH3 |
| 1964 | CF2CF2Cl | Cl | H | H |
| 1965 | CF2CF2Cl | Cl | H | Me |
| 1966 | CF2CF2Cl | Cl | H | Et |
| 1967 | CF2CF2Cl | Cl | H | Pr |
| 1968 | CF2CF2Cl | Cl | H | iPr |
| 1969 | CF2CF2Cl | Cl | H | cPr |
| 1970 | CF2CF2Cl | Cl | H | Bu |
| 1971 | CF2CF2Cl | Cl | H | cBu |
| 1972 | CF2CF2Cl | Cl | H | tBu |
| 1973 | CF2CF2Cl | Cl | Me | Me |
| 1974 | CF2CF2Cl | Cl | Et | Et |
| 1975 | CF2CF2Cl | Cl | H | CH2—cPr |
| 1976 | CF2CF2Cl | Cl | H | CH2—C(CH3)3 |
| 1977 | CF2CF2Cl | Cl | H | CH2CH(CH3)2 |
| 1978 | CF2CF2Cl | Cl | H | CH2CH(CH2CH3)2 |
| 1979 | CF2CF2Cl | Cl | H | CH2CH2CH(CH3)2 |
| 1980 | CF2CF2Cl | Cl | H | CH2CH2C(CH3)3 |
| 1981 | CF2CF2Cl | Cl | H | CH2CH=CH2 |
| 1982 | CF2CF2Cl | Cl | Me | CH2CH=CH2 |
| 1983 | CF2CF2Cl | Cl | H | CH2—C(CH3)=CH2 |
| 1984 | CF2CF2Cl | Cl | H | CH2—CCH |
| 1985 | CF2CF2Cl | Cl | Me | CH2—CCH |
| 1986 | CF2CF2Cl | Cl | H | CH(CH3)CH2CH3 |
| 1987 | CF2CF2Cl | Cl | H | CH(CH3)cPr |
| 1988 | CF2CF2Cl | Cl | H | CH(CH3)(CH2)2CH3 |
| 1989 | CF2CF2Cl | Cl | H | CH(CH3)(CH2)4CH3 |
| 1990 | CF2CF2Cl | Cl | H | CH(CH3)CH2CH(CH3)2 |
| 1991 | CF2CF2Cl | Cl | H | CH(CH3)C(CH3)3 |
| 1992 | CF2CF2Cl | Cl | H | CH(CH3)CH(CH3)2 |
| 1993 | CF2CF2Cl | Cl | H | CH(CH2CH3)2 |
| 1994 | CF2CF2Cl | Cl | H | CH2—CH(OMe)2 |
| 1995 | CF2CF2Cl | Cl | H | CH2—CH(OEt)2 |
| 1996 | CF2CF2Cl | Cl | H | CH2CH2—OH |
| 1997 | CF2CF2Cl | Cl | H | CH2CH2—OMe |
| 1998 | CF2CF2Cl | Cl | Me | CH2CH2—OMe |
| 1999 | CF2CF2Cl | Cl | H | CH(CH3)CH2—OMe |
| 2000 | CF2CF2Cl | Cl | H | CH2CH2CH2—OMe |
| 2001 | CF2CF2Cl | Cl | H | CH2—COOCH3 |
| 2002 | CF2CF2Cl | Cl | Me | CH2—COOCH3 |
| 2003 | CF2CF2Cl | Cl | H | CH(CH3)COOMe |
| 2004 | CF2CF2Cl | Cl | H | CH(CH3)COOEt |
| 2005 | CF2CF2Cl | Cl | H | CH2CH2—COOCH3 |
| 2006 | CF2CF2Cl | Br | H | H |
| 2007 | CF2CF2Cl | Br | H | Me |
| 2008 | CF2CF2Cl | Br | H | Et |
| 2009 | CF2CF2Cl | Br | H | Pr |
| 2010 | CF2CF2Cl | Br | H | iPr |
| 2011 | CF2CF2Cl | Br | H | cPr |
| 2012 | CF2CF2Cl | Br | H | Bu |
| 2013 | CF2CF2Cl | Br | H | cBu |
| 2014 | CF2CF2Cl | Br | H | tBu |
| 2015 | CF2CF2Cl | Br | Me | Me |
| 2016 | CF2CF2Cl | Br | Et | Et |
| 2017 | CF2CF2Cl | Br | H | CH2—cPr |
| 2018 | CF2CF2Cl | Br | H | CH2—C(CH3)3 |
| 2019 | CF2CF2Cl | Br | H | CH2CH(CH3)2 |
| 2020 | CF2CF2Cl | Br | H | CH2CH(CH2CH3)2 |
| 2021 | CF2CF2Cl | Br | H | CH2CH2CH(CH3)2 |
| 2022 | CF2CF2Cl | Br | H | CH2CH2C(CH3)3 |
| 2023 | CF2CF2Cl | Br | H | CH2CH=CH2 |
| 2024 | CF2CF2Cl | Br | Me | CH2CH=CH2 |
| 2025 | CF2CF2Cl | Br | H | CH2—C(CH3)=CH2 |
| 2026 | CF2CF2Cl | Br | H | CH2—CCH |
| 2027 | CF2CF2Cl | Br | Me | CH2—CCH |
| 2028 | CF2CF2Cl | Br | H | CH(CH3)CH2CH3 |
| 2029 | CF2CF2Cl | Br | H | CH(CH3)cPr |
| 2030 | CF2CF2Cl | Br | H | CH(CH3)(CH2)2CH3 |
| 2031 | CF2CF2Cl | Br | H | CH(CH3)(CH2)4CH3 |
| 2032 | CF2CF2Cl | Br | H | CH(CH3)CH2CH(CH3)2 |
| 2033 | CF2CF2Cl | Br | H | CH(CH3)C(CH3)3 |
| 2034 | CF2CF2Cl | Br | H | CH(CH3)CH(CH3)2 |
| 2035 | CF2CF2Cl | Br | H | CH(CH2CH3)2 |
| 2036 | CF2CF2Cl | Br | H | CH2—CH(OMe)2 |
| 2037 | CF2CF2Cl | Br | H | CH2—CH(OEt)2 |
| 2038 | CF2CF2Cl | Br | H | CH2CH2—OH |
| 2039 | CF2CF2Cl | Br | H | CH2CH2—OMe |
| 2040 | CF2CF2Cl | Br | Me | CH2CH2—OMe |
| 2041 | CF2CF2Cl | Br | H | CH(CH3)CH2—OMe |
| 2042 | CF2CF2Cl | Br | H | CH2CH2CH2—OMe |
| 2043 | CF2CF2Cl | Br | H | CH2—COOCH3 |
| 2044 | CF2CF2Cl | Br | Me | CH2—COOCH3 |
| 2045 | CF2CF2Cl | Br | H | CH(CH3)COOMe |
| 2046 | CF2CF2Cl | Br | H | CH(CH3)COOEt |
| 2047 | CF2CF2Cl | Br | H | CH2CH2—COOCH3 |
| 2048 | CF2CF2Cl | I | H | H |
| 2049 | CF2CF2Cl | I | H | Me |
| 2050 | CF2CF2Cl | I | H | Et |
| 2051 | CF2CF2Cl | I | H | Pr |
| 2052 | CF2CF2Cl | I | H | iPr |
| 2053 | CF2CF2Cl | I | H | cPr |
| 2054 | CF2CF2Cl | I | H | Bu |
| 2055 | CF2CF2Cl | I | H | cBu |
| 2056 | CF2CF2Cl | I | H | tBu |
| 2057 | CF2CF2Cl | I | Me | Me |
| 2058 | CF2CF2Cl | I | Et | Et |
| 2059 | CF2CF2Cl | I | H | CH2—cPr |
| 2060 | CF2CF2Cl | I | H | CH2—C(CH3)3 |
| 2061 | CF2CF2Cl | I | H | CH2CH(CH3)2 |
| 2062 | CF2CF2Cl | I | H | CH2CH(CH2CH3)2 |

TABLE 1-continued

Compounds of the formula (I)

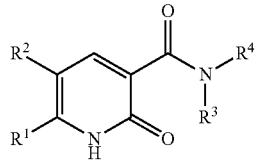

| Ex. | R¹ | R² | R³ | R⁴ |
|---|---|---|---|---|
| 2063 | CF2CF2Cl | I | H | CH2CH2CH(CH3)2 |
| 2064 | CF2CF2Cl | I | H | CH2CH2C(CH3)3 |
| 2065 | CF2CF2Cl | I | H | CH2CH=CH2 |
| 2066 | CF2CF2Cl | I | Me | CH2CH=CH2 |
| 2067 | CF2CF2Cl | I | H | CH2—C(CH3)=CH2 |
| 2068 | CF2CF2Cl | I | H | CH2—CCH |
| 2069 | CF2CF2Cl | I | Me | CH2—CCH |
| 2070 | CF2CF2Cl | I | H | CH(CH3)CH2CH3 |
| 2071 | CF2CF2Cl | I | H | CH(CH3)cPr |
| 2072 | CF2CF2Cl | I | H | CH(CH3)(CH2)2CH3 |
| 2073 | CF2CF2Cl | I | H | CH(CH3)(CH2)4CH3 |
| 2074 | CF2CF2Cl | I | H | CH(CH3)CH2CH(CH3)2 |
| 2075 | CF2CF2Cl | I | H | CH(CH3)C(CH3)3 |
| 2077 | CF2CF2Cl | I | H | CH(CH3)CH(CH3)2 |
| 2078 | CF2CF2Cl | I | H | CH(CH2CH3)2 |
| 2079 | CF2CF2Cl | I | H | CH2—CH(OMe)2 |
| 2080 | CF2CF2Cl | I | H | CH2—CH(OEt)2 |
| 2081 | CF2CF2Cl | I | H | CH2CH2—OH |
| 2082 | CF2CF2Cl | I | Me | CH2CH2—OMe |
| 2083 | CF2CF2Cl | I | H | CH2CH2—OMe |
| 2084 | CF2CF2Cl | I | H | CH(CH3)CH2—OMe |
| 2085 | CF2CF2Cl | I | H | CH2CH2CH2—OMe |
| 2086 | CF2CF2Cl | I | Me | CH2—COOCH3 |
| 2087 | CF2CF2Cl | I | H | CH2—COOCH3 |
| 2088 | CF2CF2Cl | I | H | CH(CH3)COOMe |
| 2089 | CF2CF2Cl | I | H | CH(CH3)COOEt |
| 2090 | CFClCF3 | H | H | CH2CH2—COOCH3 |
| 2091 | CFClCF3 | H | H | H |
| 2092 | CFClCF3 | H | H | Me |
| 2093 | CFClCF3 | H | H | Et |
| 2094 | CFClCF3 | H | H | Pr |
| 2095 | CFClCF3 | H | H | iPr |
| 2096 | CFClCF3 | H | H | cPr |
| 2097 | CFClCF3 | H | H | Bu |
| 2098 | CFClCF3 | H | H | tBu |
| 2099 | CFClCF3 | H | Me | Me |
| 2100 | CFClCF3 | H | Et | Et |
| 2101 | CFClCF3 | H | H | CH2—cPr |
| 2102 | CFClCF3 | H | H | CH2—C(CH3)3 |
| 2103 | CFClCF3 | H | H | CH2CH(CH3)2 |
| 2104 | CFClCF3 | H | H | CH2CH(CH2CH3)2 |
| 2105 | CFClCF3 | H | H | CH2CH2CH(CH3)2 |
| 2106 | CFClCF3 | H | H | CH2CH2C(CH3)3 |
| 2107 | CFClCF3 | H | H | CH2CH=CH2 |
| 2108 | CFClCF3 | H | Me | CH2CH=CH2 |
| 2109 | CFClCF3 | H | H | CH2—C(CH3)=CH2 |
| 2110 | CFClCF3 | H | H | CH2—CCH |
| 2111 | CFClCF3 | H | Me | CH2—CCH |
| 2112 | CFClCF3 | H | H | CH(CH3)CH2CH3 |
| 2113 | CFClCF3 | H | H | CH(CH3)cPr |
| 2114 | CFClCF3 | H | H | CH(CH3)(CH2)2CH3 |
| 2115 | CFClCF3 | H | H | CH(CH3)(CH2)4CH3 |
| 2116 | CFClCF3 | H | H | CH(CH3)CH2CH(CH3)2 |
| 2117 | CFClCF3 | H | H | CH(CH3)C(CH3)3 |
| 2118 | CFClCF3 | H | H | CH(CH3)CH(CH3)2 |
| 2119 | CFClCF3 | H | H | CH(CH2CH3)2 |

TABLE 1-continued

Compounds of the formula (I)

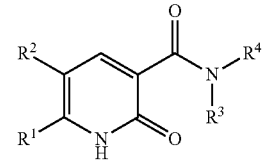

| Ex. | R¹ | R² | R³ | R⁴ |
|---|---|---|---|---|
| 2120 | CFClCF3 | H | H | CH—CH(OMe)2 |
| 2121 | CFClCF3 | H | H | CH—CH(OEt)2 |
| 2122 | CFClCF3 | H | H | CH2CH2—OH |
| 2123 | CFClCF3 | H | H | CH2CH2—OMe |
| 2124 | CFClCF3 | H | Me | CH2CH2—OMe |
| 2125 | CFClCF3 | H | H | CH(CH3)CH2—OMe |
| 2126 | CFClCF3 | H | H | CH2CH2CH2—OMe |
| 2127 | CFClCF3 | H | H | CH2—COOCH3 |
| 2128 | CFClCF3 | H | Me | CH2—COOCH3 |
| 2129 | CFClCF3 | H | H | CH(CH3)COOMe |
| 2130 | CFClCF3 | H | H | CH(CH3)COOEt |
| 2131 | CFClCF3 | H | H | CH2CH2—COOCH3 |
| 2132 | CFClCF3 | Br | H | H |
| 2133 | CFClCF3 | Br | H | Me |
| 2134 | CFClCF3 | Br | H | Et |
| 2135 | CFClCF3 | Br | H | Pr |
| 2136 | CFClCF3 | Br | H | iPr |
| 2137 | CFClCF3 | Br | H | cPr |
| 2138 | CFClCF3 | Br | H | Bu |
| 2139 | CFClCF3 | Br | H | cBu |
| 2140 | CFClCF3 | Br | H | tBu |
| 2141 | CFClCF3 | Br | Me | Me |
| 2142 | CFClCF3 | Br | Et | Et |
| 2143 | CFClCF3 | Br | H | CH2—cPr |
| 2144 | CFClCF3 | Br | H | CH2—C(CH3)3 |
| 2145 | CFClCF3 | Br | H | CH2CH(CH3)2 |
| 2146 | CFClCF3 | Br | H | CH2CH(CH2CH3)2 |
| 2147 | CFClCF3 | Br | H | CH2CH2CH(CH3)2 |
| 2148 | CFClCF3 | Br | H | CH2CH2C(CH3)3 |
| 2149 | CFClCF3 | Br | H | CH2CH=CH2 |
| 2150 | CFClCF3 | Br | Me | CH2CH=CH2 |
| 2151 | CFClCF3 | Br | H | CH2—C(CH3)=CH2 |
| 2152 | CFClCF3 | Br | H | CH2—C≡CH |
| 2153 | CFClCF3 | Br | Me | CH2—C≡CH |
| 2154 | CFClCF3 | Br | H | CH(CH3)CH2CH3 |
| 2155 | CFClCF3 | Br | H | CH(CH3)cPr |
| 2156 | CFClCF3 | Br | H | CH(CH3)(CH2)2CH3 |
| 2157 | CFClCF3 | Br | H | CH(CH3)(CH2)4CH3 |
| 2158 | CFClCF3 | Br | H | CH(CH3)CH2CH(CH3)2 |
| 2159 | CFClCF3 | Br | H | CH(CH3)C(CH3)3 |
| 2160 | CFClCF3 | Br | H | CH(CH3)CH(CH3)2 |
| 2161 | CFClCF3 | Br | H | CH(CH2CH3)2 |
| 2162 | CFClCF3 | Br | H | CH2—CH(OMe)2 |
| 2163 | CFClCF3 | Br | H | CH2—CH(OEt)2 |
| 2164 | CFClCF3 | Br | H | CH2CH2—OH |
| 2165 | CFClCF3 | Br | H | CH2CH2—OMe |
| 2166 | CFClCF3 | Br | Me | CH2CH2—OMe |
| 2167 | CFClCF3 | Br | H | CH(CH3)CH2—OMe |
| 2168 | CFClCF3 | Br | H | CH2CH2CH2—OMe |
| 2169 | CFClCF3 | Br | H | CH2—COOCH3 |
| 2170 | CFClCF3 | Br | Me | CH2—COOCH3 |
| 2171 | CFClCF3 | Br | H | CH(CH3)COOMe |
| 2172 | CFClCF3 | Br | H | CH(CH3)COOEt |
| 2173 | CFClCF3 | Br | H | CH2CH2—COOCH3 |

TABLE 2

NMR data of compounds from Table 1

| Ex. No. | 1H-NMR data |
|---|---|
| 1 | [CDCl3] 3.03 (d, 3H); 6.88 (d, 1H); 8.65 (d, 1H); 9.22 (br, 1H) |
| 2 | [CDCl3] 1.25 (t, 3H); 3.5 (m, 2H); 6.92 (d, 1H); 8.72 (d, 1H); 9.33 (br, 1H), 13.4 (br, 1H) |

TABLE 2-continued

NMR data of compounds from Table 1

| Ex. No. | 1H-NMR data |
|---|---|
| 3 | [CDCl3] 1.02 (t, 3H); 1.62 (m, 2H); 3.42 (m, 2H); 6.90 (d, 1H); 8.70 (d, 1H); 9.35 (br, 1H); 13.3 (br, 1H) |
| 4 | [CDCl3] 1.25 (d, 6H); 4.22 (m, 1H); 6.90 (d, 1H); 8.68 (d, 1H); 9.22 (d, br, 1H) |
| 5 | [CDCl3] 0.61 (m, 2H); 0.89 (m, 2H); 3.00 (m, 1H); 6.90 (d, 1H); 8.68 (d, 1H), 9.31 (br, 1H) |
| 6 | [CDCl3] 0.96 (t, 3H); 1.41 (m, 2H); 1.61 (m, 2H); 3.48 (q, 2H); 6.90 (d, 1H); 8.70 (d, 1H); 9.31 (br, 1H); 13.3 (br, 1H) |
| 7 | [CDCl3] 1.80 (m, 2H); 2.00 (m, 2H); 2.42 (m, 2H); 4.55 (m, 1H); 6.88 (d, 1H); 8.65 (d, 1H); 9.50 (br, 1H) |
| 8 | [CDCl3] 1.44 (s, 9H); 6.90 (d, 1H); 8.62 (d, 1H); 9.32 (br, 1H); 13.4 (br, 1H) |
| 9 | [CDCl3] 3.05 (s, 6H); 7.10 (d, 1H); 7.77 (d, 1H) |
| 10 | [CDCl3] 1.22 (t, 3H); 3.02 (s, 3H); 3.46 (m, 2H); 7.08 (d, 1H); 7.77 (d, 1H) |
| 11 | [CDCl3] 0.90 (t, 3H); 1.30 (br, 2H); 1.60 (m, 2H); 3.03 (s, 3H); 3.42 (br, 2H); 7.10 (d, 1H); 7.74 (d, 1H) |
| 13 | [CDCl3] 1.20 (d, 6H); 2.90 (s, 3H); 4.05 (m, br, 1H); 7.03 (d, 1H); 8.68 (d, 1H); 11.2 (br) |
| 14 | [CDCl3] 1.20 (t, 6H); 3.40 (m, 4H); 7.05 (d, 1H); 8.70 (d, 1H); 11.1 (br) |
| 16 | [CDCl3] 1.21 (m, 9H); 3.39 (q, 2H); 4.0 (br, 1H); 7.04 (d, 1H); 7.68 (d, 1H); 10.6 (br, 1H) |
| 18 | [CDCl3] 1.5-1.8 (m, 8H); 4.40 (m, 1H); 6.90 (d, 1H); 8.68 (d, 1H); 9.40 (d, br, 1H); 13.5 (br) |
| 19 | [CDCl3] 1.2-1.5 (m, 6H); 1.76 (m, 2H); 2.00 (m, 2H); 4.00 (m, 1H); 6.90 (d, 1H); 8.68 (d, 1H); 9.30 (d, br, 1H); 13.4 (br, 1H) |
| 20 | [CDCl3] 0.90 (t, 3H); 1.38 (m, 4H); 1.61 (m, 2H); 3.41 (m, 2H); 6.86 (d, 1H); 8.63 (d, 1H); 9.20 (t, 1H) |
| 22 | [CDCl3] 0.30 (m, 2H); 0.60 (m, 2H); 1.05 (m, 1H); 3.30 (m, 2H); 6.90 (d, 1H), 8.70 (d, 1H); 9.38 (br, 1H) |
| 24 | [CDCl3] 1.00 (s, 9H); 3.28 (d, 2H); 6.90 (d, 1H); 8,73 (d, 1H); 9.4 (br, 1H); 13.2 (br, 1H) |
| 25 | [CDCl3] 4.18 (dt, 2H); 6.92 (d, 1H); 8.72 (d, 1H); 9.8 (t, br, 1H) |
| 26 | [CDCl3] 4.11 (m, 2H); 6.90 (d, 1H); 8.70 (d, 1H); 9.80 (br, 1H); 12.16 (br, 1H) |
| 27 | [CDCl3] 4.22 (dt; 2H); 6.93 (d, 1H); 8.72 (d, 1H); 9.80 (t, br, 1H) |
| 30 | [CDCl3] 1.00 (d, 6H); 1.87 (m, 1H); 3.29 (t, 2H); 6.88 (d, 1H); 8.64 (d, 1H); 9.32 (br, 1H); 12.5 (br, 1H) |
| 32 | [CDCl3] 0.95 (d, 6H); 1.48 (m, 2H); 1.70 (m, 1H); 3.48 (m, 2H); 6.88 (d, 1H); 8.65 (d, 1H); 9.22 (br, 1H), 12.6 (br) |
| 34 | [CDCl3] 4.10 (t, 2H); 5.22 (dd, 2H); 5.95 (m, 1H); 6.90 (d, 1H); 8.70 (d, 1H); 9.40 (br, 1H); 12.7 (br, 1H) |
| 36 | [CDCl3] 4.0 (m, 4H); 5.21 (d, 4H); 5.80 (m, 2H); 7.04 (d, 1H); 7.78 (d, 1H); 11.0 (br) |
| 38 | [CDCl3] 1.80 (s, 3H); 4.02 (d, 2H); 4.93 (d, 2H); 6.89 (d 1H); 8.70 (d, 1H); 9.43 (br, 1H); 13.2 (br, 1H) |
| 39 | [CDCl3] 2.24 (t, 1H); 4.22 (m, 2H); 6.88 (d, 1H); 8.68 (d, 1H); 9.50 (br, 1H) |
| 40 | [CDCl3] 2.30 (s, 1H); 3.12 (s, 3H); 4.22 (br, 2H); 7.04 (d, 1H); 7.84 (d, 1H); 10.9 (br) |
| 41 | [CDCl3] 0.95 (t, 3H); 1.22 (d, 3H); 1.58 (m, 2H); 4.10 (m, 1H); 6.88 (d, 1H); 8.66 (d, 1H); 9.20 (br, 1H); 13.0 (br, 1H) |
| 43 | [DMSO] 0.93 (t, 3H); 1.16 (d, 3H); 1.30 (m, 2H); 1.48 (m, 2H); 4.00 (m, 1H); 7.35 (br, 1H); 7.39 (d, 1H); 8.40 (d, 1H); 13.40 (br) |
| 44 | [DMSO] 0.87 (t, 3H); 1.15 (d, 3H); 1.27 (m, 6H); 1.48 (m, 2H); 4.00 (m, 1H); 7.33 (d, 1H); 8.40 (d, 1H); 8.80 (br, 1H), 13.4 (br, 1H) |
| 47 | [CDCl3] 0.93 (d, 6H); 1.22 (d, 3H); 1.35 (m, 1H); 1.50 (m, 1H); 1.65 (m, 1H); 4.23 (m, 1H); 6.90 (d, 1H); 8.64 (d, 1H); 9.20 (d, br, 1H); 13.3 (br, 1H) |
| 48 | [CDCl3] 0.96 (s, 9H); 1.18 (d, 3H); 4.10 (m, 1H); 6.90 (d, 1H); 8.74 (d, 1H); 9.37 (d, br, 1H), 13.6 (br, 1H) |
| 49 | [CDCl3] 0.95 (dt, 6H); 1.20 (d, 3H); 1.80 (m, 1H); 4.07 (m, 1H); 6.90 (d, 1H); 8.70 (d, 1H); 9.30 (d, br, 1H); 13.6 (br) |
| 51 | [DMSO] 0.85 (t, 6H); 1.45 (m, 2H); 1.55 (m, 2H); 3.80 (m, 1H); 7.33 (d, br, 1H); 8.38 (d, 1H); 8.65 (br, 1H); 13.5 (br, 1H) |
| 54 | [CDCl3] 3.40 (s, 6H); 3.62 (t, 2H); 4.50 (t, 1H); 6.89 (d, 1H); 8.65 (d, 1H); 9.30 (br, 1H); 12.4 (br, 1H) |
| 55 | [CDCl3] 1.21 (t, 6H); 3.60 (m, 4H); 3.72 (m, 2H); 4.61 (t, 1H); 6.88 (d, 1H); 8.61 (d, 1H); 9.28 (br, 1H), 12.0 (br) |
| 56 | [DMSO] 3.40 (m, 2H); 3.53 (m, 2H); 7.32 (d, br, 1H); 8.45 (d, 1H); 9.05 (br, 1H); 13.6 (br, 1H) |
| 57 | [CDCl3] 3.40 (s, 3H); 3.56 (t, 2H); 3.64 (m, 2H); 6.90 (d, 1H); 8.65 (d, 1H); 9.35 (br, 1H) |
| 64 | [CDCl3] 1.25 (d, 3H); 3.40 (s, 3H); 3.43 (d, 2H); 4.37 (m, 1H); 6.89 (d, 1H); 8.64 (d, 1H); 9.30 (d, br, 1H); 13.0 (br, 1H) |
| 66 | [CDCl3] 1.90 (m, 2H); 3.34 (s, 3H); 3.46 (t, 2H); 3.55 (q, 2H); 6.90 (d, 1H); 8.60 (d, 1H); 9.23 (br, 1H); 12.5 (br) |
| 71 | [CDCl3] 3.80 (s, 3H); 4.22 (d, 2H); 6.88 (d, 1H); 8.64 (d, 1H); 9.62 (t, 1H), |
| 72 | [CDCl3] 3.10 (s, 3H); 3.75 (s, 3H); 4.25 (s, 2H); 7.18 (d, 1H); 7.80 (d, 1H) |
| 75 | [CDCl3] 2.64 (t, 2H); 3.69 (s, 3H); 3.73 (m, 2H); 6.88 (d, 1H); 8.61 (d, 1H); 9.41 (t, br, 1H); 12.2 (br, 1H) |
| 76 | [CDCl3] 3.83 (s, 6H); 5.42 (d, 1H); 6.90 (d, 1H); 8.63 (d, 1H), 10.2 (br, 1H), |
| 77 | [CDCl3] 0.99 (t, 6H); 1.25 (t, 3H)1.75 (m, 3H); 4.20 (m, 2H); 4.72 (m, 1H); 6.90 (d, 1H); 8.64 (d, 1H); 9.60 (d, br, 1H) |
| 78 | [CDCl3] 1.05 (t, 6H); 2.30 (m, 3H); 3.78 (s, 3H); 4.72 (m, 1H); 6.90 (d, 1H); 8.70 (d, 1H); 9.76 (d, br, 1H); 13.6 (br, 1H) |
| 79 | [CDCl3] 1.35 (t, 3H); 4.10 (q, 2H); 6.91 (d, 1H); 8.71 (d, 1H); 11.46 (s, 1H) |
| 80 | [CDCl3] 3.41 (s, 3H); 3.68 (s, 3H); 7.18 (d, 1H); 8.32 (d, 1H) |
| 81 | [CDCl3] 4.50 (d, 2H); 5.3 (m, 2H); 6.0 (m, 1H); 6.90 (d, 1H); 8.70 (d, 1H); 11.43 (s, 1H) |
| 82 | [CDCl3] 1.36 (s, 9H); 6.92 (d, 1H); 8.72 (d, 1H); 11.22 (s, 1H); 13.0 (br, 1H) |

TABLE 2-continued

NMR data of compounds from Table 1

| Ex. No. | 1H-NMR data |
|---|---|
| 92 | [CDCl3] 4.62 (d, 2H), 6.84 (d, 1H); 7.3 (m, 5H); 8.70 (d, 1H); 9.65 (br, 1H), 13.0 (br, 1H) |
| 93 | [CDCl3] 2.95 (s, 3H); 4.65 (br, 2H); 7.05 (d, 1H); 7.3 (m, 5H); 7.82 (d, 1H); 11.7 (br) |
| 94 | [DMSO] 4.55 (d, 2H); 7.33 (d, 1H); 7.37 (dd, 1H); 7.75 (dt, 1H); 8.40 (d, 1H); 8.48 (dd, 1H); 8.58 (s, 1H); 9.45 (br, 1H); 13.4 (br, 1H) |
| 95 | [DMSO] 4.55 (d, 2H); 7.30 (d, br, 1H); 7.50 (d, 1H); 7.80 (dd, 1H); 8.37 (m, 2H); 9.55 (br, 1H); 13.4 (br, 1H) |
| 96 | [CDCl3] 1.59 (d, 3H); 5.25 (m, 1H); 6.88 (d, 1H); 7.2-7.4 (m, 5H); 8.68 (d, 1H); 9.75 (d, br, 1H); 13.5 (br, 1H) |
| 97 | [CDCl3] 2.94 (t, 2H); 3.70 (m, 2H); 6.85 (d, 1H); 7.2-7.4 (m, 5H); 8.62 (d, 1H); 9.24 (br, 1H) |
| 98 | [CDCl3] 4.81 (d, 2H); 6.85 (d, 1H); 7.40 (t, 1H); 7.52 (t, 1H); 7.61 (d, 1H); 7.67 (d, 1H); 8.68 (d, 1H); 9.68 (t, br, 1H) |
| 99 | [DMSO] 2.28 (q, 2H); 3.20 (q, 2H); 4.03 (t, 1H); 7.1-7.4 (m, 11H); 8.35 (d, 1H); 9.0 (br), 13.4 (br, 1H) |
| 100 | [CDCl3] 3.45-3.55 (br, 4H); 3.75 (m, 4H); 7.03 (d, 1H); 7.80 (d, 1H); 11.3 (br, 1H) |
| 101 | [CDCl3] 1.65 (m, 6H); 3.52 (m, 4H); 7.10 (d, 1H); 7.72 (d, 1H) |
| 102 | [CDCl3] 3.06 (t, 2H); 3.90 (m, 2H); 4.65 (m, 2H); 7.08 (d, 1H); 7.90 (d, 1H); 11.0 (br) |
| 103 | [CDCl3] 2.00 (m, 4H); 3.67 (m, 4H); 7.20 (d, 1H); 7.97 (d, 1H), 11.7 (br, 1H) |
| 104 | [CDCl3] 1.30 (m, 3H); 1.65 (m, 1H); 1.85 (m, 1H); 2.00 (m, 1H); 2.19 (m, 1H); 3.62 (m, 2H); 4.30 (m, 1H); 7.10 (d, 1H); 7.89 (d, 1H) |
| 105 | [CDCl3] 3.25 (s, 3H); 3.35 (3.3H); 7.25 (d, 1H); 8.58 (d, 1H); 8.76 (s, 1H) |
| 112 | [CDCl3] 1.95 (m, 2H); 2.65 (m, 1H); 2.90 (m, 1H); 3.05 (m, 1H); 5.60 (m, 1H); 6.85 (d, 1H); 7.2-7.4 (m, 4H); 8.68 (d, 1H); 9.52 (d, br, 1H) |
| 113 | [CDCl3] 1.60 (m, 1H), 1.90 (m, 2H); 2.01 (m, 1H); 3.42 (m, 1H), 3.65-3.82 (m, 2H); 3.90 (m, 1H), 4.09 (m, 1H); 6.88 (d, 1H); 8.63 (d, 1H); 9.37 (br, 1H) |
| 114 | [DMSO] 7.35 (d, 1H); 8.10 (br, 1H); 8.40 (d, 1H); 8.41 (br, 1H); 13.6 (br, 1H) |
| 115 | [CDCl3] 3.01 (d, 3H); 6.81 (d, 1H); 8.63 (d, 1H); 9.22 (br, 1H); 11.7 (br, 1H) |
| 116 | [CDCl3] 1.25 (t, 3H); 3.5 (m, 2H); 6.85 (d, 1H); 8.66 (d, 1H), 9.33 (br, 1H), 13.0 (br, 1H) |
| 117 | [CDCl3] 1.01 (t, 3H); 1.62 (m, 2H); 3.42 (m, 2H); 6.86 (d, 1H); 8.66 (d, 1H); 9.35 (br, 1H); 12.6 (br, 1H) |
| 118 | [CDCl3] 1.27 (d, 6H); 4.25 (m, 1H); 6.85 (d, 1H); 8.64 (d, 1H); 9.27 (br, 1H); 13.1 (br, 1H) |
| 119 | [CDCl3] 0.62 (m, 2H); 0.85 (m, 2H); 3.02 (m, 1H); 6.84 (d, 1H); 8.78 (d, 1H), 9.33 (br, 1H) |
| 120 | [CDCl3] 0.98 (t, 3H); 1.41 (m, 2H); 1.61 (m, 2H); 3.45 (q, 2H); 6.83 (d, 1H); 8.65 (d, 1H); 9.33 (br, 1H); 12.9 (br, 1H) |
| 121 | [CDCl3] 1.80 (m, 2H); 2.05 (m, 2H); 2.44 (m, 2H); 4.58 (m, 1H); 6.84 (d, 1H); 8.63 (d, 1H); 9.60 (br, 1H); 13.1 (br) |
| 122 | [CDCl3] 1.46 (s, 9H); 6.86 (d, 1H); 8.62 (d, 1H); 9.34 (br, 1H); 13.4 (br, 1H) |
| 123 | [CDCl3] 3.08 (s, 6H); 7.06 (d, 1H); 7.79 (d, 1H) |
| 124 | [CDCl3] 1.23 (t, 3H); 3.04 (s, 3H); 3.46 (m, 2H); 7.02 (d, 1H); 7.72 (d, 1H) |
| 125 | [CDCl3] 0.92 (t, 3H); 1.30 (br, 2H); 1.60 (m, 2H); 3.04 (s, 3H); 3.41 (br, 2H); 7.04 (d, 1H); 7.71 (d, 1H) |
| 127 | [CDCl3] 1.20 (d, 6H); 2.90 (s, 3H); 4.05 (m, br, 1H); 7.00 (d, 1H); 7.68 (d, 1H) |
| 128 | [CDCl3] 1.20 (t, 6H); 3.41 (m, 4H); 6.98 (d, 1H); 7.66 d, 1H); 11.0 (br) |
| 130 | [CDCl3] 1.20 (m, 9H); 3.40 (q, 2H); 4.06 (m, br, 1H); 6.98 (d, 1H); 8.64 (d, 1H); 10.2 (br) |
| 132 | [CDCl3] 1.5-1.8 (m, 8H); 4.40 (m, 1H); 6.85 (d, 1H); 8.65 (d, 1H); 9.40 (d, br, 1H); 13.1 (br, 1H) |
| 133 | [CDCl3] 1.2-1.7 (m, 6H); 1.80 (m, 2H); 2.00 (m, 2H); 3.98 (m, 1H); 6.85 (d, 1H); 8.64 (d, 1H); 9.30 (d, br, 1H); 13.0 (br) |
| 134 | [CDCl3] 0.90 (t, 3H); 1.40 (m, 4H); 1.62 (m, 2H); 3.44 (m, 2H); 6.84 (d, 1H); 8.64 (d, 1H); 9.30 (br, 1H) |
| 136 | [CDCl3] 0.30 (m, 2H); 0.59 (m, 2H); 1.05 (m, 1H); 3.32 (m, 2H); 6.86 (d, 1H), 8.65 (d, 1H); 9.40 (br) |
| 138 | [CDCl3] 1.00 (s, 9H); 3.26 (d, 2H); 6.86 (d, 1H); 8.70 (d, 1H); 9.42 (br, 1H); 12.5 (br, 1H) |
| 139 | [DMSO] 4.25 (dt, 2H); 7.25 (d, 1H); 8.40 (d, 1H); 9.35 (br, 1H); 13.5 (br, 1H) |
| 140 | [CDCl3] 4.15 (m, 2H); 6.88 (d, 1H); 8.70 (d, 1H); 9.80 (br, 1H) |
| 141 | [CDCl3] 4.20 (dt; 2H); 6.90 (d, 1H); 8.70 (d, 1H); 9.83 (t, br, 1H); 12.80 (br) |
| 144 | [CDCl3] 1.00 (d, 6H); 1.90 (m, 1H); 3.30 (t, 2H); 6.83 (d, 1H); 8.65 (d, 1H); 9.35 (br, 1H); 12.2 (br) |
| 146 | [CDCl3] 0.96 (d, 6H); 1.50 (m, 2H); 1.70 (m, 1H); 3.48 (m, 2H); 6.83 (d, 1H); 8.67 (d, 1H); 9.30 (br, 1H), 12.9 (br, 1H) |
| 148 | [CDCl3] 4.62 (d, 2H); 5.36 (dd, 2H); 5.95 (m, 1H); 7.80 (d, 1H); 8.65 (d, 1H) |
| 150 | [CDCl3] 4.0 (m, 4H); 5.22 (d, 4H); 5.80 (m, 2H); 6.93 (d, 1H); 7.72 (d, 1H) |
| 152 | [CDCl3] 1.80 (s, 3H); 4.02 (d, 2H); 4.90 (d, 2H); 6.85 (d 1H); 8.68 (d, 1H); 9.48 (br, 1H); 12.8 (br, 1H) |
| 153 | [CDCl3] 2.26 (t, 1H); 4.23 (m, 2H); 6.84 (d, 1H); 8.64 (d, 1H); 9.58 (br, 1H); 12.4 (br) |
| 154 | [CDCl3] 2.30 (s, 1H); 3.12 (s, 3H); 4.24 (br, 2H); 7.01 (d, 1H); 7.82 (d, 1H); 10.9 (br) |
| 155 | [CDCl3] 0.98 (t, 3H); 1.22 (d, 3H); 1.59 (m, 2H); 4.10 (m, 1H); 6.85 (d, 1H); 8.65 (d, 1H); 9.26 (d, br, 1H); 13.4 (br, 1H) |
| 157 | [CDCl3] 0.92 (t, 3H); 1.22 (d, 3H); 1.40 (m, 2H); 1.55 (m, 2H); 4.20 (m, 1H); 6.85 (d, 1H); 8.68 (d, 1H); 9.30 (d, br, 1H) |
| 158 | [CDCl3] 0.87 (t, 3H); 1.12 (d, 3H); 1.30 (m, 4H); 1.58 (m, 4H); 4.15 (m, 1H); 6.84 (d, 1H); 8.65 (d, 1H); 9.24 (br, 1H), 13.1 (br) |
| 161 | [CDCl3] 0.90 (d, 6H); 1.22 (d, 3H), 1.30 (m, 1H); 1.55 (m, 2H); 4.23 (m, 1H); 6.86 (d, 1H); 8.64 (d, 1H); 9.20 (d, br, 1H); 13.0 (br, 1H) |
| 162 | [CDCl3] 0.98 (s, 9H); 1.20 (d, 3H); 4.10 (m, 1H); 6.87 (d, 1H); 8.70 (d, 1H); 9.38 (d, br, 1H), 13.2 (br, 1H) |

TABLE 2-continued

NMR data of compounds from Table 1

| Ex. No. | 1H-NMR data |
|---|---|
| 163 | [CDCl3] 0.95 (dt, 6H); 1.20 (d, 3H); 1.82 (m, 1H); 4.05 (m, 1H); 6.84 (d, 1H); 8.68 (d, 1H); 9.30 (d, br, 1H); 13.1 (br) |
| 165 | [CDCl3] 0.96 (t, 6H); 1.50 (m, 2H); 1.65 (m, 2H); 4.00 (m, 1H); 6.85 (d, 1H); 8.68 (d, 1H); 9.22 (d, br, 1H); 13.5 (br, 1H) |
| 166 | [CDCl3] 0.90 (t, 3H); 1.41 (s; 6H); 1.85 (q, 2H); 6.82 (d, 1H); 8.61 (d, 1H); 9.20 (br, 1H); 13.1 (br) |
| 168 | [CDCl3] 3.40 (s, 6H); 3.63 (t, 2H); 4.50 (t, 1H); 6.85 (d, 1H); 8.65 (d, 1H); 9.40 (br, 1H); 12.4 (br, 1H) |
| 169 | [CDCl3] 1.21 (t, 6H); 3.60 (m, 4H); 3.74 (m, 1H); 4.62 (t, 1H); 6.84 (d, 1H); 8.60 (d, 1H); 9.35 (br, 1H), 11.5 (br) |
| 171 | [CDCl3] 3.40 (s, 3H); 3.58 (m, 2H); 3.67 (m, 2H); 6.84 (d, 1H); 8.62 (d, 1H); 9.40 (br, 1H) |
| 178 | [CDCl3] 1.24 (d, 3H); 3.40 (s, 3H); 3.42 (d, 2H); 4.40 (m, 1H); 6.86 (d, 1H); 8.64 (d, 1H); 9.35 (br, 1H); 13.0 (br) |
| 180 | [DMSO] 1.75 (m, 2H); 3.22 (s, 3H); 3.36 (m, 4H); 7.3 (br, 1H); 8.4 (d, 1H); 9.0 (br); 13.4 (br, 1H) |
| 185 | [DMSO] 3.65 (s, 3H); 4.12 (d, 2H); 7.28 (d, br, 1H); 8.42 (d, 1H); 9.25 (t, br, 1H), 13.6 (br, 1H) |
| 189 | [CDCl3] 2.66 (t, 2H); 3.70 (s, 3H); 3.76 (m, 2H); 6.83 (d, 1H); 8.61 (d, 1H); 9.51 (t, br, 1H); 12.4 (br, 1H) |
| 193 | [CDCl3] 1.37 (t, 3H); 4.08 (q, 2H); 6.88 (d, 1H); 8.69 (d, 1H); 11.48 (s, 1H) |
| 194 | [CDCl3] 3.88 (s, 3H); 6.88 (d, 1H); 8.65 (d, 1H); 11.5 (s, 1H) |
| 195 | [CDCl3] 4.50 (d, 2H); 5.34 (m, 2H); 6.05 (m, 1H); 6.88 (d, 1H); 8.70 (d, 1H); 11.44 (s, 1H) |
| 196 | [CDCl3] 1.39 (s, 9H); 6.88 (d, 1H); 8.70 (d, 1H); 11.22 (s, 1H) |
| 206 | [CDCl3] 4.62 (d, 2H), 6.82 (d, 1H); 7.2-7.3 (m, 5H); 8.68 (d, 1H); 9.65 (t, br, 1H), 12.8 (br, 1H) |
| 207 | [CDCl3] 2.99 (s, 3H); 4.67 (br, 2H); 7.00 (d, 1H); 7.3-7.4 (m, 5H); 7.78 (d, 1H); 10.2 (br) |
| 210 | [CDCl3] 1.60 (d, 3H); 5.30 (m, 1H); 6.85 (d, 1H); 7.2-7.4 (m, 5H); 8.65 (d, 1H); 9.78 (d, br, 1H); 13.2 (br, 1H) |
| 211 | [CDCl3] 2.95 (t, 2H); 3.70 (m, 2H); 6.82 (d, 1H); 7.2-7.35 (m, 5H); 8.63 (d, 1H); 9.40 (t, br, 1H); 12.2 (br, 1H) |
| 214 | [CDCl3] 3.45-3.55 (br, 4H); 3.75 (m, 4H); 6.96 (d, 1H); 7.78 (d, 1H) |
| 215 | [CDCl3] 1.65 (m, 6H); 3.53 (m, 4H); 7.00 (d, 1H); 7.70 (d, 1H) |
| 216 | [CDCl3] 3.05 (t, 2H); 3.92 (m, 2H); 4.66 (m, 2H); 7.04 (d, 1H); 7.86 (d, 1H); 10.4 (br) |
| 217 | [CDCl3] 2.00 (m, 4H); 3.70 (m, 4H); 7.16 (d, 1H); 7.97 (d, 1H), 11.7 (br, 1H) |
| 218 | [CDCl3] 1.30 (m, 3H); 1.65 (m, 1H); 1.85 (m, 1H); 2.04 (m, 1H); 2.20 (m, 1H); 3.63 (m, 2H); 4.33 (m, 1H); 7.12 (d, 1H); 7.89 (d, 1H); 11.5 (br, 1H) |
| 227 | [CDCl3] 1.60 (m, 1H); 1.90 (m, 2H), 2.00 (m, 1H); 3.42 (m, 1H); 3.65-3.82 (m, 2H); 3.90 (m, 1H); 4.10 (m, 1H); 6.88 (d, 1H); 8.65 (d, 1H); 9.5 (br, 1H) |
| 228 | [DMSO] 6.80 (br, 1H); 6.90 (t, 1H); 7.72 (br, 1H); 8.40 (d, 1H); 8.90 (br, 1H); 13.20 (br, 1H) |
| 229 | [DMSO] 2.82 (d, 3H); 6.75 (d, br, 1H); 6.90 (t, 1H); 8.89 (d, 1H); 9.50 (br, 1H); 13.2 (br, 1H) |
| 230 | [DMSO] 1.11 (t, 3H); 3.32 (m, 2H); 6.75 (d, br, 1H); 6.90 (t, 1H); 8.39 (d, 1H), 9.60 (br, 1H), 13.2 (br, 1H) |
| 232 | [CDCl3] 1.25 (d, 6H); 4.22 (m, 1H); 6.55 (t, 1H); 6.69 (d, 1H); 8.64 (d, 1H); 9.42 (d, br, 1H); 13.0 (br, 1H) |
| 233 | [DMSO] 0.51 (m, 2H); 0.74 (m, 2H); 2.84 (m, 1H); 6.79 (d, br, 1H); 6.90 (t, 1H); 8.37 (d, 1H); 9.65 (br, 1H); 13.1 (br, 1H) |
| 250 | [DMSO] 0.23 (m, 2H); 0.46 (m, 2H); 1.02 (m, 1H); 3.20 (m, 2H); 6.75 (br, 1H); 6.92 (t, 1H); 8.40 (d, 1H); 9.70 (br, 1H); 13.1 (br, 1H) |
| 252 | [DMSO] 0.91 (s, 9H); 3.15 (d, 2H); 6.80 (br, 1H); 6.91 (t, 1H); 8.40 (d, 1H); 9.85 (br, 1H); 13.2 (br, 1H) |
| 258 | [DMSO] 0.90 (d, 6H); 1.80 (m, 1H); 3.15 (t, 2H); 6.80 (br, 1H); 6.91 (t, 1H); 8.40 (d, 1H); 9.73 (br, 1H); 13.1 (br, 1H |
| 262 | [DMSO] 3.96 (m, 2H); 5.15 (dd, 2H); 5.94 (m, 1H); 6.80 (br, 1H); 6.92 (t, 1H); 8.40 (d, 1H); 9.75 (br, 1H); 13.2 (br, 1H) |
| 271 | [CDCl3] 0.92 (t, 3H); 1.25 (d, 3H); 1.42 (m, 2H); 1.55 (m, 2H); 4.19 (m, 1H); 6.60 (t, 1H); 6.73 (d, 1H); 8.66 (d, 1H); 9.50 (d, br, 1H) |
| 272 | [CDCl3] 0.90 (t, 3H); 1.2-1.4 (m, 9H); 1.58 (m, 2H); 4.17 (m, 1H); 6.60 (t, 1H); 6.75 (d, 1H); 8.68 (d, 1H); 9.48 (d, br, 1H) |
| 279 | [CDCl3] 0.85 (t, 6H); 1.45 (m, 2H); 1.55 (m, 2H); 3.80 (m, 1H); 6.80 (br, 1H); 6.91 (t, 1H); 8.40 (d, 1H); 9.51 (br, 1H); 13.1 (br, 1H) |
| 280 | [DMSO] 0.86 (t, 3H); 1.12 (d, 3H); 1.50 (m, 2H); 3.90 (m, 1H); 6.75 (br, 1H); 6.91 (t, 1H); 8.39 (d, 1H); 9.57 (br, 1H); 13.1 (br, 1H) |
| 285 | [DMSO] 3.29 (s, 3H); 3.46 (m, 4H); 6.76 (br, 1H); 6.91 (t, 1H); 8.50 (d, 1H); 9.73 (br, 1H), 13.1 (br, 1H) |
| 291 | [DMSO] 1.14 (d, 3H); 3.27 (s, 3H); 3.35 (m, 2H); 4.15 (m, 1H); 6.80 (br, 1H); 6.91 (t, 1H); 8.40 (d, 1H); 9.70 (br, 1H); 13.1 (br, 1H)) |
| 293 | [DMSO] 1.72 (m, 2H); 3.22 (s, 3H); 3.37 (m, 4H); 6.75 (br, 1H); 6.90 (t, 1H); 8.40 (d, 1H); 9.70 (br, 1H)); 13.2 (br, 1H) |
| 341 | [DMSO] 7.45 (d, 1H); 8.15 (br, 1H); 8.45 (br, 1H); 8.50 (d, 1H); 13.7 (br, 1H) |
| 342 | [CDCl3] 3.01 (d, 3H); 6.90 (d, 1H); 8.72 (d, 1H); 9.34 (br, 1H) |
| 343 | [DMSO] 1.11 (t, 3H); 3.31 (m, 2H); 7.41 (d, 1H); 8.42 (d, 1H); 8.85 (br, 1H), 13.4 (br, 1H) |
| 344 | [CDCl3] 1.02 (t, 3H); 1.61 (m, 2H); 3.42 (q, 2H); 6.88 (d, 1H); 8.72 (d, 1H); 9.38 (br, 1H) |
| 345 | [CDCl3] 1.25 (d, 6H); 4.25 (m, 1H); 6.90 (d, 1H); 8.72 (d, 1H); 9.30 (d, br, 1H); 13.8 (br, 1H) |
| 346 | [CDCl3] 0.60 (m, 2H); 0.88 (m, 2H); 3.02 (m, 1H); 6.90 (d, 1H); 8.72 (d, 1H); 9.42 (br, 1H); 13.4 (br) |

TABLE 2-continued

NMR data of compounds from Table 1

| Ex. No. | 1H-NMR data |
|---|---|
| 347 | [DMSO] 0.88 (t, 3H); 1.34 (m, 2H); 1.50 (m, 2H); 3.31 (q, 2H); 7.27 (d, 1H); 8.35 (d, 1H); 9.21 (br, 1H); 12.4 (br, 1H) |
| 348 | [DMSO] 1.70 (m, 2H); 2.02 (m, 2H); 2.27 (m, 2H); 4.40 (m, 1H); 7.41 (d, 1H); 8.48 (d, 1H); 9.00 (br, 1H); 13.4 (br, 1H) |
| 349 | [DMSO] 1.36 (s, 9H); 7.35 (d, br, 1H); 8.40 (d, 1H); 8.60 (br, 1H); 13.3 (br, 1H) |
| 350 | [CDCl3] 3.08 (s, 6H); 7.08 (d, 1H); 7.81 (d, 1H) |
| 355 | [CDCl3] 1.21 (t, 6H); 3.42 (m, 4H); 7.04 (d, 1H); 7.71 (d, 1H); 10.8 (br) |
| 363 | [DMSO] 0.27 (m, 2H); 0.46 (m, 2H); 1.05 (m, 1H); 3.15 (m, 2H); 7.45 (d, br, 1H); 8.45 (d, 1H); 8.95 (br, 1H); 13.4 (br, 1H) |
| 365 | [DMSO] 0.91 (s, 9H); 3.15 (d, 2H); 7.38 (d, br, 1H); 8.40 (d, 1H); 8.83 (br, 1H); 13.4 (br, 1H) |
| 373 | [DMSO] 0.90 (d, 6H); 1.42 (m, 2H); 1.63 (m, 1H); 3.33 (m, 2H); 7.40 (d, br, 1H); 8.40 (d, 1H); 8.83 (br, 1H); 13.4 (br, 1H) |
| 375 | [DMSO] 3.95 (m, 2H); 5.15 (dd, 2H); 5.90 (m, 1H); 7.40 (d, 1H); 8.41 (d, 1H); 8.98 (br, 1H); 13.4 (br, 1H) |
| 379 | [DMSO] 1.73 (s, 3H); 3.88 (m, 2H); 4.75 (d, 2H); 7.40 (d, br, 1H); 8.41 (d, 1H); 8.97 (br, 1H); 13.4 (br, 1H) |
| 380 | [DMSO] 3.15 (t, 1H); 4.21 (m, 2H); 7.40 (d, 1H); 8.40 (d, 1H); 9.12 (br, 1H); 13.3 (br, 1H) |
| 382 | [CDCl3] 0.97 (t, 3H); 1.22 (d, 3H); 1.59 (m, 2H); 4.10 (m, 1H); 6.88 (d, 1H); 8.72 (d, 1H); 9.24 (d, br, 1H); 13.6 (br) |
| 384 | [CDCl3] 0.92 (t, 3H); 1.21 (d, 3H); 1.40 (m, 2H); 1.50 (m, 2H); 4.20 (m, 1H); 6.88 (d, 1H); 8.72 (d, 1H); 9.28 (d, br, 1H) |
| 385 | [DMSO] 0.85 (t, 3H); 1.1-1.35 (m, 9H); 1.50 (m, 2H); 4.00 (m, 1H); 7.41 (d, 1H); 8.40 (d, 1H); 8.65 (br, 1H); 13.4 (br, 1H) |
| 388 | [DMSO] 0.88 (d, 6H); 1.15 (d, 3H), 1.28 (m, 1H); 1.48 (m, 1H); 1.62 (m, 1H); 4.11 (m, 1H); 7.40 (d, br, 1H); 8.40 (d, 1H); 8.52 (d, br, 1H); 13.4 (br, 1H) |
| 389 | [DMSO] 0.90 (s, 9H); 1.10 (d, 3H); 3.90 (m, 1H); 7.38 (d, br, 1H); 8.40 (d, 1H); 8.70 (br, 1H), 13.4 (br, 1H) |
| 390 | [DMSO] 0.79 (dt, 6H); 1.10 (d, 3H); 1.75 (m, 1H); 3.87 (m, 1H); 7.40 (d, br, 1H); 8.41 (d, 1H); 8.65 (d, br, 1H); 13.4 (br, 1H) |
| 392 | [CDCl3] 0.95 (t, 6H); 1.50 (m, 2H); 1.65 (m, 2H); 4.00 (m, 1H); 6.90 (d, 1H); 8.75 (d, 1H); 9.20 (d, br, 1H); 13.7 (br, 1H) |
| 395 | [DMSO] 3.30 (s, 6H); 3.42 (t, 2H); 4.50 (t, 1H); 7.40 (d, br, 1H); 8.45 (d, 1H); 8.90 (br, 1H); 13.4 (br, 1H) |
| 397 | [DMSO] 3.38 (m, 2H); 3.52 (m, 2H); 4.80 (t, 1H); 7.40 (d, br, 1H); 8.43 (d, 1H); 8.95 (br, 1H); 13.4 (br, 1H) |
| 398 | [CDCl3] 3.38 (s, 3H); 3.58 (m, 2H); 3.65 (m, 2H); 6.88 (d, 1H); 8.70 (d, 1H); 9.43 (br, 1H) |
| 405 | [CDCl3] 1.25 (d, 3H); 3.38 (s, 3H); 3.42 (d, 2H); 4.40 (m, 1H); 6.88 (d, 1H); 8.70 (d, 1H); 9.38 (d, br, 1H) |
| 407 | [CDCl3] 1.89 (m, 2H); 3.32 (s, 3H); 3.48 (t, 2H); 3.58 (m, 2H); 6.92 (d, 1H); 8.64 (d, 1H); 9.30 (br, 1H) |
| 455 | [DMSO] 8.25 (br, 1H); 8.35 (br, 1H); 8.50 (s, 1H); 13.8 (br, 1H) |
| 456 | [DMSO] 2.84 (d, 3H); 8.40 (s, 1H); 8.72 (d, br, 1H) |
| 457 | [DMSO] 1.12 (t, 3H); 3.35 (q, 2H); 8.40 (s, 1H); 8.75 (t, br, 1H); 13.5 (br, 1H) |
| 458 | [DMSO] 0.89 (t, 3H); 1.52 (m, 2H); 3.25 (m, 2H); 8.41 (s, 1H); 8.73 (t, br, 1H); 13.4 (br, 1H) |
| 459 | [DMSO] 1.19 (d, 6H); 4.08 (m, 1H); 8.43 (s, 1H); 8.59 (d, br, 1H); 13.4 (br, 1H) |
| 460 | [DMSO] 0.59 (m, 2H); 0.75 (m, 2H); 2.87 (m, 1H); 8.39 (s, 1H); 8.73 (d, br, 1H) |
| 461 | [DMSO] 0.90 (t, 3H); 1.32 (m, 2H); 1.50 (m, 2H); 3.30 (m, 2H); 8.41 (s, 1H); 8.74 (t, br, 1H); 13.5 (br, 1H) |
| 462 | [DMSO] 1.70 (m, 2H); 2.03 (m, 2H); 2.25 (m, 2H); 4.40 (m, 1H); 8.41 (s, 1H); 8.90 (d, br, 1H); 13.5 (br, 1H) |
| 477 | [DMSO] 0.25 (m, 2H); 0.47 (m, 2H); 1.02 (m, 1H); 3.19 (t, 2H); 8.45 (s, 1H); 8.80 (t, br, 1H) |
| 479 | [DMSO] 0.90 (s, 9H); 3.14 (d, 2H); 8.38 (s, 1H); 8.60 (t, br, 1H); 13.7 (br, 1H) |
| 485 | [DMSO] 0.89 (d, 6H); 1.82 (m, 1H); 3.13 (t, 2H); 8.40 (s, 1H); 8.72 (t, br, 1H) |
| 487 | [DMSO] 0.90 (d, 6H); 1.41 (q, 2H); 1.62 (m, 1H); 3.32 (m, 2H); 8.40 (s, 1H); 8.72 (t, br, 1H); 13.5 (br, 1H) |
| 489 | [CDCl3] 4.10 (d, 2H); 5.25 (dd, 2H); 5.93 (m, 1H); 8.60 (s, 1H); 9.10 (br, 1H); 12.4 (br, 1H) |
| 493 | [DMSO] 1.71 (s, 3H); 3.86 (d, 2H); 4.84 (d, 2H); 8.40 (s, 1H); 8.85 (t, br, 1H); 13.5 (br) |
| 494 | [DMSO] 3.17 (m, 1H); 4.11 (m, 2H); 8.39 (s, 1H); 8.98 (t, br, 1H), 13.4 (br) |
| 496 | [CDCl3] 0.95 (t, 3H); 1.25 (d, 3H); 1.60 (m, 2H); 4.12 (m, 1H); 8.48 (s, 1H); 8.52 (br, 1H) |
| 498 | [CDCl3] 0.95 (t, 3H); 1.25 (d, 3H); 1.40 (m, 2H); 1.55 (m, 2H); 4.17 (m, 1H); 8.53 (s, 1H); 8.70 (br, 1H) |
| 499 | [CDCl3] 0.87 (t, 3H); 1.21 (d, 3H); 1.32 (m, 6H); 1.53 (m, 2H); 4.15 (m, 1H); 8.62 (s, 1H); 8.99 (d, br, 1H); 13.0 (br) |
| 502 | [CDCl3] 0.91 (d, 6H); 1.23 (d, 3H); 1.35 (m, 1H); 1.48 (m, 1H); 1.66 (m, 1H); 4.25 (m, 1H); 8.62 (s, 1H); 8.96 (d, br, 1H); 12.9 (br, 1H) |
| 504 | [CDCl3] 0.95 (m, 6H); 1.18 (d, 3H); 1.81 (m, 1H); 4.07 (m, 1H); 8.61 (s, 1H); 8.97 (d, br, 1H); 12.9 (br, 1H) |
| 506 | [CDCl3] 0.94 (t, 6H); 1.50 (m, 2H); 1.65 (m, 2H), 4.00 (m, 1H); 8.56 (s, 1H); 8.73 (d, br, 1H) |
| 512 | [DMSO] 3.28 (s, 3H); 3.48 (m, 4H); 8.42 (s, 1H); 8.78 (br, 1H); 13.7 (br, 1H) |
| 519 | [DMSO] 1.16 (d, 3H); 3.30 (s, 3H); 3.42 (m, 2H); 4.18 (m, 1H); 8.42 (s, 1H); 8.60 (d, br, 1H); 13.7 (br, 1H) |
| 521 | [DMSO] 1.74 (m, 2H); 3.26 (s, 3H); 3.39 (m, 4H); 8.40 (s, 1H); 8.80 (t, br, 1H); 13.6 (br, 1H) |
| 569 | [DMSO] 8.25 (br, 1H); 8.35 (br, 1H); 8.50 (s, 1H); 13.7 (br, 1H) |
| 570 | [DMSO] 2.82 (d, 3H); 8.40 (s, 1H); 8.71 (br, 1H); 13.5 (br, 1H) |
| 571 | [DMSO] 1.12 (t, 3H); 3.35 (q, 2H); 8.40 (s, 1H); 8.75 (t, br, 1H); 13.7 (br, 1H) |
| 572 | [DMSO] 0.89 (t, 3H); 1.52 (m, 2H); 3.26 (m, 2H); 8.39 (s, 1H); 8.82 (br, 1H) |

TABLE 2-continued

NMR data of compounds from Table 1

| Ex. No. | 1H-NMR data |
|---|---|
| 573 | [DMSO] 1.18 (d, 6H); 4.09 (m, 1H); 8.42 (s, 1H); 8.53 (d, br, 1H); 13.5 (br, 1H) |
| 574 | [DMSO] 0.59 (m, 2H); 0.74 (m, 2H); 2.85 (m, 1H); 8.37 (s, 1H); 8.72 (d, br, 1H) |
| 575 | [DMSO] 0.89 (t, 3H); 1.35 (m, 2H); 1.50 (m, 2H); 3.35 (m, 2H); 8.39 (s, 1H); 8.75 (br, 1H) |
| 576 | [DMSO] 1.70 (m, 2H); 2.05 (m, 2H); 2.25 (m, 2H); 4.40 (m, 1H); 8.40 (s, 1H); 8.94 (br, 1H) |
| 591 | [DMSO] 0.25 (m, 2H); 0.45 (m, 2H); 1.03 (m, 1H); 3.21 (t, 2H); 8.40 (s, 1H); 8.84 (br, 1H) |
| 599 | [DMSO] 0.89 (d, 6H); 1.82 (m, 1H); 3.14 (m, 2H); 8.38 (s, 1H); 8.74 (br, 1H) |
| 601 | [CDCl3] 0.96 (d, 6H); 1.51 (m, 2H); 1.70 (m, 1H); 3.49 (m, 2H); 8.59 (s, 1H); 9.02 (br, 1H); 12.2 (br) |
| 603 | [DMSO] 3.95 (t, 2H); 5.18 (dd, 2H); 5.89 (m, 1H); 8.40 (s, 1H); 8.85 (t, br, 1H); 13.6 (br, 1H) |
| 612 | [CDCl3] 0.91 (t, 3H); 1.24 (d, 3H); 1.40 (m, 2H); 1.54 (m, 2H); 4.18 (m, 1H); 8.57 (s, 1H); 8.90 (d, br, 1H); 12.2 (br, 1H) |
| 620 | [CDCl3] 0.94 (t, 6H); 1.51 (m, 2H); 1.67 (m, 2H); 3.99 (m, 1H); 8.57 (s, 1H); 8.82 (d, br, 1H) |
| 626 | [DMSO] 3.29 (s, 3H); 3.48 (m, 4H); 8.41 (s, 1H); 8.78 (br, 1H); 13.7 (br, 1H) |
| 633 | [CDCl3] 1.28 (d, 3H); 3.40 (s, 3H); 3.45 (m, 2H); 4.37 (m, 1H); 8.48 (s, 1H); 8.78 (br, 1H) |
| 635 | [DMSO] 1.75 (m, 2H); 3.25 (s, 3H); 3.39 (m, 4H); 8.40 (s, 1H); 8.81 (br, 1H); 13.6 (br, 1H) |
| 797 | [DMSO] 8.27 (br, 1H); 8.38 (br, 1H); 8.52 (s, 1H); 13.7 (br, 1H) |
| 798 | [DMSO] 2.82 (d, 3H); 8.40 (s, 1H); 8.75 (d, br, 1H); 13.6 (br, 1H) |
| 799 | [DMSO] 1.12 (t, 3H); 3.33 (m, 2H); 8.41 (s, 1H); 8.78 (t, br, 1H); 13.6 (br, 1H) |
| 800 | [DMSO] 0.89 (t, 3H); 1.52 (m, 2H); 3.27 (q, 2H); 8.41 (s, 1H); 8.76 (t, br, 1H); 13.5 (br, 1H) |
| 801 | [DMSO] 1.18 (d, 6H); 4.09 (m, 1H); 8.42 (s, 1H); 8.60 (d, br, 1H) |
| 802 | [DMSO] 0.55 (m, 2H); 0.75 (m, 2H); 2.85 (m, 1H); 8.31 (s, 1H); 9.24 (br, 1H); 13.4 (br, 1H) |
| 803 | [DMSO] 0.89 (t, 3H); 1.33 (m, 2H); 1.51 (m, 2H); 3.30 (m, 2H); 8.40 (s, 1H); 8.75 (t, br, 1H), 13.4 (br) |
| 804 | [DMSO] 1.70 (m, 2H); 2.04 (m, 2H); 2.25 (m, 2H); 4.39 (m, 1H); 8.43 (s, 1H); 8.95 (d, br, 1H); 13.4 (br, 1H) |
| 806 | [DMSO] 2.82 (s, 3H); 2.98 (s, 3H); 8.06 (s, 1H); 12.6 (s, br, 1H) |
| 811 | [CDCl3] 1.24 (t, 6H); 3.44 (m, 4H); 7.72 (s, 1H) |
| 819 | [DMSO] 0.25 (m, 2H); 0.46 (m, 2H); 1.03 (m, 1H); 3.20 (t, 2H); 8.45 (s, 1H); 8.87 (t, br, 1H); 13.4 (br, 1H) |
| 821 | [DMSO] 0.90 (s, 9H); 3.13 (d, 2H); 8.37 (s, 1H); 8.61 (t, br, 1H); 13.4 (br, 1H) |
| 827 | [DMSO] 0.88 (d, 6H); 1.82 (m, 1H); 3.13 (t, 2H); 8.40 (s, 1H); 8.76 (t, br, 1H); 13.5 (br, 1H) |
| 829 | [DMSO] 0.90 (d, 6H); 1.42 (m, 2H); 1.61 (m, 1H); 3.30 (m, 2H); 8.41 (s, 1H); 8.76 (t, br, 1H); 13.5 (br, 1H) |
| 831 | [DMSO] 3.95 (t, 2H); 5.19 (dd, 2H); 5.89 (m, 1H); 8.41 (s, 1H); 8.88 (t, br, 1H); 13.5 (br, 1H) |
| 835 | [DMSO] 1.72 (s, 3H); 3.87 (d, 2H); 4.86 (d, 2H); 8.39 (s, 1H); 8.90 (t, br, 1H); 13.4 (br, 1H) |
| 836 | [DMSO] 3.18 (m, 1H); 4.10 (m, 2H); 8.36 (s, 1H); 9.01 (t, br, 1H); 13.4 (br, 1H) |
| 838 | [DMSO] 0.88 (t, 3H); 1.14 (d, 3H); 1.51 (m, 2H); 3.91 (m, 1H); 8.41 (s, 1H); 8.54 (d, br, 1H); 13.5 (br, 1H) |
| 840 | [DMSO] 0.88 (t, 3H); 1.14 (d, 3H); 1.33 (m, 2H); 1.47 (m, 2H); 4.01 (m, 1H); 8.42 (s, 1H); 853 (d, br, 1H); 13.5 (br, 1H) |
| 841 | [DMSO] 0.85 (t, 3H); 1.14 (d, 3H); 1.28 (m, 6H); 1.49 (m, 2H); 3.98 (m, 1H); 8.41 (s, 1H); 8.60 (d, br, 1H); 13.5 (br, 1H) |
| 844 | [DMSO] 0.87 (d, 6H); 1.14 (d, 3H); 1.27 (m, 1H); 1.48 (m, 1H); 1.62 (m, 1H); 4.09 (m, 1H); 8.41 (s, 1H); 8.52 (d, br, 1H); 13.5 (br, 1H) |
| 845 | [DMSO] 0.90 (s, 9H); 1.08 (d, 3H); 3.90 (m, 1H); 8.35 (s, 1H); 8.38 (d, br, 1H); 13.4 (br) |
| 846 | [DMSO] 0.89 (d, 6H); 1.12 (d, 3H); 1.75 (m, 1H); 3.87 (m, 1H); 8.40 (s, 1H); 8.50 (d, br, 1H); 13.5 (br) |
| 848 | [DMSO] 0.87 (t, 6H); 1.44 (m, 2H); 1.55 (m, 2H); 3.79 (m, 1H); 8.40 (s, 1H); 8.42 (d, br, 1H); 13.4 (br, 1H) |
| 851 | [CDCl3] 3.42 (s, 6H); 3.63 (t, 2H); 4.50 (t, 1H); 8.55 (s, 1H); 8.95 (t, br, 1H); 12.1 (br, 1H) |
| 853 | [CDCl3] 3.65 (m, 2H); 3.86 (m, 2H); 8.47 (s, 1H); 8.98 (br, 1H) |
| 854 | [CDCl3] 3.39 (s, 3H); 3.58 (m, 2H); 3.69 (m, 2H); 8.49 (s, 1H); 8.80 (br, 1H); 11.9 (br, 1H) |
| 861 | [CDCl3] 1.28 (d, 3H); 3.38 (s, 3H); 3.45 (m, 2H); 4.39 (m, 1H); 8.51 (s, 1H); 8.85 (br, 1H); 12.4 (br, 1H) |
| 863 | [CDCl3] 1.90 (m, 2H); 3.40 (s, 3H); 3.57 (m, 4H); 8.30 (s, 1H); 8.70 (br, 1H) |
| 868 | [CDCl3] 3.80 (s, 3H); 4.25 (d, 2H); 8.52 (s, 1H); 9.16 (br, 1H) |
| 909 | [DMSO] 8.22 (br, 1H); 8.32 (br, 1H); 8.61 (s, 1H); 13.8 (br, 1H) |
| 910 | [DMSO] 2.83 (d, 3H); 8.51 (s, 1H); 8.74 (br, 1H); 13.7 (br, 1H) |
| 911 | [DMSO] 1.12 (t, 3H); 3.32 (q, 2H); 8.54 (s, 1H); 8.75 (t, br, 1H); 13.7 (br, 1H) |
| 912 | [DMSO] 0.89 (t, 3H); 1.52 (m, 2H); 3.25 (q, 2H); 8.54 (s, 1H); 8.75 (t, br, 1H); 13.6 (br, 1H) |
| 913 | [CDCl3] 1.25 (d, 6H); 4.25 (m, 1H); 8.54 (br, 1H); 8.70 (s, 1H) |
| 914 | [DMSO] 0.58 (m, 2H); 0.75. (m, 2H); 2.86 (m, 1H); 8.50 (s, 1H); 8.75 (d, br, 1H); 13.6 (br, 1H) |
| 915 | [DMSO] 0.89 (t, 3H); 1.32 (m, 2H); 1.50 (m, 2H); 3.32 (m, 2H); 8.53 (s, 1H); 8.74 (t, br, 1H), 13.5 (br) |
| 916 | [DMSO] 1.70 (m, 2H); 2.05 (m, 2H); 2.25 (m, 2H); 4.40 (m, 1H); 8.52 (s, 1H); 8.98 (d, br, 1H); 13.5 (br, 1H) |
| 917 | [CDCl3] 1.50 (s, 9H); 8.65 (s, 1H); 8.80 (s, br, 1H); 12.3 (br, 1H) |
| 918 | [DMSO] 2.82 (s, 3H); 2.99 (s, 3H); 8.14 (s, 1H); 12.6 (br, 1H) |
| 923 | [DMSO] 1.02 (t, 3H); 1.12 (t, 3H); 3.10 (q, 2H); 3.40 (9, 2H); 8.15 (s, 1H); 12.5 (br, 1H) |
| 931 | [DMSO] 0.24 (m, 2H); 0.46 (m, 2H); 1.04 (m, 1H); 3.18 (t, 2H); 8.55 (s, 1H); 8.82 (t, br, 1H) |
| 933 | [DMSO] 0.90 (s, 9H); 3.13 (d, 2H); 8.50 (s, 1H); 8.61 (t, br, 1H) |
| 939 | [DMSO] 0.88 (d, 6H); 1.83 (m, 1H); 3.14 (t, 2H); 8.52 (s, 1H); 8.72 (t, br, 1H); 13.6 (br, 1H) |
| 941 | [DMSO] 0.90 (d, 6H); 1.43 (m, 2H); 1.62 (m, 1H); 3.35 (m, 2H); 8.52 (s, 1H); 8.72 (t, br, 1H); 13.5 (br, 1H) |
| 943 | [DMSO] 3.94 (t, 2H); 5.18 (dd, 2H); 5.89 (m, 1H); 8.52 (s, 1H); 8.85 (t, br, 1H) |
| 947 | [DMSO] 1.72 (s, 3H); 3.87 (d, 2H); 4.85 (d, 2H); 8.51 (s, 1H); 8.87 (t, br, 1H); 13.5 (br) |

TABLE 2-continued

NMR data of compounds from Table 1

| Ex. No. | 1H-NMR data |
|---|---|
| 948 | [DMSO] 3.18 (m, 1H); 4.12 (m, 2H); 8.50 (s, 1H); 9.00 (t, br, 1H) |
| 950 | [DMSO] 0.92 (t, 3H); 1.21 (d, 3H); 1.57 (m, 2H); 3.97 (m, 1H); 8.55 (d, br, 1H); 8.60 (s, 1H); 13.7 (br, 1H) |
| 952 | [CDCl3] 0.90 (t, 3H); 1.24 (d, 3H); 1.40 (m, 2H); 1.55 (m, 2H); 4.18 (m, 1H); 8.72 (s, 1H); 8.90 (d, br, 1H) |
| 953 | [DMSO] 0.77 (t, 3H); 1.15 (d, 3H); 1.27 (m, 6H); 1.49 (m, 2H); 3.99 (m, 1H); 8.50 (d, br, 1H); 8.55 (s, 1H); 13.6 (br) |
| 956 | [DMSO] 0.88 (d, 6H); 1.15 (d, 3H); 1.27 (m, 1H); 1.48 (m, 1H); 1.62 (m, 1H); 4.10 (m, 1H); 8.50 (d, br, 1H); 8.55 (s, 1H); 13.6 (br, 1H) |
| 957 | [DMSO] 0.91 (s, 9H); 1.09 (d, 3H); 3.80 (m, 1H); 8.39 (d, br, 1H); 8.49 (s, 1H); 13.6 (br, 1H) |
| 958 | [DMSO] 0.89 (d, 6H); 1.11 (d, 3H); 1.75 (m, 1H); 3.86 (m, 1H); 8.48 (d, br, 1H); 8.52 (s, 1H); 13.6 (br) |
| 960 | [CDCl3] 0.95 (t, 6H); 1.50 (m, 2H); 1.62 (m, 2H); 4.00 (m, 1H); 8.73 (s, 1H); 8.90 (d, br, 1H) |
| 963 | [CDCl3] 3.43 (s, 6H); 3.65 (t, 2H); 4.50 (t, 1H); 8.62 (s, 1H); 8.78 (br, 1H) |
| 965 | [DMSO] 3.40 (m, 2H); 3.52 (m, 2H); 8.57 (s, 1H); 8.78 (t, br, 1H); 13.6 (br, 1H) |
| 966 | [DMSO] 3.29 (s, 3H); 3.48 (m, 4H); 8.54 (s, 1H); 8.78 (br, 1H); 13.6 (br, 1H) |
| 973 | [CDCl3] 1.29 (d, 3H); 3.40 (s, 3H); 3.45 (m, 2H); 4.36 (m, 1H); 8.60 (s, 1H); 8.72 (br, 1H) |
| 975 | [DMSO] 1.75 (m, 2H); 3.20 (s, 3H); 3.38 (m, 4H); 8.51 (s, 1H); 8.81 (t, br, 1H); 13.6 (br) |
| 1023 | [DMSO] 8.22 (br, 1H); 8.35 (br, 1H); 8.61 (s, 1H); 13.8 (br, 1H) |
| 1024 | [DMSO] 2.82 (d, 3H); 8.50 (s, 1H); 8.75 (br, 1H); 13.7 (br, 1H) |
| 1025 | [DMSO] 1.13 (t, 3H); 3.35 (m, 2H); 8.52 (s, 1H); 8.75 (br, 1H); 13.5 (br, 1H) |
| 1026 | [DMSO] 0.90 (t, 3H); 1.53 (m, 2H); 3.25 (m, 2H); 8.52 (s, 1H); 8.75 (t, br, 1H); 13.5 (br, 1H) |
| 1027 | [DMSO] 1.18 (d, 6H); 4.08 (m, 1H); 8.54 (s, 1H); 8.56 (br, 1H) |
| 1028 | [DMSO] 0.58 (m, 2H); 0.75 (m, 2H); 3.86 (m, 1H); 8.48 (s, 1H); 8.75 (br, 1H) |
| 1029 | [DMSO] 0.89 (t, 3H); 1.34 (m, 2H); 1.50 (m, 2H); 3.26 (m, 2H); 8.51 (s, 1H); 8.81 (br, 1H); 13.6 (br, 1H) |
| 1030 | [DMSO] 1.70 (m, 2H); 2.04 (m, 2H); 2.25 (m, 2H); 4.39 (m, 1H); 8.53 (s, 1H); 8.91 (d, br, 1H); 13.4 (br, 1H) |
| 1031 | [CDCl3] 1.46 (s, 9H); 8.63 (s, 1H); 8.83 (br, 1H); 111.9 (br, 1H) |
| 1032 | [DMSO] 2.82 (s, br, 3H); 2.96 (s, br, 3H); 8.11 (s, 1H); 12.5 (br, 1H) |
| 1037 | [CDCl3] 1.23 (t, 6H); 3.42 (br, 4H); 7.88 (s, 1H) |
| 1045 | [DMSO] 0.25 (m, 2H); 0.46 (m, 2H); 1.04 (m, 1H); 3.20 (t, 2H); 8.55 (s, 1H); 8.82 (t, br, 1H); 13.6 (br, 1H) |
| 1047 | [DMSO] 0.90 (s, 9H); 3.13 (d, 2H); 8.48 (s, 1H); 8.61 (t, br, 1H) |
| 1053 | [DMSO] 0.90 (d, 6H); 1.82 (m, 1H); 3.13 (m, 2H); 8.50 (s, 1H); 8.75 (br, 1H); 13.5 (br, 1H) |
| 1055 | [DMSO] 0.89 (d, 6H); 1.41 (m, 2H); 1.61 (m, 1H); 3.31 (m, 2H); 8.49 (s, 1H); 8.90 (br, 1H); 13.5 (br, 1H) |
| 1057 | [DMSO] 3.95 (t, 2H); 5.18 (dd, 2H); 5.90 (m, 1H); 8.50 (s, 1H); 8.85 (t, br, 1H) |
| 1061 | [CDCl3] 1.80 (s, 3H); 4.03 (d, 2H); 4.93 (d, 2H); 8.76 (s, 1H); 9.22 (t, br, 1H); |
| 1062 | [DMSO] 3.18 (m, 1H); 4.10 (m, 2H); 8.48 (s, 1H); 9.00 (br, 1H) |
| 1064 | [DMSO] 0.88 (t, 3H); 1.16 (d, 3H); 1.51 (m, 2H); 3.93 (m, 1H); 8.50 (d, br, 1H); 8.55 (s, 1H); 13.6 (br, 1H) |
| 1066 | [DMSO] 0.86 (t, 3H); 1.15 (d, 3H); 1.30 (m, 2H); 1.48 (m, 2H); 4.00 (m, 1H); 8.50 (d, br, 1H); 8.52 (s, 1H); 13.6 (br, 1H) |
| 1067 | [CDCl3] 0.86 (t, 3H); 1.22 (d, 3H); 1.25 (m, 6H); 1.48 (m, 2H); 4.16 (m, 1H); 8.62 (s, 1H); 8.68 (br, 1H) |
| 1070 | [CDCl3] 0.93 (d, 6H); 1.23 (d, 3H); 1.27 (m, 1H); 1.50 (m, 1H); 1.70 (m, 1H); 4.25 (m, 1H); 8.63 (br, 2H) |
| 1071 | [CDCl3] 0.95 (s, 9H); 1.17 (d, 3H); 4.08 (m, 1H); 8.70 (s, 1H); 9.00 (d, br, 1H) |
| 1072 | [CDCl3] 0.95 (m, 6H); 1.20 (d, 3H); 1.82 (m, 1H); 4.07 (m, 1H); 8.76 (s, 1H); 9.13 (br, 1H) |
| 1074 | [CDCl3] 0.92 (t, 6H); 1.50 (m, 2H); 1.65 (m, 2H); 3.96 (m, 1H); 8.72 (s, 1H); 9.00 (d, br, 1H) |
| 1077 | [CDCl3] 3.42 (s, 6H); 3.62 (t, 2H); 4.50 (t, 1H); 8.62 (s, 1H); 8.90 (br, 1H) |
| 1079 | [CDCl3] 3.65 (m, 2H); 3.85 (m, 2H); 8.64 (s, 1H); 9.22 (br, 1H) |
| 1080 | [DMSO] 3.30 (s, 3H); 3.46 (m, 4H); 8.52 (s, 1H); 8.75 (br, 1H) |
| 1087 | [CDCl3] 1.29 (d, 3H); 3.39 (s, 3H); 3.45 (m, 2H); 4.37 (m, 1H); 8.66 (s, 1H); 8.98 (br, 1H); 12.50 (br, 1H) |
| 1089 | [DMSO] 1.75 (m, 2H); 3.23 (s, 3H); 3.38 (m, 4H); 8.52 (s, 1H); 8.80 (t, br, 1H) |
| 1094 | [CDCl3] 3.80 (s, 3H); 4.24 (d, 2H); 8.61 (s, 1H); 9.19 (br, 1H) |
| 1138 | [DMSO] 2.83 (d, 3H); 7.07 (t, 1H); 8.40 (s, 1H); 8.94 (br, 1H); 13.4 (br, 1H) |
| 1139 | [DMSO] 1.12 (t, 3H); 3.33 (m, 2H); 7.08 (t, 1H); 8.40 (s, 1H); 9.00 (br, 1H); 13.4 (br, 1H) |
| 1171 | [DMSO] 3.90 (t, 2H); 5.15 (dd, 2H); 5.90 (m, 1H); 7.10 (t, 1H); 8.40 (s, 1H); 9.16 (br, 1H); 13.4 (br, 1H) |
| 1178 | [CDCl3] 0.95 (t, 3H); 1.21 (d, 3H); 1.58 (m, 2H); 4.08 (m, 1H); 6.86 (t, 1H); 8.70 (s, 1H); 9.34 (d, br, 1H); 12.9 (br, 1H) |
| 1180 | [CDCl3] 0.93 (t, 3H); 1.21 (d, 3H); 1.40 (m, 2H); 1.52 (m, 2H); 4.16 (m, 1H); 6.87 (t, 1H); 8.70 (s, 1H); 9.31 (d, br, 1H); 12.9 (br, 1H) |
| 1188 | [CDCl3] 0.92 (t, 6H); 1.50 (m, 2H); 1.65 (m, 2H); 3.98 (m, 1H); 6.86 (t, 1H); 8.71 (s, 1H); 9.28 (d, br, 1H); 12.9 (br, 1H) |
| 1201 | [CDCl3] 1.27 (d, 3H); 3.40 (s, 3H); 3.43 (m, 2H); 4.37 (m, 1H); 6.85 (t, 1H); 8.68 (s, 1H); 9.42 (d, br, 1H); 12.7 (br, 1H) |
| 1251 | [DMSO] 8.26 (br, 1H); 8.42 (br, 1H); 8.62 (s, 1H) |
| 1252 | [CDCl3] 3.00 (d, 3H); 8.66 (s, 1H); 8.82 (br, 1H) |
| 1253 | [CDCl3] 1.24 (t, 3H); 3.50 (m, 2H); 8.68 (s, 1H); 8.86 (br, 1H) |
| 1254 | [CDCl3] 1.00 (t, 3H); 1.62 (m, 2H); 3.42 (m, 2H); 8.67 (s, 1H); 8.90 (br, 1H) |
| 1255 | [CDCl3] 1.25 (d, 6H); 4.25 (m, 1H); 8.70 (s, 1H); 8.84 (br, 1H) |
| 1256 | [CDCl3] 0.60 (m, 2H); 0.89. (m, 2H); 3.00 (m, 1H); 8.70 (s, 1H); 9.00 (br, 1H) |

TABLE 2-continued

NMR data of compounds from Table 1

| Ex. No. | 1H-NMR data |
|---|---|
| 1257 | [CDCl3] 0.96 (t, 3H); 1.42. (m, 2H); 1.60 (m, 2H); 3.45 (m, 2H); 8.70 (s, 1H); 8.88 (br, 1H); 12.1 (br, 1H) |
| 1258 | [CDCl3] 1.77 (m, 2H); 1.98. (m, 2H); 2.43 (m, 2H); 4.55 (m, 1H); 8.68 (s, 1H); 9.13 (br, 1H); 12.5 (br, 1H) |
| 1259 | [CDCl3] 1.45 (s, 9H); 8.67 (s, 1H); 8.78 (br, 1H); 12.4 (br, 1H) |
| 1260 | [CDCl3] 3.11 (s, 6H); 7.95 (s, 1H) |
| 1265 | [CDCl3] 1.25 (t, 6H); 3.45 (br, 4H); 7.89 (s, 1H) |
| 1273 | [CDCl3] 0.27 (m, 2H); 0.56. (m, 2H); 1.04 (m, 1H); 3.32 (m, 2H); 8.67 (s, 1H); 8.92 (br, 1H); 12.3 (br, 1H) |
| 1275 | [CDCl3] 0.97 (s, 9H); 3.29 (d, 2H); 8.73 (s, 1H); 9.00 (br, 1H); 11.9 (br, 1H) |
| 1281 | [CDCl3] 0.98 (d, 6H); 1.89 (m, 1H); 3.29 (t, 2H); 8.70 (s, 1H); 8.98 (br, 1H); 12.1 (br, 1H) |
| 1283 | [CDCl3] 0.95 (d, 6H); 1.50 (m, 2H); 1.68 (m 1H); 3.46 (m, 2H); 8.69 (s, 1H); 8.83 (br, 1H); 12.1 (br, 1H) |
| 1285 | [CDCl3] 4.09 (t, 2H); 5.22 (dd, 2H); 5.91 (m, 1H); 8.70 (s, 1H); 9.01 (br, 1H); 12.2 (br, 1H) |
| 1289 | [DMSO] 0.26 (m, 2H); 0.47 (m, 2H); 1.05 (m, 1H); 3.20 (m, 2H); 6.85 (tt, 1H); 7.25 (br, 1H); 8.45 (d, 1H); 9.15 (br, 1H), 13.4 (br, 1H) |
| 1290 | [CDCl3] 2.25 (m, 1H); 4.23 (m, 2H); 8.72 (s, 1H); 9.20 (br, 1H), 12.0 (br, 1H) |
| 1292 | [CDCl3] 0.95 (t, 3H); 1.21 (d, 3H); 1.55 (m 2H); 4.10 (m, 1H); 8.70 (s, 1H); 8.82 (br, 1H) |
| 1294 | [CDCl3] 0.93 (t, 3H); 1.22 (d, 3H); 1.38 (m, 2H); 1.52 (m, 2H); 4.18 (m, 1H); 8.70 (s, 1H); 8.79 (br, 1H); 12.4 (br, 1H) |
| 1295 | [CDCl3] 0.89 (t, 3H); 1.20 (d, 3H); 1.25-1.4 (m, 6H); 1.50 (m, 2H); 4.16 (m, 1H); 8.70 (s, 1H); 8.75 (br, 1H) |
| 1298 | [CDCl3] 0.92 (t, 6H); 1.40 (d, 3H); 1.32 (m, 1H); 1.45 (m, 1H); 1.55 (m, 1H); 4.25 (m, 1H); 8.70 (s, 1H); 8.75 (br, 1H); 12.4 (br, 1H) |
| 1299 | [CDCl3] 0.95 (s, 9H); 1.15 (d, 3H); 4.10 (m, 1H); 8.72 (s, 1H); 8.88 (br, 1H); 11.9 (br, 1H) |
| 1300 | [CDCl3] 0.95 (m, 6H); 1.15 (d, 3H); 1.77 (m, 1H); 4.05 (m, 1H); 8.71 (s, 1H); 8.85 (br, 1H) |
| 1302 | [CDCl3] 0.93 (t, 6H); 1.48 (m, 2H); 1.65 (m, 2H); 3.99 (m, 1H); 8.71 (s, 1H); 8.76 (br, 1H); 12.4 (br, 1H) |
| 1305 | [CDCl3] 3.40 (s, 6H); 3.62 (t, 2H); 4.50 (t, 1H); 8.60 (s, 1H); 8.74 (br, 1H); 11.7 (br, 1H) |
| 1307 | [CDCl3] 3.65 (m, 2H); 3.87 (m, 2H); 4.50 (t, 1H); 8.66 (s, 1H); 9.11 (br, 1H) |
| 1308 | [CDCl3] 3.40 (s, 3H); 3.58 (m, 2H); 3.67 (m, 2H); 8.60 (s, 1H); 8.75 (br, 1H); 11.7 (br, 1H) |
| 1315 | [CDCl3] 1.48 (d, 3H); 3.38 (s, 3H); 3.44 (m, 2H); 4.38 (m, 1H); 8.62 (s, 1H); 8.72 (br, 1H); 12.1 (br, 1H) |
| 1317 | [CDCl3] 1.90 (m, 2H); 3.40 (s, 3H); 3.58 (m, 4H); 8.39 (s, 1H); 8.62 (br, 1H) |
| 1322 | [CDCl3] 3.79 (s, 3H); 4.25 (d, 2H); 8.65 (s, 1H); 9.18 (br, 1H) |
| 1365 | [DMSO] 8.24 (br, 1H), 8.42 (br, 1H); 8.81 (s, 1H); 13.6 (br, 1H) |
| 1366 | [DMSO] 8.19 (br, 1H), 8.34 (br, 1H); 8.78 (s, 1H); 13.7 (br, 1H) |
| 1368 | [DMSO] 2.83 (d, 3H); 6.81 (tt, 1H); 7.22 (br, 1H); 8.41 (d, 1H); 9.00 (br, 1H); 13.4 (br, 1H) |
| 1369 | [DMSO] 1.12 (t, 3H); 3.35 (m, 2H); 6.85 (tt, 1H); 7.20 (br, 1H); 8.41 (d, 1H); 9.20 (br, 1H); 13.4 (br, 1H) |
| 1370 | [DMSO] 0.89 (t, 3H); 1.52 (m, 2H); 3.27 (q, 2H); 6.82 (tt, 1H); 7.20 (br, 1H); 8.40 (d, 1H); 9.20 (br, 1H); 13.4 (br, 1H) |
| 1371 | [DMSO] 1.18 (d, 6H); 4.09 (m, 1H); 6.82 (tt, 1H); 7.20 (br, 1H); 8.42 (d, 1H); 8.95 (br, 1H); 13.4 (br, 1H) |
| 1372 | [DMSO] 0.56 (m, 2H); 0.75 (m, 2H); 2.85 (m, 1H); 6.83 (tt, 1H); 7.21 (br, 1H); 8.40 (d, 1H); 9.05 (br, 1H); 13.4 (br, 1H) |
| 1373 | [DMSO] 0.89 (t, 3H); 1.32 (m, 2H); 1.50 (m, 2H); 3.30 (q, 2H); 6.84 (tt, 1H); 7.20 (br, 1H); 8.41 (d, 1H); 9.10 (br, 1H); 13.4 (br, 1H) |
| 1389 | [DMSO] 0.26 (m, 2H); 0.47 (m, 2H); 1.05 (m, 1H); 3.20 (m, 2H); 6.85 (tt, 1H); 7.25 (br, 1H); 8.45 (d, 1H); 9.15 (br, 1H), 13.4 (br, 1H) |
| 1391 | [DMSO] 0.91 (s, 9H); 3.16 (d, 2H); 6.82 (tt, 1H); 7.10 (br, 1H); 8.41 (d, 1H); 9.20 (br, 1H); 13.3 (br, 1H) |
| 1397 | [DMSO] 0.90 (d, 6H); 1.82 (m, 1H); 3.15 (m, 2H); 6.82 (tt, 1H); 7.20 (br, 1H); 8.40 (d, 1H); 9.15 (br, 1H), 13.4 (br, 1H) |
| 1401 | [DMSO] 3.95 (m, 2H); 5.18 (dd, 2H); 5.92 (m, 1H); 6.82 (tt, 1H); 7.20 (d, 1H); 8.42 (d, 1H); 9.20 (br, 1H); 13.3 (br, 1H) |
| 1406 | [DMSO] 3.15 (t, 1H); 4.13 (m, 2H); 6.82 (tt, 1H); 7.18 (br, 1H); 8.41 (d, 1H); 9.35 (br, 1H); 13.3 (br, 1H) |
| 1408 | [DMSO] 0.87 (t, 3H); 1.14 (d, 3H); 1.51 (m, 2H); 3.92 (m, 1H); 6.82 (tt, 1H); 7.20 (br, 1H); 8.41 (d, 1H); 8.90 (br, 1H); 13.4 (br, 1H) |
| 1410 | [DMSO] 0.86 (t, 3H); 1.15 (d, 3H); 1.30 (m, 2H); 1.48 (m, 2H); 4.02 (m, 1H); 6.83 (tt, 1H); 7.20 (br, 1H); 8.42 (d, 1H); 8.90 (br, 1H); 13.4 (br, 1H) |
| 1411 | [DMSO] 0.88 (t, 3H); 1.15 (d, 3H); 1.27 (m, 6H); 1.49 (m, 2H); 4.00 (m, 1H); 6.82 (tt, 1H); 7.20 (br, 1H); 8.42 (d, 1H); 8.92 (br, 1H); 13.4 (br, 1H) |
| 1414 | [DMSO] 0.88 (d, 6H); 1.15 (d, 3H); 1.28 (m, 1H); 1.46 (m, 1H); 1.60 (m, 1H); 4.10 (m, 1H); 6.81 (tt, 1H); 7.20 (br, 1H); 8.42 (d, 1H); 8.90 (br, 1H), 13.4 (br, 1H) |
| 1418 | [CDCl3] 0.93 (t, 6H); 1.50 (m, 2H); 1.65 (m, 2H); 4.00 (m, 1H); 6.83 (d, 1H); 8.69 (d, 1H); 9.21 (d, br, 1H); 13.0 (br, 1H) |
| 1421 | [CDCl3] 3.41 (s, 6H); 3.52 (t, 2H); 4.50 (t, 1H); 6.12 (tt, 1H); 6.81 (d, 1H); 8.64 (d, 1H); 9.41 (br, 1H); 12.5 (br, 1H) |
| 1424 | [CDCl3] 3.37 (s, 3H); 3.56 (m, 2H); 3.67 (m, 2H); 6.11 (tt, 1H); 6.84 (d, 1H); 8.65 (d, 1H); 9.46 (br, 1H); 12.2 (br, 1H) |
| 1431 | [CDCl3] 1.28 (d, 3H); 3.39 (s, 3H); 3.45 (m, 2H); 4.40 (m, 1H); 6.10 (tt, 1H); 6.83 (d, 1H); 8.67 (d, 1H); 9.39 (d, br, 1H); 13.0 (br, 1H) |
| 1433 | [DMSO] 1.75 (m, 2H); 3.24 (s, 3H); 3.38 (m, 4H); 6.83 (tt, 1H); 7.20 (br, 1H); 8.42 (d, 1H); 9.15 (br, 1H), 13.4 (br, 1H) |

TABLE 2-continued

NMR data of compounds from Table 1

| Ex. No. | 1H-NMR data |
|---|---|
| 1481 | [DMSO] 7.42 (br, 1H); 8.10 (br, 1H); 8.40 (br, 1H); 8.46 (d, 1H), 13.6 (br, 1H) |
| 1482 | [CDCl3] 3.01 (d, 3H); 6.88 (d, 1H); 8.67 (d, 1H); 9.34 (br, 1H); 12.5 (br, 1H) |
| 1483 | [CDCl3] 1.27 (t, 3H); 3.50 (m, 2H); 6.88 (d, 1H); 8.68 (d, 1H); 9.32 (br, 1H); 12.6 (br, 1H) |
| 1484 | [CDCl3] 1.00 (t, 3H); 1.63 (m, 2H); 3.41 (m, 2H); 6.88 (d, 1H); 8.70 (d, 1H); 9.38 (br, 1H); 12.9 (br, 1H) |
| 1485 | [CDCl3] 1.25 (d, 6H); 4.27 (m, 1H); 6.88 (d, 1H); 8.70 (d, 1H); 9.30 (d, br, 1H); 13.4 (br, 1H) |
| 1486 | [CDCl3] 0.62 (m, 2H); 0.86 (m, 2H); 3.01 (m, 1H); 6.88 (d, 1H); 8.70 (d, 1H); 9.41 (br, 1H); 12.6 (br, 1H) |
| 1487 | [CDCl3] 0.95 (t, 3H); 1.44 (m, 2H); 1.61 (m, 2H); 3.45 (m, 2H); 6.88 (d, 1H); 8.70 (d, 1H); 9.35 (t, br, 1H); 12.7 (br, 1H) |
| 1488 | [CDCl3] 1.78 (m, 2H); 2.00 (m, 2H); 2.42 (m, 2H); 4.58 (m, 1H); 6.88 (d, 1H); 8.68 (d, 1H); 9.60 (d, br, 1H); 13.3 (br, 1H) |
| 1503 | [CDCl3] 0.26 (m, 2H); 0.55 (m, 2H); 1.06 (m, 1H); 3.33 (m, 2H); 6.88 (d, 1H); 8.70 (d, 1H); 9.45 (br, 1H); 12.9 (br, 1H) |
| 1505 | [CDCl3] 0.98 (s, 9H); 3.30 (d, 2H); 6.88 (d, 1H); 8.72 (d, 1H); 9.43 (t, br, 1H); 12.5 (br, 1H) |
| 1511 | [CDCl3] 0.98 (d, 6H); 1.90 (m, 1H); 3.30 (m, 2H); 6.88 (d, 1H); 8.70 (d, 1H); 9.42 (t, br, 1H) |
| 1513 | [CDCl3] 0.85 (d, 6H); 1.51 (m, 2H); 1.70 (m, 1H); 3.47 (m, 2H); 6.88 (d, 1H); 8.70 (d, 1H); 9.32 (t, br, 1H); 12.7 (br, 1H) |
| 1515 | [CDCl3] 4.10 (t, 2H); 5.25 (dd, 2H); 5.91 (m, 1H); 6.88 (d, 1H); 8.70 (d, 1H); 9.47 (br, 1H); 12.8 (br, 1H) |
| 1519 | [DMSO] 1.71 (s, 3H); 3.88 (d, 2H); 4.84 (d, 2H); 7.35 (br, 1H); 8.41 (d, 1H); 9.02 (br, 1H); 13.4 (br, 1H) |
| 1520 | [DMSO] 3.15 (m, 1H); 4.12 (m, 2H); 7.36 (d, br, 1H); 8.42 (d, 1H); 9.15 (br, 1H), 13.4 (br, 1H) |
| 1522 | [CDCl3] 0.95 (t, 3H); 1.22 (d, 3H); 1.59 (m, 2H); 4.11 (m, 1H); 6.88 (d, 1H); 8.71 (d, 1H); 9.28 (d, br, 1H); 13.4 (br, 1H) |
| 1524 | [CDCl3] 0.92 (t, 3H); 1.23 (d, 3H); 1.40 (m, 2H); 1.52 (m, 2H); 4.20 (m, 1H); 6.89 (d, 1H); 8.71 (d, 1H); 9.27 (d, br, 1H); 13.4 (br, 1H) |
| 1525 | [CDCl3] 0.88 (t, 3H); 1.23 (d, 3H); 1.25-1.4 (m, 6H); 1.55 (m, 2H); 4.18 (m, 1H); 7.89 (d, 1H); 8.70 (d, 1H); 9.28 (br, 1H); 13.2 (br, 1H) |
| 1528 | [CDCl3] 0.92 (d, 6H); 1.22 (d, 3H), 1.35 (m, 1H); 1.50 (m, 1H); 1.68 (m, 1H); 4.28 (m, 1H); 6.89 (d, 1H); 8.71 (d, 1H); 9.26 (d, br, 1H); 13.3 (br, 1H) |
| 1529 | [CDCl3] 0.95 (s, 9H); 1.17 (d, 3H); 4.12 (m, 1H); 6.89 (d, 1H); 8.73 (d, 1H); 9.30 (d, br, 1H), 12.8 (br, 1H) |
| 1530 | [CDCl3] 0.95 (dt, 6H); 1.17 (d, 3H); 1.82 (m, 1H); 4.08 (m, 1H); 6.89 (d, 1H); 8.72 (d, 1H); 9.31 (d, br, 1H); 13.2 (br, 1H) |
| 1532 | [CDCl3] 0.95 (t, 6H); 1.50 (m, 2H); 1.66 (m, 2H); 4.00 (m, 1H); 6.89 (d, 1H); 8.72 (d, 1H); 9.21 (d, br, 1H); 13.3 (br, 1H) |
| 1535 | [DMSO] 3.32 (s, 6H); 3.45 (t, 2H); 4.50 (t, 1H); 7.33 (d, br, 1H); 8.43 (d, 1H); 8.92 (br, 1H); 13.4 (br, 1H) |
| 1537 | [DMSO] 3.38 (m, 2H); 3.52 (m, 2H); 4.80 (m, 1H); 7.37 (br, 1H); 8.45 (d, 1H); 8.96 (br, 1H); 13.4 (br, 1H) |
| 1538 | [DMSO] 3.25 (s, 3H); 3.49 (m, 4H); 7.37 (d, br, 1H); 8.44 (d, 1H); 8.97 (br, 1H); 13.5 (br, 1H) |
| 1545 | [DMSO] 1.15 (d, 3H); 3.27 (s, 3H); 3.40 (m, 2H); 4.19 (m, 1H); 7.35 (d, br, 1H); 8.43 (d, 1H); 8.82 (br, 1H); 13.4 (br, 1H) |
| 1547 | [DMSO] 1.75 (m, 2H); 3.25 (s, 3H); 3.40 (m, 4H); 7.38 (br, 1H); 8.40 (d, 1H); 8.94 (br, 1H); 13.4 (br, 1H) |
| 1595 | [DMSO] 7.45 (d, 1H); 8.15 (br, 1H); 8.40 (br, 1H); 8.50 (d, 1H); 13.7 (br, 1H) |
| 1596 | [DMSO] 2.82 (d, 3H); 7.42 (d, 1H); 8.41 (d, 1H); 8.80 (br, 1H); 13.4 (br, 1H) |
| 1597 | [DMSO] 1.12 (t, 3H); 3.31 (m, 2H); 7.41 (d, 1H); 8.41 (d, 1H); 8.85 (br, 1H); 13.45 (br, 1H) |
| 1598 | [DMSO] 0.90 (t, 3H); 1.54 (m, 2H); 3.25 (q, 2H); 7.41 (d, 1H); 8.40 (d, 1H); 8.85 (br, 1H); 13.45 (br) |
| 1599 | [DMSO] 1.17 (d, 6H); 4.10 (m, 1H); 7.40 (d, 1H); 8.41 (d, 1H); 8.67 (d, br, 1H); 13.4 (br, 1H) |
| 1600 | [DMSO] 0.57 (m, 2H); 0.75 (m, 2H); 2.86 (m, 1H); 7.41 (d, 1H); 8.37 (d, 1H); 8.80 (br, 1H); 13.35 (br, 1H) |
| 1601 | [CDCl3] 0.95 (t, 3H); 1.40 (m, 2H); 1.60 (m, 2H); 3.45 (q, 2H); 6.88 (d, 1H); 8.71 (d, 1H); 9.28 (br, 1H); 12.9 (br, 1H) |
| 1602 | [CDCl3] 1.78 (m, 2H); 1.95 (m, 2H); 2.40 (m, 2H); 4.57 (m, 1H); 6.86 (d, 1H); 8.70 (d, 1H); 9.45 (d, br, 1H); 12.9 (br, 1H) |
| 1603 | [CDCl3] 1.45 (s, 9H); 6.85 (d, 1H); 8.67 (d, 1H); 9.15 (br, 1H); 12.6 (br, 1H) |
| 1604 | [CDCl3] 3.05 (s, 6H); 7.07 (d, 1H); 7.80 (d, 1H) |
| 1609 | [CDCl3] 1.22 (t, 6H); 3.40 (m, 4H); 7.02 (d, 1H); 7.72 (d, 1H) |
| 1617 | [DMSO] 0.25 (m, 2H); 0.46 (m, 2H); 1.05 (m, 1H); 3.22 (m, 2H); 7.45 (d, br, 1H); 8.45 (d, 1H); 8.95 (br, 1H); 13.4 (br, 1H) |
| 1619 | [DMSO] 0.90 (s, 9H), 3.15 (d, 2H); 7.38 (d, br, 1H); 8.40 (d, 1H); 8.80 (br, 1H); 13.4 (br, 1H) |
| 1625 | [DMSO] 0.90 (d, 6H); 1.82 (m, 1H); 3.14 (t, 2H); 7.39 (d, 1H); 8.40 (d, 1H); 8.91 (t, br, 1H) |
| 1627 | [CDCl3] 0.92 (d, 6H); 1.49 (m, 2H); 1.68 (m, 1H); 3.46 (m, 2H); 6.87 (d, 1H); 8.70 (d, 1H); 9.22 (br, 1H); 12.8 (br, 1H) |
| 1629 | [DMSO] 3.95 (m, 2H); 5.15 (dd, 2H); 5.90 (m, 1H); 7.40 (d, 1H); 8.40 (d, 1H); 8.95 (br, 1H); 13.4 (br, 1H) |
| 1633 | [CDCl3] 1.78 (s, 3H); 4.02 (d, 2H); 4.88 (d, 2H); 6.87 (d 1H); 8.72 (d, 1H); 9.42 (br, 1H); 12.7 (br, 1H) |
| 1634 | [CDCl3] 2.23 (m, 1H); 4.23 (m, 2H); 6.88 (d, 1H); 8.73 (d, 1H); 9.51 (br, 1H), 12.8 (br, 1H) |
| 1636 | [DMSO] 0.89 (t, 3H); 1.14 (d, 3H); 1.51 (m, 2H); 3.95 (m, 1H); 7.41 (d, 1H); 8.40 (d, 1H); 8.60 (br, 1H); 13.6 (br, 1H) |

TABLE 2-continued

NMR data of compounds from Table 1

| Ex. No. | 1H-NMR data |
|---|---|
| 1638 | [DMSO] 0.87 (t, 3H); 1.15 (d, 3H); 1.32 (m, 2H); 1.46 (m, 2H); 4.03 (m, 1H); 7.40 (d, 1H); 8.40 (d, 1H); 8.51 (br, 1H); 13.4 (br, 1H) |
| 1639 | [CDCl3] 0.88 (t, 3H); 1.21 (d, 3H); 1.32 (m, 6H); 1.50 (m, 2H); 4.18 (m, 1H); 6.88 (d, 1H); 8.71 (d, 1H); 9.12 (d, br, 1H), 12.9 (br, 1H) |
| 1642 | [CDCl3] 0.92 (t, 6H); 1.20 (d, 3H); 1.32 (m, 1H); 1.46 (m, 1H); 1.67 (m, 1H); 4.27 (m, 1H); 6.88 (d, 1H); 8.71 (d, 1H); 9.12 (d, br, 1H), 12.9 (br, 1H) |
| 1643 | [CDCl3] 0.93 (s, 9H); 1.15 (d, 3H); 4.12 (m, 1H); 6.88 (d, 1H); 8.72 (d, 1H); 9.22 (d, br, 1H) |
| 1644 | [CDCl3] 0.95 (m, 6H); 1.15 (d, 3H); 1.78 (m, 1H); 4.05 (m, 1H); 6.88 (d, 1H); 8.72 (d, 1H); 9.18 (d, br, 1H); 12.7 (br, 1H) |
| 1646 | [DMSO] 0.87 (t, 6H); 1.45 (m, 2H); 1.55 (m, 2H); 3.81 (m, 1H); 7.40 (d, 1H); 8.40 (d, 1H); 8.52 (d, br, 1H); 13.4 (br, 1H) |
| 1649 | [CDCl3] 3.40 (s, 6H); 3.61 (t, 2H); 4.50 (t, 1H); 6.87 (d, 1H); 8.69 (d, 1H); 9.32 (br, 1H); 12.3 (br, 1H) |
| 1651 | [CDCl3] 3.63 (m, 2H); 3.84 (m, 2H); 6.88 (d, 1H); 8.68 (d, 1H); 9.60 (br, 1H) |
| 1652 | [DMSO] 3.25 (s, 3H); 3.50 (m, 4H); 7.40 (d, br, 1H); 8.45 (d, 1H); 8.92 (br, 1H); 13.5 (br, 1H) |
| 1659 | [DMSO] 1.15 (d, 3H); 3.25 (s, 3H); 3.38 (m, 2H); 4.17 (m, 1H); 7.40 (d, br, 1H); 8.43 (d, 1H); 8.75 (br, 1H); 13.5 (br, 1H) |
| 1661 | [DMSO] 1.74 (m, 2H); 3.22 (s, 3H); 3.37 (m, 4H); 7.42 (d, br, 1H); 8.42 (d, 1H); 8.90 (br, 1H); 13.4 (br, 1H) |
| 1666 | [CDCl3] 3.77 (s, 3H); 4.23 (d, 2H); 6.87 (d, 1H); 8.67 (d, 1H); 9.65 (br, 1H); 12.1 (br, 1H) |
| 1711 | [DMSO] 2.83 (d, 3H); 8.39 (s, 1H); 8.72 (d, br, 1H); 13.5 (br) |
| 1712 | [DMSO] 1.11 (t, 3H); 3.30 (m, 2H); 8.40 (s, 1H); 8.75 (t, br, 1H) |
| 1713 | [CDCl3] 0.99 (t, 3H); 1.62 (m, 2H); 3.41 (q, 2H); 8.56 (s, 1H); 9.00 (br, 1H) |
| 1714 | [CDCl3] 1.24 (d, 6H); 4.22 (m, 1H); 8.41 (s, 1H); 9.17 (br, 1H) |
| 1715 | [CDCl3] 0.61 (m, 2H); 0.90 (m, 2H); 2.95 (m, 1H); 8.57 (s, 1H); 9.02 (br, 1H) |
| 1716 | [CDCl3] 0.94 (t, 3H); 1.41 (m, 2H); 1.58 (m, 2H); 3.45 (m, 2H); 8.54 (s, 1H); 9.05 (br, 1H) |
| 1717 | [CDCl3] 1.80 (m, 2H); 1.98 (m, 2H); 2.42 (m, 2H); 4.55 (m, 1H); 8.55 (s, 1H); 9.01 (br, 1H); 12.0 (br, 1H) |
| 1719 | [DMSO] 2.83 (s, 3H); 2.97 (s, 3H); 8.04 (s, 1H); 12.6 (br, 1H) |
| 1720 | [DMSO] 1.03 (t, 3H); 1.15 (t, 3H); 3.12 (q, 2H); 3.45 (q, 2H); 8.05 (s, 1H); 12.5 (br, 1H) |
| 1721 | [CDCl3] 0.25 (m, 2H); 0.55 (m, 2H); 1.05 (m, 1H); 3.32 (m, 2H); 8.57 (s, 1H); 8.93 (br, 1H); 12.1 (br, 1H) |
| 1722 | [CDCl3] 0.96 (s, 9H); 3.28 (d, 2H); 8.59 (s, 1H); 9.05 (br, 1H) |
| 1723 | [CDCl3] 0.95 (d, 6H); 1.90 (m, 1H); 3.29 (t, 2H); 8.59 (s, 1H); 9.00 (br, 1H); 12.0 (br, 1H) |
| 1725 | [CDCl3] 0.94 (d, 6H); 1.49 (q, 2H); 1.65 (m, 1H); 3.45 (m, 2H); 8.59 (s, 1H); 8.93 (br, 1H); 12.1 (br, 1H) |
| 1727 | [CDCl3] 4.08 (m, 2H); 5.21 (dd, 2H); 5.90 (m, 1H); 8.60 (s, 1H); 9.05 (br, 1H); 12.1 (br, 1H) |
| 1728 | [CDCl3] 1.78 (s, 3H); 4.01 (d, 2H); 4.90 (d, 2H); 8.61 (s, 1H); 9.09 (bt, 1H); 11.9 (br, 1H) |
| 1729 | [CDCl3] 2.25 (m, 1H); 4.23 (m, 2H); 8.63 (s, 1H); 9.23 (br, 1H); 11.9 (br, 1H) |
| 1731 | [CDCl3] 0.95 (t, 3H); 1.23 (d, 3H); 1.58 (m, 2H); 4.11 (m, 1H); 8.55 (s, 1H); 8.60 (br, 1H) |
| 1733 | [CDCl3] 0.92 (t, 3H); 1.23 (d, 3H); 1.39 (m, 2H); 1.52 (m, 2H); 4.20 (m, 1H); 8.55 (s, 1H); 8.66 (br, 1H) |
| 1734 | [CDCl3] 0.87 (t, 3H); 1.22 (d, 3H); 1.35 (m, 6H); 1.52 (m, 2H); 4.17 (m, 1H); 8.52 (s, 1H); 8.61 (br, 1H) |
| 1735 | [CDCl3] 0.94 (m, 6H); 1.23 (d, 3H); 1.33 (m, 1H); 1.45 (m, 1H); 1.65 (m, 1H); 4.27 (m, 1H); 8.56 (s, 1H); 8.63 (br, 1H); 11.9 (br) |
| 1736 | [CDCl3] 0.96 (s, 9H); 1.17 (d, 3H); 4.08 (m, 1H); 8.57 (s, 1H); 8.80 (d, br, 1H) |
| 1737 | [CDCl3] 0.95 (m, 6H); 1.18 (d, 3H); 1.80 (m, 1H); 4.05 (m, 1H); 8.57 (s, 1H); 8.73 (d, br, 1H) |
| 1738 | [DMSO] 0.87 (t, 6H); 1.45 (m, 2H), 1.55 (m, 2H); 3.80 (m, 1H); 8.40 (s, 1H); 8.42 (d, br, 1H); 13.4 (br, 1H) |
| 1739 | [CDCl3] 3.42 (s, 6H); 3.63 (t, 2H); 4.50 (t, 1H); 8.49 (s, 1H); 8.74 (br, 1H); 11.4 (br, 1H) |
| 1741 | [CDCl3] 3.65 (m, 2H); 3.85 (m, 2H); 8.55 (s, 1H); 9.16 (br, 1H) |
| 1742 | [CDCl3] 3.40 (s, 3H); 3.57 (m, 2H); 3.67 (m, 2H); 8.47 (s, 1H); 8.75 (br, 1H); 11.5 (br, 1H) |
| 1744 | [CDCl3] 1.27 (d, 3H); 3.39 (s, 3H); 3.45 (m, 2H); 4.37 (m, 1H); 8.45 (s, 1H); 8.57 (br, 1H); 11.6 (br, 1H) |
| 1745 | [CDCl3] 1.90 (m, 2H); 3.40 (s, 3H); 3.56 (m, 4H); 8.27 (s, 1H); 8.65 (br, 1H); 11.8 (br, 1H) |
| 1746 | [DMSO] 3.67 (s, 3H); 4.13 (d, 2H); 8.38 (s, 1H); 9.12 (br, 1H); 13.6 (br, 1H) |
| 1751 | [DMSO] 8.24 (br, 1H); 8.38 (br, 1H); 8.61 (br, 1H); 13.7 (br, 1H) |
| 1752 | [CDCl3] 3.00 (d, 3H); 8.71 (s, 1H); 8.91 (br, 1H); 12.2 (br, 1H) |
| 1753 | [CDCl3] 1.23 (t, 3H); 3.49 (m, 2H); 8.71 (s, 1H); 8.89 (br, 1H); 12.1 (br, 1H) |
| 1754 | [CDCl3] 0.98 (t, 3H); 1.62 (m, 2H); 3.40 (q, 2H); 8.70 (s, 1H); 8.90 (br, 1H) |
| 1755 | [CDCl3] 1.25 (d, 6H); 4.25 (m, 1H); 8.68 (br, 2H); 12.0 (br, 1H) |
| 1756 | [CDCl3] 0.61 (m, 2H); 0.89 (m, 2H); 2.95 (m, 1H); 8.70 (s, 1H); 8.97 (br, 1H) |
| 1757 | [CDCl3] 0.94 (t, 3H); 1.40 (m, 2H); 1.58 (m, 2H); 3.45 (m, 2H); 8.69 (s, 1H); 8.88 (br, 1H); 12.0 (br, 1H) |
| 1758 | [CDCl3] 1.80 (m, 2H); 1.98 (m, 2H); 2.41 (m, 2H); 4.55 (m, 1H); 8.67 (s, 1H); 8.98 (br, 1H); 12.1 (br, 1H) |
| 1759 | [CDCl3] 1.32 (s, 9H); 8.50 (br, 1H); 8.60 (s, 1H) |
| 1760 | [CDCl3] 3.12 (s, 6H); 7.99 (s, 1H) |
| 1761 | [CDCl3] 1.24 (t, 6H); 3.43 (m, 4H); 7.89 (s, 1H) |
| 1762 | [CDCl3] 0.28 (m, 2H); 0.55 (m, 2H); 1.03 (m, 1H); 3.31 (m, 2H); 8.67 (s, 1H); 8.85 (br, 1H); 11.9 (br, 1H) |
| 1763 | [CDCl3] 0.96 (s, 9H); 3.27 (d, 2H); 8.71 (s, 1H); 9.00 (br, 1H) |
| 1764 | [CDCl3] 0.95 (d, 6H); 1.89 (m, 1H); 3.28 (t, 2H); 8.70 (s, 1H); 8.97 (br, 1H) |
| 1766 | [CDCl3] 0.95 (d, 6H); 1.48 (q, 2H); 1.65 (m, 1H); 3.45 (m, 2H); 8.69 (s, 1H); 8.85 (br, 1H); 12.0 (br, 1H) |

TABLE 2-continued

NMR data of compounds from Table 1

| Ex. No. | 1H-NMR data |
|---|---|
| 1768 | [CDCl3] 4.08 (m, 2H); 5.21 (dd, 2H); 5.89 (m, 1H); 8.71 (s, 1H); 9.02 (br, 1H); 12.1 (br, 1H) |
| 1769 | [CDCl3] 1.77 (s, 3H); 4.01 (d, 2H); 4.87 (d, 2H); 8.71 (s, 1H); 9.03 (br, 1H) |
| 1770 | [CDCl3] 2.23 (m, 1H); 4.23 (m, 2H); 8.72 (s, 1H); 9.20 (br, 1H); 12.0 (br, 1H) |
| 1772 | [CDCl3] 0.95 (t, 3H); 1.21 (d, 3H); 1.55 (m, 2H); 4.10 (m, 1H); 8.67 (br, 1H); 8.70 (s, 1H); 12.1 (br, 1H) |
| 1774 | [CDCl3] 0.91 (t, 3H); 1.21 (d, 3H); 1.38 (m, 2H); 1.50 (m, 2H); 4.19 (m, 1H); 8.64 (br, 1H); 8.69 (s, 1H); 12.0 (br, 1H) |
| 1775 | [CDCl3] 0.89 (t, 3H); 1.21 (d, 3H); 1.33 (m, 6H); 1.51 (m, 2H); 4.17 (m, 1H); 8.60 (br, 1H); 8.68 (s, 1H) |
| 1776 | [CDCl3] 0.90 (m, 6H); 1.21 (d, 3H); 1.31 (m, 1H); 1.45 (m, 1H); 1.64 (m, 1H); 4.25 (m, 1H); 8.60 (br, 1H); 8.69 (s, 1H) |
| 1777 | [CDCl3] 0.94 (s, 9H); 1.15 (d, 3H); 4.08 (m, 1H); 8.69 (s, 1H); 8.79 (br, 1H) |
| 1778 | [CDCl3] 0.93 (m, 6H); 1.17 (d, 3H); 1.79 (m, 1H); 4.05 (m, 1H); 8.67 (s, 1H); 8.71 (br, 1H) |
| 1780 | [CDCl3] 0.92 (t, 6H); 1.48 (m, 2H); 1.62 (m, 2H); 3.96 (m, 1H); 8.61 (s, 1H); 9.16 (d, br, 1H) |
| 1781 | [CDCl3] 3.40 (s, 6H); 3.61 (t, 2H); 4.50 (t, 1H); 8.63 (s, 1H); 8.76 (br, 1H) |
| 1783 | [CDCl3] 3.64 (m, 2H); 3.86 (m, 2H); 8.68 (s, 1H); 9.17 (br, 1H) |
| 1784 | [CDCl3] 3.49 (s, 3H); 3.55 (m, 2H); 3.66 (m, 2H); 8.62 (s, 1H); 8.77 (br, 1H) |
| 1785 | [CDCl3] 1.27 (d, 3H); 3.39 (s, 3H); 3.44 (m, 2H); 4.37 (m, 1H); 8.56 (br, 1H); 8.60 (s, 1H); 11.9 (br, 1H) |
| 1786 | [CDCl3] 1.90 (m, 2H); 3.40 (s, 3H); 3.58 (m, 4H); 8.40 (s, 1H); 8.65 (br, 1H) |
| 1787 | [CDCl3] 3.78 (s, 3H); 4.24 (d, 2H); 8.69 (s, 1H); 9.25 (br, 1H); 11.5 (br, 1H) |
| 1792 | [DMSO] 8.22 (br, 1H); 8.37 (br, 1H); 8.81 (br, 1H); 13.7 (br, 1H) |
| 1793 | [CDCl3] 3.00 (d, 3H); 8.80 (s, br, 2H); 12.0 (br, 1H) |
| 1794 | [CDCl3] 1.24 (t, 3H); 3.49 (m, 2H); 8.40 (s, br, 2H); 12.0 (br, 1H) |
| 1795 | [DMSO] 0.89 (t, 3H); 1.53 (m, 2H); 3.26 (q, 2H); 8.72 (s, 1H); 8.78 (t, br, 1H); 13.4 (br, 1H) |
| 1796 | [DMSO] 1.18 (d, 6H); 4.08 (m, 1H); 8.60 (d, br, 2H); 13.4 (br, 1H) |
| 1797 | [DMSO] 0.60 (m, 2H); 0.75 (m, 2H); 2.88 (m, 1H); 8.68 (s, 1H); 8.77 (d, br, 1H); 13.3 (br, 1H) |
| 1798 | [CDCl3] 0.94 (t, 3H); 1.40 (m, 2H); 1.59 (m, 2H); 3.44 (m, 2H); 8.79 (s, br, 2H) |
| 1799 | [DMSO] 1.70 (m, 2H); 2.05 (m, 2H); 2.27 (m, 2H); 4.39 (m, 1H); 8.71 (s, 1H); 8.95 (d, br, 1H); 13.4 (br, 1H) |
| 1800 | [CDCl3] 1.43 (s, 9H); 8.70 (br, 1H); 8.85 (s, 1H); 11.5 (br) |
| 1801 | [CDCl3] 3.10 (s, 6H); 8.20 (s, 1H) |
| 1802 | [CDCl3] 1.23 (t, 6H); 3.43 (m, br, 4H); 8.12 (s, 1H) |
| 1803 | [DMSO] 0.26 (m, 2H); 0.50 (m, 2H); 1.05 (m, 1H); 3.19 (t, 2H); 8.76 (s, 1H); 8.87 (br, 1H); 13.5 (br, 1H) |
| 1804 | [DMSO] 0.91 (s, 9H); 3.13 (d, 2H); 8.61 (t, br, 1H); 8.68 (s, 1H); 13.4 (br, 1H) |
| 1805 | [DMSO] 0.89 (d, 6H); 1.84 (m, 1H); 3.14 (t, 2H); 8.70 (s, 1H); 8.75 (t, br, 1H); 13.4 (br, 1H) |
| 1807 | [DMSO] 0.89 (d, 6H); 1.40 (q, 2H); 1.62 (m, 1H); 3.30 (m, 2H); 8.71 (s, 1H); 8.73 (t, br, 1H); 13.4 (br, 1H) |
| 1809 | [DMSO] 3.93 (m, 2H); 5.18 (dd, 2H); 5.90 (m, 1H); 8.71 (s, 1H); 8.89 (t, br, 1H); 13.4 (br, 1H) |
| 1810 | [DMSO] 1.72 (s, 3H); 3.87 (d, 2H); 4.85 (d, 2H); 8.71 (s, 1H); 8.87 (t, br, 1H); 13.3 (br, 1H) |
| 1811 | [DMSO] 3.18 (m, 1H); 4.10 (m, 2H); 8.69 (s, 1H); 9.01 (t, br, 1H); 13.4 (br, 1H) |
| 1813 | [DMSO] 0.87 (t, 3H); 1.14 (d, 3H); 1.50 (m, 2H); 3.90 (m, 1H); 8.52 (d, br, 1H); 8.72 (s, 1H); 13.4 (br, 1H) |
| 1815 | [DMSO] 0.89 (t, 3H); 1.15 (d, 3H); 1.30 (m, 2H); 1.47 (m, 2H); 4.00 (m, 1H); 8.54 (br, 1H); 8.72 (s, 1H); 13.4 (br, 1H) |
| 1816 | [CDCl3] 0.89 (t, 3H); 1.20 (d, 3H); 1.27-1.37 (m, 6H); 1.51 (m, 2H); 4.16 (m, 1H); 8.75 (br, 1H); 8.90 (s, 1H); 12.1 (br, 1H) |
| 1817 | [CDCl3] 0.91 (m, 6H); 1.20 (d, 3H); 1.32 (m, 1H); 1.45 (m, 1H); 1.65 (m, 1H); 4.25 (m, 1H); 8.66 (br, 1H); 8.90 (s, 1H); 11.9 (br, 1H) |
| 1818 | [CDCl3] 0.94 (s, 9H); 1.14 (d, 3H); 4.07 (m, 1H); 8.85 (br, 1H); 8.90 (s, 1H) |
| 1819 | [CDCl3] 0.95 (m, 6H); 1.18 (d, 3H); 1.79 (m, 1H); 4.04 (m, 1H); 8.75 (br, 1H); 8.89 (s, 1H) |
| 1820 | [CDCl3] 0.93 (t, 6H); 1.48 (m, 2H); 1.64 (m, 2H); 3.98 (m, 1H); 8.63 (br, 1H); 8.90 (s, 1H); 11.6 (br, 1H) |
| 1821 | [CDCl3] 3.40 (s, 6H); 3.60 (t, 2H); 4.49 (t, 1H); 8.85 (s, br, 2H); 11.4 (br, 1H) |
| 1823 | [CDCl3] 3.63 (m, 2H); 3.83 (m, 2H); 8.86 (s, 1H); 9.17 (br, 1H) |
| 1824 | [CDCl3] 3.38 (s, 3H); 3.55 (m, 2H); 3.65 (m, 2H); 8.82 (s, 1H); 8.84 (br, 1H); 11.4 (br, 1H) |
| 1826 | [CDCl3] 1.25 (d, 3H); 3.39 (s, 3H); 3.43 (m, 2H); 4.38 (m, 1H); 8.67 (br, 1H); 8.82 (s, 1H); 11.5 (br, 1H) |
| 1827 | [CDCl3] 1.89 (m, 2H); 3.40 (s, 3H); 3.55 (m, 4H); 8.67 (s, 1H); 8.74 (br, 1H); 11.8 (br, 1H) |
| 1828 | [CDCl3] 3.78 (s, 3H); 4.24 (d, 2H); 8.89 (s, 1H); 9.30 (br, 1H) |
| 1833 | [DMSO] 2.85 (d, 3H); 8.69 (s, 1H); 8.71 (br, 1H); 13.5 (br, 1H) |
| 1834 | [DMSO] 1.12 (t, 3H); 3.30 (m, 2H); 8.70 (s, 1H); 8.75 (t, br, 1H); 13.5 (br, 1H) |
| 1835 | [DMSO] 0.89 (t, 3H); 1.52 (m, 2H); 3.25 (q, 2H); 8.70 (s, 1H); 8.75 (t, br, 1H); 13.5 (br, 1H) |
| 1837 | [DMSO] 0.59 (m, 2H); 0.76 (m, 2H); 2.86 (m, 1H); 8.66 (s, 1H); 8.76 (br, 1H); 13.3 (br) |
| 1838 | [CDCl3] 0.95 (t, 3H); 1.42 (m, 2H); 1.60 (m, 2H); 3.45 (m, 2H); 8.86 (s, 1H); 8.95 (br, 1H) |
| 1839 | [CDCl3] 1.81 (m, 2H); 2.00 (m, 2H); 2.42 (m, 2H); 4.54 (m, 1H); 8.84 (s, 1H); 9.17 (d, br, 1H); 12.2 (br, 1H) |
| 1845 | [CDCl3] 0.29 (m, 2H); 0.57 (m, 2H); 1.05 (m, 1H); 3.32 (t, 2H); 8.87 (s, 1H); 9.05 (br, 1H); 12.3 (br, 1H) |
| 1847 | [CDCl3] 1.00 (d, 6H); 1.90 (m, 1H); 3.30 (t, 2H); 8.85 (s, 1H); 9.00 (br, 1H) |
| 1849 | [CDCl3] 0.95 (d, 6H); 1.51 (q, 2H); 1.68 (m, 1H); 3.46 (m, 2H); 8.85 (s, 1H); 8.91 (br, 1H) |
| 1851 | [DMSO] 3.94 (m, 2H); 5.16 (dd, 2H); 5.90 (m, 1H); 8.70 (s, 1H); 8.85 (t, br, 1H); 13.4 (br, 1H) |

TABLE 2-continued

NMR data of compounds from Table 1

| Ex. No. | 1H-NMR data |
|---|---|
| 1852 | [CDCl3] 1.79 (s, 3H); 4.02 (m, 2H); 4.92 (m, 2H); 8.88 (s, 1H); 9.10 (t, br, 1H) |
| 1853 | [CDCl3] 2.26 (m, 1H); 4.22 (m, 2H); 8.86 (s, 1H); 9.25 (br, 1H) |
| 1854 | [DMSO] 0.87 (t, 3H); 1.13 (d, 3H); 1.50 (m, 2H); 3.91 (m, 1H); 8.55 (d, br, 1H); 8.70 (br, 1H); 13.5 (br, 1H) |
| 1856 | [DMSO] 0.89 (t, 3H); 1.15 (d, 3H); 1.30 (m, 2H); 1.49 (m, 2H); 4.01 (m, 1H); 8.51 (d, br, 1H); 8.71 (s, 1H); 13.6 (br, 1H) |
| 1857 | [CDCl3] 0.87 (t, 3H); 1.22 (8, 3H); 1.25-1.35 (m, 6H); 1.53 (m, 2H); 4.14 (m, 1H); 8.81 (d, br, 1H); 8.88 (s, 1H) |
| 1858 | [CDCl3] 0.92 (m, 6H); 1.22 (d, 3H); 1.33 (m, 1H); 1.48 (m, 1H); 1.65 (m, 1H); 4.25 (m, 1H); 8.84 (br, 1H); 8.88 (s, 1H); 12.3 (br, 1H) |
| 1860 | [CDCl3] 0.95 (m, 6H); 1.18 (d, 3H); 1.81 (m, 1H); 4.05 (m, 1H); 8.90 (s, 1H); 9.01 (d, br, 1H) |
| 1861 | [DMSO] 0.88 (t, 6H); 1.45 (m, 2H); 1.55 (m, 2H); 3.79 (m, 1H); 8.40 (d, br, 1H); 8.70 (s, 1H); 13.5 (br, 1H) |
| 1867 | [DMSO] 3.29 (s, 3H); 3.47 (m, 4H); 8.73 (s, 1H); 8.79 (br, 1H); 13.6 (br, 1H) |
| 1869 | [CDCl3] 1.28 (d, 3H); 3.39 (s, 3H); 3.45 (m, 2H); 4.35 (m, 1H); 8.81 (s, 1H); 8.86 (br, 1H); 12.0 (br, 1H) |
| 1870 | [CDCl3] 1.90 (m, 2H); 3.41 (s, 3H); 3.56 (m, 4H); 8.62 (s, 1H); 8.76 (br, 1H); 11.9 (br, 1H) |
| 1876 | [DMSO] 8.18 (br, 1H); 8.35 (br, 1H); 8.79 (s, 1H); 13.7 (br, 1H) |
| 1877 | [DMSO] 2.83 (d, 3H); 8.70 (br, 2H); 13.5 (br, 1H) |
| 1878 | [DMSO] 1.12 (t, 3H); 3.32 (m, 2H); 8.71 (s, 1H); 8.76 (t, br, 1H); 13.4 (br, 1H) |
| 1879 | [DMSO] 0.90 (t, 3H); 1.51 (m, 2H); 3.25 (q, 2H); 8.70 (s, 1H); 8.78 (t, br, 1H); 13.5 (br, 1H) |
| 1880 | [DMSO] 1.18 (d, 6H); 4.07 (m, 2H); 8.57 (d, br, 1H); 8.72 (s, 1H); 13.4 (br, 1H) |
| 1881 | [DMSO] 0.58 (m, 2H); 0.74 (m, 2H); 2.85 (m, 1H); 8.66 (s, 1H); 8.74 (br, 1H); 13.4 (br, 1H) |
| 1882 | [DMSO] 0.89 (t, 3H); 1.31 (m, 2H); 1.50 (m, 2H); 3.30 (m, 2H); 8.70 (s, 1H); 8.75 (br, 1H) |
| 1883 | [DMSO] 1.69 (m, 2H); 2.02 (m, 2H); 2.25 (m, 2H); 4.39 (m, 1H); 8.70 (s, 1H); 8.95 (br, 1H) |
| 1884 | [CDCl3] 1.47 (s, 9H); 8.87 (s, 1H); 9.02 (br, 1H); 12.2 (br, 1H) |
| 1885 | [CDCl3] 3.12 (s, 6H); 8.16 (s, 1H) |
| 1886 | [DMSO] 0.23 (m, 2H); 0.45 (m, 2H); 1.02 (m, 1H); 3.19 (t, 2H); 8.72 (s, 1H); 8.83 (br, 1H); 13.4 (br, 1H) |
| 1887 | [DMSO] 0.90 (s, 9H); 3.14 (d, 2H); 8.72 (br, 1H); 8.67 (s, 1H); 13.4 (br, 1H) |
| 1888 | [DMSO] 0.90 (d, 6H); 1.84 (m, 1H); 3.12 (t, 2H); 8.68 (s, 1H); 8.73 (t, br, 1H); 13.4 (br, 1H) |
| 1890 | [DMSO] 0.90 (d, 6H); 1.41 (m, 2H); 1.60 (m, 1H); 3.30 (m, 2H); 8.69 (s, 1H); 8.72 (t, br, 1H); 13.5 (br, 1H) |
| 1892 | [DMSO] 3.94 (m, 2H); 5.15 (dd, 2H); 5.89 (m, 1H); 8.70 (s, 1H); 8.85 (t, br, 1H) |
| 1894 | [DMSO] 1.70 (s, 3H); 3.86 (d, 2H); 4.84 (d, 2H); 8.68 (s, 1H); 8.95 (br, 1H); 13.4 (br, 1H) |
| 1895 | [DMSO] 3.10 (t, 1H); 4.05 (m, 2H); 8.25 (br, 1H); 8.30 (s, 1H); 11.5 (br, 1H) |
| 1897 | [CDCl3] 0.95 (t, 3H); 1.24 (d, 3H); 1.60 (m, 2H); 4.10 (m, 1H); 8.87 (br, 2H) |
| 1899 | [CDCl3] 0.92 (t, 3H); 1.23 (d, 3H); 1.40 (m, 2H); 1.52 (m, 2H); 4.17 (m, 1H); 8.88 (s, 1H); 8.91 (br, 1H) |
| 1900 | [DMSO] 0.86 (t, 3H); 1.15 (d, 3H); 1.25 (m, 6H); 1.48 (m, 2H); 4.00 (m, 1H); 8.53 (d, br, 1H); 8.71 (s, 1H); 13.4 (br, 1H) |
| 1903 | [DMSO] 0.89 (d, 6H); 1.13 (d, 3H); 1.27 (m, 1H); 1.48 (m, 1H); 1.62 (m, 1H); 4.09 (m, 1H); 8.50 (d, br, 1H); 8.71 (s, 1H); 13.5 (br, 1H) |
| 1904 | [DMSO] 0.81 (s, 9H); 1.07 (d, 3H); 3.90 (m, 1H); 8.43 (d, br, 1H); 8.67 (s, 1H); 13.4 (br, 1H) |
| 1905 | [DMSO] 0.88 (d, 6H); 1.10 (d, 3H); 1.75 (m, 1H); 1.48 (m, 1H); 3.85 (m, 1H); 8.49 (d, br, 1H); 8.70 (s, 1H); 13.5 (br, 1H) |
| 1907 | [DMSO] 0.87 (t, 6H); 1.43 (m, 2H); 1.55 (m, 2H); 3.78 (m, 1H); 8.55 (br, 1H); 8.67 (s, 1H); 13.5 (br, 1H) |
| 1910 | [CDCl3] 3.41 (s, 6H); 3.62 (t, 2H); 4.50 (t, 2H); 8.82 (s, 1H); 8.95 (br, 1H); 11.2 (br, 1H) |
| 1912 | [DMSO] 3.39 (m, 2H); 3.52 (m, 2H); 4.83 (br, 1H); 8.76 (s, 1H); 8.80 (t, br, 1H); 13.6 (br, 1H) |
| 1913 | [DMSO] 3.26 (s, 3H); 3.47 (m, 4H); 8.71 (s, 1H); 8.79 (br, 1H) |
| 1916 | [CDCl3] 1.27 (d, 3H); 3.39 (s, 3H); 3.44 (m, 2H); 4.38 (m, 1H); 8.83 (s, 1H); 8.95 (br, 1H); 12.1 (br, 1H) |
| 1917 | [DMSO] 1.75 (m, 2H); 3.24 (s, 3H); 3.39 (m, 4H); 8.70 (s, 1H); 8.81 (br, 1H); 13.4 (br, 1H) |
| 1918 | [DMSO] 3.66 (s, 3H); 4.12 (d, 2H); 8.71 (s, 1H); 9.02 (t, br, 1H), 13.5 (br, 1H) |
| 1923 | [DMSO] 2.81 (d, 3H); 8.72 (s, 1H); 8.77 (br, 1H); 13.4 (br) |
| 1924 | [DMSO] 1.14 (t, 3H); 3.35 (m, 2H); 8.74 (s, 1H); 8.82 (t, br, 1H); 13.4 (br) |
| 1925 | [DMSO] 0.89 (t, 3H); 1.53 (m, 2H); 3.28 (q, 2H); 8.73 (s, 1H); 8.80 (t, br, 1H) |
| 1926 | [DMSO] 1.18 (d, 6H); 4.10 (m, 1H); 8.63 (d, br, 1H); 8.75 (s, 1H); 13.4 (br, 1H) |
| 1927 | [DMSO] 0.60 (m, 2H); 0.75 (m, 2H); 2.87 (m, 1H); 8.69 (s, 1H); 8.80 (br, 1H) |
| 1928 | [DMSO] 0.89 (t, 3H); 1.34 (m, 2H); 1.51 (m, 2H); 3.30 (m, 2H); 8.72 (s, 1H); 8.79 (br, 1H) |
| 1929 | [DMSO] 1.72 (m, 2H); 2.05 (m, 2H); 2.27 (m, 2H); 4.38 (m, 1H); 8.73 (s, 1H); 9.00 (d, br, 1H); 13.3 (br) |
| 1930 | [DMSO] 1.37 (s, 9H); 8.30 (br, 1H); 8.66 (s, 1H); 13.4 (br) |
| 1931 | [DMSO] 2.80 (s, 3H); 2.96 (s, 3H); 8.27 (s, 1H); 12.4 (br, 1H) |
| 1932 | [DMSO] 1.01 (t, 3H); 1.11 (t, 3H); 3.10 (q, 2H); 3.42 (q, 2H); 8.25 (s, 1H); 12.3 (br, 1H) |
| 1933 | [DMSO] 0.26 (m, 2H); 0.47 (m, 2H); 1.04 (m, 1H); 3.20 (m, 2H); 8.77 (s, 1H); 8.87 (t, br, 1H); 13.5 (br, 1H) |
| 1934 | [DMSO] 0.90 (s, 9H); 3.13 (d, 2H); 8.62 (t, br, 1H); 8.70 (s, 1H); 13.3 (br, 1H) |
| 1935 | [DMSO] 0.90 (d, 6H); 1.85 (m, 1H); 3.13 (m, 2H); 8.71 (s, 1H); 8.75 (t, br, 1H); 13.4 (br, 1H) |
| 1937 | [CDCl3] 0.94 (d, 6H); 1.49 (q, 2H); 1.66 (m, 1H); 3.46 (m, 2H); 8.75 (br, 1H); 8.85 (s, 1H); 11.5 (br) |
| 1939 | [DMSO] 3.93 (m, 2H); 5.19 (dd, 2H); 5.89 (m, 1H); 8.72 (s, 1H); 8.90 (t, br, 1H); 13.3 (br, 1H) |
| 1941 | [DMSO] 1.72 (s, 3H); 3.87 (d, 2H); 4.87 (d, 2H); 8.73 (s, 1H); 8.89 (t, br, 1H); 13.3 (br) |
| 1942 | [DMSO] 3.18 (m, 1H); 4.10 (m, 2H); 8.70 (s, 1H); 9.04 (t, br, 1H); 13.3 (br, 1H) |

TABLE 2-continued

NMR data of compounds from Table 1

| Ex. No. | 1H-NMR data |
|---|---|
| 1944 | [DMSO] 0.89 (t, 3H); 1.14 (d, 3H); 1.51 (m, 2H); 3.91 (m, 1H); 8.55 (d, br, 1H); 8.75 (s, 1H); 13.4 (br, 1H) |
| 1946 | [DMSO] 0.89 (t, 3H); 1.15 (d, 3H); 1.31 (m, 2H); 1.47 (m, 2H); 4.01 (m, 1H); 8.56 (br, 1H); 8.74 (s, 1H); 13.4 (br, 1H) |
| 1947 | [DMSO] 0.85 (t, 3H); 1.15 (d, 3H); 1.20-1.35 (m, 6H); 1.49 (m, 2H); 4.00 (m, 1H); 8.58 (d, br, 1H); 8.74 (s, 1H); 13.4 (br, 1H) |
| 1948 | [DMSO] 0.88 (d, 6H); 1.15 (d, 3H); 1.27 (m, 1H); 1.48 (m, 1H); 1.61 (m, 1H); 4.10 (m, 1H); 8.56 (d, br, 1H); 8.74 (s, 1H); 13.5 (br, 1H) |
| 1949 | [CDCl3] 0.94 (s, 1H); 1.15 (d, 3H); 4.09 (m, 1H); 8.89 (br, 1H); 8.91 (s, 1H) |
| 1950 | [CDCl3] 0.94 (m, 6H); 1.17 (d, 3H); 1.80 (m, 1H); 4.05 (m, 1H); 8.88 (br, 1H); 8.92 (s, 1H) |
| 1951 | [CDCl3] 0.92 (t, 6H); 1.49 (m, 2H); 1.65 (m, 2H); 3.99 (m, 1H); 8.78 (br, 1H); 8.92 (s, 1H) |
| 1952 | [CDCl3] 3.41 (s, 6H); 3.61 (t, 2H); 4.50 (t, 1H); 8.84 (s, br, 2H); 11.4 (br, 1H) |
| 1954 | [DMSO] 3.39 (m, 2H); 3.52 (m, 2H); 4.80 (br, 1H); 8.79 (s, 1H); 8.82 (t, br, 1H); 13.5 (br, 1H) |
| 1955 | [CDCl3] 3.38 (s, 3H); 3.55 (m, 2H); 3.66 (m, 2H); 8.78 (s, br, 1H); 8.82 (s, 1H); 11.5 (br) |
| 1957 | [CDCl3] 1.27 (d, 3H); 3.38 (s, 3H); 3.42 (m, 2H); 4.38 (m, 1H); 8.75 (br, 1H); 8.84 (s, 1H); 12.3 (br, 1H) |
| 1958 | [CDCl3] 1.89 (m, 2H); 3.41 (s, 3H); 3.56 (m, 4H); 8.61 (s, 1H); 8.68 (br, 1H); 11.8 (br, 1H) |
| 1959 | [DMSO] 3.67 (s, 3H); 4.12 (d, 2H); 8.73 (s, 1H); 9.04 (t, br, 1H); 13.5 (br, 1H) |
| 1964 | [DMSO] 8.25 (br, 1H); 8.37 (br, 1H); 8.47 (s, 1H); 13.7 (br, 1H) |
| 1965 | [DMSO] 2.82 (d, 3H); 8.37 (s, 1H); 8.72 (d, br, 1H); 13.5 (br, 1H) |
| 1966 | [DMSO] 1.13 (t, 3H); 3.34 (m, 2H); 8.39 (s, 1H); 8.76 (t, br, 1H); 13.5 (br, 1H) |
| 1967 | [DMSO] 0.90 (t, 3H); 1.53 (m, 2H); 3.26 (q, 2H); 8.39 (s, 1H); 8.75 (t, br, 1H); 13.5 (br, 1H) |
| 1968 | [DMSO] 1.18 (d, 6H); 4.09 (m, 1H); 8.41 (s, 1H); 8.58 (d, br, 1H); 13.5 (br, 1H) |
| 1969 | [DMSO] 0.59 (m, 2H); 0.75 (m, 2H); 2.86 (m, 1H); 8.34 (s, 1H); 8.73 (d, br, 1H); 13.4 (br, 1H) |
| 1970 | [DMSO] 0.89 (t, 3H); 1.33 (m, 2H); 1.51 (m, 2H); 3.31 (m, 2H); 8.39 (s, 1H); 8.73 (t, br, 1H); 13.5 (br, 1H) |
| 1971 | [DMSO] 1.70 (m, 2H); 2.04 (m, 2H); 2.25 (m, 2H); 4.38 (m, 1H); 8.39 (s, 1H); 8.92 (d, br, 1H); 13.4 (br, 1H) |
| 2006 | [DMSO] 8.25 (br, 1H); 8.35 (br, 1H); 8.61 (s, 1H); 13.7 (br, 1H) |
| 2007 | [DMSO] 2.82 (d, 3H); 8.51 (s, 1H); 8.74 (d, br, 1H); 13.5 (br, 1H) |
| 2008 | [DMSO] 1.13 (t, 3H); 3.33 (m, 2H); 8.53 (s, 1H); 8.78 (t, br, 1H); 13.5 (br, 1H) |
| 2009 | [DMSO] 0.89 (t, 3H); 1.53 (m, 2H); 3.26 (q, 2H); 8.51 (s, 1H); 8.76 (t, br, 1H); 13.5 (br, 1H) |
| 2010 | [DMSO] 1.18 (d, 6H); 4.07 (m, 1H); 8.53 (s, 1H); 8.61 (d, br, 1H); 13.5 (br, 1H) |
| 2011 | [DMSO] 0.58 (m, 2H); 0.74 (m, 2H); 2.86 (m, 1H); 8.48 (s, 1H); 8.77 (d, br, 1H); 13.4 (br, 1H) |
| 2012 | [DMSO] 0.90 (t, 3H); 1.33 (m, 2H); 1.51 (m, 2H); 3.30 (m, 2H); 8.52 (s, 1H); 8.77 (t, br, 1H); 13.5 (br, 1H) |
| 2013 | [DMSO] 1.72 (m, 2H); 2.05 (m, 2H); 2.25 (m, 2H); 4.39 (m, 1H); 8.51 (s, 1H); 8.95 (d, br, 1H); 13.4 (br, 1H) |
| 2014 | [DMSO] 1.37 (s, 9H); 8.31 (br, 1H); 8.45 (s, 1H); 13.4 (br, 1H) |
| 2015 | [DMSO] 2.82 (s, 3H); 2.95 (s, 3H); 8.12 (s, 1H); 12.5 (br, 1H) |
| 2017 | [DMSO] 0.26 (m, 2H); 0.47 (m, 2H); 1.04 (m, 1H); 3.30 (m, 2H); 8.56 (s, 1H); 8.86 (t, br, 1H); 13.5 (br, 1H) |
| 2018 | [DMSO] 0.91 (s, 9H); 3.13 (d, 2H); 8.47 (s, 1H); 8.63 (t, br, 1H); 13.5 (br, 1H) |
| 2019 | [DMSO] 0.90 (d, 6H); 1.83 (m, 1H); 3.13 (m, 2H); 8.50 (s, 1H); 8.73 (t, br, 1H); 13.4 (br, 1H) |
| 2021 | [DMSO] 0.89 (d, 6H); 1.42 (q, 2H); 1.62 (m, 1H); 3.31 (m, 2H); 8.51 (s, 1H); 8.75 (t, br, 1H); 13.5 (br, 1H) |
| 2023 | [DMSO] 3.94 (m, 2H); 5.18 (dd, 2H); 5.89 (m, 1H); 8.52 (s, 1H); 8.88 (t, br, 1H); 13.4 (br, 1H) |
| 2025 | [DMSO] 1.72 (s, 3H); 3.86 (d, 2H); 4.85 (d, 2H); 8.50 (s, 1H); 8.87 (t, br, 1H); 13.4 (br, 1H) |
| 2026 | [DMSO] 3.18 (m, 1H); 4.10 (m, 2H); 8.48 (s, 1H); 9.02 (t, br, 1H); 13.3 (br, 1H) |
| 2030 | [CDCl3] 0.93 (t, 3H); 1.23 (d, 3H); 1.40 (m, 2H); 1.52 (m, 2H); 4.21 (m, 1H); 8.74 (s, 1H); 8.97 (d, br, 1H); 12.9 (br, 1H) |
| 2031 | [DMSO] 0.85 (t, 3H); 1.15 (d, 3H); 1.20-1.35 (m, 6H); 1.48 (m, 2H); 3.99 (m, 1H); 8.52 (s, 1H); 8.54 (d, br, 1H); 13.5 (br, 1H) |
| 2032 | [DMSO] 0.88 (d, 6H); 1.14 (d, 3H); 1.27 (m, 1H); 1.48 (m, 1H); 1.62 (m, 1H); 4.10 (m, 1H); 8.51 (s, 1H); 8.53 (d, br, 1H); 13.5 (br, 1H) |
| 2035 | [DMSO] 0.86 (t, 6H); 1.45 (m, 2H); 1.55 (m, 2H); 3.78 (m, 1H); 8.82 (d, br, 1H); 8.51 (s, 1H); 13.5 (br, 1H) |
| 2036 | [CDCl3] 3.41 (s, 6H); 3.61 (t, 2H); 4.50 (t, 1H); 8.67 (s, 1H); 9.00 (br, 1H); 11.7 (br, 1H) |
| 2038 | [DMSO] 3.35 (m, 2H); 3.53 (m, 2H); 4.81 (br, 1H); 8.56 (s, 1H); 8.80 (t, br, 1H); 13.6 (br, 1H) |
| 2039 | [CDCl3] 3.38 (s, 3H); 3.56 (m, 2H); 3.65 (m, 2H); 8.65 (s, 1H); 9.01 (s, 1H); 11.8 (br, 1H) |
| 2041 | [DMSO] 1.15 (d, 3H); 3.30 (s, 3H); 3.40 (m, 2H); 4.18 (m, 1H); 8.52 (s, 1H); 8.64 (d, br, 1H); 13.4 (br, 1H) |
| 2048 | [DMSO] 8.20 (br, 1H); 8.37 (br, 1H); 8.81 (s, 1H); 13.7 (br, 1H) |
| 2090 | [DMSO] 7.45 (d, 1H); 8.14 (br, 1H); 8.42 (br, 1H); 8.48 (d, 1H); 13.7 (br, 1H) |
| 2091 | [DMSO] 2.84 (d, 3H); 7.42 (d, 1H); 8.41 (d, 1H); 8.79 (br, 1H); 13.4 (br, 1H) |
| 2092 | [DMSO] 1.12 (t, 3H); 3.32 (m, 2H); 7.42 (d, 1H); 8.42 (d, 1H); 8.83 (br, 1H); 13.4 (br, 1H) |
| 2093 | [DMSO] 0.89 (t, 3H); 1.54 (m, 2H); 3.27 (q, 2H); 7.42 (d, 1H); 8.41 (d, 1H); 8.82 (br, 1H); 13.4 (br, 1H) |
| 2094 | [DMSO] 1.18 (d, 6H); 4.11 (m, 1H); 7.41 (d, 1H); 8.41 (d, 1H); 8.63 (br, 1H); 13.4 (br, 1H) |
| 2095 | [CDCl3] 0.61 (m, 2H); 0.88 (m, 2H); 3.00 (m, 1H); 6.89 (d, 1H); 8.68 (d, 1H); 9.35 (br, 1H); 12.5 (br, 1H) |
| 2096 | [DMSO] 0.89 (t, 3H); 1.33 (m, 2H); 1.52 (m, 2H); 3.32 (m, 2H); 7.42 (d, 1H); 8.41 (d, 1H); 8.81 (br, 1H); 13.3 (br, 1H) |

TABLE 2-continued

NMR data of compounds from Table 1

| Ex. No. | 1H-NMR data |
|---|---|
| 2097 | [DMSO] 1.72 (m, 2H); 2.05 (m, 2H); 2.46 (m, 2H); 4.41 (m, 1H); 7.43 (d, 1H); 8.39 (d, 1H); 8.96 (br, 1H); 13.3 (br, 1H) |
| 2101 | [DMSO] 0.26 (m, 2H), 0.47 (m, 2H); 1.06 (m, 1H); 3.22 (m, 2H); 7.45 (d, 1H); 8.45 (d, 1H); 8.91 (br, 1H); 13.4 (br, 1H) |
| 2102 | [DMSO] 0.92 (s, 9H); 3.15 (d, 2H); 7.40 (d, 1H); 8.41 (d, 1H); 8.75 (br, 1H); 13.3 (br, 1H) |
| 2103 | [DMSO] 0.90 (d, 6H); 1.83 (m, 1H); 3.14 (t, 2H); 7.40 (d, 1H); 8.40 (d, 1H); 8.81 (t, br, 1H); 13.3 (br, 1H) |
| 2105 | [DMSO] 0.90 (d, 6H); 1.42 (m, 2H); 1.62 (m, 1H); 3.33 (m, 2H); 7.41 (d, 1H); 8.40 (d, 1H); 8.80 (br, 1H); 13.3 (br, 1H) |
| 2107 | [DMSO] 3.95 (t, 2H); 5.17 (dd, 2H); 5.90 (m, 1H); 7.41 (d, 1H); 8.41 (d, 1H); 8.93 (br, 1H); 13.3 (br, 1H) |
| 2109 | [DMSO] 1.72 (s, 3H); 3.88 (d, 2H); 4.85 (d, 2H); 7.42 (d 1H); 8.42 (d, 1H); 8.94 (br, 1H); 13.3 (br, 1H) |
| 2110 | [DMSO] 3.17 (m, 1H); 4.11 (m, 2H); 7.41 (d, 1H); 8.40 (d, 1H); 9.06 (br, 1H), 13.3 (br, 1H) |
| 2112 | [DMSO] 0.89 (t, 3H); 1.15 (d, 3H); 1.53 (m, 2H); 3.95 (m, 1H); 7.42 (d, 1H); 8.42 (d, 1H); 8.60 (br, 1H); 13.4 (br, 1H) |
| 2114 | [DMSO] 0.88 (t, 3H); 1.15 (d, 3H); 1.32 (m, 2H); 1.48 (m, 2H); 4.04 (m, 1H); 7.42 (d, 1H); 8.41 (d, 1H); 8.59 (br, 1H); 13.4 (br, 1H) |
| 2115 | [DMSO] 0.85 (t, 3H); 1.16 (d, 3H); 1.20-1.35 (m, 6H); 1.50 (m, 2H); 4.02 (m, 1H); 7.42 (d, 1H); 8.44 (d, 1H); 8.62 (d, br, 1H), 13.4 (br, 1H) |
| 2116 | [DMSO] 0.88 (d, 6H); 1.14 (d, 3H); 1.25 (m, 1H); 1.48 (m, 1H); 1.63 (m, 1H); 4.21 (m, 1H); 6.92 (d, 1H); 8.42 (d, 1H); 8.59 (d, br, 1H), 13.4 (br, 1H) |
| 2122 | [DMSO] 3.40 (m, 2H); 3.52 (m, 2H); 4.82 (br, 1H); 7.44 (d, 1H); 8.46 (d, 1H); 8.88 (br, 1H); 13.4 (br, 1H) |
| 2133 | [DMSO] 2.83 (d, 3H); 8.58 (s, 1H); 8.82 (d, br, 1H); 13.4 (br, 1H) |
| 2134 | [DMSO] 1.14 (t, 3H); 3.34 (m, 2H); 8.60 (s, 1H); 8.86 (t, br, 1H); 13.5 (br, 1H) |
| 2135 | [DMSO] 0.89 (t, 3H); 1.54 (m, 2H); 3.26 (q, 2H); 8.59 (s, 1H); 8.85 (t, br, 1H); 13.5 (br, 1H) |
| 2137 | [DMSO] 0.60 (m, 2H); 0.75 (m, 2H); 2.88 (m, 1H); 8.55 (s, 1H); 8.85 (d, br, 1H); 13.4 (br, 1H) |
| 2138 | [DMSO] 0.90 (t, 3H); 1.33 (m, 2H); 1.51 (m, 2H); 3.31 (m, 2H); 8.59 (s, 1H); 8.84 (t, br, 1H); 13.4 (br, 1H) |
| 2139 | [DMSO] 1.71 (m, 2H); 2.05 (m, 2H); 2.25 (m, 2H); 4.40 (m, 1H); 8.62 (s, 1H); 9.04 (d, br, 1H); 13.4 (br, 1H) |
| 2143 | [DMSO] 0.26 (m, 2H); 0.47 (m, 2H); 1.05 (m, 1H); 3.20 (m, 2H); 8.63 (s, 1H); 8.94 (t, br, 1H); 13.4 (br, 1H) |
| 2144 | [DMSO] 0.91 (s, 9H); 3.15 (d, 2H); 8.55 (s, 1H); 8.66 (t, br, 1H); 13.3 (br, 1H) |

3. Biological Examples 3.1 Scoring of the Damage

The damage to the plants is scored visually using a scale of 0-100%, in comparison to control plants:

0%=no noticeable effect compared to the untreated plant
100%=the treated plants dies.

3.2 Post-Emergence Herbicide Action and Safener Action

Seeds or rhizome pieces of monocotyledonous and dicotyledonous harmful plants and crop plants are placed in sandy loam soil in plastic pots, covered with soil and cultivated in the greenhouse under good growth conditions. Alternatively, harmful plants encountered in paddy rice cultivation are cultivated in pots in which the surface of the soil is covered by up to 2 cm of water. Three weeks after sowing, the test plants are treated at the three-leaf stage. The herbicide/safener active compound combinations according to the invention, formulated as emulsion concentrates, and in parallel tests the individual active compounds formulated in a corresponding manner, are sprayed at various dosages at a water application rate of 3001 l/ha (converted) onto the green parts of the plants, and, after the test plants were left to stand in the greenhouse for about 2 to 3 weeks under optimum growth conditions, the effect of the preparations is scored visually in comparison to untreated controls. In the case of rice or harmful plants encountered in the cultivation of rice, the active compounds are also added directly to the irrigation water (application analogously to the so-called granule application) or sprayed onto the plants and into the irrigation water.

The tests show that the safeners according to the invention in combination with herbicides, in a herbicides:safener ratio of from 2:1 to 1:20, considerably reduce the damage caused by the herbicide to crop plants such as corn, rice, wheat or barley or other cereals or dicotyledonous crop plants such as soybeans or oilseed rape compared to the application of the individual herbicides without safener, such that from 30% up to 100% less damage to the crop plant is observed. At the same time, the action of the herbicide against economically important harmful plants is not, or not essentially, adversely affected, so that good herbicidal post-emergence action against a broad spectrum of weed grasses and broad-leaved weeds can be achieved.

In barley, for example, a good safener action for the herbicide mesosulfuron-methyl could be achieved using the compounds Nos. 1, 2, 3, 5, 7, 9, 10, 13, 14, 22, 25, 26, 30, 34, 36, 40, 57, 64, 66, 79, 100, 101, 102, 105, 114, 115, 116, 117, 119, 123, 124, 128, 130, 134, 136, 138, 140, 146, 148, 153, 154, 155, 157, 163, 165, 168, 169, 171, 178, 193, 194, 214, 341, 342, 344, 345, 346, 382, 384, 392, 398, 405, 407, 455, 457, 489, 496, 498, 571, 909, 910, 911, 913, 943, 950, 960, 1023, 1026, 1029, 1030, 1201, 1481, 1487, 1598, 1599, 1600, 1636, 1907.

In corn, for example, a good safener action for the herbicide tembotrione could be achieved using the following compounds from Table 1: 4, 6, 9, 10, 14, 24, 32, 34, 36, 43, 64, 66, 71, 75, 79, 105, 114, 118, 140, 146, 148, 153, 169, 178, 210, 214, 345, 51, 95, 341, 456, 457, 489, 496, 498, 909, 911, 913, 943, 960, 1026, 1139, 1368, 1371, 1485, 1488, 1596, 1597, 1598, 1599, 1600, 1604, 1619, 1625, 1629, 1636, 1638, 1646, 1758.

In rice, for example, the following compounds from Table 1 achieved good safener action for fenoxaprop-P-ethyl and thiencarbazone or thiencarbazone-methyl:

1, 2, 3, 4, 9, 16, 20, 22, 34, 41, 47, 54, 57, 75, 76, 79, 80, 81, 101, 103, 105, 114, 115, 117, 118, 120, 127, 128, 130, 153, 154, 157, 162, 165, 169, 171, 178, 218, 271, 341, 342, 344, 345, 346, 350, 355, 392, 398, 405, 407, 456, 973, 1482, 1596, 1597, 1598, 1600, 1603, 1609, 1625, 1638, 1646, 1659.

3.3 Pre-Emergence Herbicide Action and Safener Action

Seeds or rhizome pieces of monocotyledonous and dicotyledonous weed plants and crop plants were placed in sandy loam soil in plastic pots and covered with soil. The herbicide/safener active compound combinations according to the invention, formulated as suspension emulsion concentrates, and in parallel tests the individual active compounds formulated in a corresponding manner, were then, at various dosages at a water application rate of 600 to 800 l/ha (converted), applied to the surface of the covering soil.

After the treatment, the pots were placed in the greenhouse and kept under good growth conditions for the weeds and the crop plants. Visual scoring of the plant damage or emergence damage was carried out after the test plants had emerged after a test period of 3 to 4 weeks, in comparison to untreated controls. The test results showed that the compounds according to the invention prevented or reduced herbicide damage to the crop plants without reducing, or reducing substantially, the herbicide action against the harmful plants.

For example, example Nos. 2, 19, 39, 72, 104, 122, 155, 193, 194, 217, 232, 271, 341, 380, 392, 1368, 1597, 1625, 1636 of Table 1 showed in the test in combination with the herbicide isoxaflutol a good safener action in corn. The herbicidal action of the herbicidally active compounds used was not adversely affected.

Accordingly, in many cases, the safeners, combined with herbicides, are suitable for the selective control of harmful plants in the pre-emergence treatment of crops of useful plants.

3.4 Seed Treatment

Seeds of crop plants were mixed in bottles with the safeners according to the invention, formulated as suspension or emulsion concentrates, and water, and the mixture was shaken well so that the seeds were coated evenly with the formulation of the safener in question. The seeds or the emerged plants were then tested with herbicides in the pre- or post-emergence method according to the tests of examples 3.3 and 3.2, respectively.

In the treatment of seed, too, the safeners showed good activity. The herbicidal action of the herbicidally active compounds used was not adversely affected.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of the formula (I) or a salt thereof,

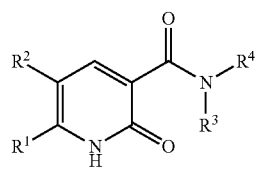

(I)

wherein the identities of $R^1$, $R^2$, $R^3$, and $R^4$ for the compound of formula (I) are selected from the group consisting of (A), (B), and (C);

wherein in (A):
  $R^1$ is a $(C_1-C_6)$-haloalkyl radical;
  $R^2$ is hydrogen or halogen; and
  the identities of $R^3$ and $R^4$ are selected from the group consisting of (i), (ii) (iii), and (iv);
where for (i):
  $R^3$ is:
    (a) hydrogen, $(C_1-C_{16})$-alkyl, $(C_2-C_{16})$-alkenyl, or $(C_2-C_{16})$-alkynyl;
      where each of the 3 last mentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]-carbonyl, and [$(C_1-C_4)$-haloalkoxy]-carbonyl; or
    (b) $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring;
      where each of the 4 lastmentioned radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted; and
  $R^4$ is:
    (a) $(C_1-C_{16})$-alkyl, $(C_2-C_{16})$-alkenyl, or $(C_2-C_{16})$-alkynyl;
      where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, and [$(C_1-C_4)$-haloalkoxy]-carbonyl; or
    (b) $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring;
      where each of the 4 lastmentioned radicals is unsubstituted or substituted by one or more radicals selected from the group consisting of halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]-amino, [$(C_1-C_4)$-alkoxy]-carbonyl, [$(C_1-C_4)$-haloalkoxy]-carbonyl, $(C_3-C_6)$-cycloalkyl, which is unsubstituted or substituted, phenyl, which is unsubstituted or substituted, and heterocyclyl, which is unsubstituted or substituted; and
where for (ii):
$R^3$ is $(C_1\text{-}C_4)$-alkoxy, $(C_2\text{-}C_4)$-alkenyloxy, $(C_2\text{-}C_6)$-alkynyloxy, or $(C_2\text{-}C_4)$-haloalkoxy; and
$R^4$ is hydrogen or $(C_1\text{-}C_4)$-alkyl; or and
where for (iii) $R^3$ and $R^4$ together with the directly attached nitrogen atom are a four- to eight-membered heterocyclic ring which, in addition to the nitrogen atom, may also comprise further hetero ring atoms, and which is unsubstituted or substituted by one or more radicals selected from the group consisting of halogen, cyano, nitro, $(C_1\text{-}C_4)$-alkyl, $(C_1\text{-}C_4)$-haloalkyl, $(C_1\text{-}C_4)$-alkoxy, $(C_1\text{-}C_4)$-haloalkoxy, and $(C_1\text{-}C_4)$-alkylthio; and
where for (iv) $R^3$ and $R^4$ together with the directly attached nitrogen atom are the group $-N=CR^5-NR^6R^7$ in which:
$R^5$ is hydrogen or $(C_1\text{-}C_6)$-alkyl, and
$R^6$, $R^7$ independently of one another are hydrogen or $(C_1\text{-}C_4)$-alkyl, or
$R^6$ and $R^7$ together with the directly attached nitrogen atom form a five- to seven-membered heterocyclic ring; and
wherein in (B):
$R^1$ is a $(C_1\text{-}C_6)$-haloalkyl radical;
$R^2$ is halogen;
$R^3$ is hydrogen; and
$R^4$ is hydrogen; and
wherein in (C):
$R^1$ is a radical of the formula $CF_2CF_3$, $CF_2CF_2H$, $CF_2CF_2Cl$, $CFClCF_3$, $CFHCF_3$, $CF(CF_3)_2$, $CH(CF_3)_2$, $CF_2CF_2CF_3$, or $C(CH_3)_2F$;
$R^2$ is hydrogen;
$R^3$ is hydrogen; and
$R^4$ is hydrogen.

2. A process for preparing compounds of the general formula (I) or salts thereof as defined in claim 1, which comprises:
(a) reacting a carboxylic acid of the general formula (II) with an amine of the formula (III) or a salt thereof to give the compound of the formula (I);
wherein the general formula (II) is:

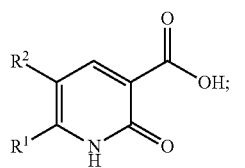

where $R^1$ and $R^2$ are as defined for the compound of the formula (I) to be prepared;
wherein the formula (III) is:

where $R^3$ and $R^4$ are as defined for the compound of the formula (I) to be prepared; or
(b) reacting a carboxylic ester of the general formula (IV) with an amine of the formula (III) or a salt thereof to give the compound of the formula (I);
wherein the general formula (IV) is:

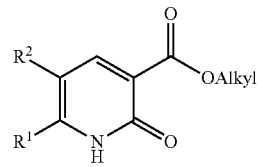

where $R^1$ and $R^2$ are as defined for the compound of the formula (I) to be prepared and "Alkyl" is an alkyl radical;
wherein the formula (III) is:

where $R^3$ and $R^4$ are as defined for the compound of the formula (I) to be prepared; or
(c) reacting a carbonyl halide or a carboxylic anhydride of the general formula (V) with an amine of the formula (III) or a salt thereof to give the compound of the formula (I);
wherein the general formula (V) is:

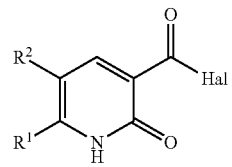

where $R^1$ and $R^2$ are as defined for the compound of the formula (I) to be prepared and Hal is a halogen atom or an acyloxy radical;
wherein the formula (III) is:

where $R^3$ and $R^4$ are as defined for the compound of the formula (I) to be prepared; or
(d) if $R^3$ and $R^4$ in the compound of the formula (I) to be prepared are each hydrogen, reacting a compound of the formula (VI) with malonamide to give the compound of the formula (I);
wherein the formula (VI) is:

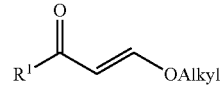

where $R^1$ is as defined for the compound of the formula (I) to be prepared, and "Alkyl" is an alkyl radical.

3. A crop protection composition comprising:
one or more compounds of the formula (I) or salts thereof as defined in claim 1; and
formulation auxiliaries.

4. A crop protection composition comprising:
one or more compounds of the formula (I) or salts thereof as defined in claim 1; and
one or more agrochemicals and, optionally, formulation auxiliaries.

5. The compound as claimed in claim 1;
wherein $R^3$ is:
   (a) hydrogen, $(C_1-C_{10})$-alkyl, $(C_1-C_{10})$-alkenyl, or $(C_2-C_{10})$-alkynyl;
      where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, $[(C_1-C_4)$-alkoxy]-carbonyl, and $[(C_1-C_4)$-haloalkoxy]-carbonyl; or
   (b) $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring;
      where each of the 4 lastmentioned radicals is unsubstituted or substituted by one or more radicals selected from the group consisting of:
         halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]-amino, $[(C_1-C_4)$-alkoxy]-carbonyl, and $[(C_1-C_4)$-haloalkoxy]-carbonyl;
         $(C_3-C_6)$-cycloalkyl, which is unsubstituted or substituted by one or more radicals selected from the group consisting of halogen, $(C_1-C_4)$-alkyl and $(C_1-C_4)$-haloalkyl;
         phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio; and
         heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo; and
wherein $R^4$ is:
   (a) $(C_1-C_{10})$-alkyl, $(C_2-C_{10})$-alkenyl, or $(C_2-C_{10})$-alkynyl;
      where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]-amino, $[(C_1-C_4)$-alkoxy]-carbonyl, and $[(C_1-C_4)$-haloalkoxy]-carbonyl; or
   (b) $(C_3-C_6)$-cycloalkyl, $(C_4-C_6)$-cycloalkenyl, $(C_3-C_6)$-cycloalkyl which is condensed at one side of the ring to a 4- to 6-membered saturated or unsaturated carbocyclic ring, or $(C_4-C_6)$-cycloalkenyl which is condensed at one side of the ring to a 4- to 6-membered saturated or unsaturated carbocyclic ring;
      where each of the 4 lastmentioned radicals is unsubstituted or substituted by one or more radicals selected from the group consisting of:
         halogen, hydroxyl, cyano, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]-amino, $[(C_1-C_4)$-alkoxy]-carbonyl, and $[(C_1-C_4)$-haloalkoxy]-carbonyl;
         $(C_3-C_6)$-cycloalkyl, which is unsubstituted or substituted by one or more radicals selected from the group consisting of halogen, $(C_1-C_4)$-alkyl and $(C_1-C_4)$-haloalkyl;
         phenyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio; and
         heterocyclyl, which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo.

6. The compound as claimed in claim 1;
wherein $R^3$ is:
   hydrogen, $(C_1-C_{10})$-alkyl, $(C_2-C_{10})$-alkenyl, or $(C_2-C_{10})$-alkynyl;
      where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]-amino, $[(C_1-C_4)$-alkoxy]-carbonyl, and $[(C_1-C_4)$-haloalkoxy]-carbonyl; or
   $(C_3-C_6)$-cycloalkyl or $(C_3-C_6)$-cycloalkyl which is condensed at one side of the ring to a 4- to 6-membered saturated or unsaturated carbocyclic ring;
      where each of the 2 lastmentioned radicals is unsubstituted or substituted by one or more radicals selected from the group consisting of $(C_1-C_4)$-alkyl; and
wherein $R^4$ is:
   $(C_1-C_{10})$-alkyl, $(C_2-C_{10})$-alkenyl, or $(C_2-C_{10})$-alkynyl;
      where each of the 3 lastmentioned radicals is unsubstituted or substituted by one or more radicals selected from the group consisting of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di$[(C_1-C_4)$-alkyl]-amino, $[(C_1-C_4)$-alkoxy]-carbonyl, and $[(C_1-C_4)$-haloalkoxy]-carbonyl; or
   $(C_3-C_6)$-cycloalkyl or $(C_3-C_6)$-cycloalkyl which is condensed at one side of the ring to a 4- to 6-membered saturated or unsaturated carbocyclic ring;
      where each of the 2 lastmentioned radicals is unsubstituted or substituted by one or more radicals selected from the group consisting of $(C_1-C_4)$-alkyl.

7. The compound as claimed in claim 1;
wherein $R^3$ is hydrogen, $(C_1-C_{10})$-alkyl, $(C_2-C_{10})$-alkenyl, or $(C_2-C_{10})$-alkynyl;
   where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio, and $[(C_1-C_4)$-alkoxy]-carbonyl; and
wherein $R^4$ is $(C_1-C_{10})$-alkyl, $(C_2-C_{10})$-alkenyl, or $(C_2-C_{10})$-alkynyl;

where each of the 3 lastmentioned radicals is unsubstituted or substituted by one or more radicals selected from the group consisting of $(C_1-C_4)$-alkoxy, $(C_1-C_4)$-haloalkoxy, $(C_1-C_4)$-alkylthio, and $[(C_1-C_4)$-alkoxy]-carbonyl.

8. The compound as claimed in claim 1;
wherein $R^1$ is $CF_3$, $CF_2Cl$, $CF_2H$, $CF_2CF_3$, $CF_2CF_2H$, $CF_2CF_2Cl$, $CF_2CF_2CF_3$, or $C(CH_3)_2F$; and
wherein $R^2$ is hydrogen or halogen.

9. The compound as claimed in claim 1;
wherein $R^1$ is a $(C_1-C_6)$-haloalkyl radical;
wherein $R^2$ is halogen;
wherein $R^3$ is hydrogen; and
wherein $R^4$ is hydrogen.

10. The compound as claimed in claim 1;
wherein $R^1$ is a radical of the formula $CF_2Cl$, $CF_2H$, $CF_2CF_3$, $CF_2CF_2H$, $CF_2CF_2Cl$, $CFClCF_3$, $CFHCF_3$, $CF(CF_3)_2$, $CH(CF_3)_2$, $CF_2CF_2CF_3$, or $C(CH_3)_2F$;
wherein $R^2$ is hydrogen;
wherein $R^3$ is hydrogen; and
wherein $R^4$ is hydrogen.

11. A method for protecting useful plants against phytotoxic side effects of agrochemicals, the method comprising:
applying an effective amount of one or more compounds as defined in claim 1 before, after, or simultaneously with the agrochemicals to the plants, parts of the plants, the plant seeds, or seed of the plants.

12. The method as claimed in claim 11;
wherein one or more compounds of the formula (I) or salts thereof are used together with one or more agrochemicals which, applied on their own, cause damage to the useful plants, optionally in the presence of formulation auxiliaries.

13. The method as claimed in claim 11;
wherein the application is by the post-emergence method.

14. The method as claimed in claim 11;
wherein the application of the compound of the formula (I) or a salt thereof is by treating the plant seeds or seed of the plants.

15. The method as claimed in claim 11;
wherein the application is by the pre-emergence method.

16. A method for the selective control of harmful plants in crops of useful plants, the method comprising:
applying an effective amount of one or more compounds of the formula (I) or salts thereof as defined in claim 1 before, after, or simultaneously with one or more herbicides to the plants, parts of plants, plant seeds, or seed of the plants.

17. The method as claimed in claim 16, further comprising:
treating the seed of the plants with one or more compounds of the formula (I) or salts thereof and applying the herbicide after sowing by the pre-emergence method or by the post-emergence method.

* * * * *